US011906519B2

(12) United States Patent
Zhang et al.

(10) Patent No.: US 11,906,519 B2
(45) Date of Patent: Feb. 20, 2024

(54) METHODS FOR IDENTIFYING LILRB-BLOCKING ANTIBODIES

(71) Applicant: THE BOARD OF REGENTS OF THE UNIVERSITY OF TEXAS SYSTEM, Austin, TX (US)

(72) Inventors: Chengcheng Zhang, Dallas, TX (US); Zhiqiang An, Houston, TX (US); Ningyan Zhang, Houston, TX (US); Mi Deng, Plano, TX (US); Jaehyup Kim, Houston, TX (US); Xun Gui, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 270 days.

(21) Appl. No.: 16/321,745

(22) PCT Filed: Jul. 27, 2017

(86) PCT No.: PCT/US2017/044171
§ 371 (c)(1),
(2) Date: Jan. 29, 2019

(87) PCT Pub. No.: WO2018/022881
PCT Pub. Date: Feb. 1, 2018

(65) Prior Publication Data

US 2021/0349096 A1 Nov. 11, 2021

Related U.S. Application Data

(60) Provisional application No. 62/368,672, filed on Jul. 29, 2016.

(51) Int. Cl.
*G01N 33/574* (2006.01)
*G01N 15/14* (2006.01)
(Continued)

(52) U.S. Cl.
CPC ....... *G01N 33/57426* (2013.01); *G01N 15/14* (2013.01); *G01N 21/6428* (2013.01);
(Continued)

(58) Field of Classification Search
CPC ....... G01N 33/57426; G01N 33/57492; G01N 33/4915; G01N 33/5023; G01N 2015/1006; G01N 2021/6439
See application file for complete search history.

(56) References Cited

FOREIGN PATENT DOCUMENTS

| | | |
|---|---|---|
| CN | 104225627 | 12/2014 |
| WO | WO 2013/033734 | 3/2013 |

(Continued)

OTHER PUBLICATIONS

Deng et al. (A motif in LILRB2 critical for Angptl2 binding and activation. Blood 124 (6): 924-935 (Aug. 2014)).*

(Continued)

*Primary Examiner* — Gailene Gabel
(74) *Attorney, Agent, or Firm* — Parker Highlander PLLC

(57) ABSTRACT

Provided herein are methods and compositions for the identification of modulators of ApoE-induced LILRB activation. Also provided herein are methods of treating cancer comprising the administration of an inhibitor of ApoE-induced LILRB activation. Also provided are methods of treating autoimmune disease or inhibiting the onset of transplant rejection or treating an inflammatory disorder comprising administering an agonist of ApoE-induced LILRB activation to a subject.

26 Claims, 73 Drawing Sheets

Specification includes a Sequence Listing.

(51) Int. Cl.
G01N 21/64 (2006.01)
G01N 33/50 (2006.01)
G01N 33/49 (2006.01)
G01N 15/00 (2006.01)
G01N 15/10 (2006.01)
(52) U.S. Cl.
CPC ...... *G01N 21/6456* (2013.01); *G01N 33/4915* (2013.01); *G01N 33/5023* (2013.01); *G01N 33/57492* (2013.01); *G01N 2015/0065* (2013.01); *G01N 2015/1006* (2013.01); *G01N 2021/6439* (2013.01)

(56) References Cited

FOREIGN PATENT DOCUMENTS

| WO | WO 2015/179633 | 11/2015 |
| WO | WO 2016/144728 | 9/2016 |

OTHER PUBLICATIONS

Deng et al. A motif in LILRB2 critical for Angptl2 binding and activation. Blood 124 (6): 924-936 (Aug. 2014).*
Chiofalo et al. Subclass specificity of the Fc receptor for human IgG on K562. Cell Immunol 114 (2): 272-81 (Jul. 1988).*
Ali, K., Middleton, M., Pure, E. & Rader, D. J. Apolipoprotein E suppresses the type I inflammatory response in vivo. Circ Res 97, 922-927, doi:10.1161/01.res.0000187467.67684.43 (2005).
Baia, Diogo, et al. "Interaction of the LILRB1 inhibitory receptor with HLA class Ia dimers." *European Journal of Immunology* 46.7: 1681-1690. (2016).
Chen, Z. et al. Signalling thresholds and negative B-cell selection in acute lymphoblastic leukaemia. Nature 521. 357-361, doi:10.1038/nature14231 (2015).
Chiofalo, Maria Stefania, et al. "Subclass specificity of the Fc receptor for human IgG on K562." *Cellular Immunology* 114.2: 272-281. (1988).
Colovai, A. I. et al. Expression of inhibitory receptor ILT3 on neoplastic B cells is associated with lymphoid tissue involvement in chronic lymphocytic leukemia. Cytometry B Clin Cytom 72, 354-362, doi:10.1002/cyto.b.20164 (2007).
Cortesini, R. Pancreas cancer and the role of soluble immunoglobulin-like transcript 3 (ILT3), JOP : Journal of the pancreas 8, 697-703 (2007).
De Goeje, P. L. et al. Immunoglobulin-like transcript 3 is expressed by myeloid-derived suppressor cells and correlates with survival in patients with non-small cell lung cancer. Oncoimmunology 4, e1014242, doi:10.1080/2162402X.2015.1014242 (2015).
Deng, Mi, et al. "A motif in LILRB2 critical for Angptl2 binding and activation." *Blood, The Journal of the American Society of Hematology* 124.6: 924-935. (2014).
Deng. Mi, et al. "LILRB4 signalling in leukaemia cells mediates T cell suppression and tumour infiltration." *Nature* 562.7728: 605-609. (2018).
Extended European Search Report issued in European Patent Application No. 17835266.2, dated Mar. 10, 2020.
Gui, Xun, et al. "Disrupting LILRB4/APOE interaction by an efficacious humanized antibody reverses T-cell suppression and blocks AML development." *Cancer immunology research* 7.8: 1244-1257, (2019).
Grainger, D. J., Reckless, J. & McKilligin, E. Apolipoprotein E modulates clearance of apoptotic bodies in vitro and in vivo, resulting in a systemic proinflammatory state in apolipoprotein E-deficient mice. J Immunol 173, 6366-6375 (2004).
Harly, C. et al. Up-regulation of cytolytic functions of human Vdelta2-gamma T lymphocytes through engagement of ILT2 expressed by tumor target cells. Blood 117, 2864-2873, doi:10.1182/blood-2010-09-309781 (2011).
Heidemeich, S. et al. Impact of the NK cell receptor LIR-1 (ILT-2/CD85j/LILRB1) on cytotoxicity against multiple myeloma. Clinical & developmental immunology 2012, 652130, doi:10.1155/2012/652130 (2012).
International Preliminary Report on Patentability issued in PCT/US2017/044171, dated Feb. 7, 2019.
International Search Report and Written Opinion issued in PCT/US2017/044171, dated Jan. 11, 2018.
Invitation to Pay Additional Fees issued in PCT/US2017/044171, dated Nov. 8, 2017.
Kang, Xunlei, et al. "Inhibitory leukocyte immunoglobulin-like receptors: immune checkpoint proteins and tumor sustaining factors." *Cell cycle* 15.1: 25-40.(2016).
Kang, X. et al. The ITIM-containing receptor LAIR1 is essential for acute myeloid leukaemia development. Nat Cell Biol 17, 665-677, doi:10.1038/ncb3158 (2015).
Lebbink, Robert Jan, et al. "The soluble leukocyte-associated Ig-like receptor (LAIR)-2 antagonizes the collagen/LAIR-1 inhibitory immune interaction." *The Journal of Immunology* 180.3: 1662-1669. (2008).
Liu, X. et al. ANGPTL2/LILRB2 signaling promotes the propagation of lung cancer cells. Oncotarget (2014).
Liu, J. et al. Inhibitory receptor immunoglobulin-like transcript 4 was highly expressed in primary ductal and lobular breast cancer and significantly correlated with IL-10. Diagnostic pathology 9, 85, doi:10.1186/1746-1596-9-85 (2014).
Ma, G. et al. Paired immunoglobin-like receptor-B regulates the suppressive function and fate of myeloid-derived suppressor cells. Immunity 34, 385-395, doi:10.1016/j.immuni.2011.02.004 (2011).
Mori, Y. et al. Inhibitory immunoglobulin-like receptors LILRB and PIR-B negatively regulate osteoclast development. J Immunol 181, 4742-4751 (2008).
Naji, A., Menier, C., Maki, G., Carosella, E. D. & Rouas-Freiss, N. Neoplastic B-cell growth is impaired bv HLA-G/ILT2 interaction. Leukemia 26, 1889-1892, doi:10.1038/leu.2012.62 (2012).
Pfistershammer, K. et al. Allogeneic disparities in immunoglobulin-like transcript 5 induce potent antibody responses in hematopoietic stem cell transplant recipients. Blood 114, 2323-2332, doi:10.1182/blood-2008-10-183814 (2009).
Suciu-Foca, N. et al. Soluble Ig-like transcript 3 inhibits tumor allograft rejection in humanized SCID mice and T cell responses in cancer patients. J Immunol 178, 7432-7441 (2007).
Sun, Y., Liu, J., Gao, P., Wang, Y. & Liu, C. Expression of Ig-like transcript 4 inhibitory receptor in human non-small cell lung cancer. Chest 134, 783-788, doi:10.1378/chest.07-1100 (2008).
Urosevic, M., Kamarashev, J., Burg, G. & Dummer, R. Primary cutaneous CD8+ and CD56+ T-cell lymphomas express HLA-G and killer-cell inhibitory ligand, ILT2. Blood 103, 1796-1798, doi:10.1182/blood-2003-10-3372 (2004).
Wang, L. et al. Co-expression of immunoglobulin-like transcript 4 and angiopoietin-like proteins in human non-small cell lung cancer. Mol Med Rep 11, 2789-2796, doi:10.3892/nmir.2014.3029 (2015).
Zhang, Y. et al. Expression of immunoglobulin-like transcript (ILT)2 and ILT3 in human gastric cancer and its clinical significance. Mol Med Rep 5, 910-916, doi:10.3892/mmr.2012.744 (2012).
Zhang, P. et al. ILT4 drives B7-H3 expression via PIK/AKT/mTOR signalling and ILT4/B7-H3 co-expression correlates with poor prognosis in non-small cell lung cancer. FEES Lett, doi:10.1016/j.febslet.2015.06.037 (2015).
Zheng, J. et al. Inhibitory receptors bind ANGPTLs and support blood stem cells and leukaemia development. Nature 485, 656-660, doi:10.1038/nature11095 (2012).
Office Communication in European Patent Application No. 17835266.2, dated Jun. 28, 2023.
Zhang, FeiFei et al. "Inhibitory leukocyte immunoglobulin-like receptors in cancer development." *Science China. Life sciences* vol. 58,12 (2015): 1216-25.

* cited by examiner

PD1:
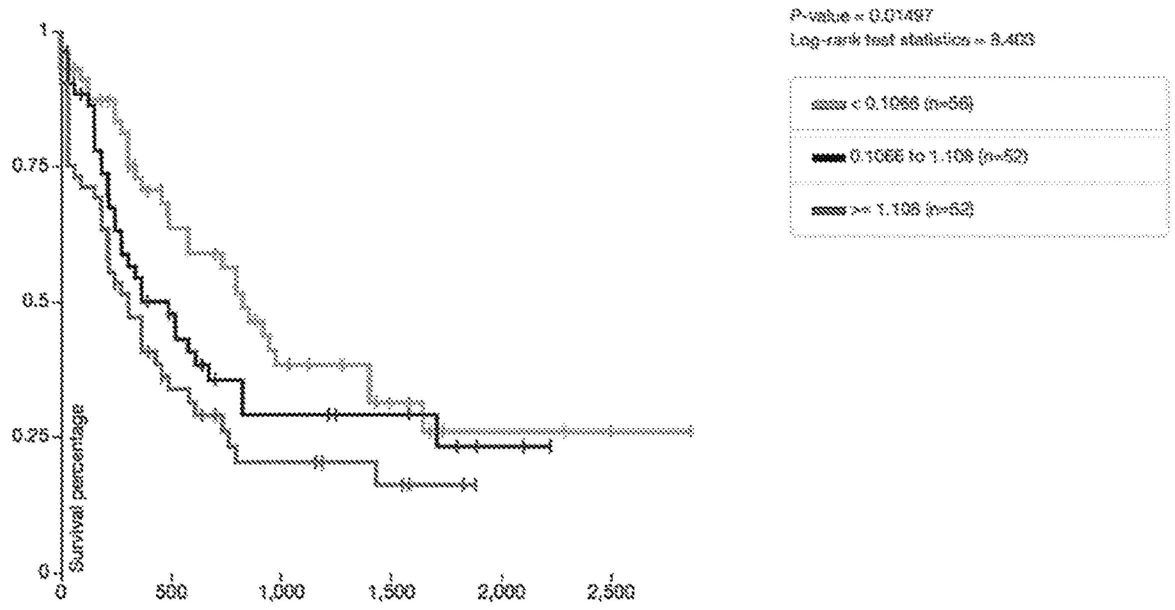
PDCD6:
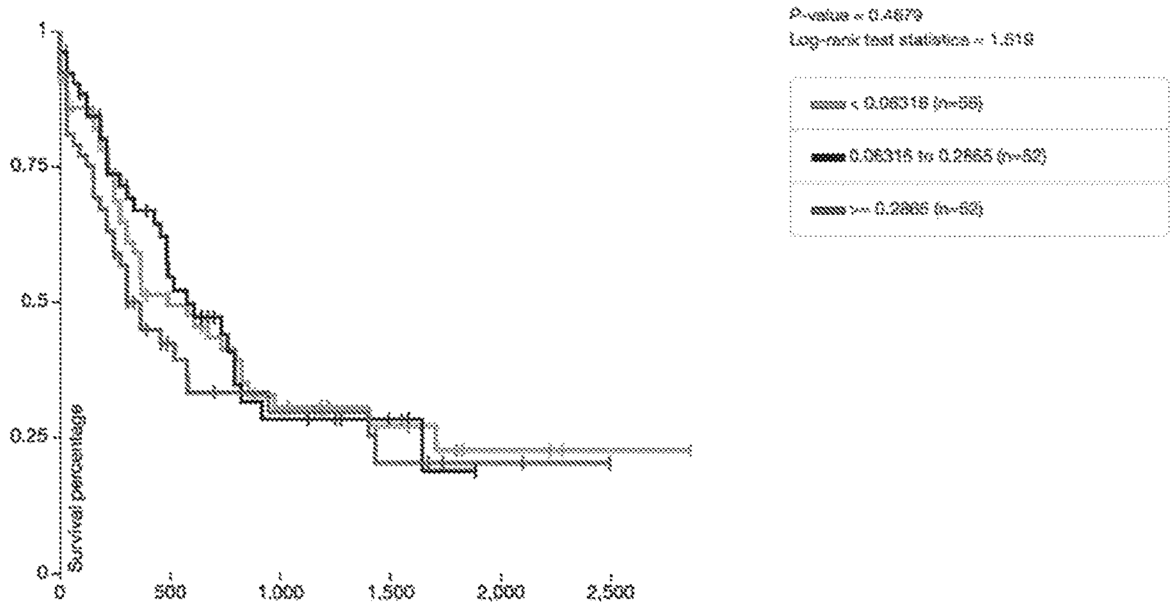
FIG. 5a

PD-L1:
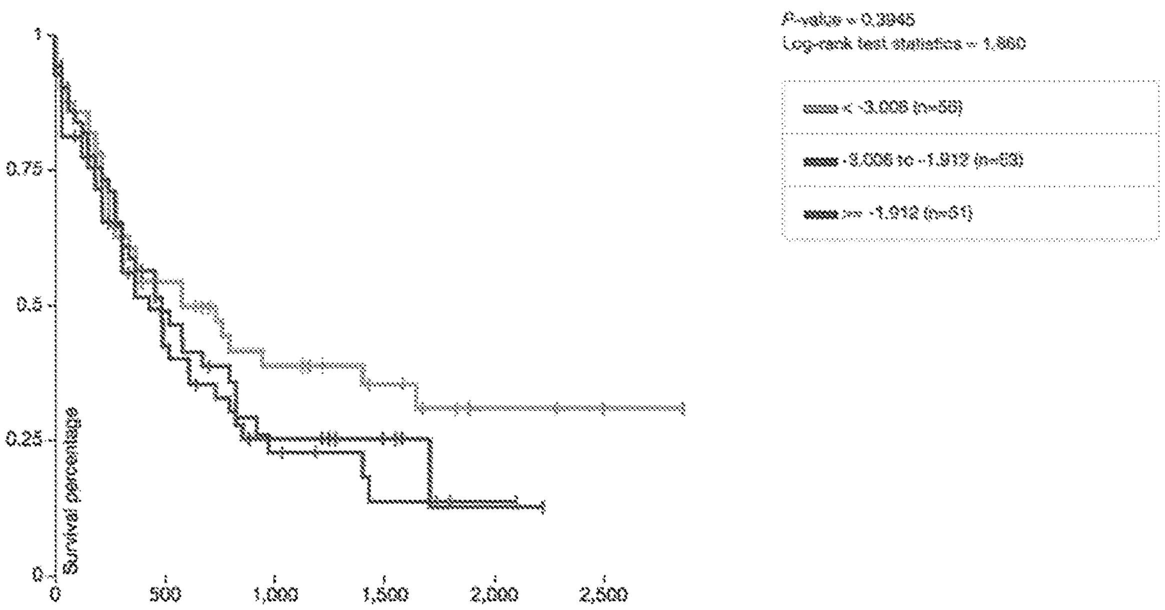
PD-L2:
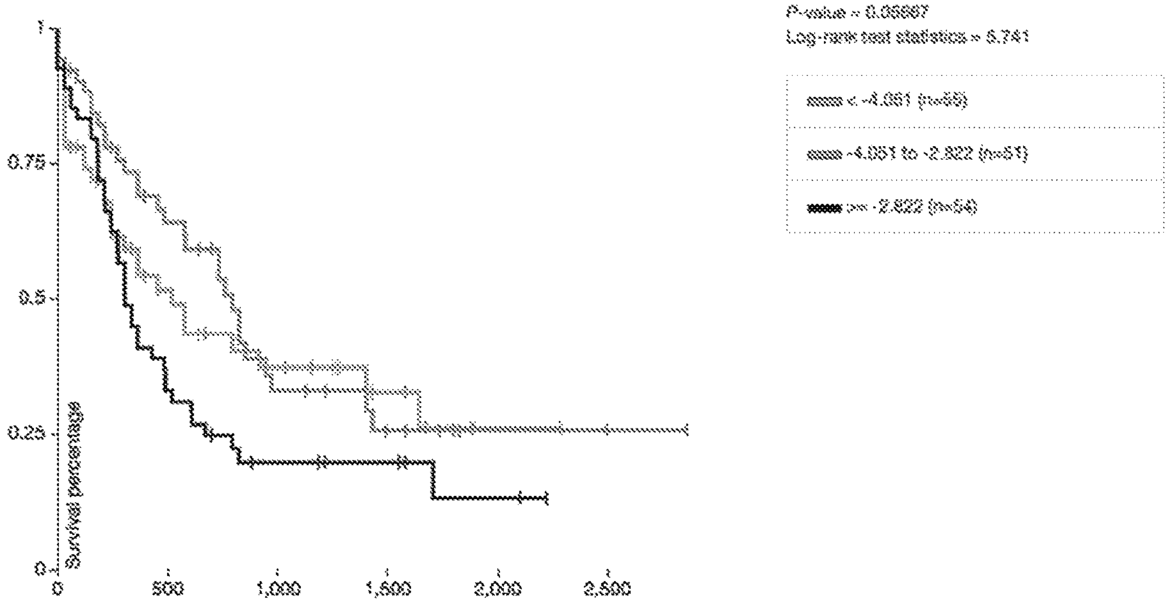
FIG. 5a (cont.)

CTLA-4:
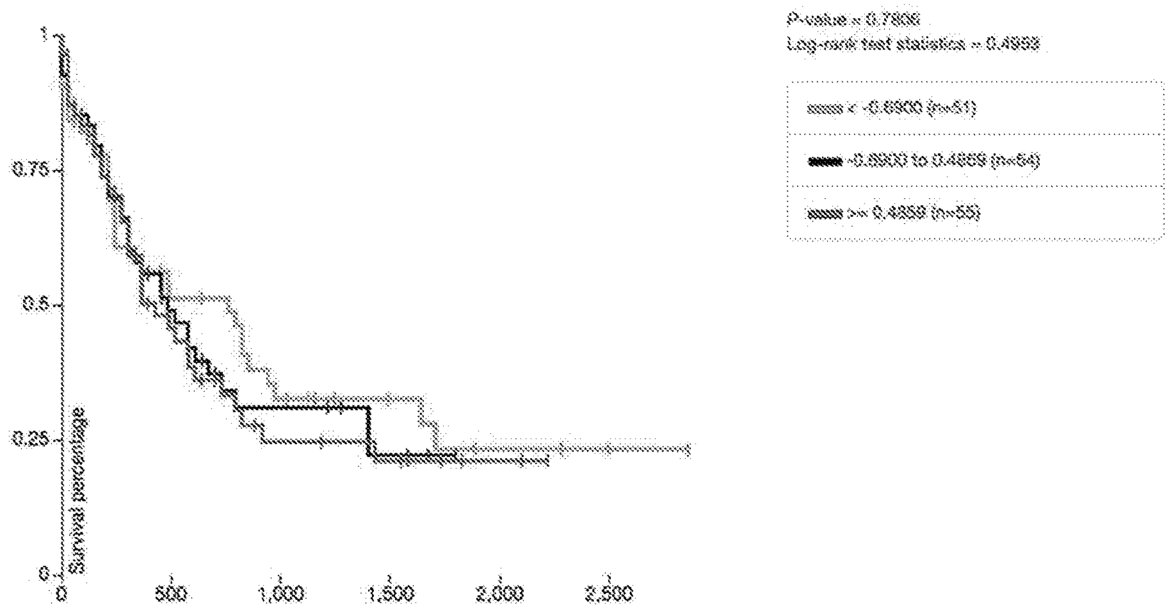
CD80:
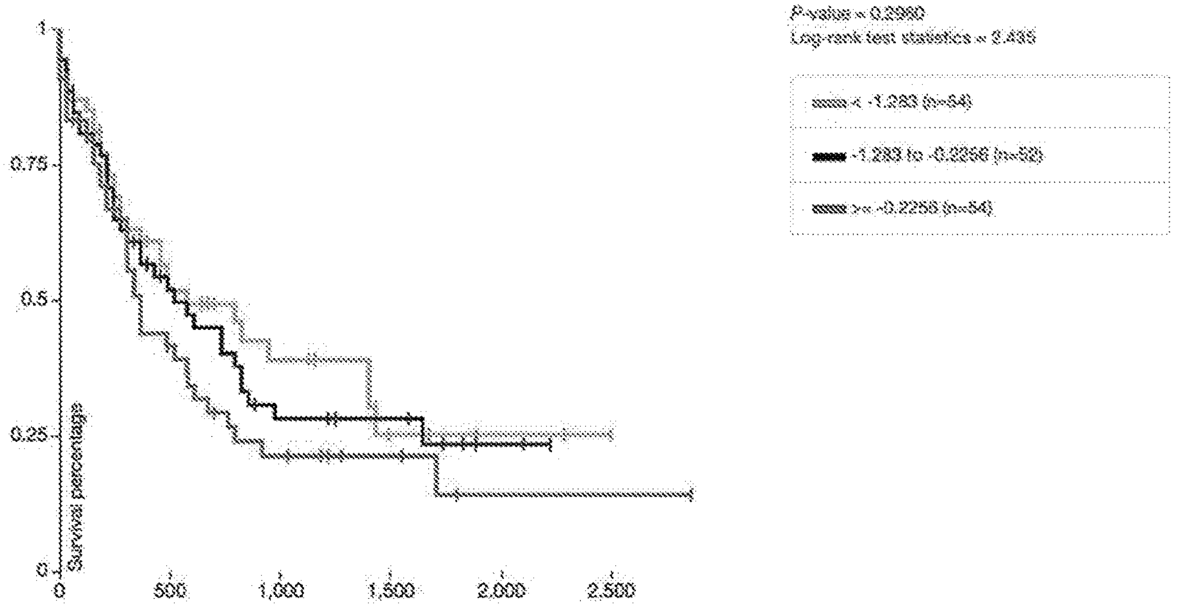
FIG. 5a (cont.)

CD86:
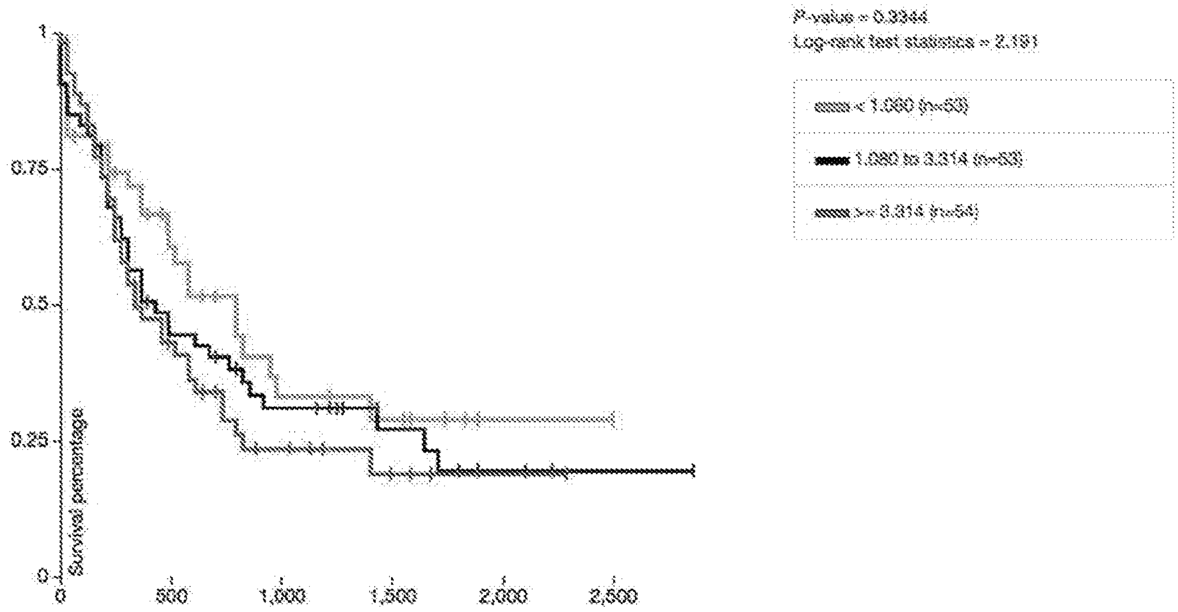
ICOS:
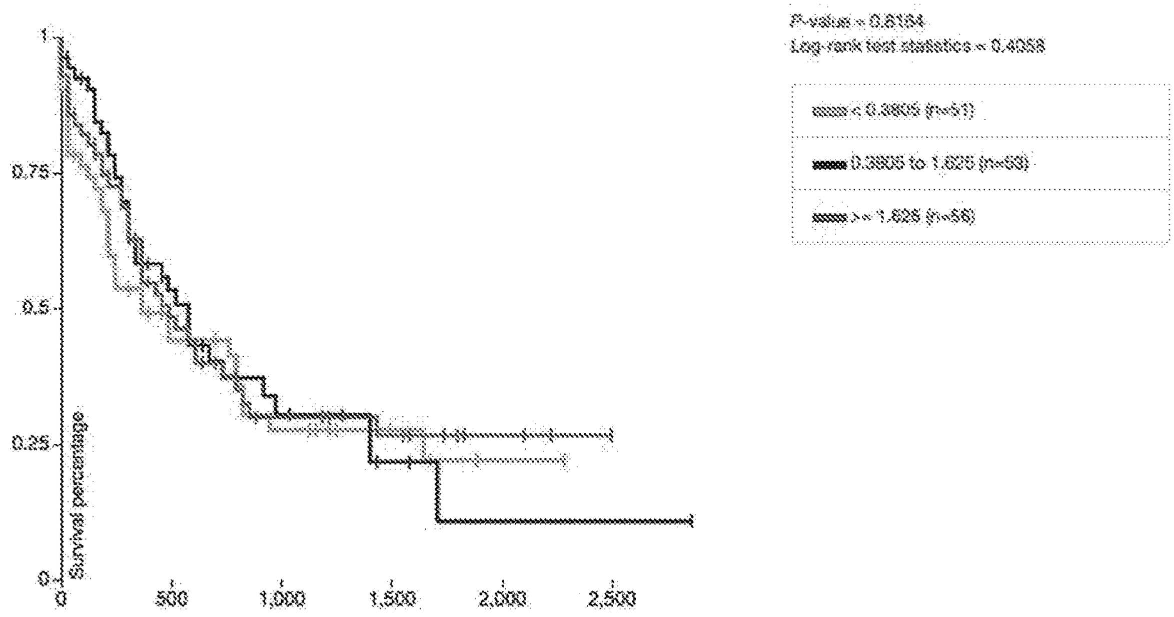
FIG. 5a (cont.)

ICOSLG:
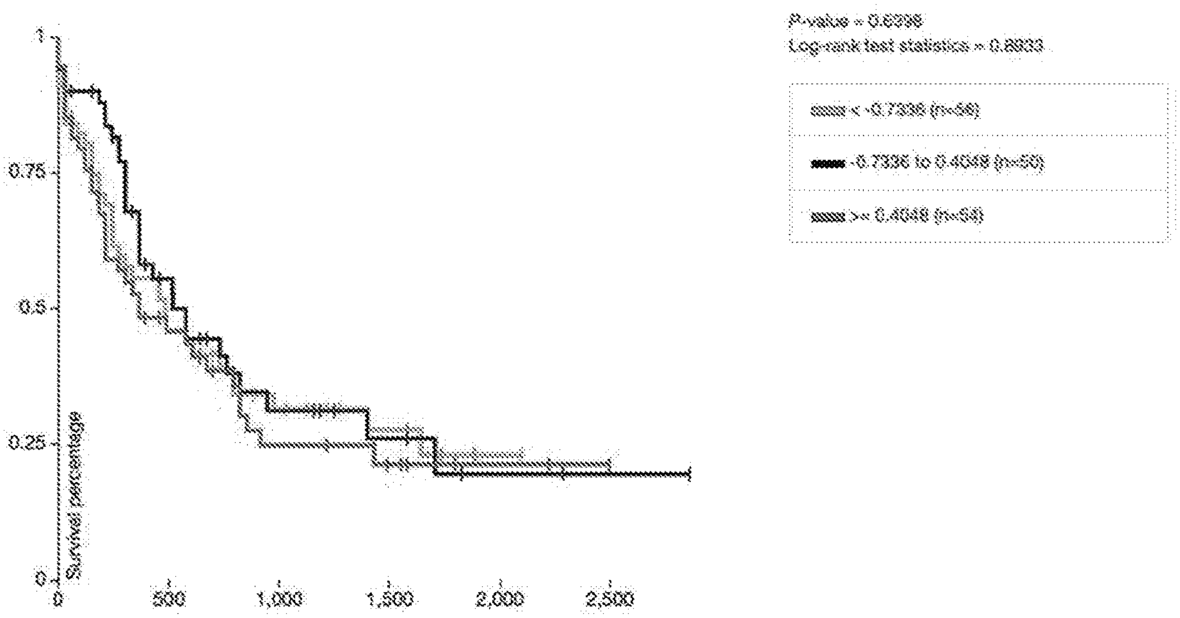
CD276:
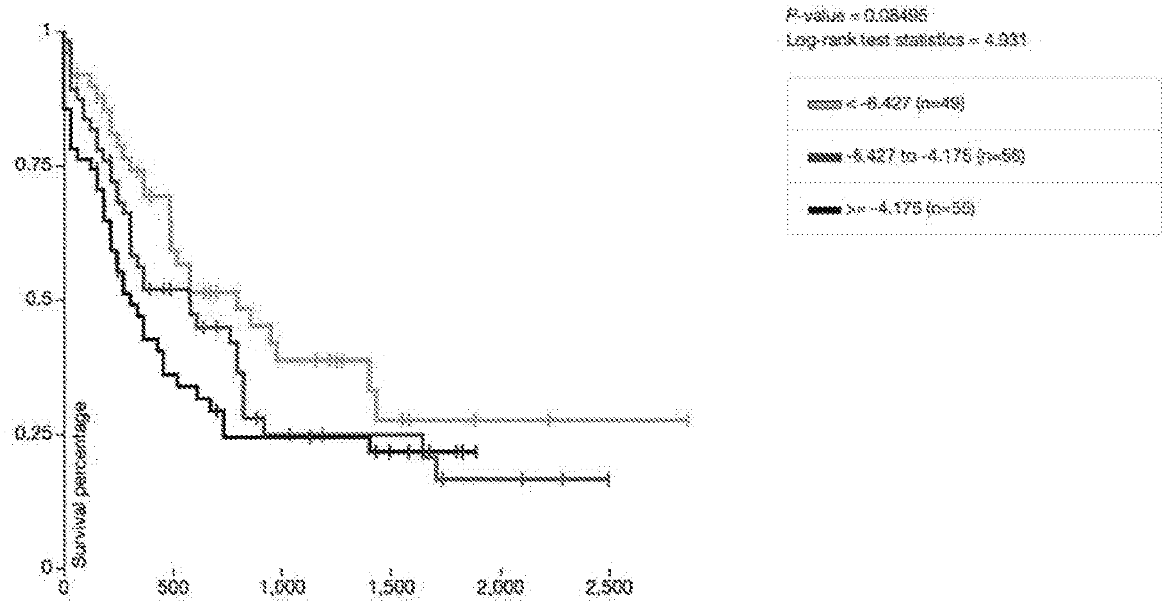
FIG. 5a (cont.)

VTCN1:
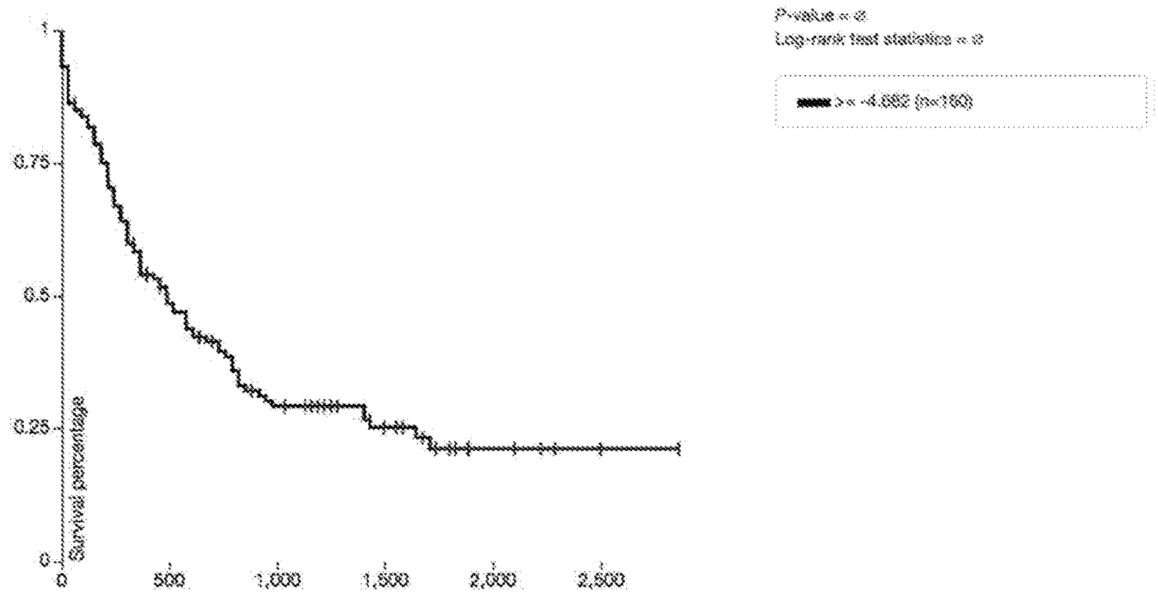
BTLA:
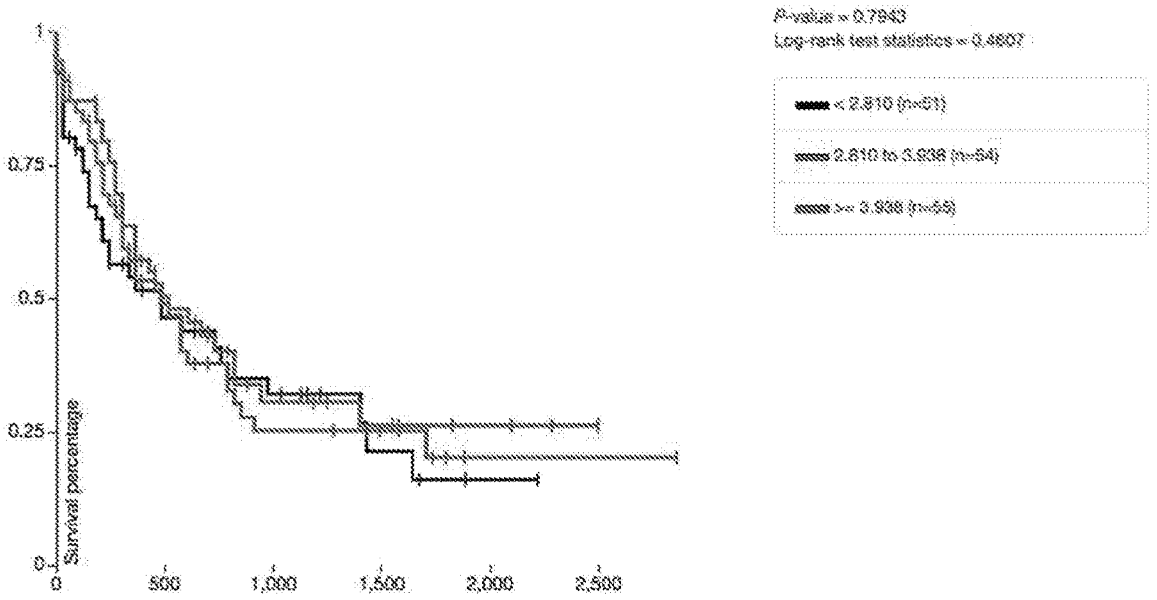
FIG. 5a (cont.)

CD28:
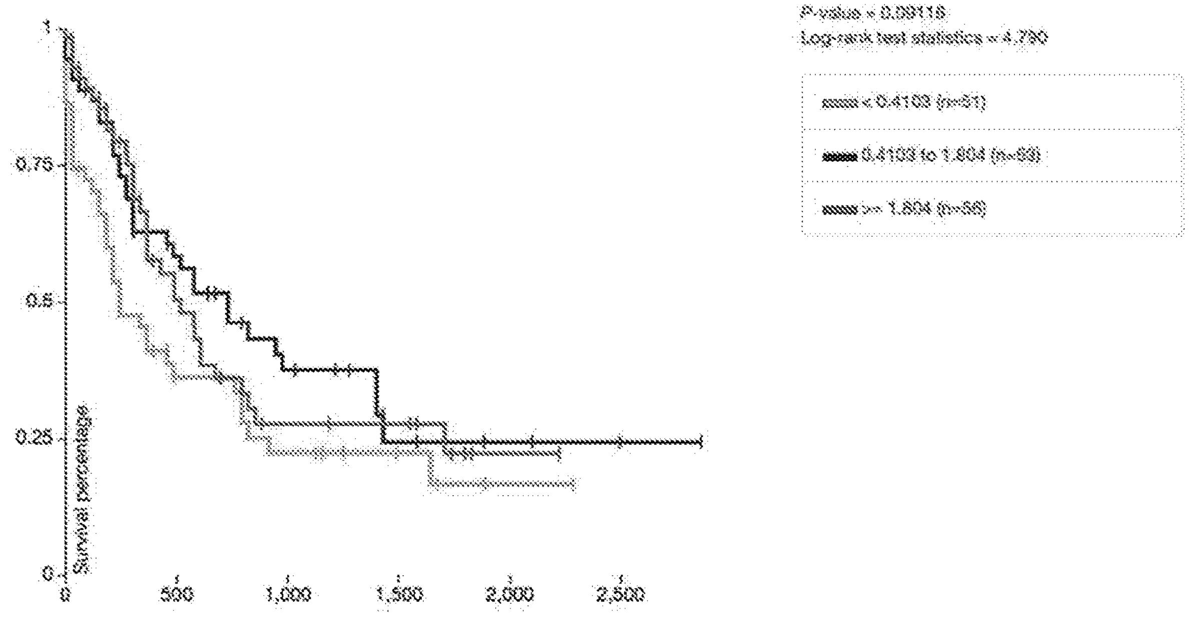
CD28H:
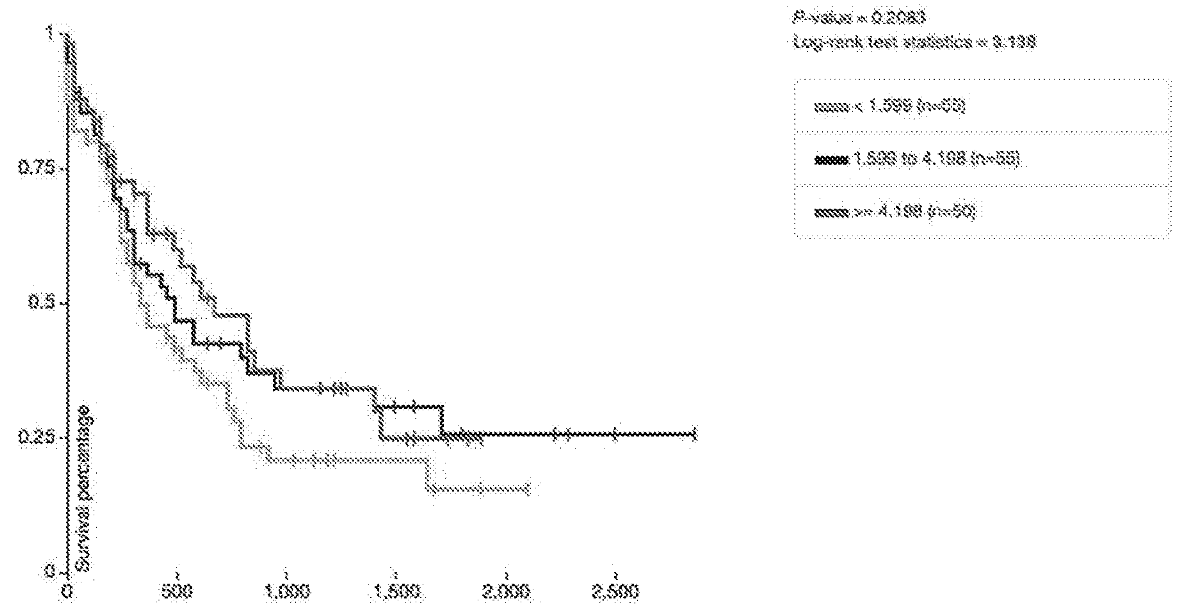
FIG. 5a (cont.)

VISTA:
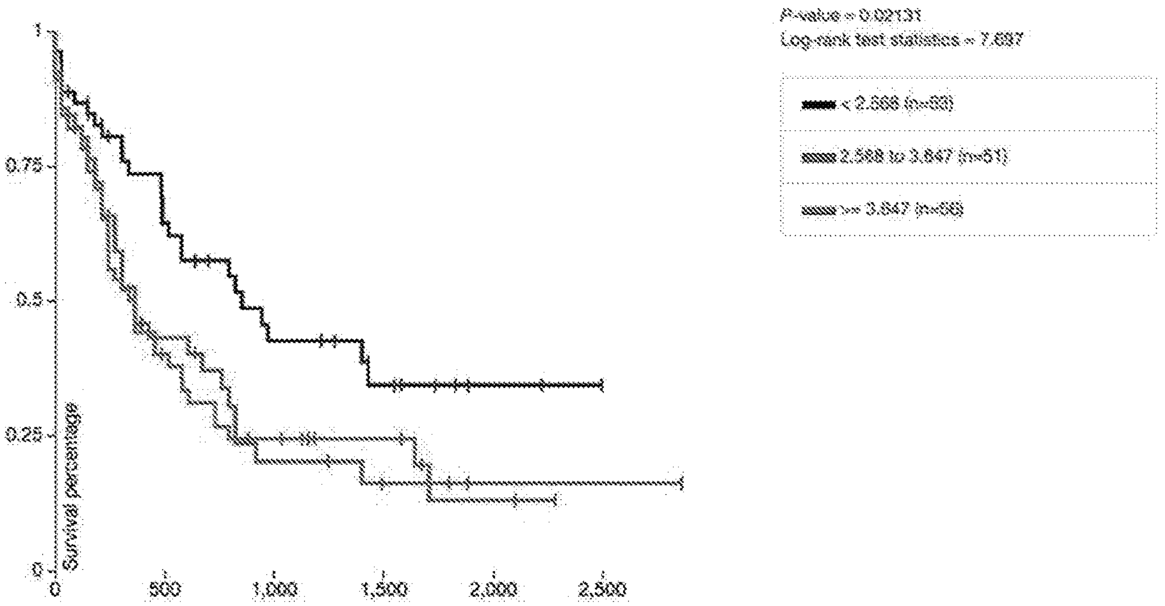
LILRA1:
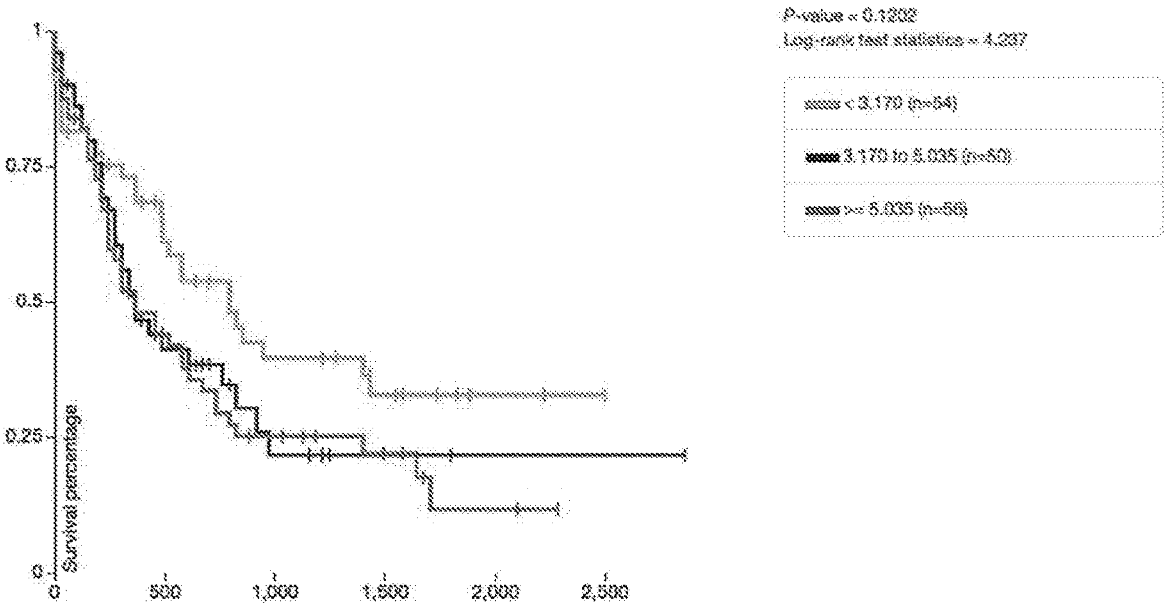
FIG. 5a (cont.)

LILRA2:
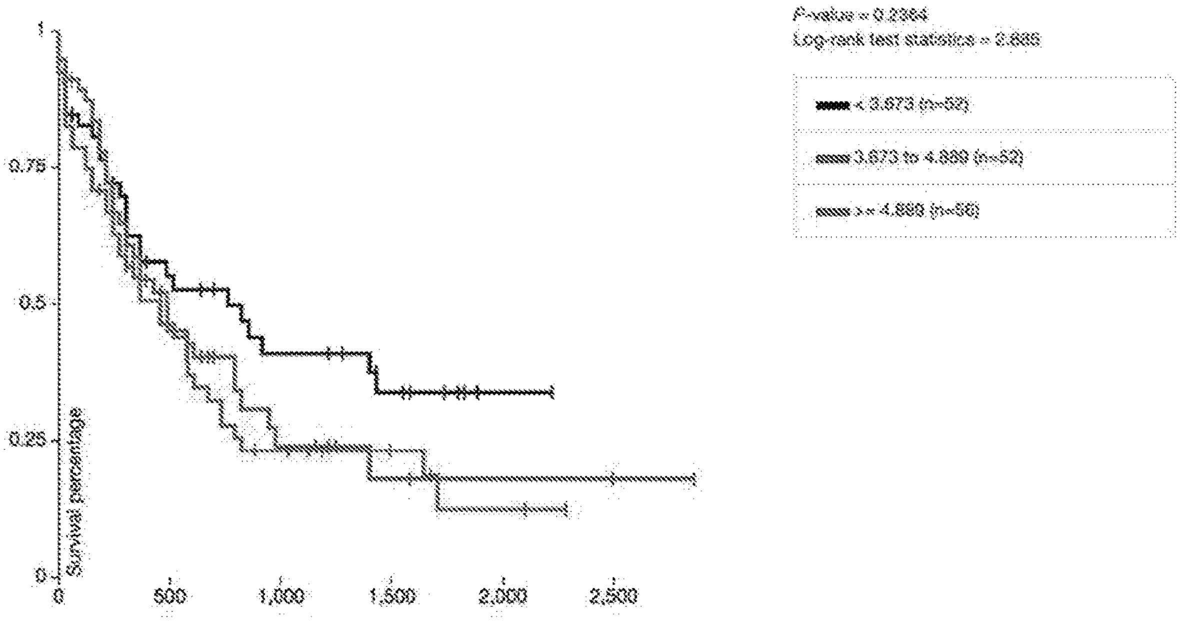
LILRA4:
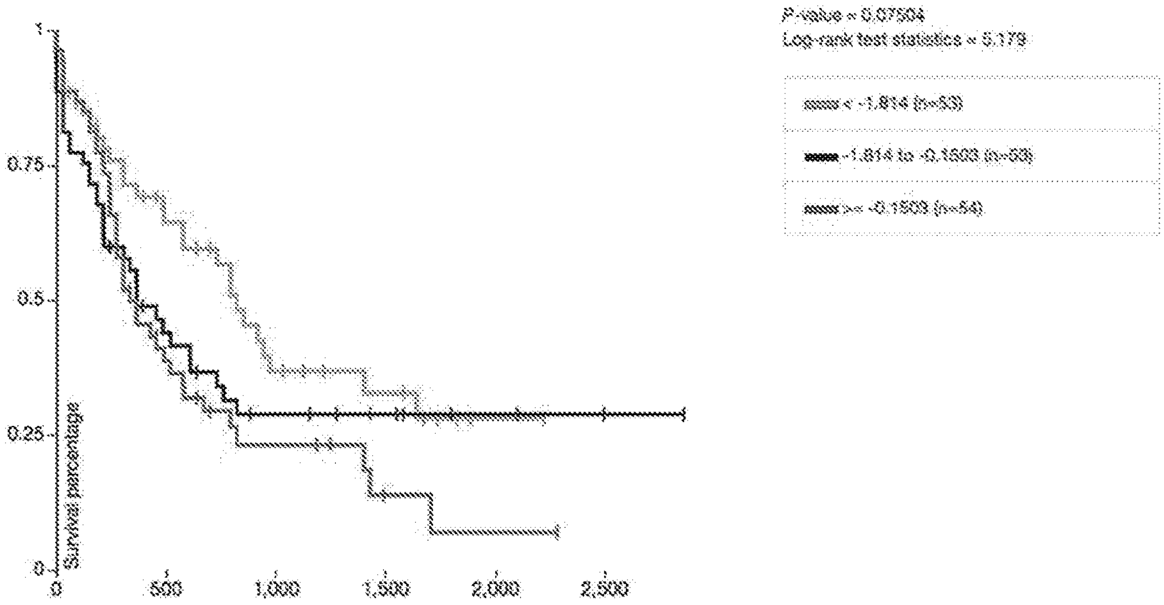
FIG. 5a (cont.)

LILRA5:
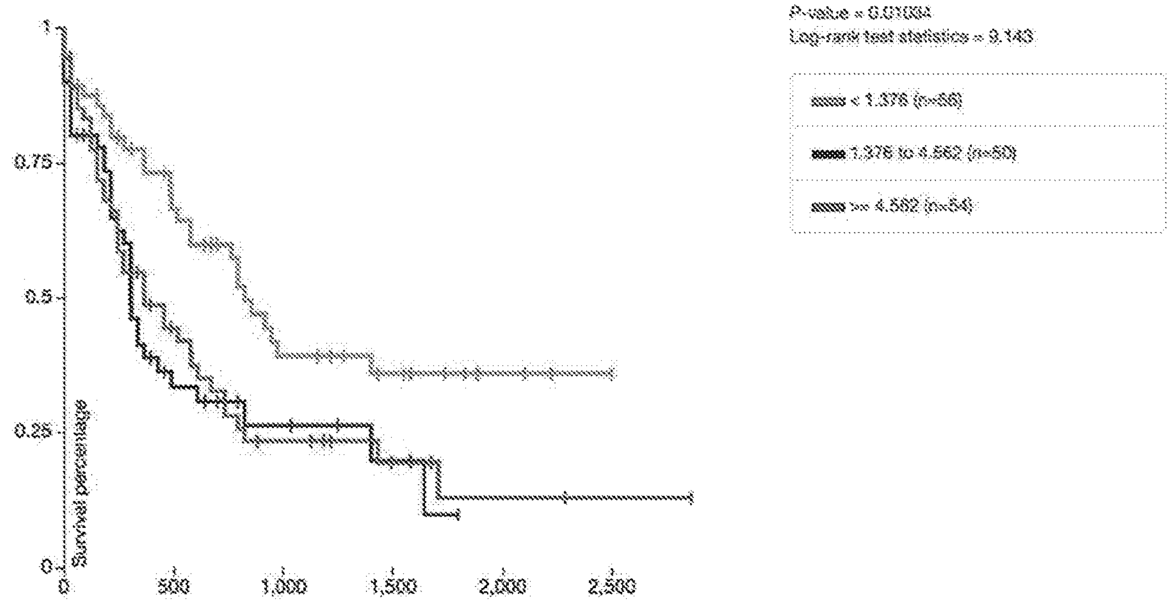
LILRA6:
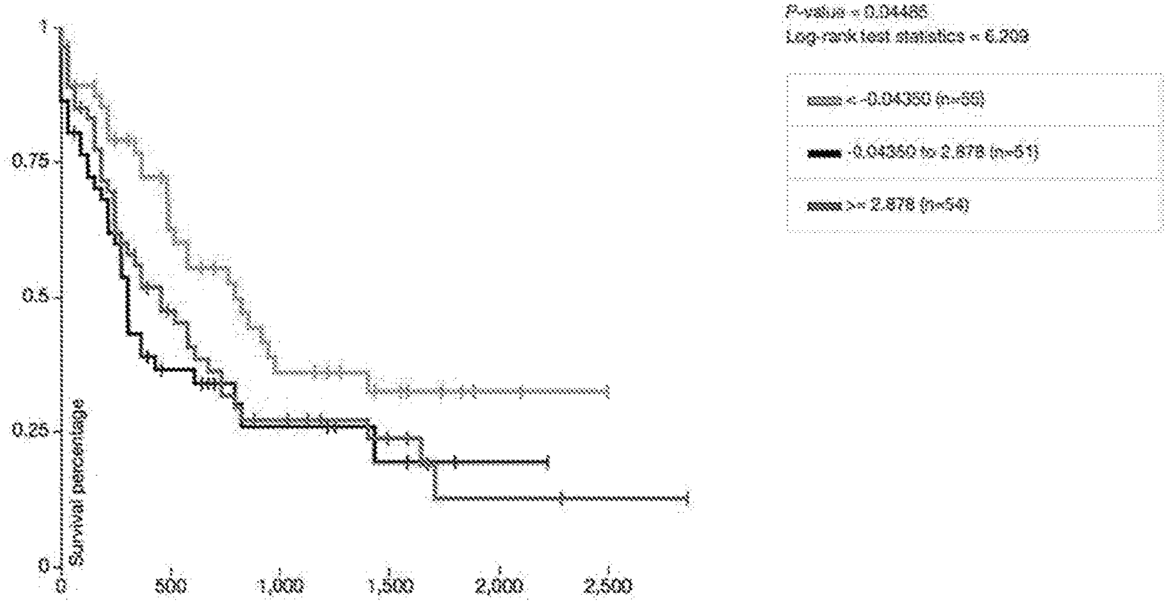
FIG. 5a (cont.)

LILRB1:
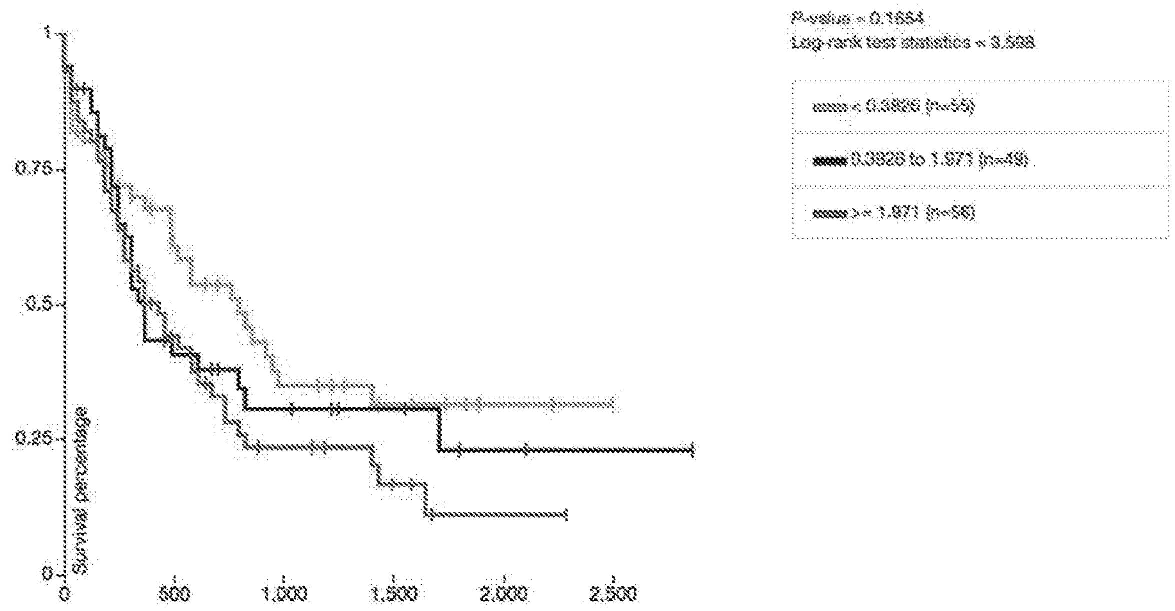
LILRB2:
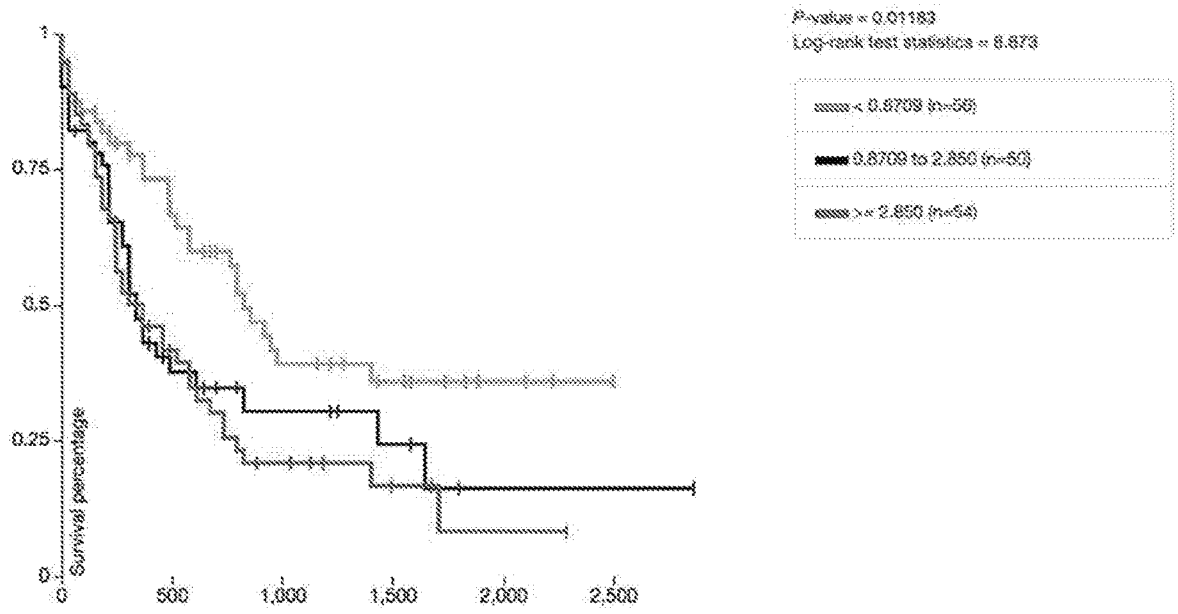
FIG. 5a (cont.)

LILRB3:
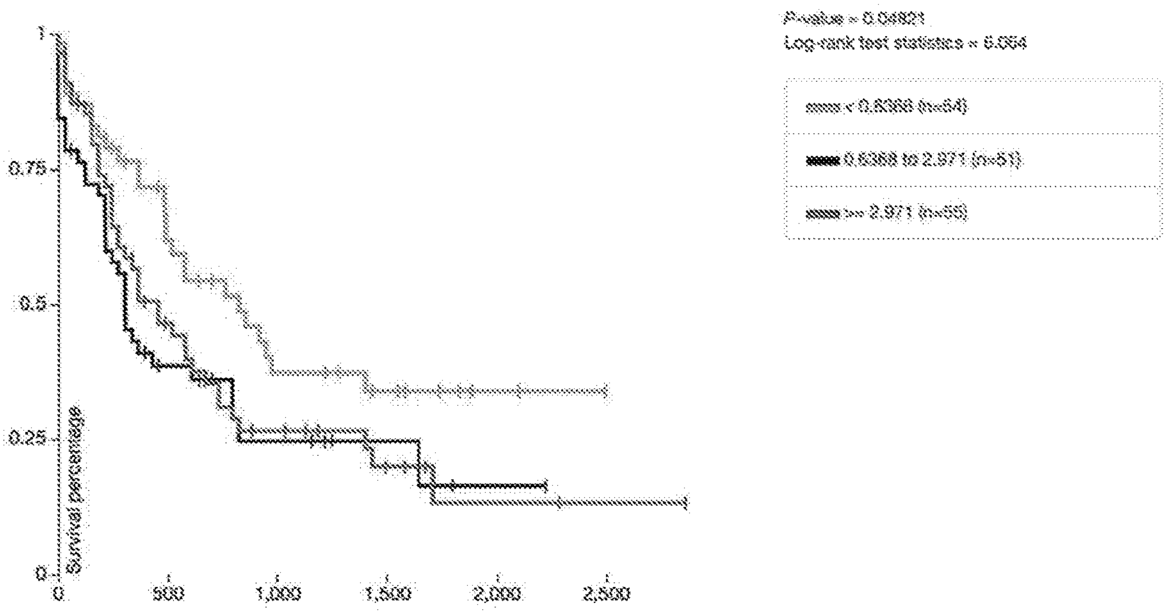
LILRB4:
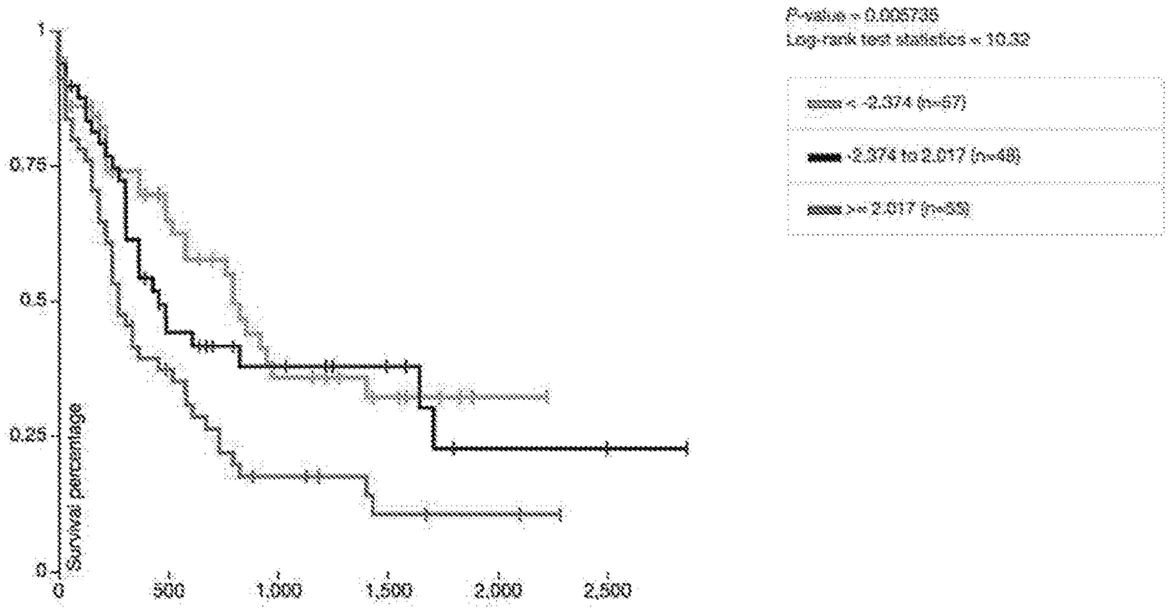
FIG. 5a (cont.)

LILRB5:
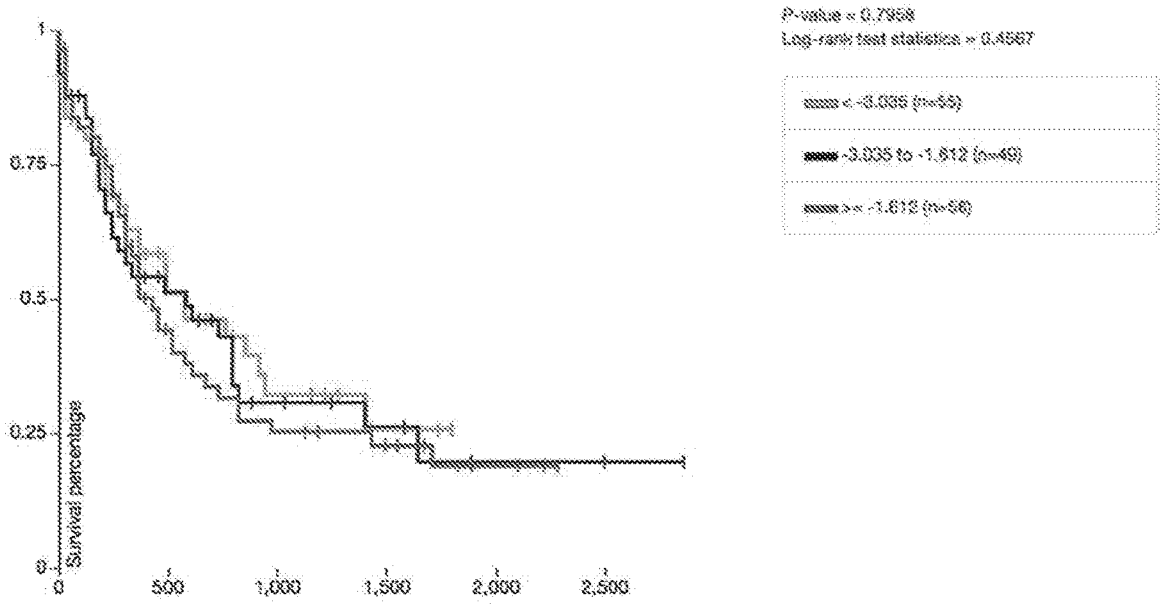
LAIR-1:
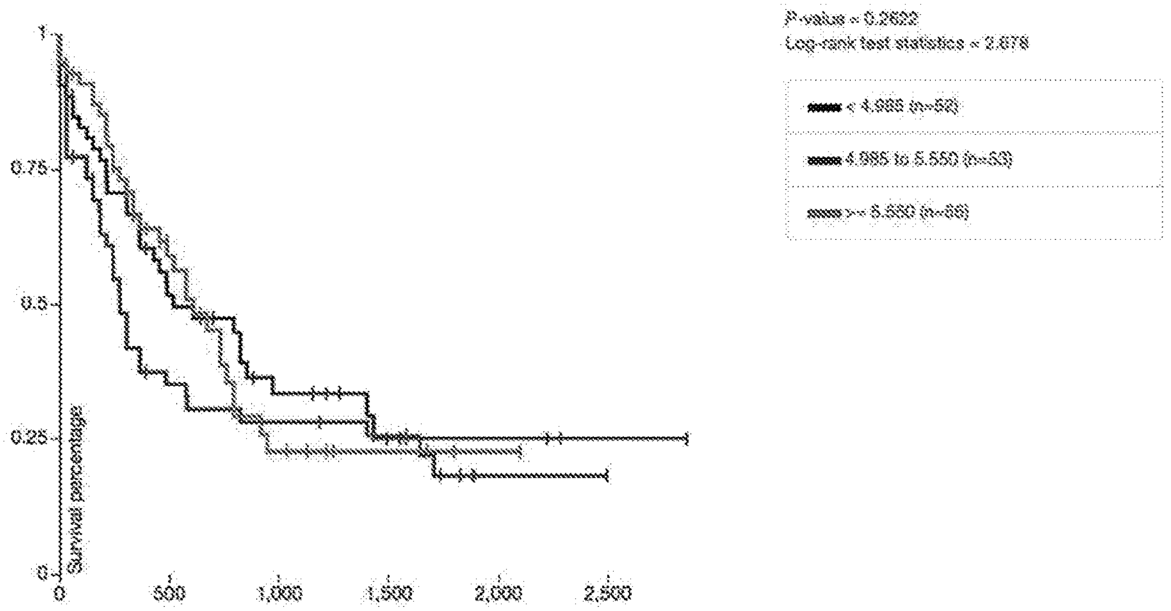
FIG. 5a (cont.)

LAIR-2:
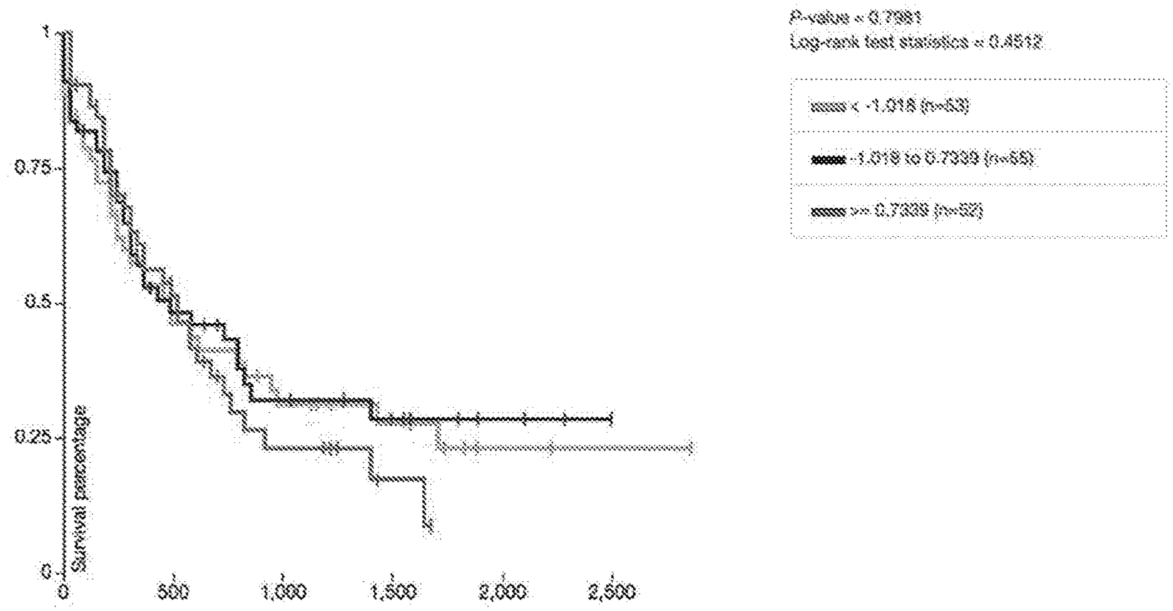
LAG-3:
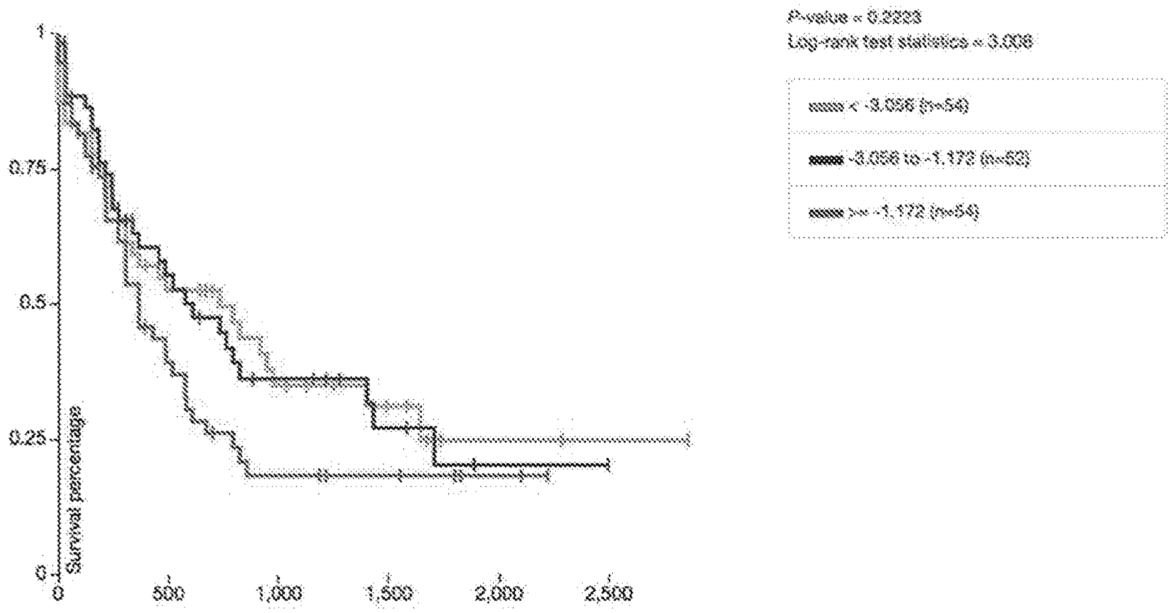
FIG. 5a (cont.)

TIM-1:
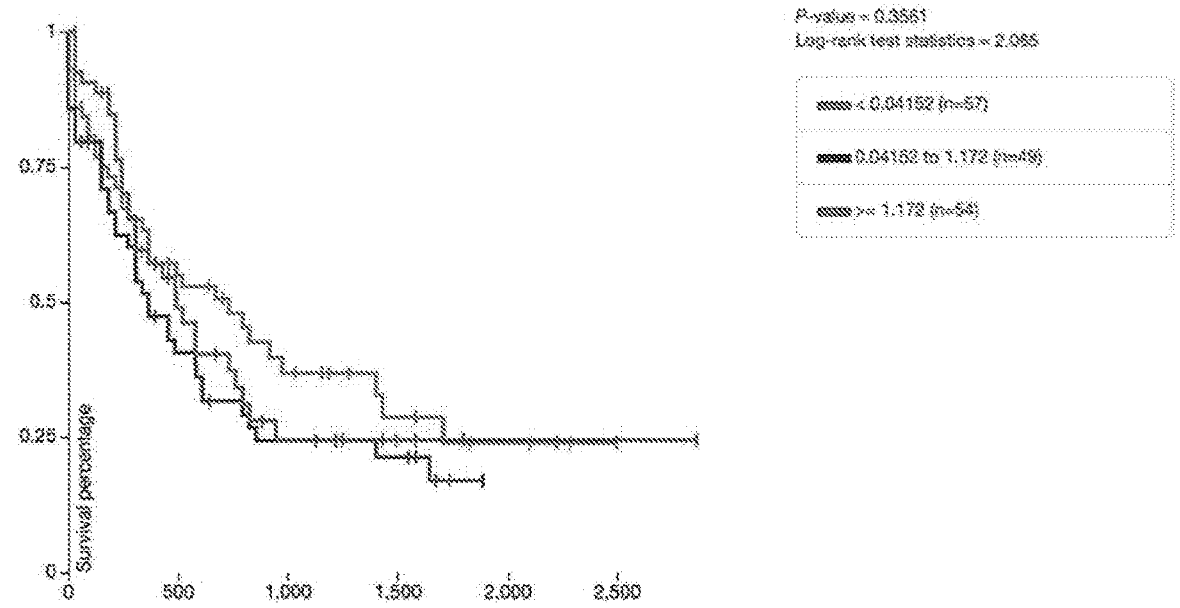
TIM-3:
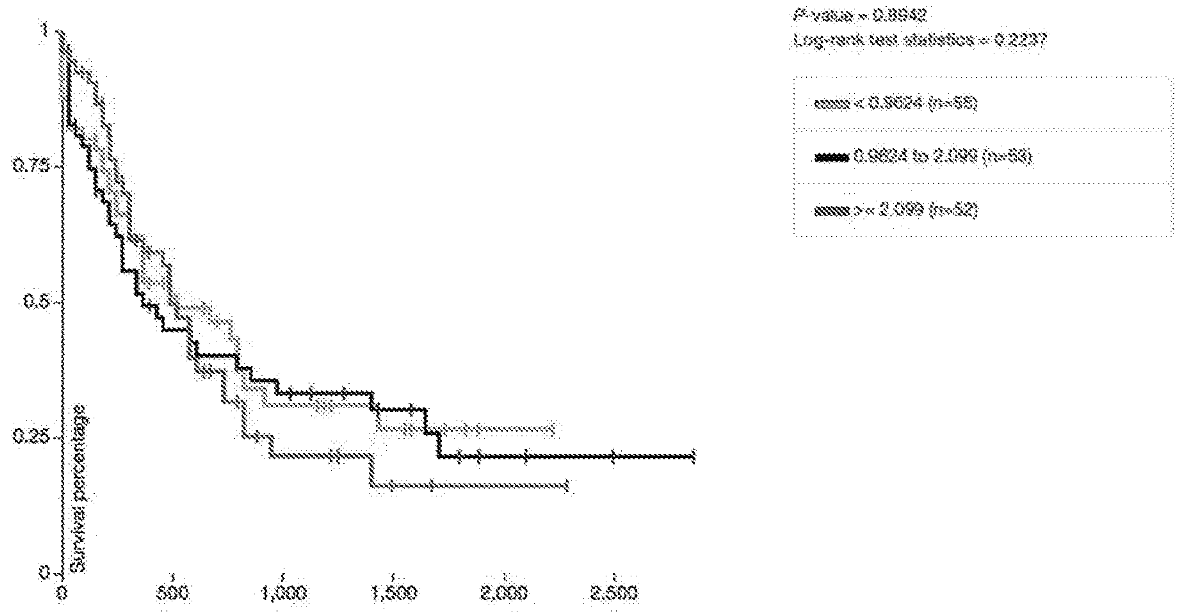
FIG. 5a (cont.)

SLAMF2:
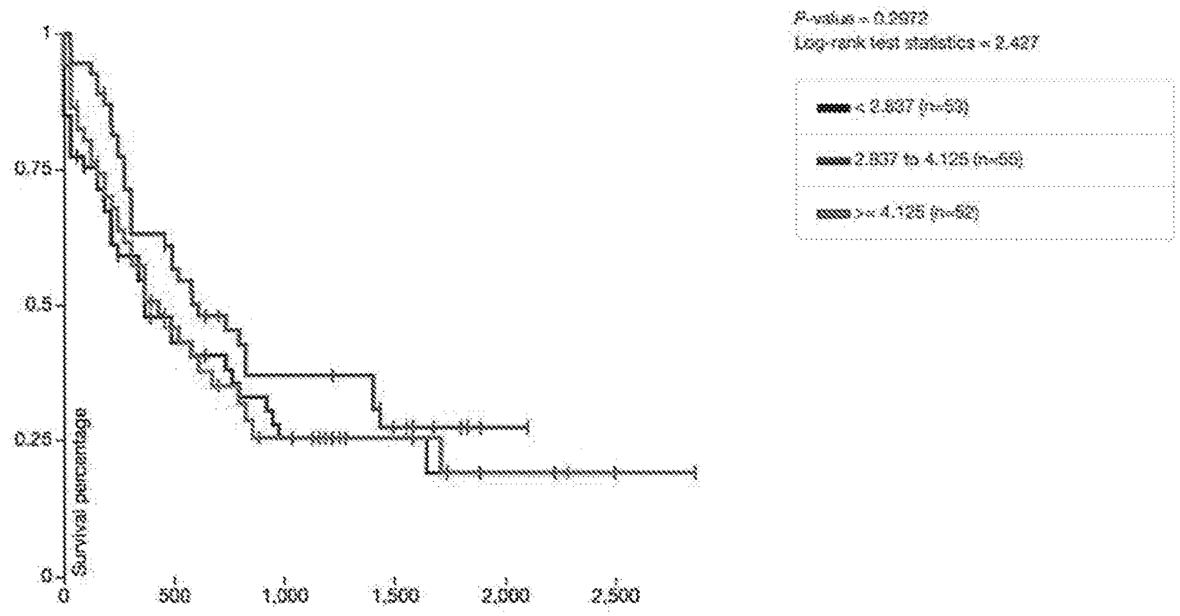
SLAMF4:
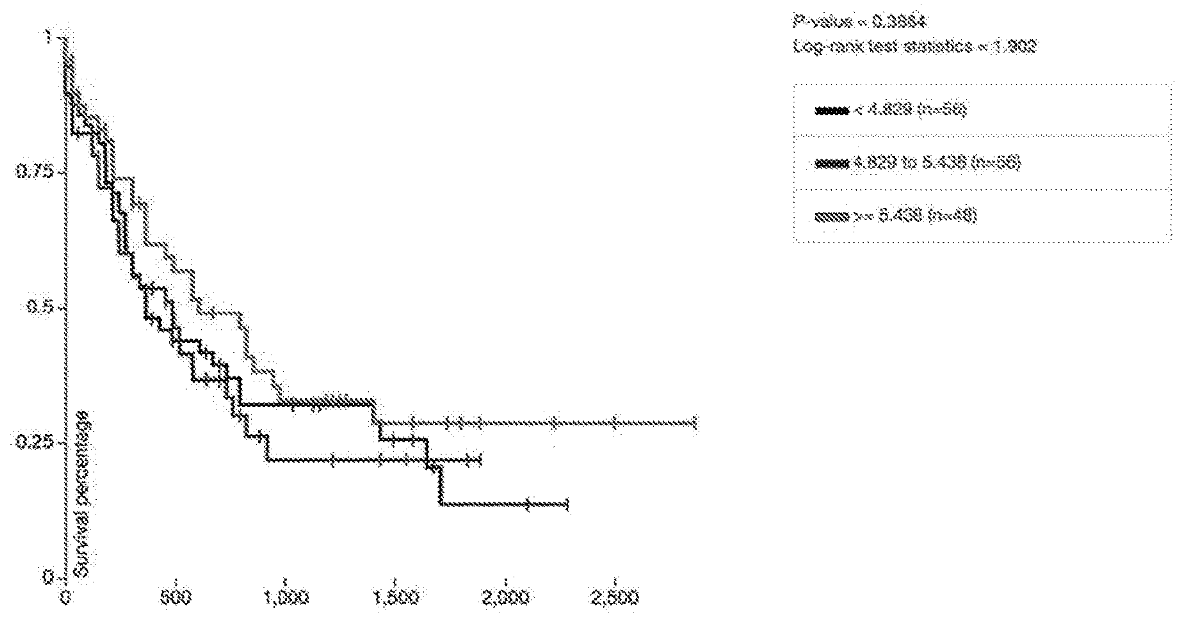
FIG. 5a (cont.)

SLAMF5:
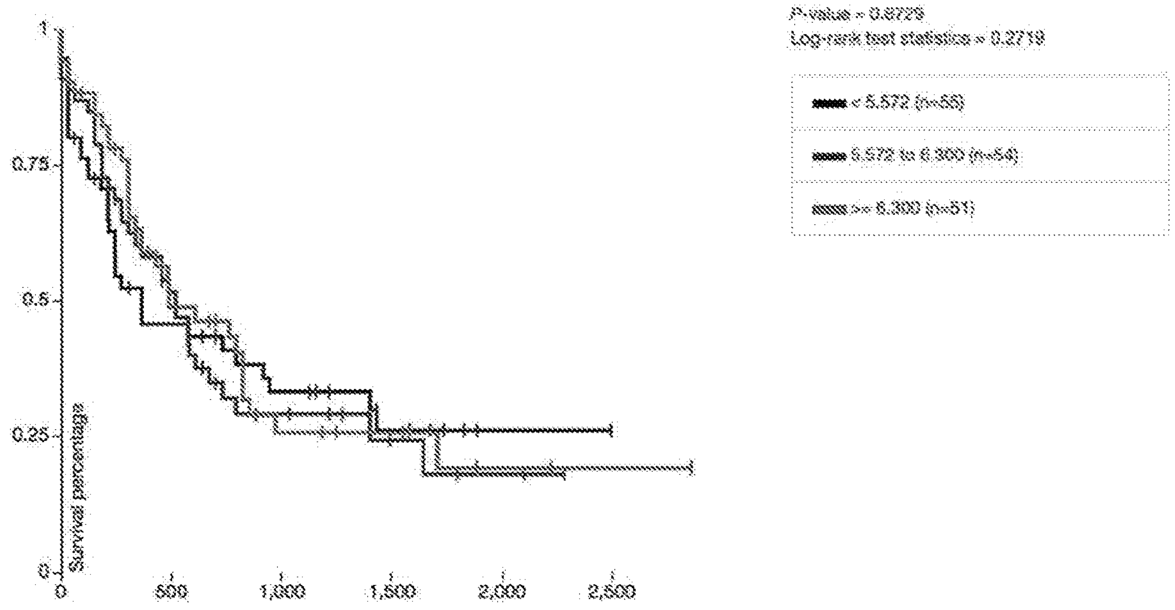
BTN1A1:
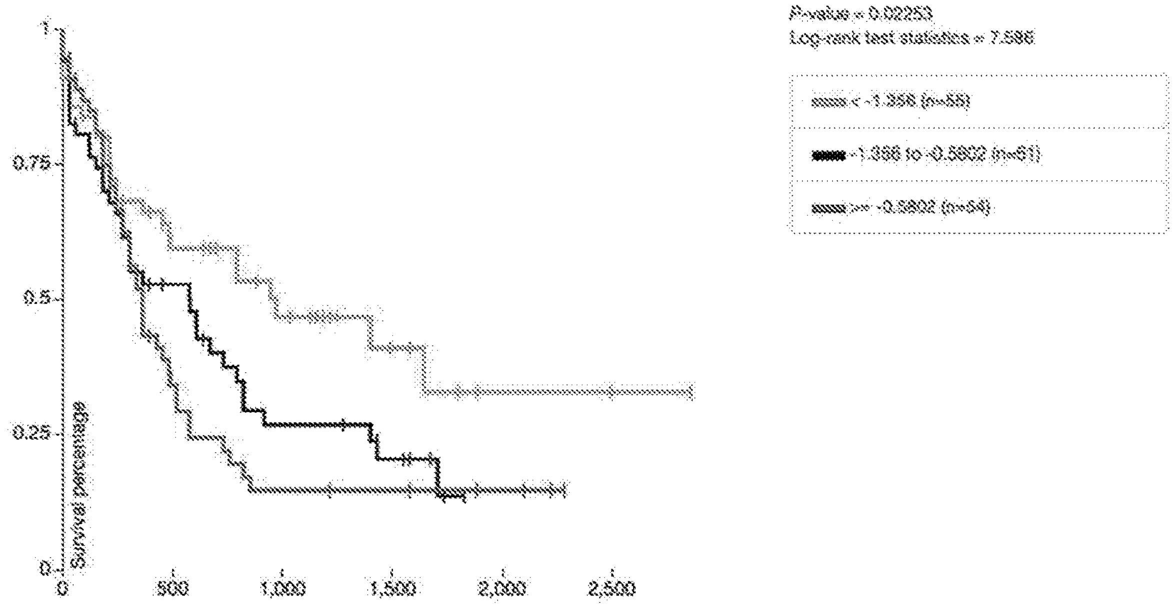
FIG. 5a (cont.)

BTN2A1:
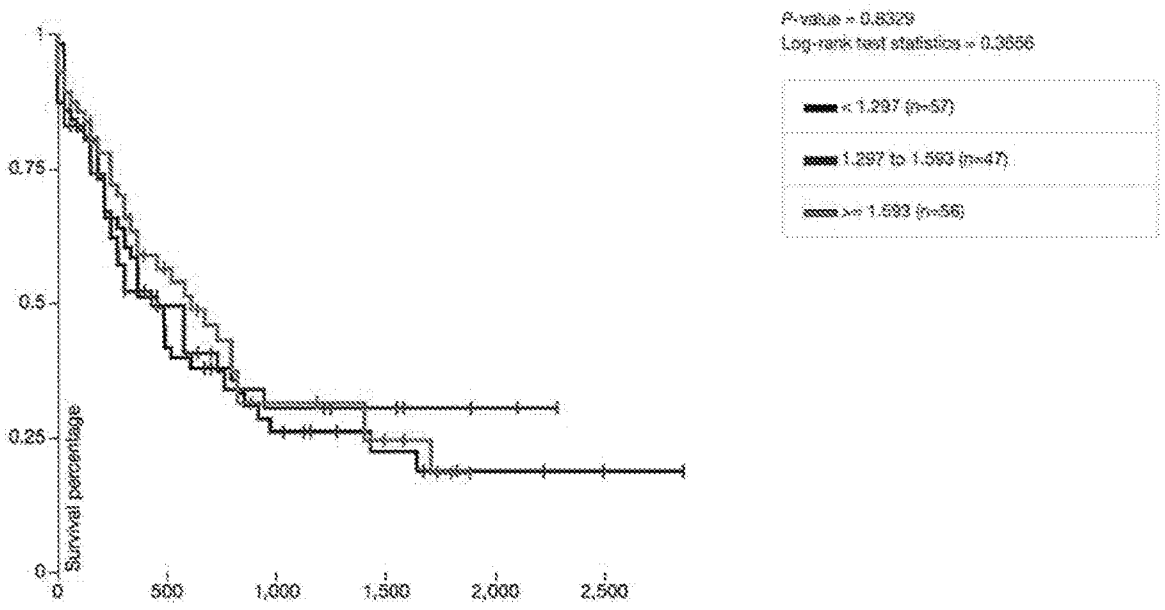
BTN2A2:
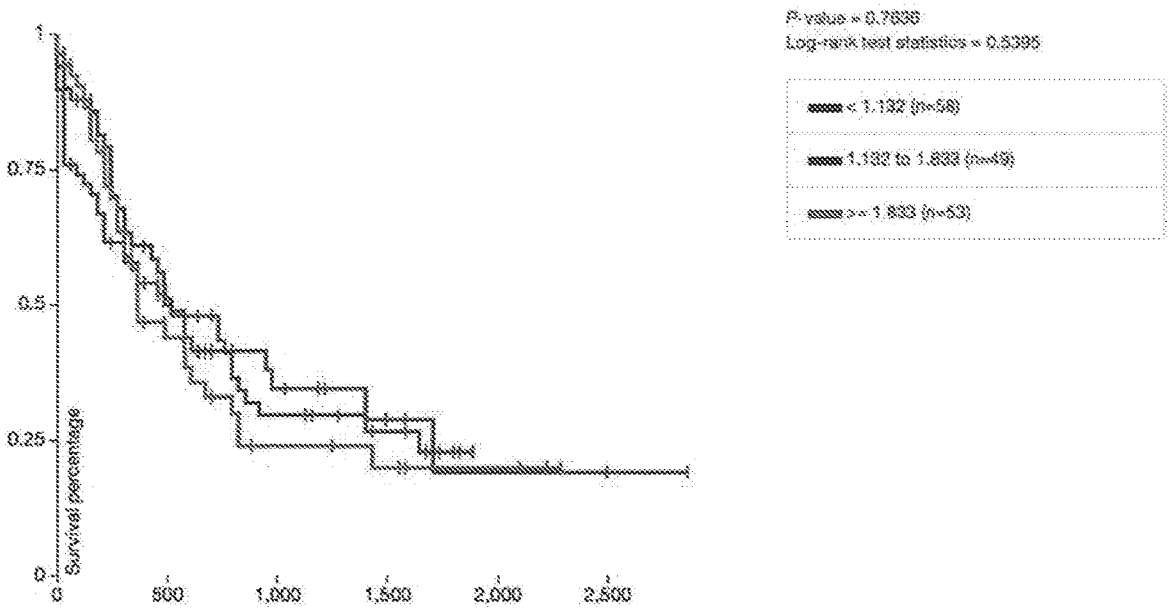
FIG. 5a (cont.)

BTN3A1:
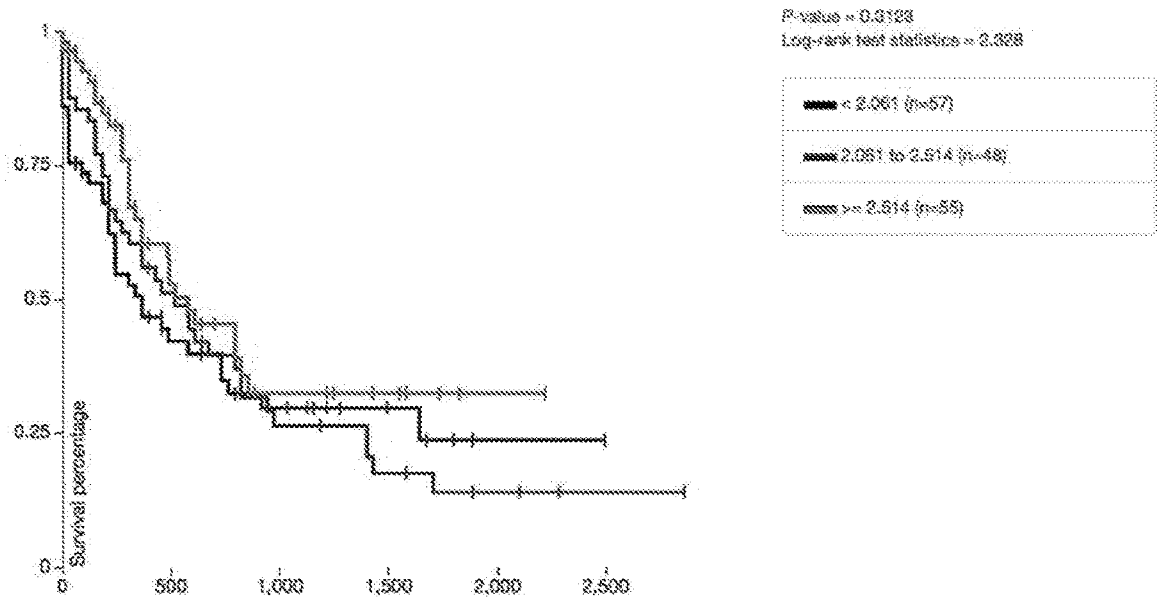
BTN3A2:
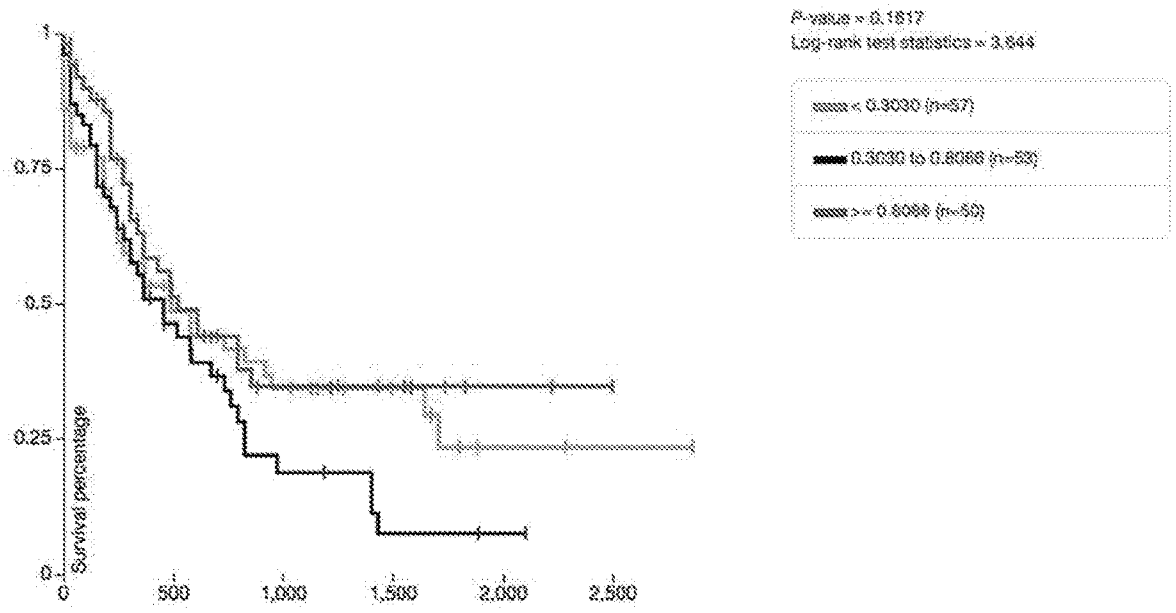
FIG. 5a (cont.)

BTN3A3:
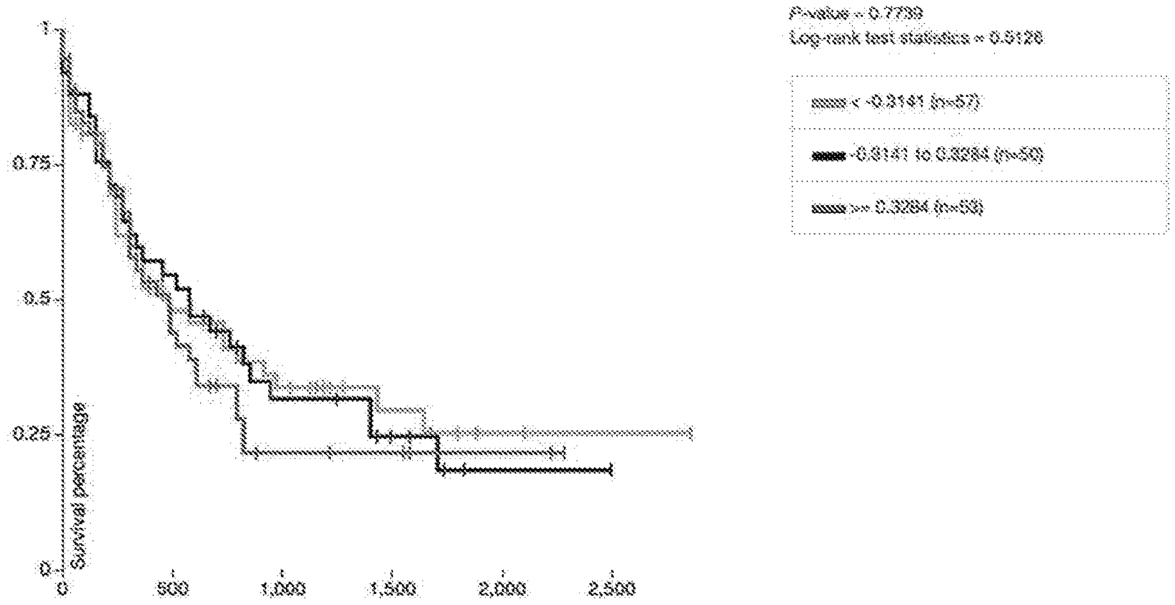
BTNL2:
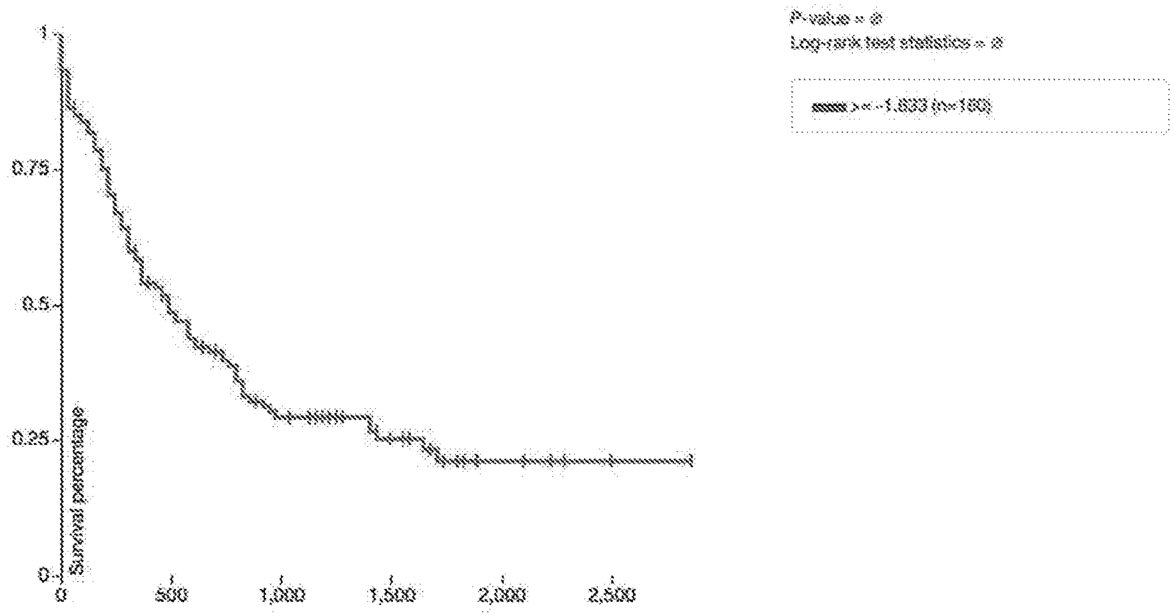
FIG. 5a (cont.)

BTNL3:
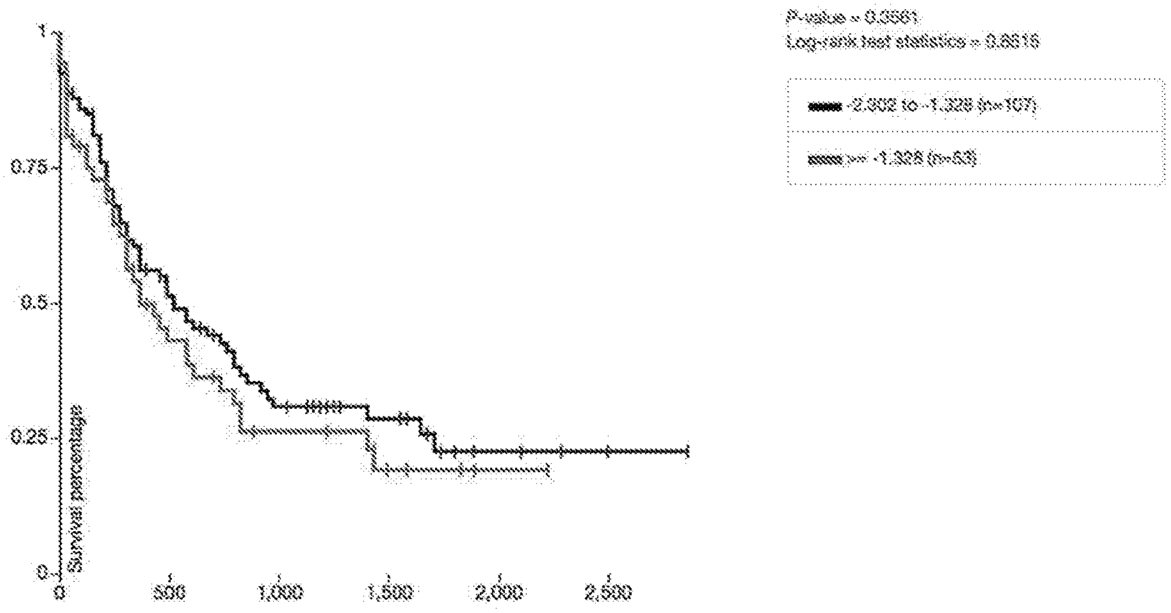
BNTL8:
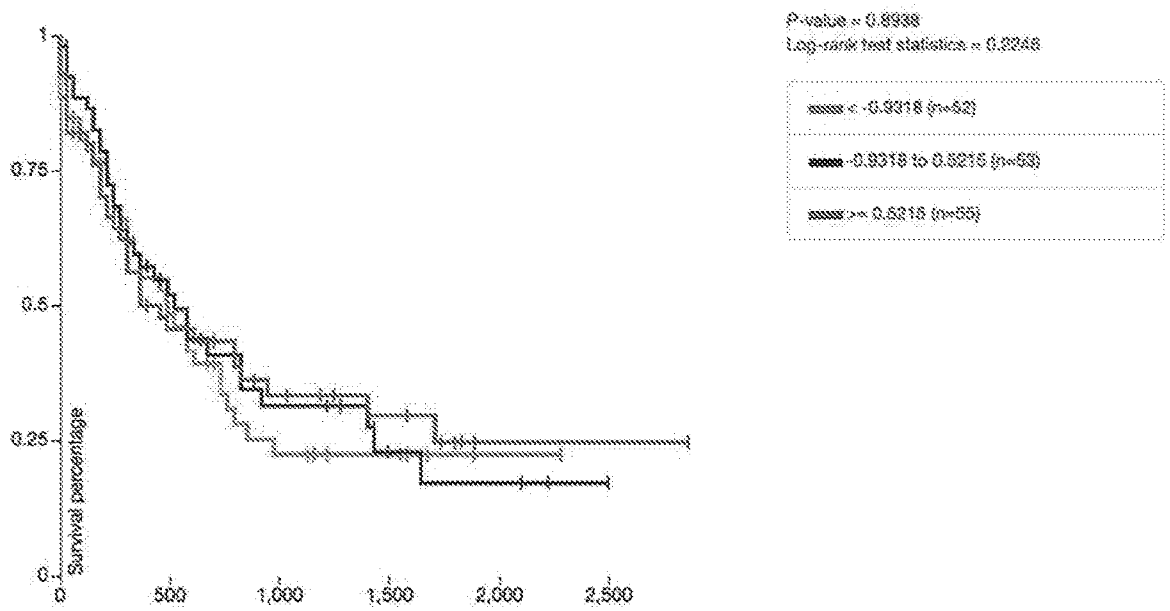
FIG. 5a (cont.)

CD96:
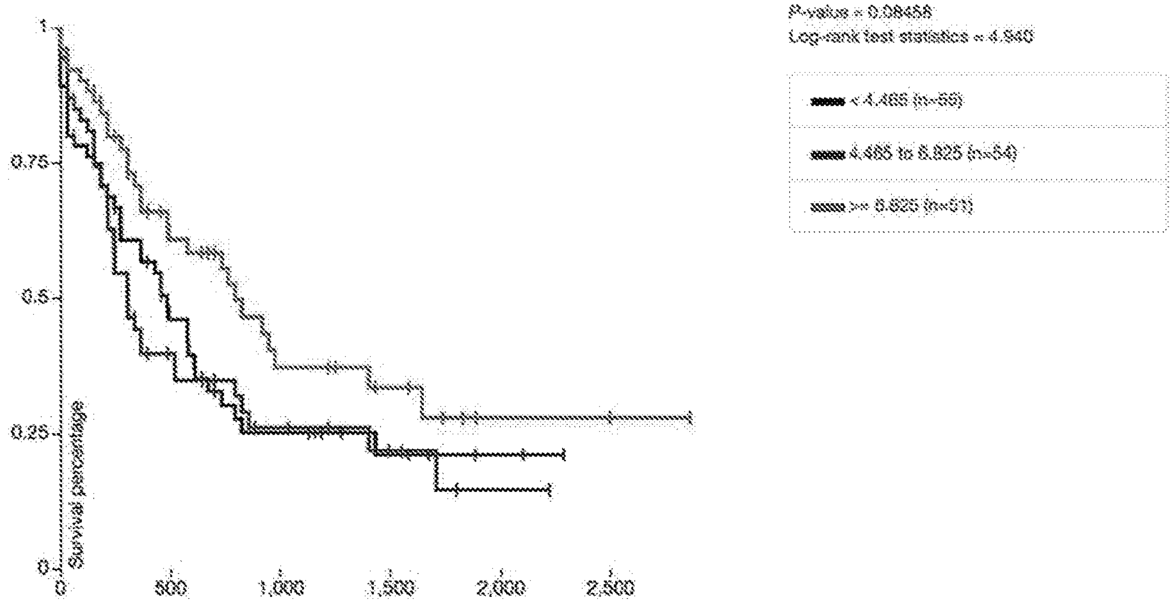
CD226:
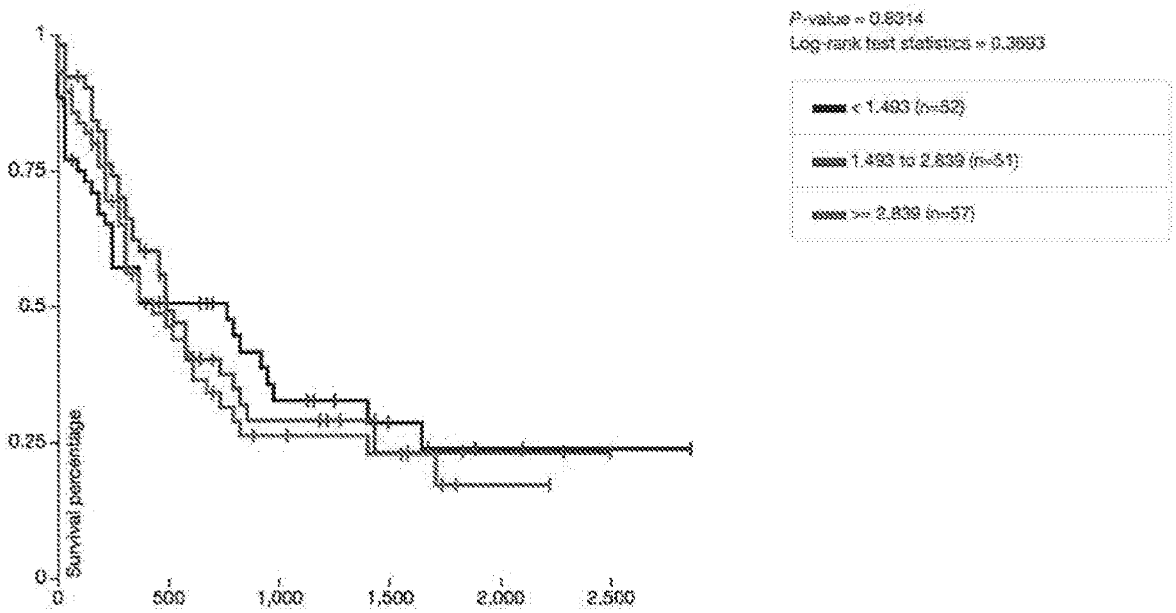
FIG. 5a (cont.)

CRTAM:
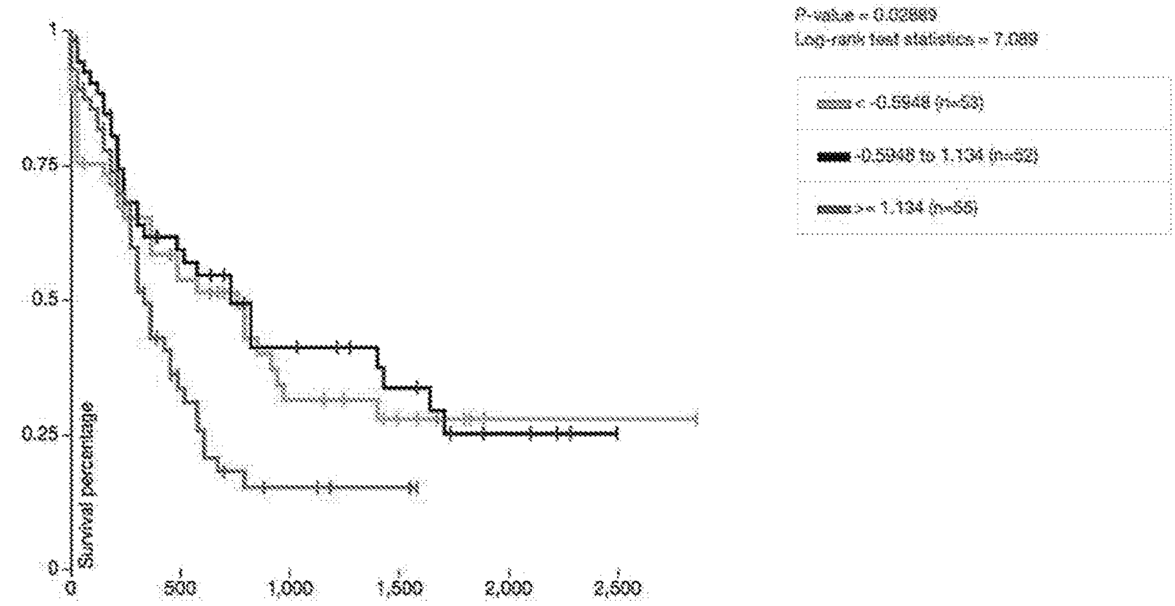
PVR:
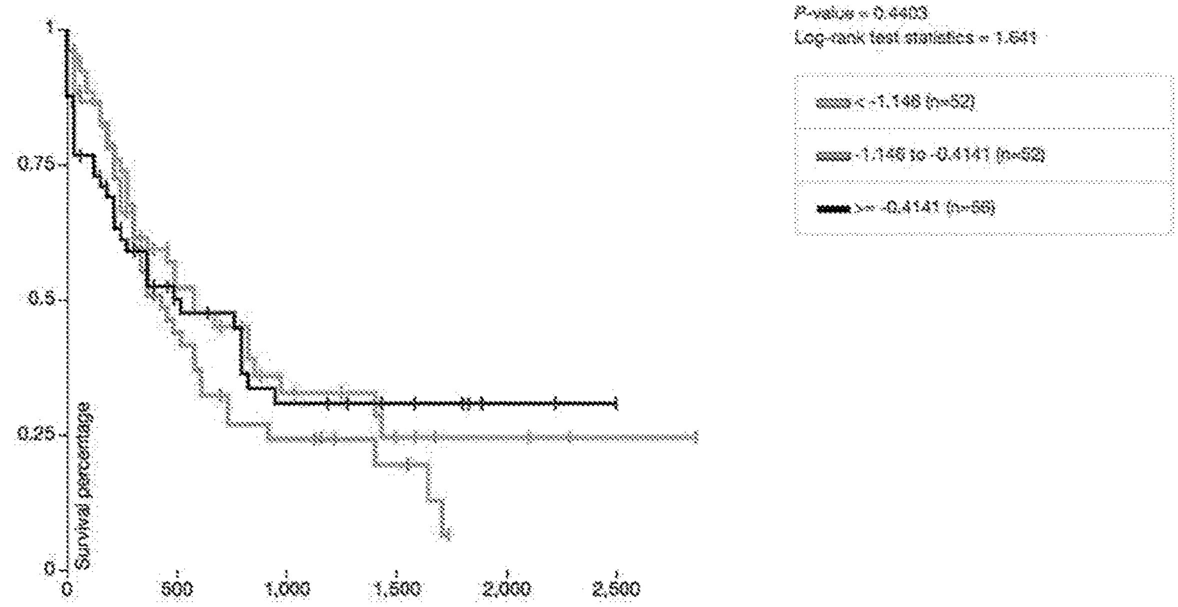
FIG. 5a (cont.)

PVRIG:
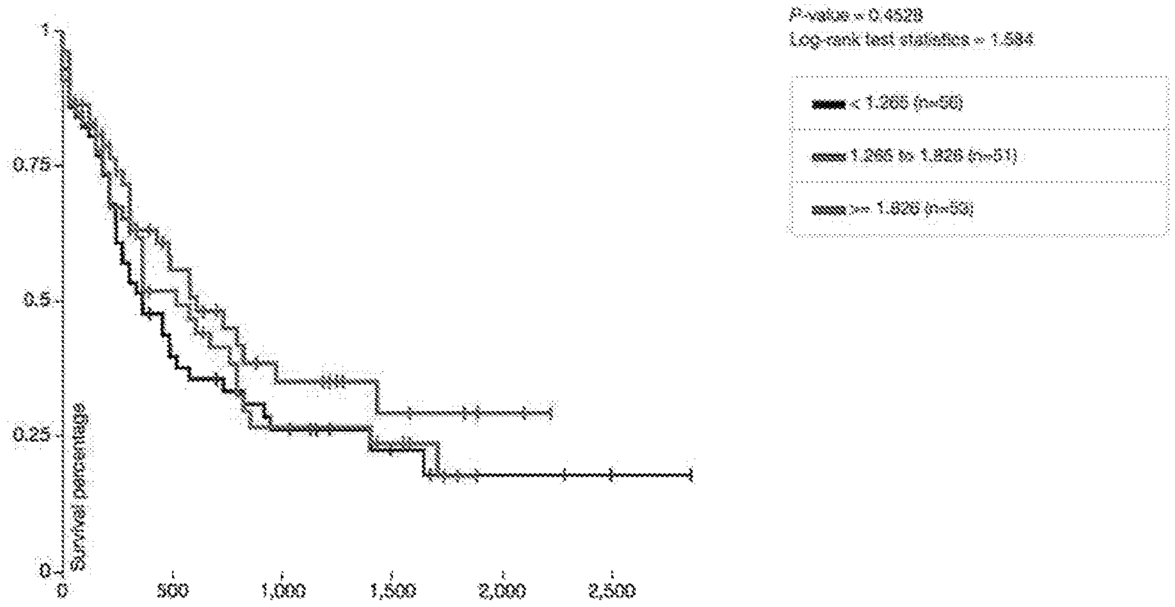
PVRL2:
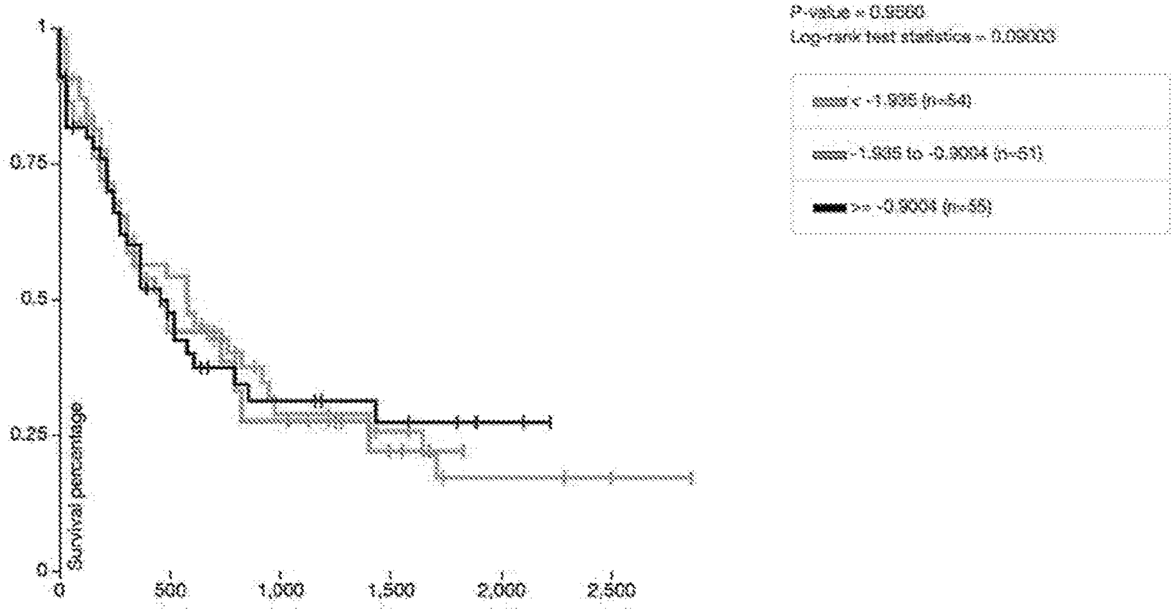
FIG. 5a (cont.)

PVRL3:
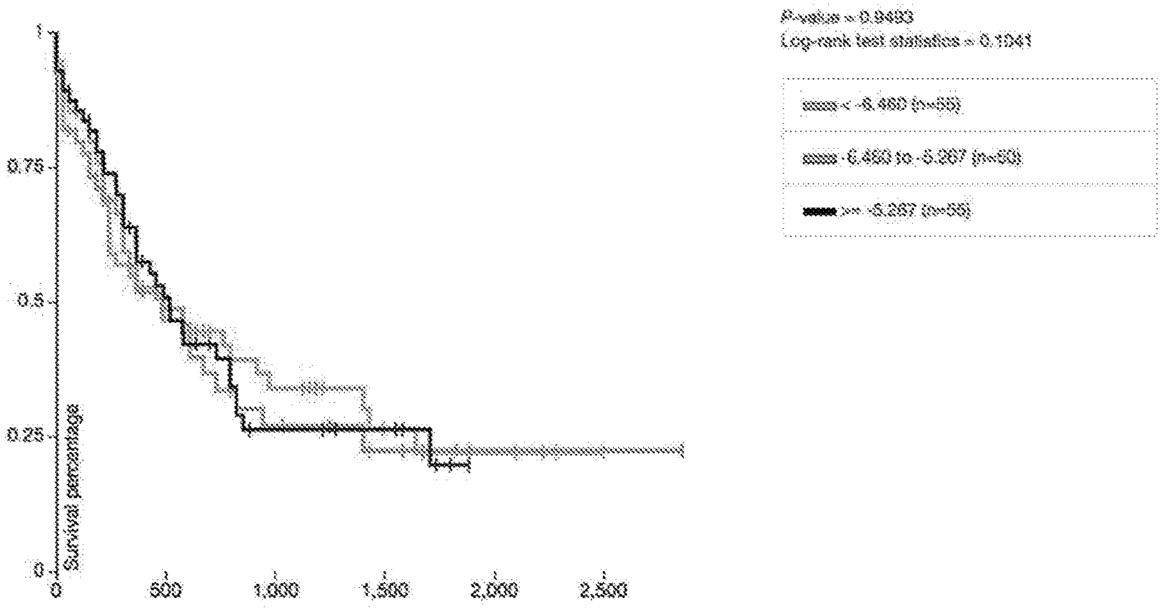
TIGIT:
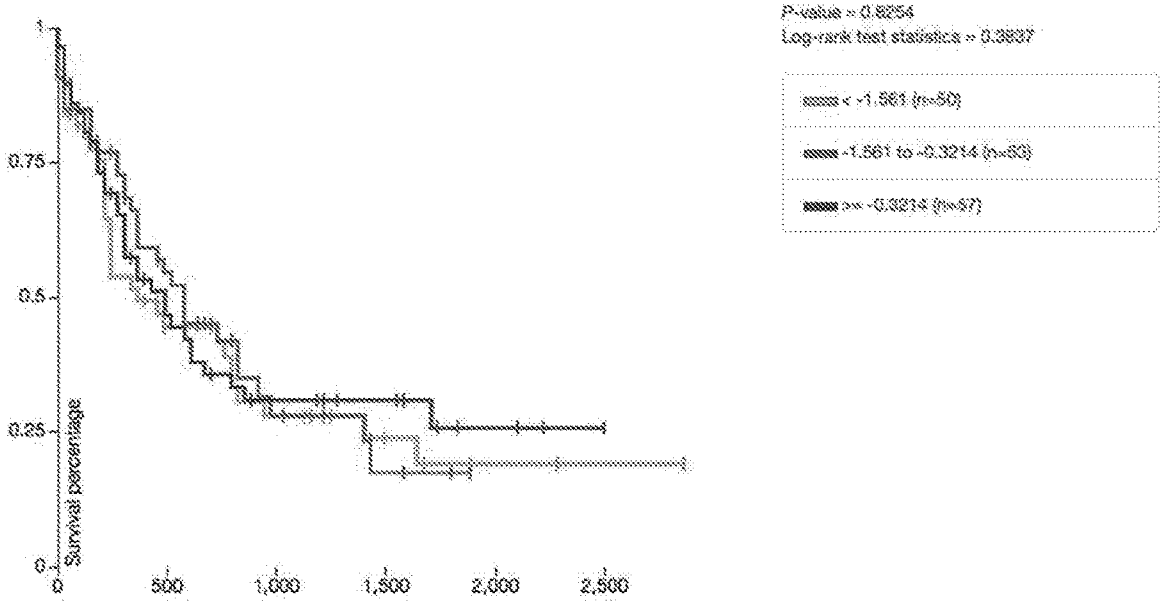
FIG. 5a (cont.)

| Gene Symbol | *p* Value |
|---|---|
| LILRB4 | 0.005733 |
| LILRA5 | 0.01034 |
| LILRB2 | 0.0118 |
| PD1 | 0.01492 |
| VISTA | 0.0217 |
| BTN1A1 | 0.02253 |
| CRTAM | 0.02889 |
| LILRA6 | 0.04485 |
| LILRB3 | 0.04821 |
| PD-L2 | 0.05667 |
| LILRA4 | 0.07504 |
| CD96 | 0.08458 |
| CD276 | 0.08499 |
| CD28 | 0.09116 |
| LILRA1 | 0.1202 |
| BTN3A2 | 0.1617 |
| LILRB1 | 0.1654 |
| CD28H | 0.2083 |
| LAG-3 | 0.2223 |
| LILRA2 | 0.2364 |
| LAIR-1 | 0.2622 |
| CD80 | 0.296 |
| SLAMF2 | 0.2972 |
| BTN3A1 | 0.3123 |
| CD86 | 0.3344 |
| BTNL3 | 0.3561 |
| TIM-1 | 0.3561 |
| SLAMF4 | 0.3864 |
| PD-L1 | 0.3945 |
| PVR | 0.4403 |
| PVRIG | 0.4528 |
| PDCD6 | 0.4679 |
| ICOSLG | 0.6398 |
| BTN2A2 | 0.7636 |
| BTN3A3 | 0.7739 |
| CTLA-4 | 0.7808 |
| BTLA | 0.7943 |
| LILRB5 | 0.7958 |
| LAIR-2 | 0.7981 |
| ICOS | 0.8164 |
| TIGIT | 0.8254 |
| CD226 | 0.8314 |
| BTN2A1 | 0.8529 |
| SLAMF5 | 0.8763 |
| BTNL8 | 0.8938 |
| TIM-3 | 0.8942 |
| PVRL3 | 0.9493 |
| PVRL2 | 0.956 |
| VTCN1 | 0.9996 |
| BTNL2 | 0.9999 |

FIG. 5b

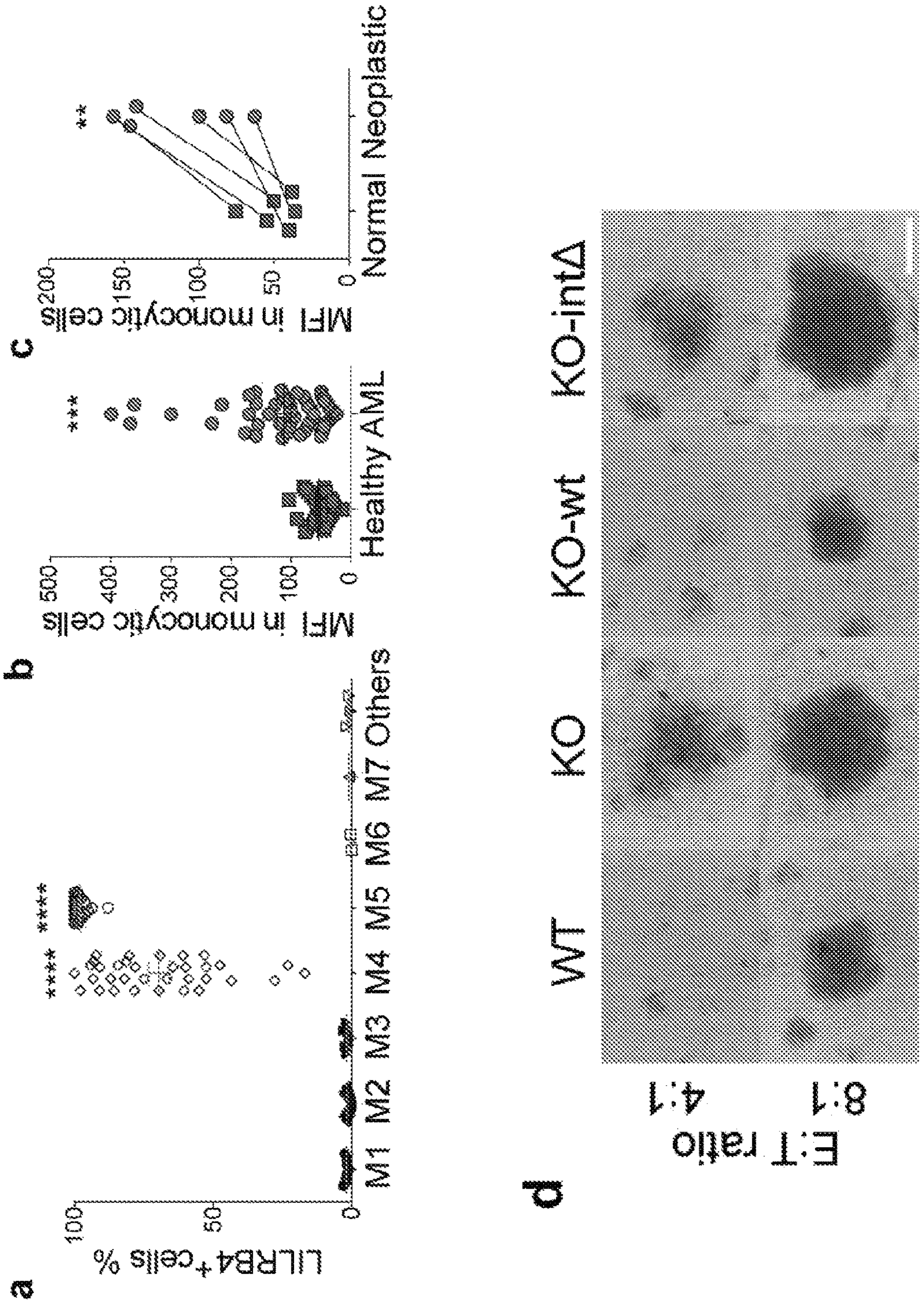
FIGS. 7a-d

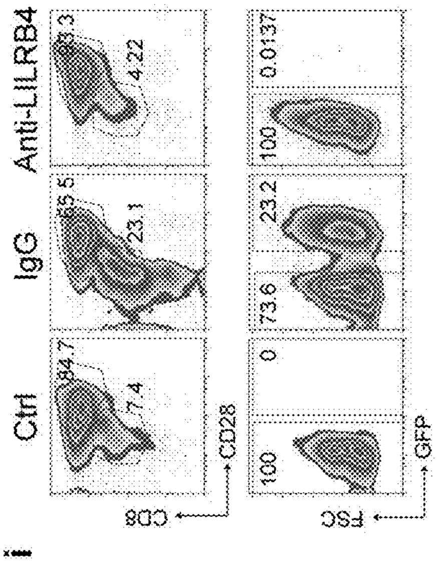
FIG 7i
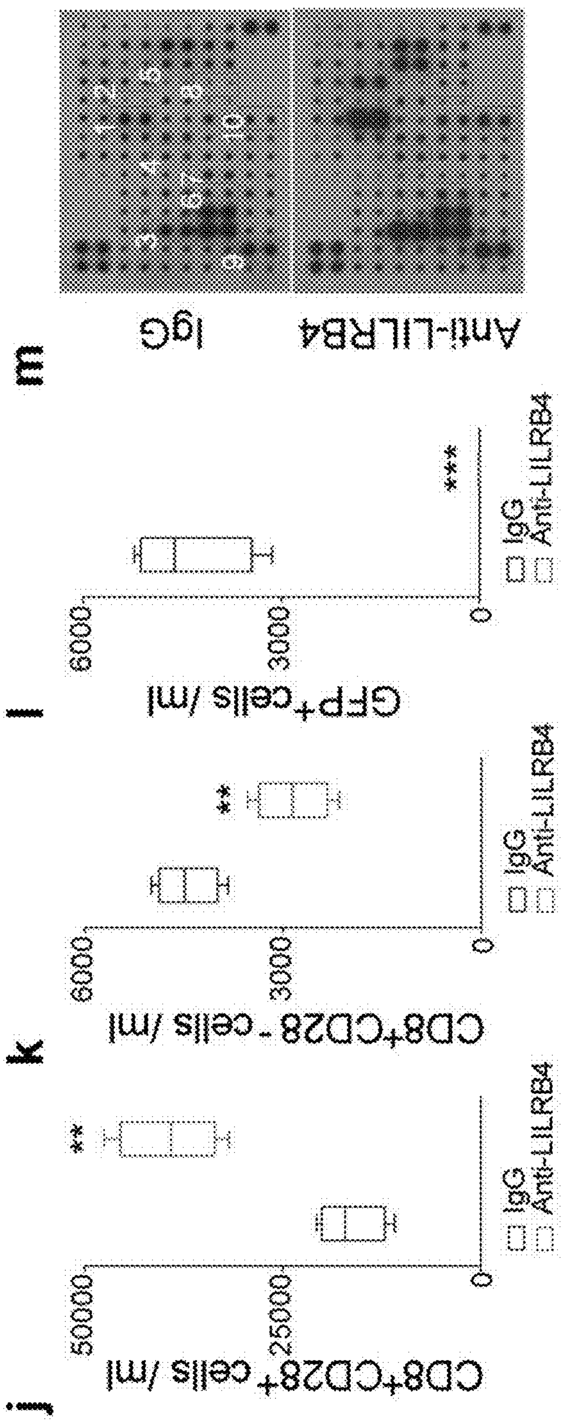
FIGS. 7j-m a

Pose #5

| Residue (LILRB4) | Interaction Energy (kcal/mol) |
|---|---|
| PHE201 (F) | -12.361279 |
| GLU64 (E) | -9.627243 |
| GLU63 (E) | -8.199759 |
| ARG97 (R) | -7.526236 |
| PRO66 (P) | -6.648518 |
| TRP106 (W) | -4.482213 |
| GLN174 (Q) | -4.325576 |
| ARG95 (R) | -4.155138 |
| SER65 (S) | -3.705189 |
| PRO68 (P) | -3.454256 |
| GLY172 (G) | -2.956375 |
| ALA67 (A) | -2.919467 |
| GLY200 (G) | -2.754843 |
| HIS199 (H) | -2.747746 |
| ALA173 (A) | -2.562305 |
| LYS62 (K) | -2.133966 |
| GLU170 (E) | -2.114094 |
| PRO109 (P) | -2.044897 |

Pose #115

| Residue (LILRB4) | Interaction Energy (kcal/mol) |
|---|---|
| TRP32 (W) | -10.162224 |
| GLU114 (E) | -6.124348 |
| THR30 (T) | -5.663048 |
| GLN50 (Q) | -4.54658 |
| PRO112 (P) | -4.35171 |
| LEU165 (L) | -4.31777 |
| PRO184 (P) | -3.930789 |
| LEU164 (L) | -3.905388 |
| ARG168 (R) | -3.671397 |
| LEU113 (L) | -3.377484 |
| HIS162 (H) | -3.349706 |
| SER183 (S) | -3.268351 |
| VAL188 (V) | -3.103813 |
| THR185 (T) | -2.416582 |

Pose #51

| Residue (LILRB4) | Interaction Energy (kcal/mol) |
|---|---|
| GLU90 (E) | -9.502012 |
| PHE201 (F) | -8.028892 |
| TYR121 (Y) | -7.288127 |
| GLU63 (E) | -7.189283 |
| GLU64 (E) | -6.94281 |
| ARG147 (R) | -6.633883 |
| PRO66 (P) | -5.140189 |
| TRP41 (W) | -4.799497 |
| ASP91 (D) | -4.351736 |
| SER148 (S) | -3.6496 |
| SER65 (S) | -3.562618 |
| SER202 (S) | -2.962636 |
| ARG95 (R) | -2.717827 |
| LEU205 (L) | -2.62092 |
| GLY119 | -2.582134 |
| SER122 (S) | -2.387931 |
| PRO149 (P) | -2.126853 |

Pose #155

| Residue (LILRB4) | Interaction Energy (kcal/mol) |
|---|---|
| LEU165 (L) | -9.812494 |
| ARG159 (R) | -8.752884 |
| ASP111 (D) | -8.496945 |
| HIS162 (H) | -8.100805 |
| TRP32 (W) | -6.589325 |
| ARG168 (R) | -5.058758 |
| LEU167 (L) | -4.187927 |
| ARG95 (R) | -4.11992 |
| CYS166 (C) | -3.41541 |
| GLU114 (E) | -3.271711 |
| GLU34 (E) | -3.268257 |
| PRO112 (P) | -3.056938 |
| GLU170 (E) | -2.692563 |
| GLN50 (Q) | -2.506593 |
| LYS28 (K) | -2.487442 |
| ALA161 (A) | -2.385419 |
| LYS157 (K) | -2.32742 |
| PRO35 (P) | -2.219545 |
| THR30 (T) | -2.148501 |

b

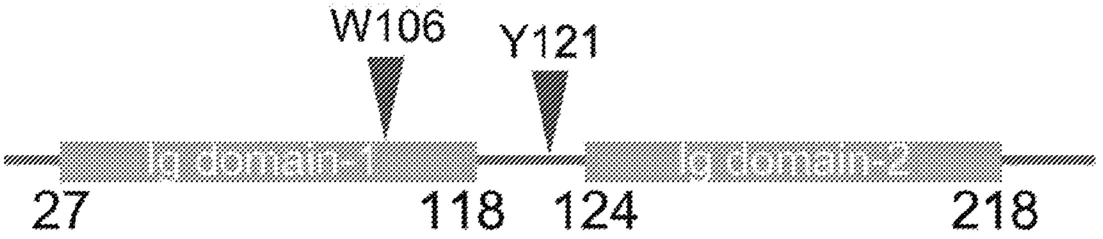

FIGS. 30a-30b

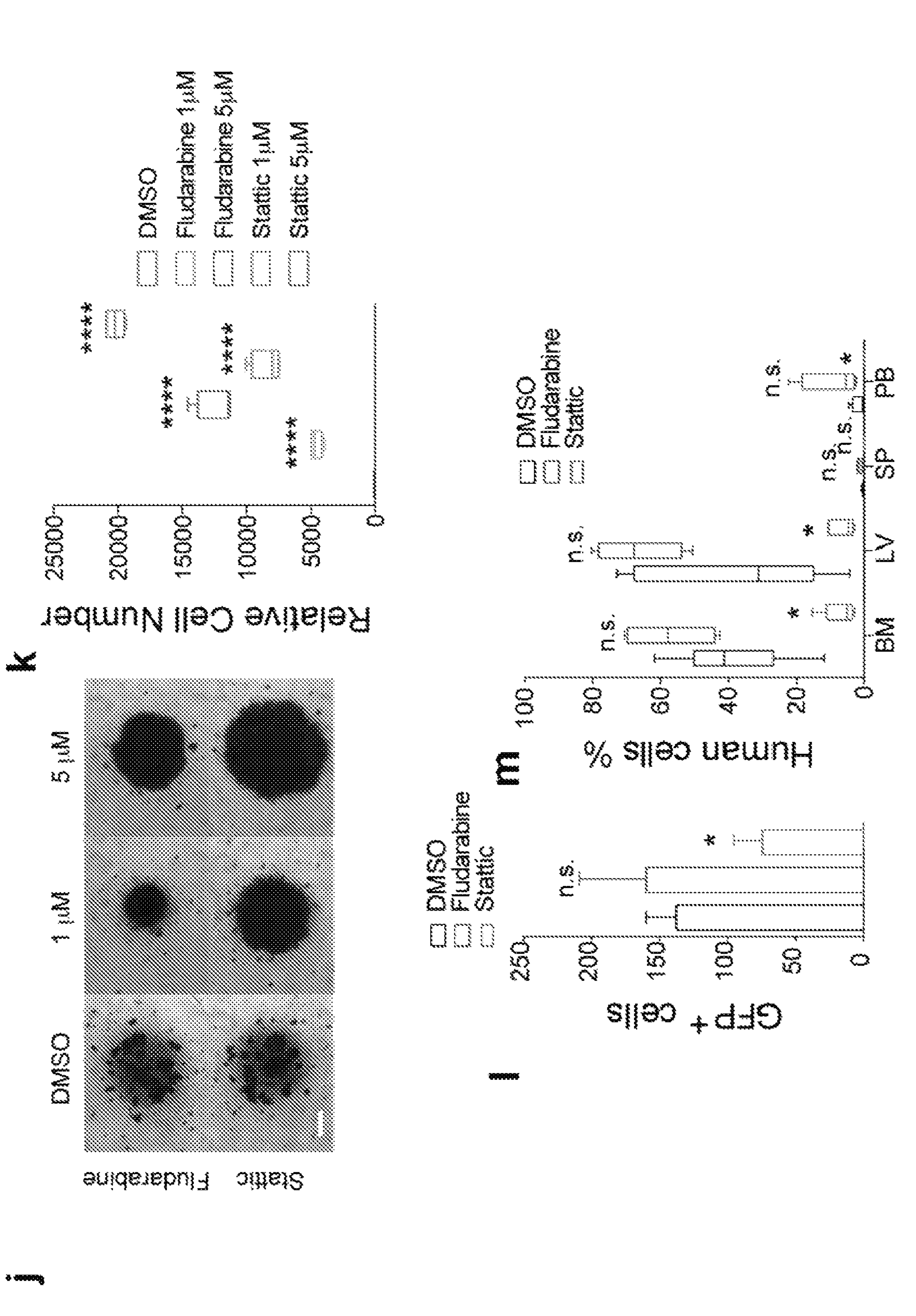
FIGS. 31j-m

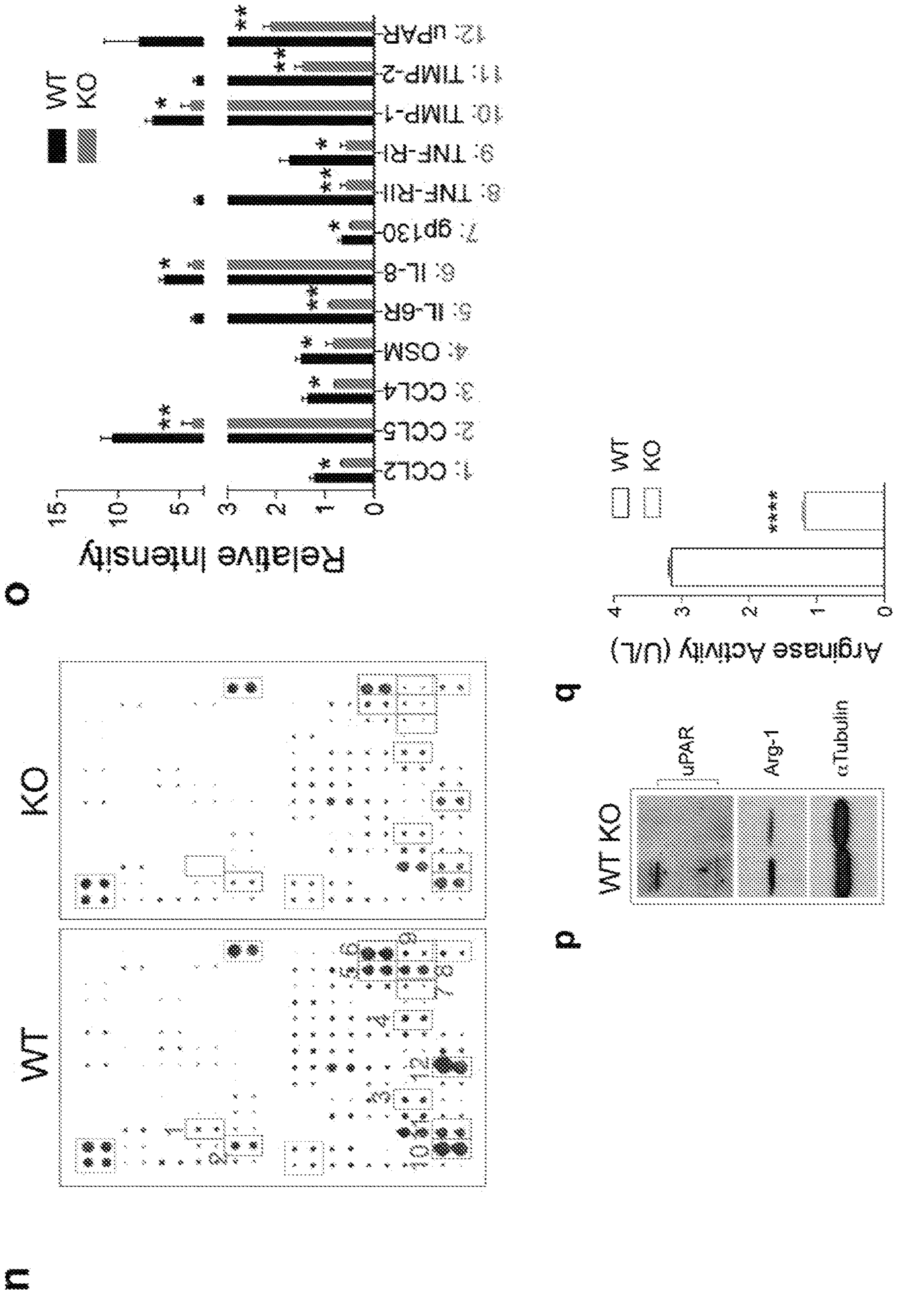
FIGS. 31n-q

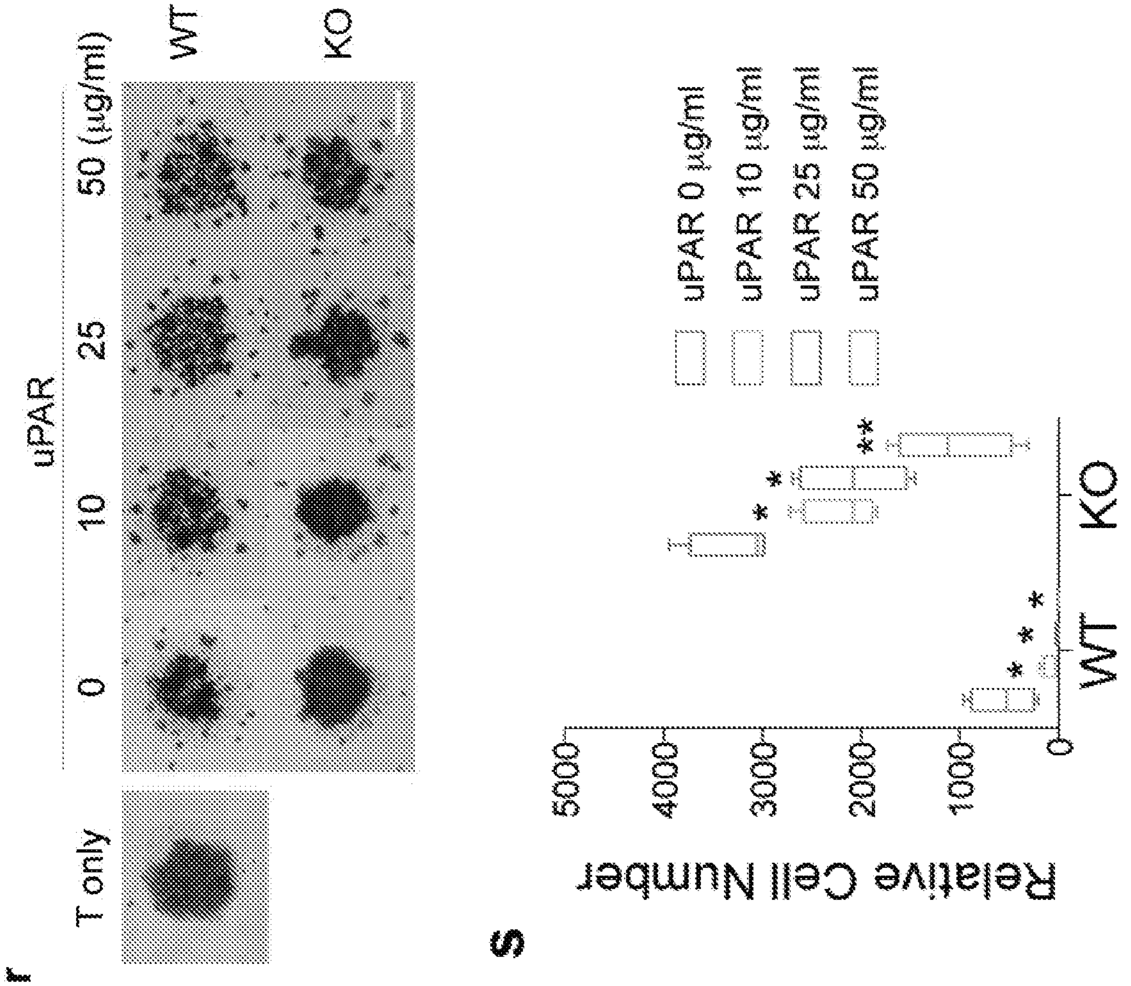
FIGS. 31r-s t
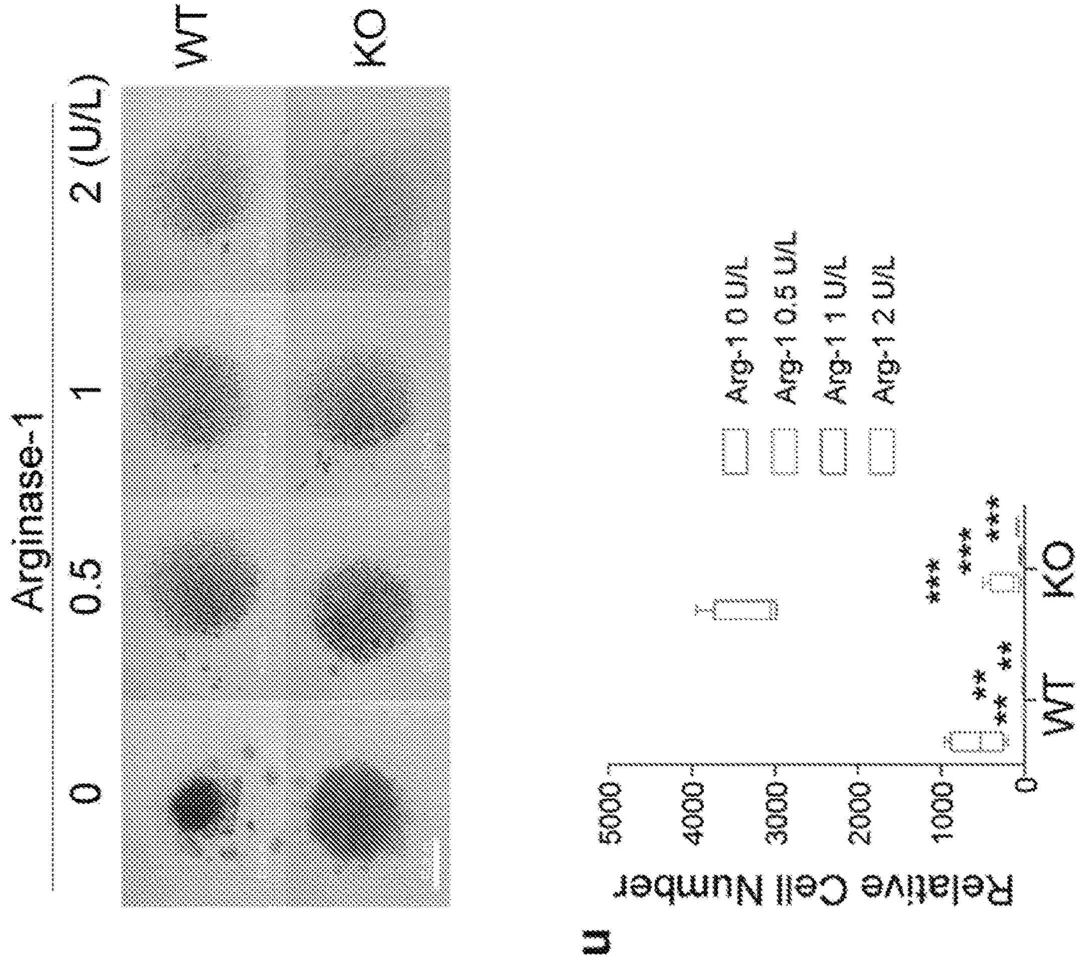
FIGS. 31t-u

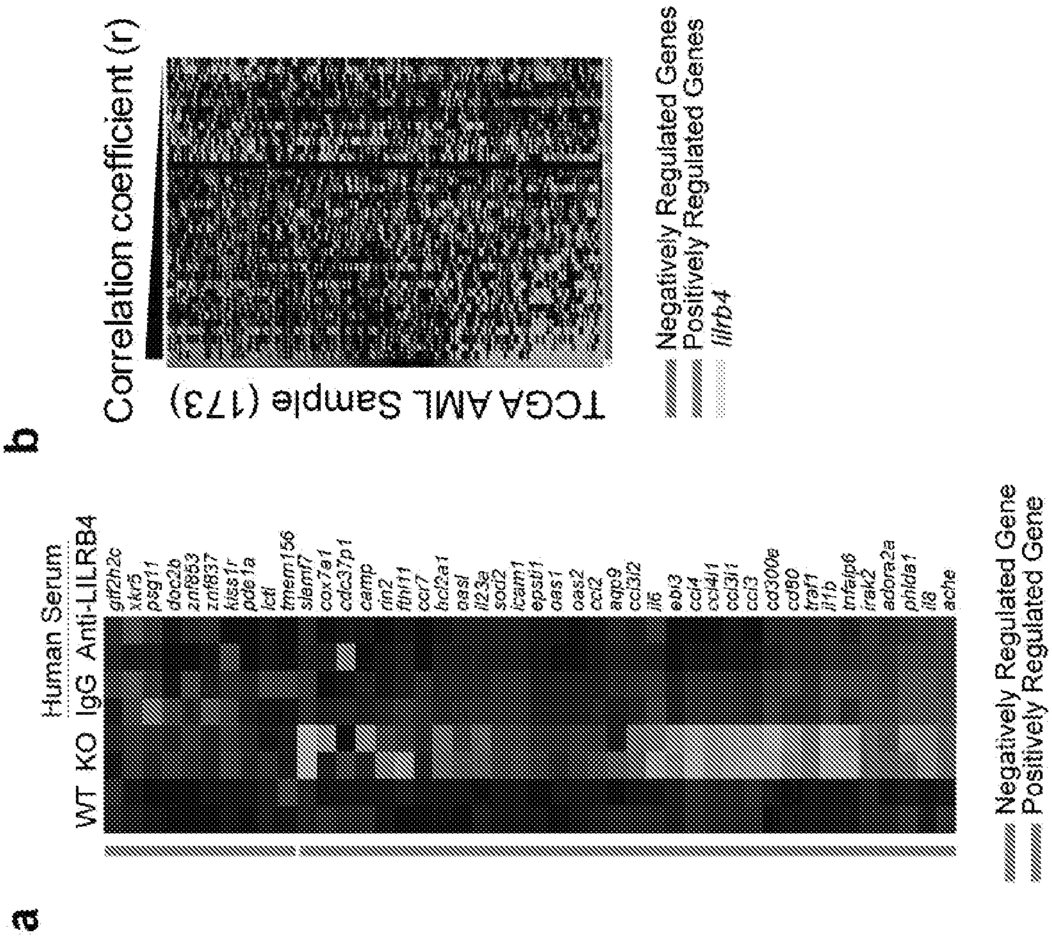
FIGS. 36a-b

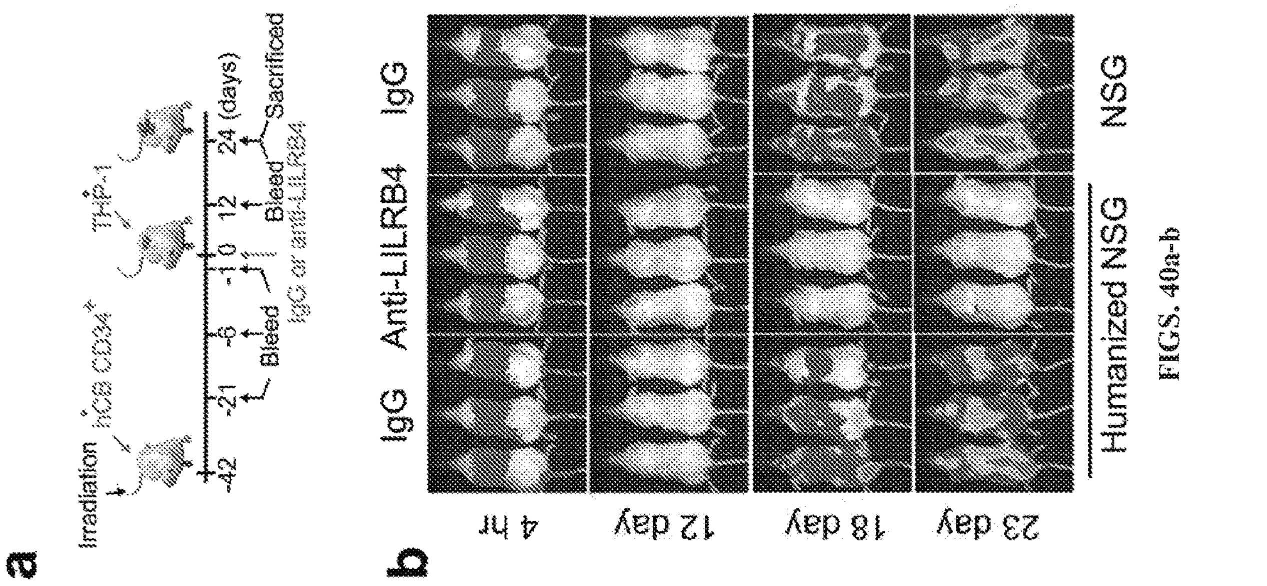
FIGS. 40a-b

C

METHODS FOR IDENTIFYING LILRB-BLOCKING ANTIBODIES

This application is a national phase application under 35 U.S.C. § 371 of International Application No. PCT/US2017/044171, filed Jul. 27, 2017, which claims benefit of priority to U.S. Provisional Application Ser. No. 62/368,672, filed Jul. 29, 2016, the entire contents of which are hereby incorporated by reference.

The invention was made with government support under Grant No. 1R01 CA172268 awarded by the National Institutes of Health. The government has certain rights in the invention.

The sequence listing that is contained in the file named "UTSHP0332US_ST25.txt", which is 176 KB (as measured in Microsoft Windows) and was created on Jan. 29, 2019, is filed herewith by electronic submission and is incorporated by reference herein.

BACKGROUND

1. Field

The present disclosure relates generally to the field of molecular biology. More particularly, it concerns methods and compositions for identifying LILRB antibodies.

2. Description of Related Art

Acute myeloid leukemia (AML) is the most common acute leukemia of adults and a common pediatric cancer. Current treatment for AML involves intensive cytotoxic chemotherapy, often times followed by myeloblative conditioning and stem cell transplant. However, despite treatment, most patients will relapse or succumb to disease within 5 years[1]. No new therapy for AML has been approved for more than 30 years. To effectively treat AML, new molecular targets and therapeutic approaches must be identified. Recently, it has been shown that inhibitory leukocyte immunoglobulin-like receptors (LILRBs) and a related immunoreceptor tyrosine-based inhibitory motif (ITIM)-containing receptor, LAIR1, have tumor-promoting functions in various hematopoietic and solid cancer cells[2, 3, 4-18, 19]. ITIM-containing receptors are expressed on a wide range of immune cells and transduce signals by recruitment of phosphatases SHP-1, SHP-2, or SHIP, leading to negative regulation of immune cell activation[20, 21, 22]. Similar to CTLA4 and PD-1[23], LILRBs are considered to be immune checkpoint factors[22].

LILRBs may inhibit activities of a number of immune cell types facilitating tumor immune escape[22]. LILRB4 is expressed on monocytes, macrophages, and dendritic cells and can inhibit innate immunity in a cell-autonomous manner and suppress T cell activation through an indirect mechanism[24, 25]. LILRB4 is a specific marker for monocytic AML including refractory and relapsed disease[26]. LILRB1-5 are primate and human specific, while there are two mouse orthologues: paired immunoglobulin-like receptor B (PirB)[27] and gp49B1[28]. The related immunoreceptor tyrosine-based inhibitory motif (ITIM)-containing receptor, LAIR1, has both human and mouse versions of the protein. Because of the limited value of mouse models and the fact that ligands for several LILRBs including LILRB4 are unknown, the biological function and clinical significance of these receptors remain poorly understood.

SUMMARY

Embodiments of the present disclosure provide methods and compositions concerning modulation of LILRB activation through its ligand. In a first embodiment, there is provided a method of identifying a modulator of LILRB activation comprising: (a) contacting a reporter cell with a ligand of LILRB and a candidate substance; and (b) detecting a level of LILRB activation in the reporter cell, wherein a change in LILRB activation as compared to a reference level indicates that the candidate substance is a modulator of LILRB activation. In certain aspects, the reporter cell is a mouse T-cell hybridoma cell.

In some aspects, the reporter cell expresses a receptor comprising the extracellular domain of LILRB. In certain aspects, the extracellular domain of LILRB is further defined as the extracellular domain of LILRB1, LILRB2, LILRB3, LILRB4, LILRBS, LAIR1 (human or mouse), PirB, or gp49B1. In particular aspects, the LILRB is further defined as LILRB4. In certain aspects, the ligand of LILRB4 is ApoE or LFA-1. In certain aspects, the ligand of LILRB is MHC I, UL18, S100A8, S100A9, Angptls, beta-amyloid, myelin inhibitor, CD1d, collagen or integrin αvβ3. In additional aspects, the receptor is a chimeric receptor comprising the intracellular domain of paired immunoglobulin-like receptor β (PILRβ).

In certain aspects, the chimeric receptor is expressed in the reporter cell through a viral expression vector. In some aspects, the viral expression vector is a retroviral expression vector. In particular aspects, the level of LILRB activation is detected based on the morphology or mobility of the cell. In certain aspect, the reporter cell further comprises a reporter gene that encodes a detectable label and is operably linked to a promoter regulated by activation of the receptor. In specific aspects, the promoter is a nuclear factor of activated T cells (NFAT) promoter. In specific aspects, the promoter is a CCL2 promoter, a CCL4 promoter, a CCL5 promoter, a IL-6R promoter, a IL-8 promoter, a gp130 promoter, a OSM promoter, a TIMP-1/2 promoter, a TNF-R1/II promoter, a uPAR promoter or an arginase-1 promoter.

In some aspects, the detectable label is a colorometric label, fluorescent label, bioluminescent label, or chemiluminescent label. In certain aspects, the detectable label is GFP, YFP, RFP, or D-luciferin. In particular aspects, the detectable label is GFP. In some aspects, the detecting step comprises flow cytometry analysis or quantification of luminescence.

In certain aspects, the candidate compound is an antibody. In some aspects, the antibody is a monoclonal antibody, a chimeric antibody, a CDR-grafted antibody, a humanized antibody, a Fab, a Fab', a F(ab')2, a Fv, or a scFv. In particular aspects, the antibody is a monoclonal antibody.

In some aspects, the reference level is obtained from a reporter cell contacted with only ApoE. In certain aspects, the ApoE is recombinant. In particular aspects, the ApoE is human ApoE. In some aspects, the human ApoE is isolated from serum. In certain aspects, the ApoE is further defined as ApoE2, ApoE3, or ApoE4.

In certain aspects, an increase in the level of LILRB activation as compared to the reference level indicates that the modulator is an agonist. In certain aspects, a decrease in the level of LILRB activation as compared to the reference level indicates that the modulator is an antagonist.

In certain aspects, the candidate substance is linked to a substrate. In certain aspects, the candidate substance is linked to a cell expressing FcR.

A further embodiment provides a composition for identifying a modulator of LILRB activation. In one aspect, the composition comprises a candidate LILRB modulator, the ligand of LILRB and a reporter cell expresses a receptor comprising an extracellular domain of LILRB, wherein the reporter cell has a phenotype indicating LILRB activation. In certain aspects, the reporter cell further comprises a reporter gene that encodes a detectable label and is operably linked to a promoter regulated by activation of the receptor. In some aspects, the receptor further comprises an intracellular domain of PILRβ. In certain aspects, the candidate LILRB inhibitor is an antibody. In some aspects, the detectable label is GFP. In certain aspects, the composition further comprises a cell expressing FcR.

A further embodiment provides a composition for identifying a modulator of LILRB activation in the absence of its known ligands. In one aspect, the composition comprises a candidate LILRB modulator, and a reporter cell expresses a receptor comprising an extracellular domain of LILRB, wherein the reporter cell has a phenotype indicating LILRB activation. In certain aspects, the reporter cell further comprises a reporter gene that encodes a detectable label and is operably linked to a promoter regulated by activation of the receptor. In some aspects, the receptor further comprises an intracellular domain of PILRβ. In certain aspects, the candidate LILRB inhibitor is an antibody. In some aspects, the detectable label is GFP. In certain aspects, the composition further comprises a cell expressing FcR.

An even further embodiment provides a method of treating cancer in a subject comprising administering an effective amount of an inhibitor of ApoE-induced LILRB activation (e.g., identified by the embodiments disclosed herein) to a subject. In some aspects, the inhibitor of ApoE-induced LILRB activation is an antibody. In particular aspects, the cancer is AML.

A further embodiment provides a method of treating autoimmune disease or inhibiting the onset of transplant rejection or treating an inflammatory disorder in a subject comprising administering an effective amount of an agonist of ApoE-induced LILRB activation to a subject.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 5*a*-5*b*-Analysis of correlation between mRNA level of immune modulating molecules and the overall survival of AML patients in TCGA database. FIG. 5*a*: Individual analysis of patient survival curve for each gene; FIG. 5*b*: Summary of p value of all 50 genes.

FIGS. 7*a*-7*m*—LILRB4 expressed on leukemia cells directly suppresses T cell proliferation in vitro. FIG. 7*a*: LILRB4 surface expression was quantified by flow cytometric analysis of samples from 105 patients at UT Southwestern. The "Other" category includes cells from patients with acute undifferentiated leukemia (AUL) and tumor-associated macrophages. FIGS. 7*b-c*: LILRB4 surface expression was compared on normal monocytes and neoplastic monocytes from healthy donors (n=25) and AML patients (n=53) respectively (FIG. 7*b*), or from the same AML patient (n=6) (shown in FIG. 7*c*). MFI: mean fluorescence intensity. FIG. 7*d*: T cells isolated from healthy donors were incubated with irradiated lilrb4-modulated THP-1 cells in indicated E:T ratios. After culture with anti-CD3/CD28/CD137-coated beads and rhIL-2 for 5 days, representative cells were photographed using an inverted microscope. E cells are effect cells; T, THP-1 cells are target cells. FIG. 7*e*: Total T cells were stained with anti-CD3 antibody and analyzed by flow cytometry. FIG. 7*f*: The percentage of CTL cells was determined using flow cytometry with staining of anti-CD3, anti-CD8 and anti-CD28 antibodies. FIGS. 7*g-h*: T cells isolated from healthy donors were incubated in the lower chambers of a 96-well transwell plate. Irradiated indicated THP-1 cells were incubated in the upper chambers. The pore size of the transwell membrane was 3 μm. E:T=2:1. After culture with anti-CD3/CD28-coated beads and rhIL-2 for 7 days, representative cells were photographed using an inverted microscope (FIG. 7*g*) and T cells were stained with anti-CD3, anti-CD4 and anti-CD8 antibodies and analyzed by flow cytometry (FIG. 7*h*). FIG. 7*i*: $CD8^+$ T cells stimulated by anti-CD3/CD28/CD137-coated beads were co-cultured with THP-1 cells that stably express GFP and treated with anti-LILRB4 antibodies or control IgG. $GFP^+$ cells are THP-1 leukemia cells, $CD8^+CD28^+$ are activated CTLs, and $CD8^+CD28^-$ cells are inactive T cells or T suppressor cells. FIGS. 7*j-l*: Quantification of the indicated cells shows that anti-LILRB4 antibody reversed LILRB4 mediated inhibition of T cell activation by upregulation of $CD8^+CD28^+$ cells and led to killing of $LILRB4^+$ AML cells. FIG. 7*m*: Anti-LILRB4 antibody increases CTL cytokine production. Numbers 1~10 represent transwell plates to which were added GM-CSF, IFNγ, IL-13, IL-1β, IL-5, MCP-3, MCP-4, MIP-3α, RANTES, and TNFβ, respectively. The red boxes indicate increases as the result of anti-LILRB4 antibody treatment and the green boxes indicate decreases as the result of anti-LILRB4 antibody treatment; blue boxes indicate internal controls in the cytokine array.

FIGS. 9*a*-9*b*: T cells isolated from individual AML (FIG. 9*a*) or B-ALL (FIG. 9*b*) patient were incubated with irradiated lilrb4-positive or negative primary leukemia cells from the same patient. FIG. 9*c*-FIG. 9*f*: T cells isolated from healthy donors were incubated with irradiated lilrb4-positive or negative primary leukemia cells from indicated AML (FIG. 9*c*, FIG. 9*e*) or B-ALL (FIG. 9*d*, FIG. 9*f*) patients. E:T=10:1. After culture with anti-CD3/CD28/CD137-coated beads and rhIL-2 for 5 days, T cells were stained with anti-CD3, anti-CD4 and anti-CD8 antibodies and analyzed by flow cytometry.

FIG. 10*a*: Schematic of the LILRB4 reporter system. FIG. 10*b*: Flow cytometry demonstrates anti-LILRB4 antibody binds to human LILRB4 reporter cells. FIG. 10*c*: The LILRB4 activation induced by 10% human serum (HS) was inhibited by anti-LILRB4 antibody. IgG was used as control. ****, $p<0.0001$.

FIG. 11*a*: The growth of THP-1 cells was not changed after 7 days of treatment of IgG or anti-LILRB4 antibody. FIG. 11*b*: The activation status of human primary $CD8^+$ cells were not affected after 5 days' treatment of IgG or anti-LILRB4 antibody in vitro. n.s., not significant.

FIG. 12*a*: Anti-LILRB4 antibody treatment inhibits subcutaneous implantation of THP-1 cells in hPBMC-transplanted humanized NSG mice. Leukemia development was monitored over time by luminescence imaging. FIG. 12***g*: Tumor weights were measured at 27 days post inoculation of tumor cells. FIG. 2*l*: Mice treated with anti-LILRB4-N297A antibodies showed no effect on mouse survival when $CD8^+$ T cells are depleted. FIG. 12*n*: $2\times10^7$ spleen cells from mice that were implanted by human LILRB4-overexpressing C1498 cells and then treated by anti-LILRB4-N297A were transferred into a wild-type C57b1/6 mouse (n=5). At the same time, $2\times10^7$ spleen cells from normal wild-type C57b1/6 mice were transferred into a wild-type C57b1/6 mouse (n=5) as naïve control. One month after adoptive transplantation, $1\times10^6$ C1498 cells were subcutaneously implanted into each mouse. Tumor size was monitored and calculated by (width×width×length). Arrow indicates the failure of rechallenge in mice which had eliminated leukemia upon adoptive transfer with $3\times10^6$ C1498 cells subcutaneously.

FIGS. 14*a*-14*dd*—LILRB4 promotes AML cells migration and supports leukemia development. FIG. 14*a*: Knockout of lilrb4 reduced THP-1 cell transmigration across endothelial cells. FIG. 14*b*: $2\times10^6$ lilrb4-knockout (KO) or scrambled control (WT) THP-1 cells were injected into NSG mice (n=5), and then mice were sacrificed at 20 hrs after transplant. The number of leukemia cells (GFP positive) in liver, spleen, and bone marrow were normalized to that in peripheral blood as determined by flow cytometry. FIG. 14*c*: NSG mice (n=5) were injected with $1\times10^6$ lilrb4-knockout (KO) or scramble control (WT) THP-1 cells. Mice were sacrificed at day 21 post-transplant for analysis. Anti-human CD45 was used to detect THP-1 cells by flow cytometry. FIG. 14*d*: Overall survival and (FIG. 14*e*) body weight of these mice have been also examined. FIG. 14*f*: Forced expression of human LILRB4 promotes transmigration of mouse AML C1498 cells. FIG. 14*g*: $3\times10^6$ human lilrb4-expressing (GFP-hlilrb4) or control (GFP) C1498 cells were injected into NSG mice (n=5), and then mice were sacrificed at 20 hrs after transplant. The number of leukemia cells (GFP positive) in liver, spleen, and bone marrow were normalized to that in peripheral blood as determined by flow cytometry. FIG. 14*h*: NSG mice (n=5) were injected with $3\times10^6$ human lilrb4-expressing (GFP-hlilrb4) or control (GFP) C1498 cells. Mice were sacrificed at day 16 post-transplant for analysis. FIG. 14*i*: Overall survival and FIG. 14*j*: body weight of these mice was determined. FIG. 14*k*: Anti-LILRB4 antibody inhibits transmigration of THP-1 cells. IgG was used as control. FIG. 14*l*: $1\times10^6$ THP-1 cells were injected into NSG mice followed immediately by IgG or anti-LILRB4 antibody treatment, and then mice (n=5) were sacrificed at 20 hrs after transplant. The number of leukemia cells (GFP positive) in liver, spleen, and bone marrow were normalized to that in peripheral blood as determined by flow cytometry. FIG. 14*m*: NSG mice (n=5) were injected with $1\times10^6$ THP-1 cells followed immediately by IgG or anti-LILRB4 antibody treatment. Mice were sacrificed at day 21 post-transplant for analysis. Anti-human CD45 was used to detect THP-1 cells by flow cytometry. Overall survival (FIG. 14*n*) and body weight (FIG. 14*o*) of these mice was also examined. FIG. 14*p*: Anti-LILRB4 antibody inhibits transmigration of MV4-11 cells. IgG was used as control. FIG. 14*q:* $5\times10^6$ CFSE-labeled MV4-11 cells were injected into NSG mice (n=5) followed immediately by IgG or anti-LILRB4 antibody treatment, and then mice were sacrificed at 20 hrs after transplant. The number of leukemia cells (CFSE positive) in liver, spleen, and bone marrow were normalized to that in peripheral blood as determined by flow cytometry. FIG. 14*r*: NSG mice (n=5) were injected with $1\times10^6$ MV4-11 cells followed immediately by IgG or anti-LILRB4 antibody treatment. Mice were sacrificed at day 21 post-transplant for analysis. Anti-human CD45 was used to detect MV4-11 cells by flow cytometry. Overall survival (FIG. 14*s*) and body weight (FIG. 14*t*) of these mice was also examined. FIG. 14*u*: THP-1 leukemia development was monitored by whole animal bioluminescence imaging. Mice were treated with control IgG or anti-LILRB4 antibodies. FIG. 14*v*: Representative mice were sacrificed at 21 days for ex vivo bioluminescence imaging of internal organs after luciferase-expressed THP-1 transplantation. 1: GI tract; 2: legs; 3: lung; 4: spleen; 5: liver; 6: kidneys; 7: brain; 8: heart. FIG. 14*w*-FIG. 14*z:* $5\times10^6$ CFSE-labeled MV4-11 cells were injected into NSG mice (n=5) that had been pre-treated to deplete innate immune cells, followed immediately by IgG or anti-LILRB4-N297A antibody treatment, and then mice were sacrificed at 20 hrs after transplant. The number of leukemia cells (CFSE positive) in liver, spleen, and bone marrow were normalized to that in peripheral blood as determined by flow cytometry. Mice in (x), (y) and (z) were pretreated with anti-asialo GM1 antibodies, clodronate liposomes and anti-Ly6G antibody, respectively. FIG. 14*aa*-FIG. 14*dd:* $1\times10^6$ lilrb4-modified THP-1 cells were injected into NSG mice followed immediately by IgG or anti-LILRB4 antibody treatment, and then mice (n=5) were sacrificed at 20 hrs after transplant. The number of leukemia cells (GFP positive) in liver, spleen, and bone marrow were normalized to that in peripheral blood as determined by flow cytometry. WT, wild-type THP-1 cells with inducible Cas9 and scramble gRNA expression; KO, lilrb4-knockout THP-1 cells selected by inducible Cas9 expression and scramble lilrb4-specific gRNA expression; KO-wt, overexpression of wild-type lilrb4 cDNA lilrb4-knockout in THP-1 cells; KO-int Δ, overexpression of intracellular domain-deleted lilrb4 cDNA lilrb4-knockout in THP-1 cells.

(FIG. 16*a*) The growth of THP-1 cells was not changed by knockout of lilrb4. WT, wild type THP-1 cells with inducible Cas9 and scramble gRNA expression; KO, lilrb4-knockout THP-1 cells selected by inducible Cas9 expression and scramble lilrb4-specific gRNA expression. (FIG. 16*b*) The growth of mouse AML C1498 cells was not changed by forced expression of human lilrb4. n.s., not significant.

(FIG. 20*a*) Schematic of antibody administration in AML xenograft. Antibodies (either control IgG or anti-LILRB4 antibodies) were administered as indicated by arrows. (FIG. 20*b*) The percentages of human leukemia (THP-1, CD45+) cells in liver (LV), bone marrow (BM), and spleen (SP) of recipient NSG mice (n=6) were determined by flow cytometry for antibody given every three days beginning on the indicated day.

FIGS. 25*a*-251—APOE binds LILRB4 and supports AML migration. FIG. 25*a*: As shown by analysis of the percentage of cells in the LILRB4 reporter system that are $GFP^+$, human serum and mouse serum specifically activate LILRB4. FIG. 25*b*: Recombinant APOE activates human LILRB4 and mouse PIRB in reporter systems. FIG. 25*c*: Serum from APOE-null mouse was unable to activate LILRB4. FIG. 25*d*: Lipid-reconstituted APOE (APOE-POPC) activates human LILRB4 as well as recombinant APOE in reporter systems. FIG. 25*e*: lilrb4-knockout THP-1 cells showed decreased APOE binding as determined by flow cytometry. Cells stained with anti-His tag-APC served as a negative control. FIG. 25*f*: Binding kinetics of human APOE-3 to LILRB4-ECD-Fc were measured using surface plasmon resonance (SPR). LILRB4-ECD-Fc was immobilized on Protein A biosensor tips and incubated with APOE-3 concentrations ranging from 1.5625 nM to 100 nM.

FIG. 26*a*: Flowchart of ligand screen. FIG. 26*b*: Fractionation of LILRB4 stimulating activities from human serum by FPLC. 10% human serum was used as a positive control. FIG. 26*c*: A list of proteins identified from the LILRB4 stimulating fractions by mass spectrometry (MS). PSMs: peptide spectrum matches.

FIG. 28*a*: APOE (20 μg/ml) purified from human plasma, His-tagged or tag-free recombinant human APOE (rhAPOE) (20 μg/ml) expressed by 293T mammalian cells, or rhAPOE (20 μg/ml) expressed by bacteria all activate the LILRB4 reporter. These APOE all represent human APOE3. FIG. 28*b*: APOE2, APOE3 and APOE4 all activate the LILRB4 reporter. 40 μg/ml APOEs were coated on plates or directly added in cell culture media (soluble).

FIGS. 29*a-c*: Binding kinetics of APOE 2, 3, and 4 to LILRB4-Fc were measured using surface plasmon resonance (SPR). LILRB4-Fc was immobilized on Protein A biosensor tips and incubated with APOE concentrations ranging from 1.5625 nM to 100 nM. The Kd of APOE2, APOE3 and APOE4 binding to LILRB4 are 5.525 nM, 2.485 nM and 3.573 nM, respectively. (FIGS. 29*d-f*) Binding kinetics of APOE 2, 3, and 4 to LILRB4-Fc were measured using Bio-layer Interferometry (Octet). LILRB4-Fc was immobilized on Protein A biosensor tips and incubated with APOE concentrations ranging from 44 nM to 1176 nM. The Kd of APOE2, APOE3 and APOE4 binding to LILRB4 are 60.68 nM, 61.67 nM and 48.39 nM, respectively. (FIG. 29*g*) Binding kinetics of APOE 3 to His-LILRB4 was measured using microscale thermophoresis (MST). The Kd of APOE3 binding to LILRB4 is 210 nM.

FIGS. 30*a*-30*b*—The role of mutated residues of LILRB4 in the possible APOE binding interface based on the known structures of LILRB4 and APOE. FIG. 30*a*: Based on the PDB structure of LILRB4 (PDBID: 3P2T) and APOE3 (PDBID: 2L7B), residues in four possible ligand binding interfaces for mutagenesis study and generated a series of mutant LILRB4 reporter cells. FIG. 30*b*: Mutation of two residues, W106 and Y121 significantly reduced activation of LILRB4 by APOE, located in the first Ig domain and in the linker between two Ig domains, respectively.

FIGS. 31*a*-31*w*—LILRB4-mediated intracellular signaling controls AML cell migration and T cell suppression. FIG. 31*a*: Western blots show shp-1, shp-2 and ship were individually knocked-out by CRISP/Cas9 in THP-1 cells. FIG. 31*b*-FIG. 31*c*: T cells isolated from healthy donors were incubated in the lower chambers of a 96-well transwell plate. Irradiated indicated THP-1 cells were incubated in the upper chambers. The pore size of the transwell membrane was 3 μm. E:T=2:1. After cultured with anti-CD3/CD28-coated beads and rhIL-2 for 7 days. Representative cells were photographed using an inverted microscope (FIG. 31*b*) and T cells were stained with anti-CD3 and anti-CD8 antibodies and analyzed by flow cytometry (FIG. 31*c*). FIG. 31*d*-FIG. 31*e*: Knockout of shp-2 reduces THP-1 cell migration and leukemia development in xenografted mice. FIG. 31*d:* $2\times10^6$ shp-1-knockout (shp-1-KO), shp-2-knockout (shp-2-KO), ship-knockout (ship-KO) or scramble control (WT) THP-1 cells were injected into NSG mice (n=5), and then mice were sacrificed at 20 hrs after transplant. The number of leukemia cells (GFP positive) in liver, spleen, and bone marrow were normalized to that in peripheral blood as determined by flow cytometry. FIG. 31*e*: NSG mice (n=5) were injected with $1\times10^6$ indicated THP-1 cells. Mice were sacrificed at day 21 post-transplant for analysis. Anti-human CD45 was used to detect THP-1 cells by flow cytometry. FIG. 31*j*-FIG. 31*k*: T cells isolated from healthy donors were incubated in the lower chambers of a 96-well transwell plate. Irradiated THP-1 cells, which were pre-treated with 1-5 μM of fludarabine or stattic for 24 hrs, were incubated in the upper chambers. The pore size of the transwell membrane was 3 μm. E:T=2:1. After culture with anti-CD3/CD28-coated beads and rhIL-2 for 7 days, representative cells were photographed using an inverted microscope (FIG. 31*j*) and T cells were stained with anti-CD3 antibody and analyzed by flow cytometry (shown in FIG. 31*k*). FIG. 31*l*: Inhibition of STAT-3 but not STAT-1 by specific inhibitors, 2.5 μM of stattic (STAT-3 inhibitor) or fludarabine, respectively, decreases THP-1 cell transmigration across endothelial cells. FIG. 31*m*: NSG mice (n=5) were injected with $1\times10^6$ THP-1 cells with pre-treatment with 2.5 uM indicated STATs inhibitors for 24 hrs. DMSO was used as control. Mice were sacrificed at day 21 post-transplant for analysis. Anti-human CD45 was used to detect THP-1 cells by flow cytometry. FIG. 31*n*: Loss of lilrb4 decreases cytokine and chemokine production in THP-1 cells. Numbers 1-12 of red boxes represent CCL2, CCL5, CCL4, OSM, IL-6R. IL-8, gp130, TNFRSF1B, TNFRSF1A, TIMP-1, TIMP-2 and uPAR, respectively. Blue boxes indicate internal controls in the cytokine arrays. FIG. 31*o*: Quantification of the intensity of blots (shown in FIG. 31*n*) by ImageJ software. FIG. 31*p*: Western blots show lilrb4-knockout (KO) decreases protein expression of uPAR and arginase-1 compared with that in scramble control (WT) THP-1 cells. FIG. 31*q*: Arginase activity was decreased in culture medium of lilrb4-knockout (KO) compared with that in scramble control (WT) THP-1 cells. FIG. 31*r*-FIG. 31*s*: T cells isolated from healthy donors were incubated with irradiated lilrb4-KO or WT THP-1 cells. These cells were supplemented with indicated concentration of uPAR proteins for 7 days. Representative cells were photographed using an inverted microscope (FIG. 31*r*) and T cells were stained with anti-CD3 antibody and analyzed by flow cytometry (FIG. 31*s*). FIG. 31*t*-FIG. 31*u*: T cells isolated from healthy donors were incubated with irradiated lilrb4-KO or WT THP-1 cells. The culture was supplemented with indicated concentration of recombinant Arginase-1 proteins for 7 days. Representative cells were photographed using an inverted microscope (FIG. 31*t*) and T cells were stained with anti-CD3 antibody and analyzed by flow cytometry (FIG. 31*u*). FIG. 31*v*-FIG. 31*w*: Supplementation of recombinant uPAR or Arginase-1 to the medium rescued the decrease of transmigration ability of lilrb4-KO THP-1 (FIG. 31*v*) or lilrb4-KO MV4-11 cells (FIG. 31*w*) across endothelium.

FIG. 35*a*: Blockade of CCL4, but not CCL2 or CCL3, by specific neutralizing antibodies decreases THP-1 cell transmigration across endothelial cells. FIG. 35*b*: NSG mice (n=5) were injected with $1\times10^6$ THP-1 cells followed immediately by 200 μg/mouse IgG, anti-CCL2, anti-CCL3 or anti-CCL4 neutralizing antibody treatment. Mice were sacrificed at day 21 post-transplant for analysis. Anti-human CD45 was used to detect THP-1 cells by flow cytometry. FIG. 35*c*: T cells isolated from healthy donors were incubated with irradiated lilrb4-KO or WT THP-1 cells. These cells were supplemented with 20 μg/ml CCL4 proteins or treated with 10 μg/ml IgG or anti-CCL4 neutralizing antibodies for 7 days. T cell number was analyzed by flow cytometry.

FIGS. 36*a*-36*d*—Correlation analyses of LILRB4-regulated genes. FIG. 36*a*: Comparison of differential gene expression patterns in lilrb4-KO versus WT and in those treated with anti-LILRB4 versus IgG identified by RNA-seq. For antibody treatments, THP-1 cells were treated with 1% human serum for 24 hrs in presence of antibodies. Blue indicates lilrb4-negatively regulated genes and red indicates lilrb4-positively regulated genes. FIG. 36*b*: Correlation analysis of mRNA expression data of lilrb4-regulated genes from the TCGA database shows that lilrb4 expression has positive correlation with expression of lilrb4-positively regulated genes; In contrast, lilrb4 expression has negative correlation with expression of lilrb4-negatively regulated genes identified from RNA-seq data. FIG. 36*c*-FIG. 36*d*: Analysis of mRNA expression data and patient survival from the TCGA database shows that expression of lilrb4-positively regulated genes (red line) has inverse correlation between gene expression and patient overall survival (FIG. 36*c*); but expression of lilrb4-negatively regulated genes (red line) shows positive correlation between gene expression and patient overall survival (FIG. 36*d*).

(FIG. 37*a*) Schematic of antibody administration. (FIG. 37*b*) The number of leukemia cells in peripheral blood (PB) was normalized to that in peripheral blood as determined by flow cytometry. (FIG. 37*c*) The number of leukemia cells in liver (LV), spleen (SP), and bone marrow (BM) were normalized to that in peripheral blood as determined by flow cytometry. Anti-human CD45 was used to detect MV4-11 cells.

FIG. 38*a*-FIG. 38*b*: Anti-LILRB4 antibody accelerates the mobilization of MV4-11 cells to peripheral blood (PB) (FIG. 38*a*) from bone marrow (BM), liver (LV) and spleen (SP) (FIG. 38*b*). Anti-human CD45 was used to detect MV4-11 cells by flow cytometry. Mice in each group, n=6. FIG. 38*c*-FIG. 38*e*: Synergistic effects of anti-LILRB4 antibody treatment in combination with the chemotherapy drug cytarabicin (FIG. 38*d*) or daunorubicin (FIG. 38*e*) inhibited AML development. Mice in each group, n=6. The administration of chemotherapy drugs and anti-LILRB4 antibody are shown in the diagram (FIG. 38*c*). Anti-human CD45 was used to detect human leukemia cells by flow cytometry.

FIGS. 40*a*-40*c*—Anti-LILRB4 antibodies inhibit leukemia development in hCB-humanized NSG mice. FIG. 40*a*: Strategy to test whether anti-LILRB4 antibody C84 inhibits leukemia development in hCB-humanized NSG mice. FIG. 40*b*: Leukemia development was monitored over time by luminescence imaging. FIG. 40*c*: Frequency of engrafted leukemia, normal human cells, including human B cells, human myeloid cells and human T cells in peripheral blood over time and hematopoietic tissues of hCB-humanized mice at the 24 days after leukemia transplantation. BM: bone marrow; LV: liver; SP: spleen; PB: peripheral blood.

DESCRIPTION OF ILLUSTRATIVE EMBODIMENTS

Figure 1:
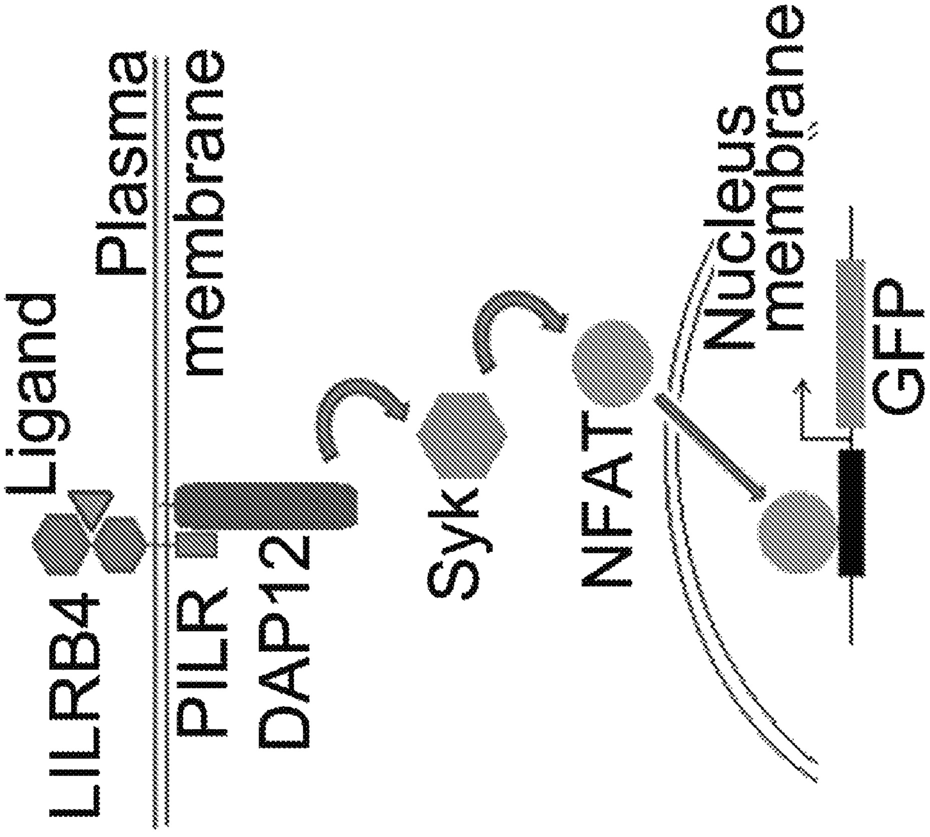
FIG. 1—Schematic of the LILRB4 reporter system.
Figure 2:
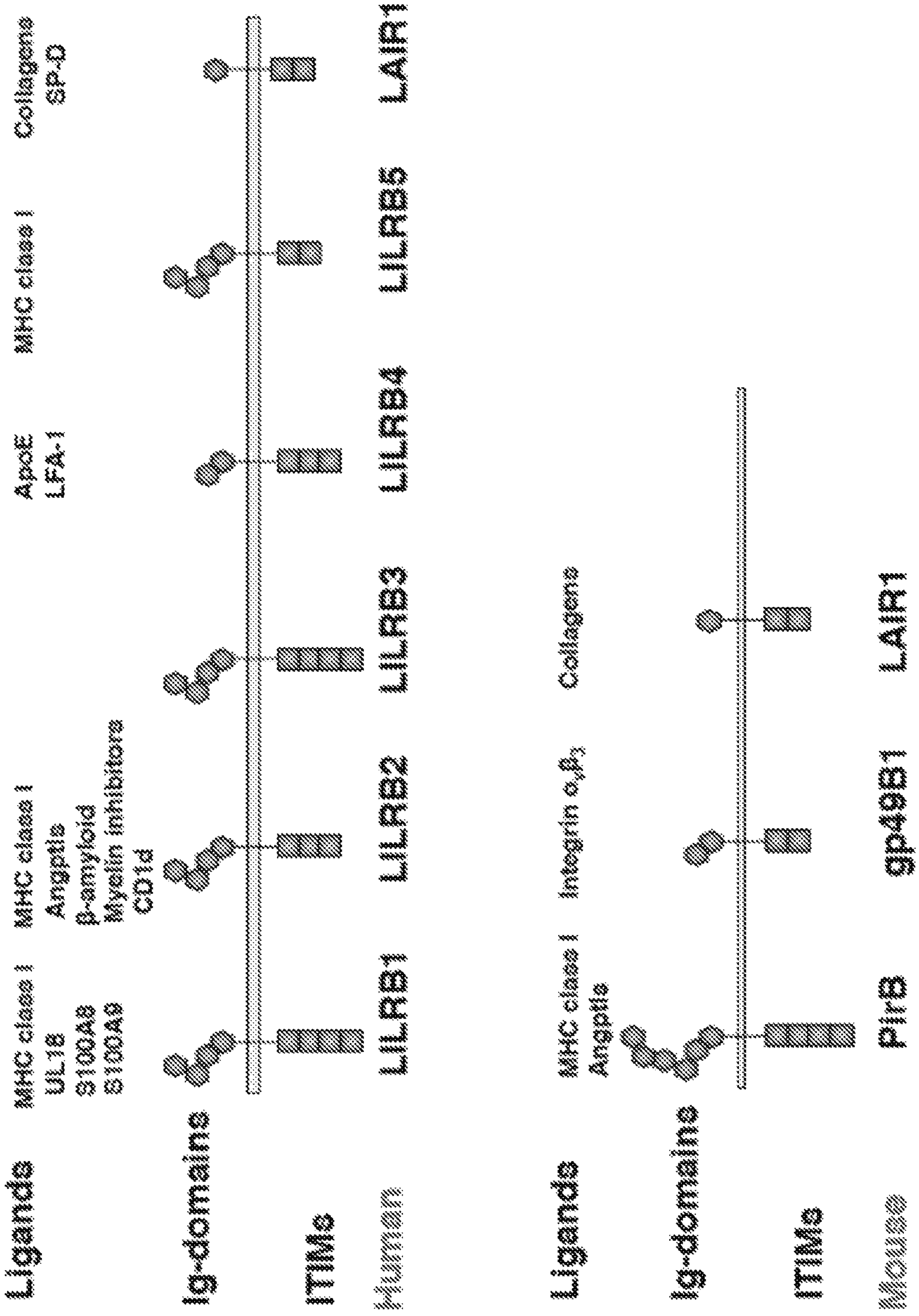
FIG. 2—Diagram of LILRBs and their ligands.
Figure 3:
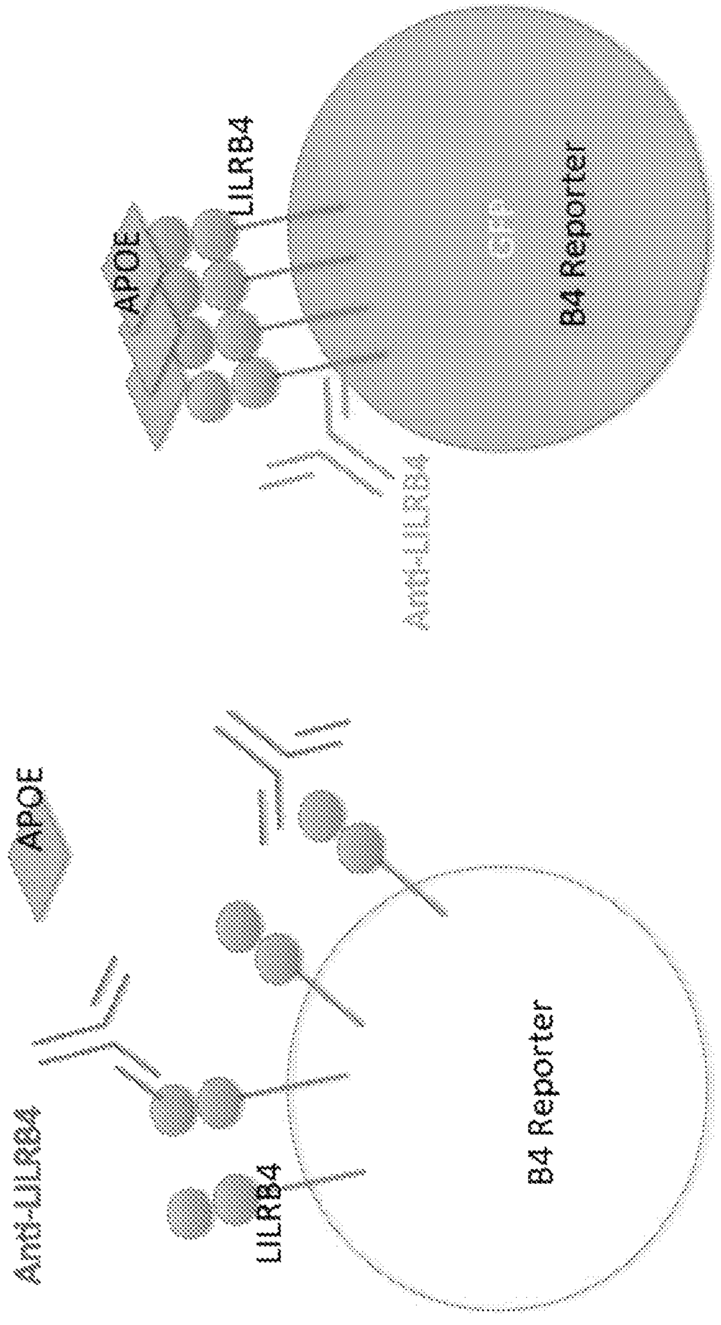
FIG. 3—Illustration of an assay for identifying an antibody that blocks the ApoE-induced LILRB4 activation. The reporter cell on the left is GFP-negative, indicating that the antibody can block ApoE binding to LILRB4 or compete with ApoE to biding to LILRB4 and blocks the GFP induction by ApoE. On the right the antibody binds to a region of LILRB4 without blocking the GFP induction by ApoE, resulting GFP-positive reporter cells.
Figure 4:
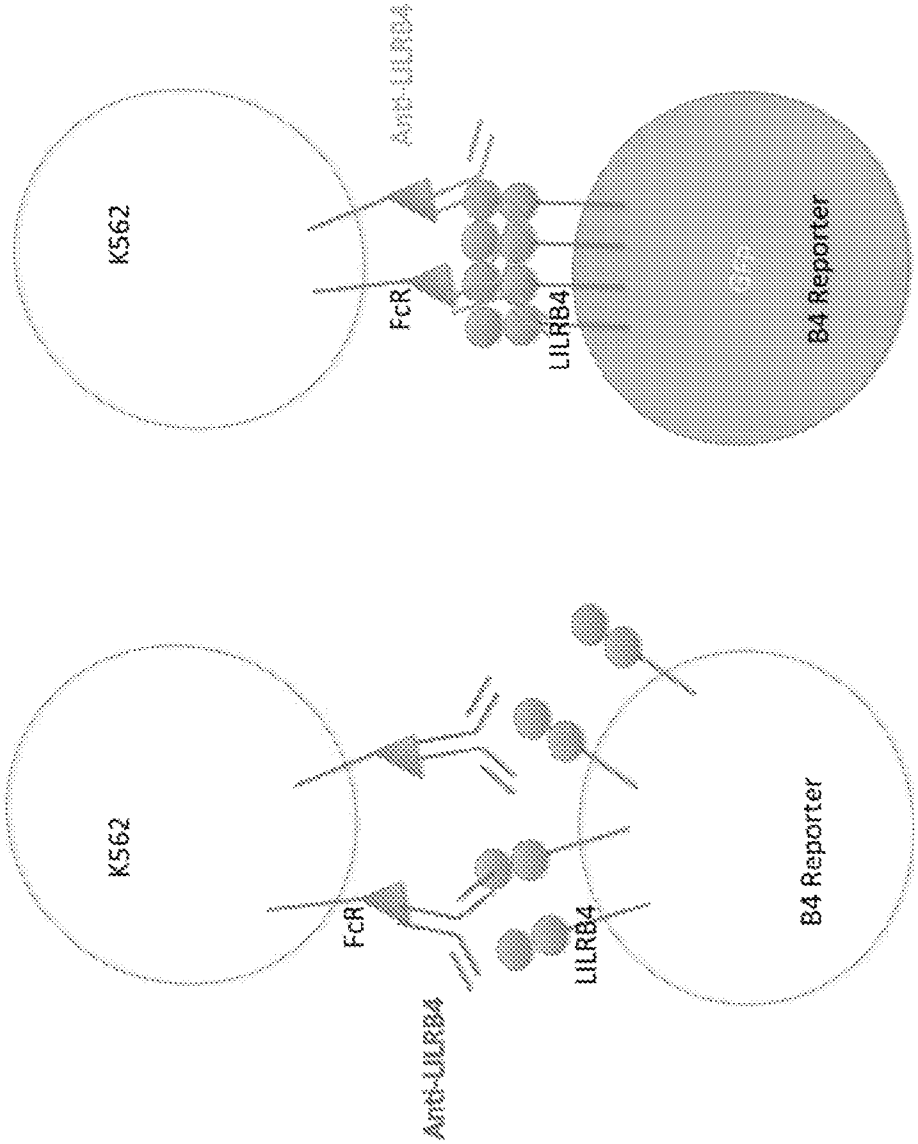
FIG. 4—Illustration of an assay for identifying an antibody that activates LILRB4. On the left, an antibody can bind to FcR on K562 cells and bind to LILRB4 on reporter cells. But it does not induce GFP. On the right, an antibody can bind to FcR on K562 cells and bind to LILRB4 on reporter cells in a way that induces GFP. The results indicate that the antibody on the right is an activating antibody.

Targeted therapy may induce rapid tumor regression, whereas immunotherapy may achieve long-lasting anti-tumor effects. Thus, it would be ideal to identify molecular targets that enable the combination of the strengths of targeted therapy and immunotherapy. The function of leukocyte immunoglobulin-like receptor family (LILRBs) that are expressed on both immune cells and leukemia cells remain to be understood. The present disclosure shows that LILRB4, a surface marker for monocytic acute myeloid leukemia (AML), sustains leukemia development. It was found that APOE binds specifically to LILRB4, activating LILRB4-mediated signalling and supporting homing of AML cells to internal organs. In the xenografted mice, inhibition of LILRB4 signalling by LILRB4 blocking antibodies eliminated AML development through direct tumor targeting, disruption of retention of leukemia cells in the microenvironment, and immune checkpoint inhibition. LILRB4 thus represents a novel target for treating monocytic AML, and anti-LILRB4 antibodies are promising drug candidates.

Accordingly, LILRB4 is an ideal target for treatment of AML and potentially other cancers. Because LILRB4 is a marker for monocytic AML and is expressed by both primitive and mature monocytic AML cells, it may be appropriate to investigate LILRB4 for potential treatment of monocytic AML. Most unexpected is that the data indicate that the anti-LILRB4 blocking antibody strategy combines targeted therapy and immunotherapy. The anti-LILRB4 blocks signalling and the interaction between LILRB4$^+$ AML cells and their microenvironment and also mediates direct tumor killing effects. In addition, the anti-LILRB4 stimulates the activation of T cells resulting in immune-system-mediated anti-cancer effects. Because LILRB4 expressed on tumor-associated macrophages and MDSCs supports cancer cell escape by immune suppression[29], anti-LILRB4 antibodies may also relieve immune suppression mediated by these myeloid cells. Moreover, the findings presented in the examples below indicate that anti-LILRB4 should enhance the efficacy of a standard chemotherapy regimen as the antibody resulted in migration of leukemia cells out of niche into the blood stream where these cells may be more susceptible to cytotoxic chemotherapy.

Further, LILRB4 targeting may have minimal toxicity. LILRB4 is expressed on monocytes and macrophages, dendritic cells, progenitor mast cells, endothelial cells, and osteoclasts. However, it is expressed at higher levels on human AML cells than on normal counterparts. Significantly, anti-LILRB4 should have no effect on HSCs, which do not express LILRB4. Although LILRB4 is expressed by osteoclasts, mice that do not express PirB, the mouse LILRB orthologue, do not have altered osteoclast function[30]. Anti-LILRB4 antibodies thus hold great promise for treatment of patients with monocytic AML and other malignancies.

Therefore, embodiments of the present disclosure provide methods of identifying LILRB antagonist (e.g., anti-LILRB antibodies) specifically targeting ApoE-induced LILRB activation. The assay provided herein comprises the administration of the LILRB ligand, ApoE, to a reporter cell or population of reporter cells along with a candidate antagonist of LILRB activation. The level of LILRB activation is then measured, such as by detecting a marker under the control of LILRB activation (e.g., NFAT-GFP). The level of LILRB activation is compared to the activation by ApoE administration alone, and a decrease in LILRB activation identifies an inhibitor of ApoE-mediated LILRB activation. Thus, the methods and compositions of the present disclosure provide methods of identifying ApoE-induced LILRB activation and their use thereof in the treatment of cancer, specifically AML.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

I. DEFINITION

As used herein, the singular forms "a", "an" and "the" include plural references unless the context clearly dictates otherwise.

Throughout this application, the term "about" is used to indicate that a value includes the inherent variation of error for the device, the method being employed to determine the value, or the variation that exists among the study subjects.

Autoimmune disease includes, without limitation, rheumatoid arthritis, Crohn's disease, multiple sclerosis, autoimmune diabetes, systemic lupus erythematosus, lupus vulgaris, thyroiditis, Addison's Disease, hemolytic anemia, antiphospbolipid syndrome, dermatitis, allergic encephalomyelitis, glomerulonephritis, Goodpasture's Syndrome, Graves' Disease, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Pulmonary Inflammation, Guillain-Barre Syndrome, and autoimmune inflammatory eye disease. Preferably, in the subject method, the subject is human. In one embodiment, the polypeptide is administered to the subject during a flare-up of an autoimmune attack. The method may further comprise administration of additional immunosuppressive drugs, e.g., cytotoxic agents, cyclosporine, methotrexate, azathioprine, and corticosteroids.

As used herein, "antagonist" or "inhibitor" of LILRB activation refers to any substance that can block or decrease the activation of LILRB in the presence of an LILRB ligand, e.g., ApoE. In certain embodiments, the antagonist or inhibitor can be protein, e.g., antibodies. In certain embodiments, the antagonist or inhibitor can be small molecule, e.g., a chemical compound. In certain embodiments, the antagonist or inhibitor decrease the activation of LILRB by at least 20%, 30%, 40%, 50%, 60%, 70%, 80% or 90% as compared to a reference level, e.g., the activation level of LILRB in the presence of LILRB ligand but in the absence of the antagonist or inhibitor.

The term "antibody" as used herein includes any immunoglobulin, monoclonal antibody, polyclonal antibody, multi-specific antibody, or bispecific (bivalent) antibody that binds to a specific antigen (or multiple antigens). A native intact antibody comprises two heavy chains and two light chains. Each heavy chain consists of a variable region ($V_H$) and a first, second, and third constant region ($C_H1$, $C_H2$, $C_H3$), while each light chain consists of a variable region ($V_L$) and a constant region (CL). Mammalian heavy chains are classified as $\alpha$, $\delta$, $\varepsilon$, $\gamma$, and $\mu$, and mammalian light chains are classified as $\lambda$ or $\kappa$. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding, and are often referred to as Fv (for variable fragment) or Fv fragment. The variable regions in both chains generally contains three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Chothia, Kabat, or Al-Lazikani (Chothia, C. et al., J Mol Biol 186(3):651-63 (1985); Chothia, C. and Lesk, A. M., J Mol Biol, 196:901 (1987); Chothia, C. et al., Nature 342 (6252):877-83 (1989); Kabat E. A. et al., National Institutes of Health, Bethesda, Md. (1991); Al-Lazikani, B., Chothia, C., Lesk, A. M., J Mol Biol 273(4):927 (1997)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain) in human, and IgG1 (γ1 heavy chain), IgG2a (γ2a heavy chain), IgG2b (γ2b heavy chain), and IgG3 (γ3 heavy chain) in mouse. As used herein, antibodies also include antigen-binding fragments, i.e., a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. Examples of antigen-binding fragment include, without limitation, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody.

The term "cancer" refers to a condition or disorder in which cells grow and divide at unregulated, quickened pace. Examples of cancer include acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, leukemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, and an alveolar macrophage; a cell from circular system or organ (e.g., myocardiocyte and pericyte); a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, and a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell; a cell from urinary system or organ (e.g., a podocyte, a juxtaglomerular cell, an intraglomerular mesangial cell, an extraglomerular mesangial cell, a kidney proximal tubule brush border cell, and a macula densa cell); and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The inflammatory disorder includes, without limitation, (i) inflammatory diseases such as chronic inflammatory pathologies (including chronic inflammatory pathologies such as, but not limited to, sarcoidosis, chronic inflammatory bowel disease, ulcerative colitis, and Crohn's pathology); (ii) vascular inflammatory pathologies such as, but not limited to, disseminated intravascular coagulation, atherosclerosis, Kawasaki's pathology and vasculitis syndromes (such as, but not limited to, polyarteritis nodosa, Wegener's granulomatosis, Henoch-Schonlein purpura, giant cell arthritis and microscopic vasculitis of the kidneys); (iii) chronic active hepatitis; (iv) Sjogren's syndrome; (v) spondyloarthropathies such as ankylosing spondylitis, psoriatic arthritis and spondylitis, enteropathic arthritis and spondylitis, reactive arthritis and arthritis associated with inflammatory bowel disease; and (vi) uveitis. Preferably, in the subject method, the subject is human. The method can also be combined with administration of additional anti-inflammatory agents. Anti-inflammatory agents include, but are not limited to, any known nonsteroidal anti-inflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal anti-inflammatory agent which include corticosteriods and biologically active synthetic analogs with respect to their relative glucocorticoid (metabolic) and mineralocorticoid (electrolyte-regulating) activities. Additionally, other drugs used in the therapy of inflammation include, but are not limited to, autocoid antagonists such as histamine, bradykinin receptor antagonists, leukotriene and prostaglandin receptor antagonists, and platelet activating factor receptor antagonists.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

II. LILRS

The leukocyte immunoglobulin-like receptors (LILR) are a family of receptors possessing extracellular immunoglobulin domains. They are also known as CD85, ILTs and LIR, and can exert immunomodulatory effects on a wide range of immune cells. The human genes encoding these receptors are found in a gene cluster at chromosomal region 19q13.4. They include, LILRA1, LILRA2, LILRA3, LILRA4, LILRA5, LILRA6, LILRB1, LILRB2, LILRB3, LILRB4, LILRBS, LILRB6 or LILRA6, and LILRB7 or LILRA5. A subset of LILRs recognize MHC class I molecules (also known as HLA class I in humans). Of these, the inhibitory receptors LILRB1 and LILRB2 show a broad specificity for classical and non-classical MHC alleles with preferential binding to β2m-associated complexes. In contrast, the activating receptors LILRA1 and LILRA3 prefer b2m-independent free heavy chains of MHC class I, and in particular HLA-C alleles. For LILRs and following descriptions of LILRB1-5 and LAIR1, see review[22].

A. LILRB1

Leukocyte immunoglobulin-like receptor subfamily B member 1 is a protein that in humans is encoded by the LILRB1 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. LILRB1 was also reported to be expressed in human gastric cancer cells and may enhance tumor growth. It is thought to control inflammatory responses and cytotoxicity to help focus the immune response and limit autoreactivity. Multiple transcript variants encoding different isoforms have been found for this gene.

B. LILRB2

Leukocyte immunoglobulin-like receptor subfamily B member 2 is a protein that in humans is encoded by the LILRB2 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. The receptor is also expressed on human non-small cell lung cancer cells. Multiple transcript variants encoding different isoforms have been found for this gene. LILRB2 has been shown to interact with PTPN6.

C. LILRB3

Leukocyte immunoglobulin-like receptor subfamily B member 3 is a protein that in humans is encoded by the LILRB3 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. Multiple transcript variants encoding different isoforms have been found for this gene.

D. LILRB4

Leukocyte immunoglobulin-like receptor subfamily B member 4 is a protein that in humans is encoded by the LILRB4 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. The receptor can also function in antigen capture and presentation. It is thought to control inflammatory responses and cytotoxicity to help focus the immune response and limit autoreactivity. LILRB4 is also expressed in human gastric cancer cells and may enhance tumor growth. Multiple transcript variants encoding different isoforms have been found for this gene. LILRB4 has been shown to interact with PTPN6.

E. LAIR1

Leukocyte-associated immunoglobulin-like receptor 1 is a protein that in humans is encoded by the LAIR1 gene. LAIR1 has also been designated as CD305 (cluster of differentiation 305). LAIR1 is a type I transmembrane glycoprotein that contains one extracellular Ig-like domain and two intracellular ITIMs. Like the genes that encode LILRBs, lair1 is localized to the leukocyte receptor complex (LRC) on human chromosome 19q13.4. LAIR1 binds collagens, and its ITIMs recruit SHP-1 and SHP-2. LAIR1 is expressed in T cells, B cells, natural killer (NK) cells, macrophages, and dendritic cells, as well as hematopoietic progenitors including human $CD34^+$ cells.

III. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

LILRB4 Expressed on Leukemia Cells Leads to T Cell Suppression

To identify novel mechanism and molecular targets for immune evasion of leukemia, the inventors analysed the correlation between gene expression of 50 known conceptual co-stimulating and co-inhibitory receptors and the overall survivals of 173 AML patients in TCGA AML database. The inventors found that the expression of lilrb4, an immune inhibitory receptor, most significantly negatively correlated with AML patient survival (FIG. 5).

Figure 6:
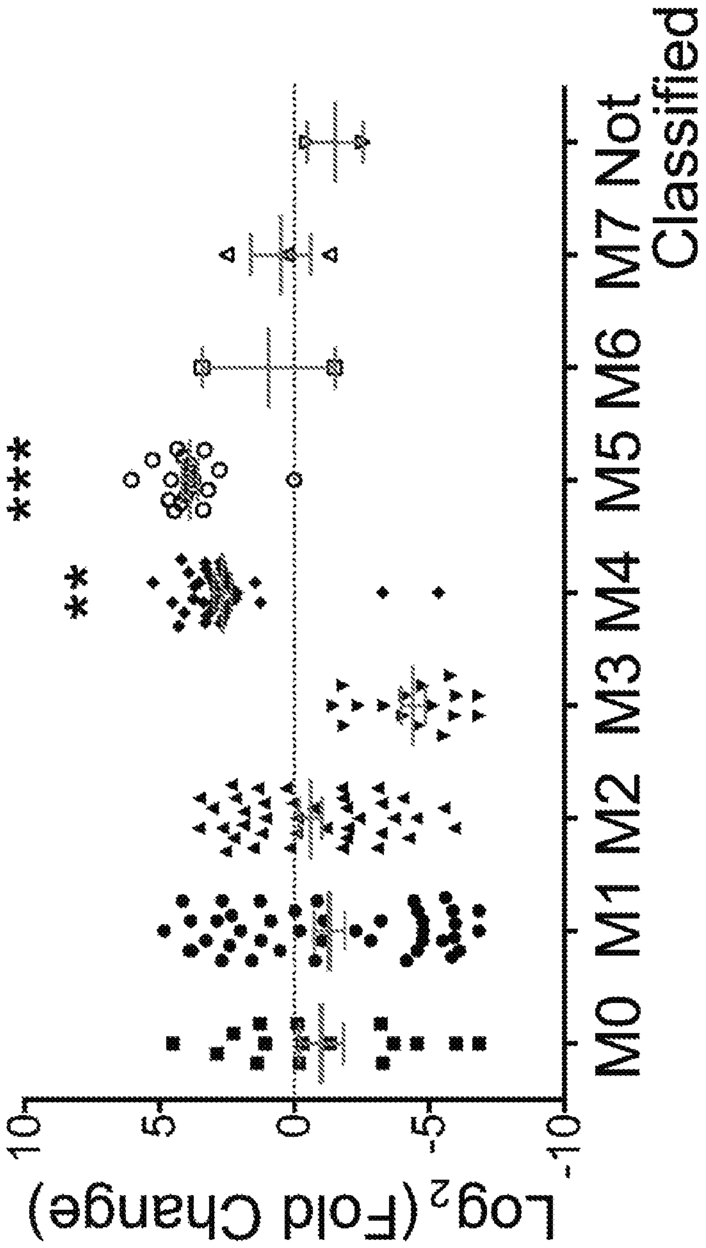
FIG. 6—Analysis of mRNA expression data from the TCGA database shows that LILRB4 mRNA is present at higher concentration in M4 and M5 AML cells than in other subtypes. , $p<0.01$,*, $p<0.001$.
Figures 7E, 7F, 7G, 7H:
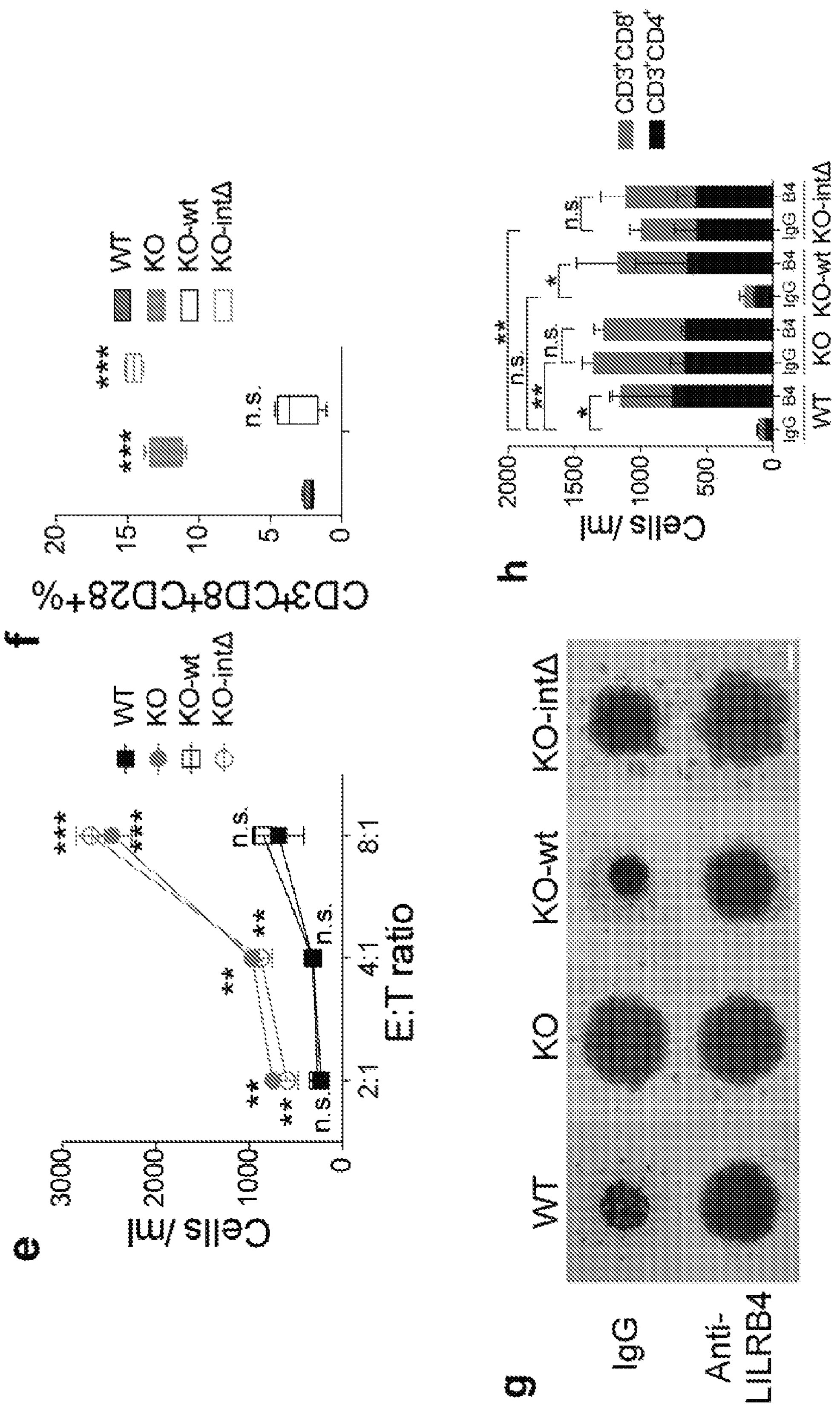
Figure 8:
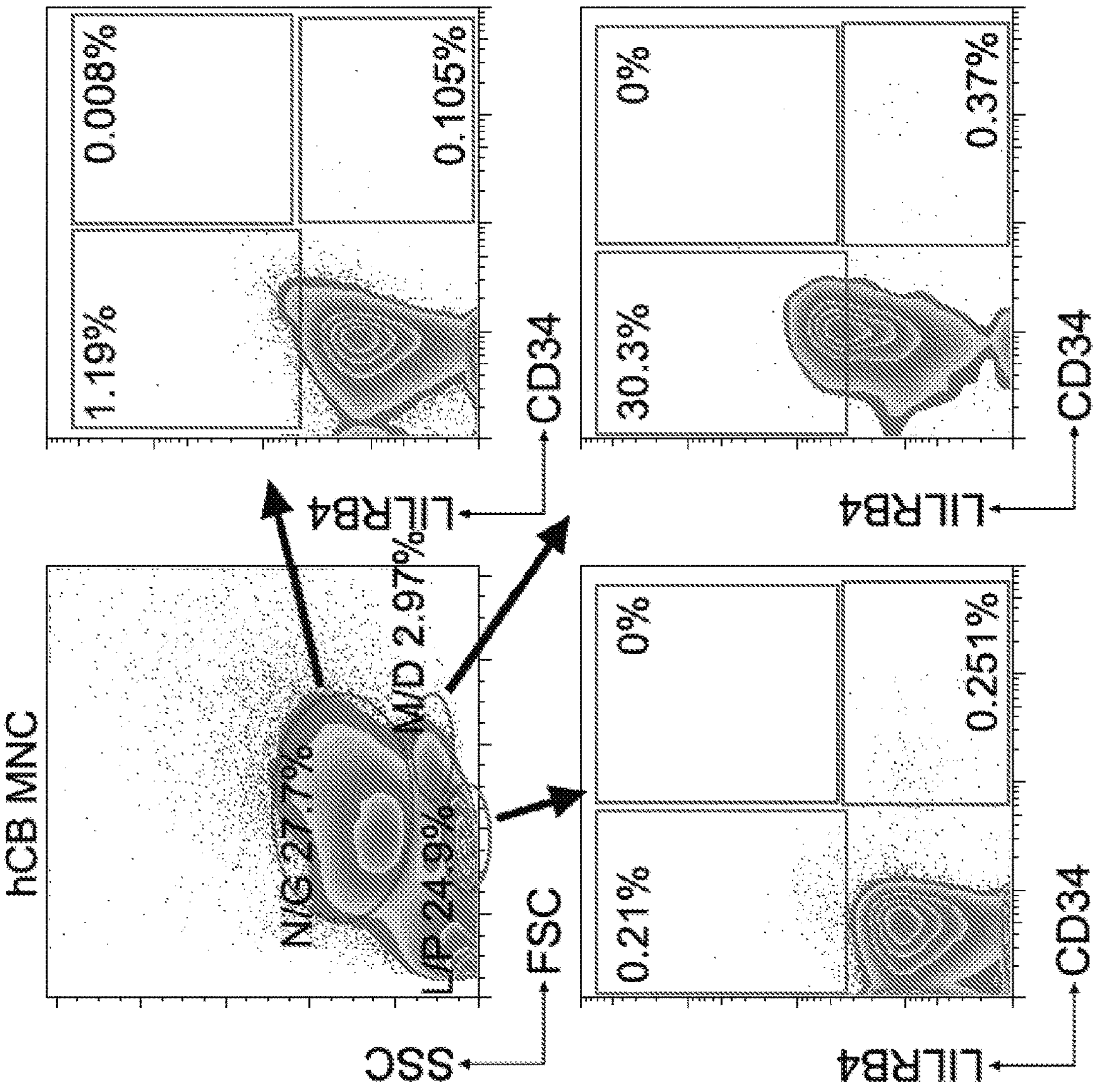
FIG. 8—LILRB4 is not expressed on normal $CD34^+$ HSCs. Shown are LILRB4 and CD34 co-staining patterns of human cord blood mononuclear cells (hCB MNCs). N/G, neutrophils and granulocytes; M/D, monocytes, macrophages and dendritic cells; L/P, lymphocytes, hematopoietic stem and progenitor cells.

LILRB4 has a restrictive expression pattern on normal monocytic cells[22], and is higher expressed in monocytic AML (or acute monocytic leukemia, which are developed from monocytic lineage and belong to FAB M4 and M5 AML subtypes) cells than in those from other subtypes of AML (FIG. 6). The inventors analysed the surface expression of LILRB4 on leukemia blasts from 118 AML patient samples from the UT Southwestern Medical Center (UTSW), and found that LILRB4 was only present on the blasts of M4 and M5 monocytic AML but not on other AML subtypes (FIG. 7*a* and Table 1). These results are consistent with a previous report that LILRB4 is a specific marker for monocytic AML[26]. Importantly, LILRB4 levels were higher on monocytic AML cells than on normal monocytes (FIGS. 7*b-c*), and is not expressed on normal hematopoietic stem cells (HSCs) (FIG. 8). These results suggest that LILRB4, a monocytic AML marker, represents an attractive target for treating this type of leukemia.

Figures 9A, 9B, 9C, 9D, 9E, 9F:
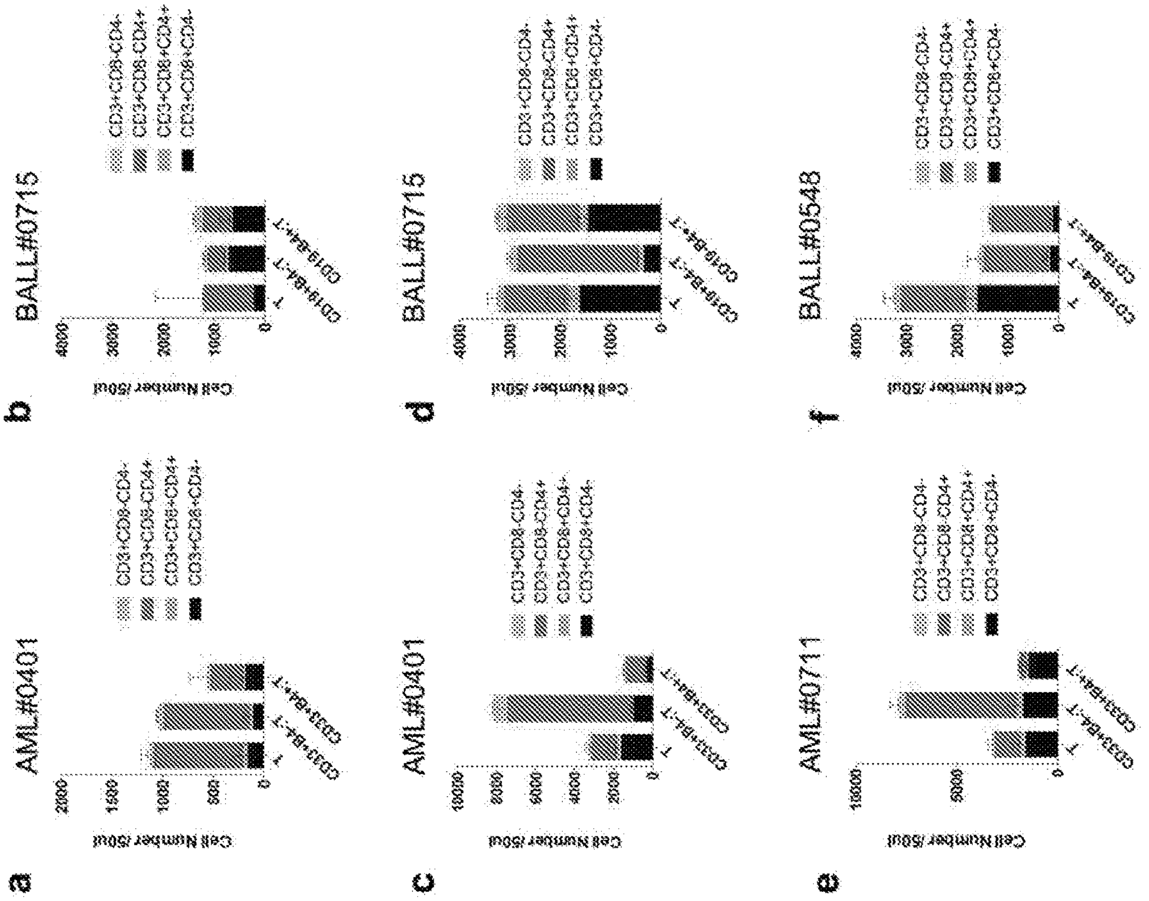
FIGS. 9*a*-9*f*—LILRB4-expressing primary AML cells suppress T cell proliferation.

To test whether LILRB4 expressed on AML cells have immune-suppressive function, the inventors co-cultured LILRB4-positive or LILRB4-negative leukemia cells, or normal hematopoietic cells with either autologous T cells or T cells from healthy donors. LILRB4-positive primary monocytic AML cells significantly suppressed T cell proliferation (FIG. 9). They then deleted LILRB4 in the human monocytic AML THP-1 cells using an inducible CRISPR/Cas9 system with lilrb4-specific guide RNA. The T cell suppressive ability of THP-1 cells was lost upon lilrb4 knockout (KO) (FIGS. 7*d-f*). Conversely, forced expression of wild-type lilrb4, but not the intracellular domain-deleted mutant lilrb4, on lilrb4-KO THP-1 cells, rescued such T cell inhibitory function (FIG. 7*d-f*). Therefore, LILRB4 on tumor cells efficiently suppresses human T cell activity, and this function of LILRB4 depends on its intracellular signalling domain. This is in contrast to a previous study reporting that the extracellular domain of LILRB4 was responsible for inhibition of T cell activities[25]. Surprisingly, the separation of wild-type THP-1 cells and human T cells in transwells still enabled T cell inhibition. In contrast, the lilrb4-KO THP-1 cells lost this ability. Again, the full-length but not the intracellular domain-deleted LILRB4 was capable of rescuing this phenotype, indicating that the non-contact T cell suppression is LILRB4 intracellular signaling dependent (FIGS. 7*g-h*).

Figures 10A, 10B, 10C:
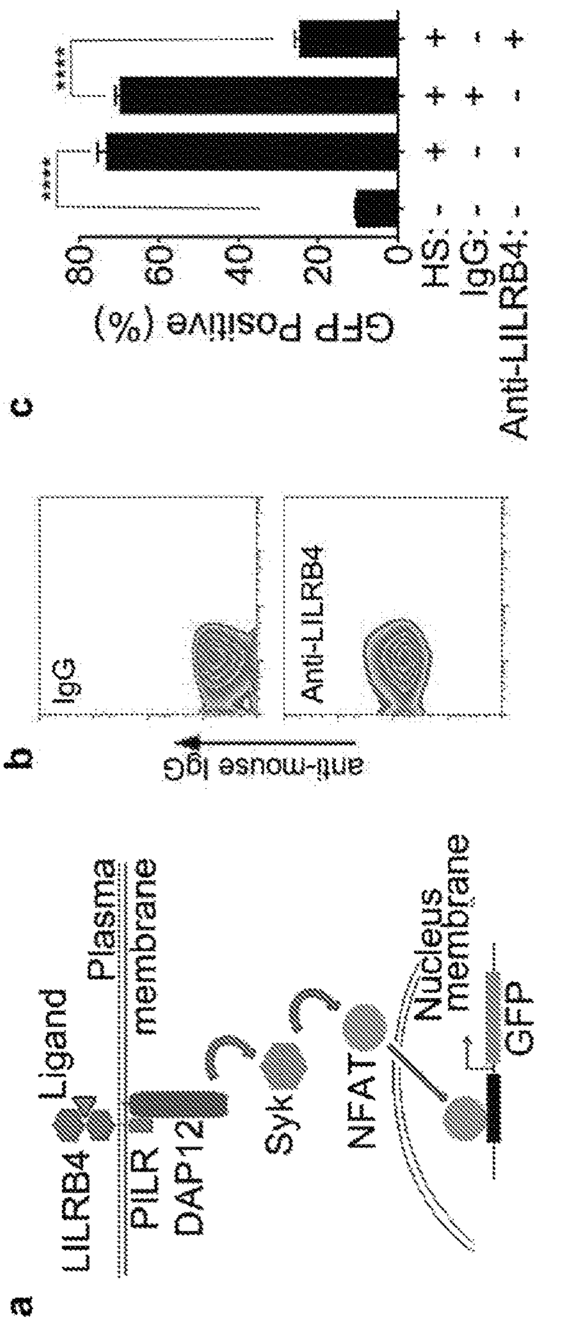
FIGS. 10*a*-10*c*-Anti-LILRB4 antibodies block human serum induced LILRB4 activation.
Figures 11A, 11B:
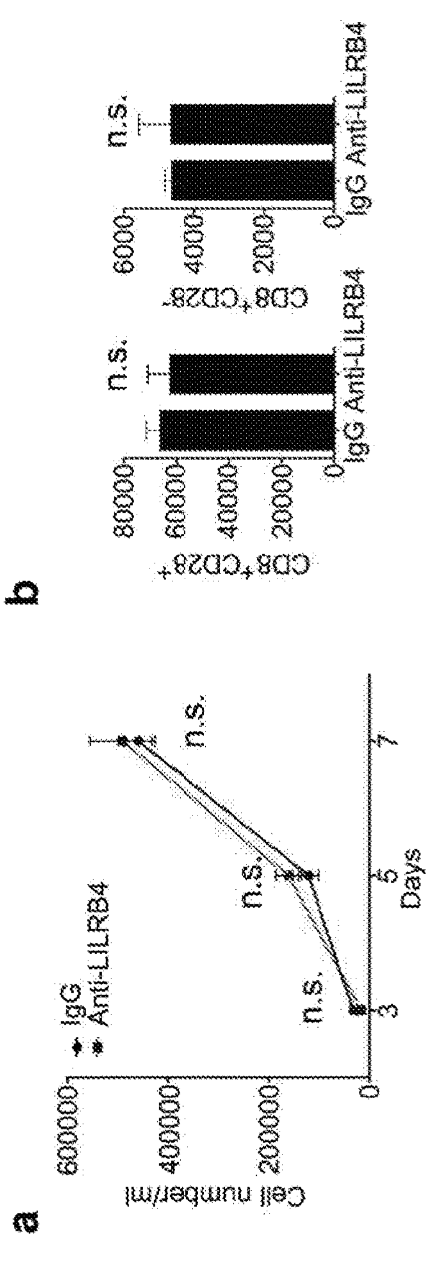
FIGS. 11*a*-11*b*-Anti-LILRB4 antibody had no effect on proliferation of THP-1 cells or cell activation or proliferation of T cells.

The inventors sought to determine if antagonizing LILRB4 could prevent AML development by reversing LILRB4-mediated immune inhibition. To identify potential agonists and antagonists of LILRBs, the inventors generated individual stable chimeric receptor reporter cells based on fusion of the extracellular domain (ECD) of individual LILRBs and their mouse orthologues PirB[27] and gp49B1[28], with the intracellular domain of paired immunoglobulin-like receptor β, which signals through the adaptor DAP-12 to activate NFAT promoter-driven GFP expression, as the inventors have described[2, 31]. With help from this system, the inventors generated novel anti-LILRB4 blocking antibodies to further assess LILRB4-mediated signaling (FIG. 10). Although anti-LILRB4 had no effect on cell activation or proliferation of T cells or THP-1 cells per se (FIG. 11), anti-LILRB4 antibody treatment blocked the LILRB4-mediated T cell suppression (FIGS. 7*g-h*). Furthermore, the treatment of this blocking antibody significantly decreased THP-1 cell number and increased CTL number and cytokine production by CTLs, in a co-culture of THP-1 cells and CTLs (FIGS. 7*i-m*). Together, these in vitro results indicate that LILRB4 expressed by AML cells inhibits T cell activity, and that anti-LILRB4 blocking antibody reverses this immune checkpoint function, making tumor cells susceptible to cytotoxic killing by T cells.

Figures 12A, 12B, 12C, 12D, 12E, 12F, 12G:
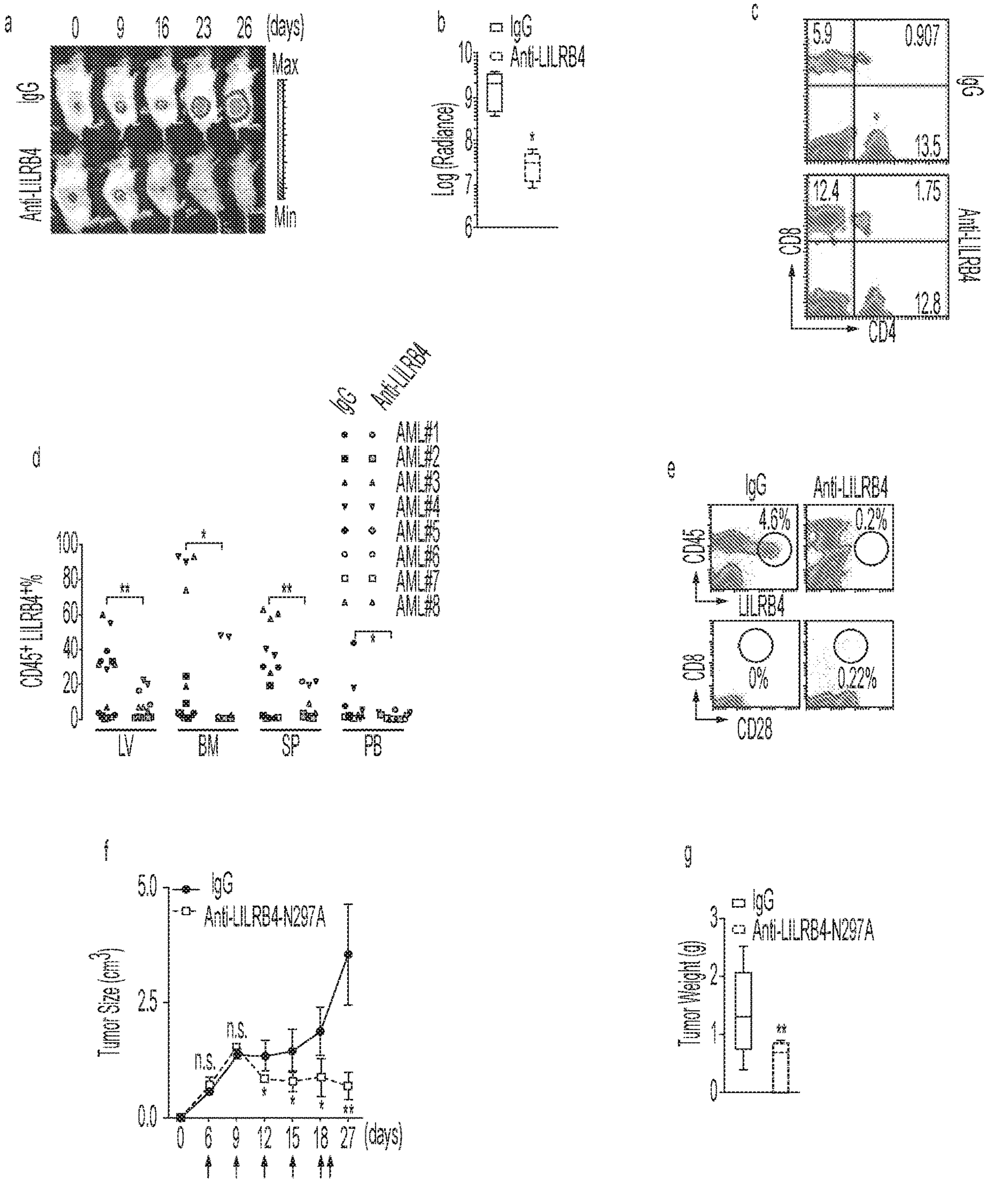
FIGS. 12*a*-12*n* LILRB4 expressed on leukemia cells suppresses T cell proliferation in vivo.
FIG. 12*b*: Luminescence flux was determined at day 26 after implantation of leukemia cells.
FIG. 12*c*: $CD8^+$ T cells were increased in anti-LILRB4-treated hPBMC-humanized NSG mice at day 26.
FIG. 12*d*: Percentage of human CD45+LILRB4+ cells detected by flow cytometry of cells harvested from the indicated organs from mice injected with primary monocytic AML cells obtained from different patients followed by injection of control mIgG or anti-LILRB4 antibody (C84). AML #1~8 were from patients #1402903, #1403615, #1403605, #1403986, #1500237, #1500245, #1500401, and #1502990 respectively as shown in Table 1.
FIG. 12*e*: Engraftment of primary human AML cells in NSG mouse bone marrow was examined by flow cytometry. CD45+LILRB4+ represents AML leukemia cells derived from a human patient; CD8+ CD28+ represents active tumor-killing T cells which were derived from the same human patient.
FIG. 12*f*: C57b1/6 mice were subcutaneously implanted with human LILRB4-expressing mouse AML C1498 cells ($3\times10^6$ cells/mouse). Anti-LILRB4-N297A antibodies or control IgG were intravascularly injected at 6, 9, 12, 15, 18 and 21 days post inoculation of tumor cells. Tumor size was monitored every 3 days. Tumor size was calculated by (width×width×length). n.s., not significant; *, $p<0.05$, , $p<0.01$.

The inventors tried to confirm the function of LILRB4 in immune checkpoint blockade in vivo using humanized mouse xenograft models and an immunocompetent mouse model. To generate the humanized mouse model, immune compromised NOD-SCID Il2rg-knockout (NSG) mice were sub-lethally irradiated and transplanted with human peripheral blood mononuclear cells (hPBMC), enabling analysis of human T cells function on tumor biology[32]. LILRB4 blockade by anti-LILRB4 inhibited tumor development from subcutaneously implanted THP-1 cells (FIG. 12*a-b*) and increased cytotoxic T cells in humanzied NSG mice (FIG. 12*c*). Importantly, the blockade of LILRB4 significantly reduced leukemia development in eight primary human monocytic AML-derived xenografts (FIG. 12*d*) and, meanwhile, increased allogeneic human CTL cells (FIG. 12*e*). These results confirm that anti-LILRB4 antibody reverses T cell immune suppression mediated by tumor cell-expressed LILRB4.

Figures 12H, 12I, 12J, 12K, 12L, 12M, 12N:
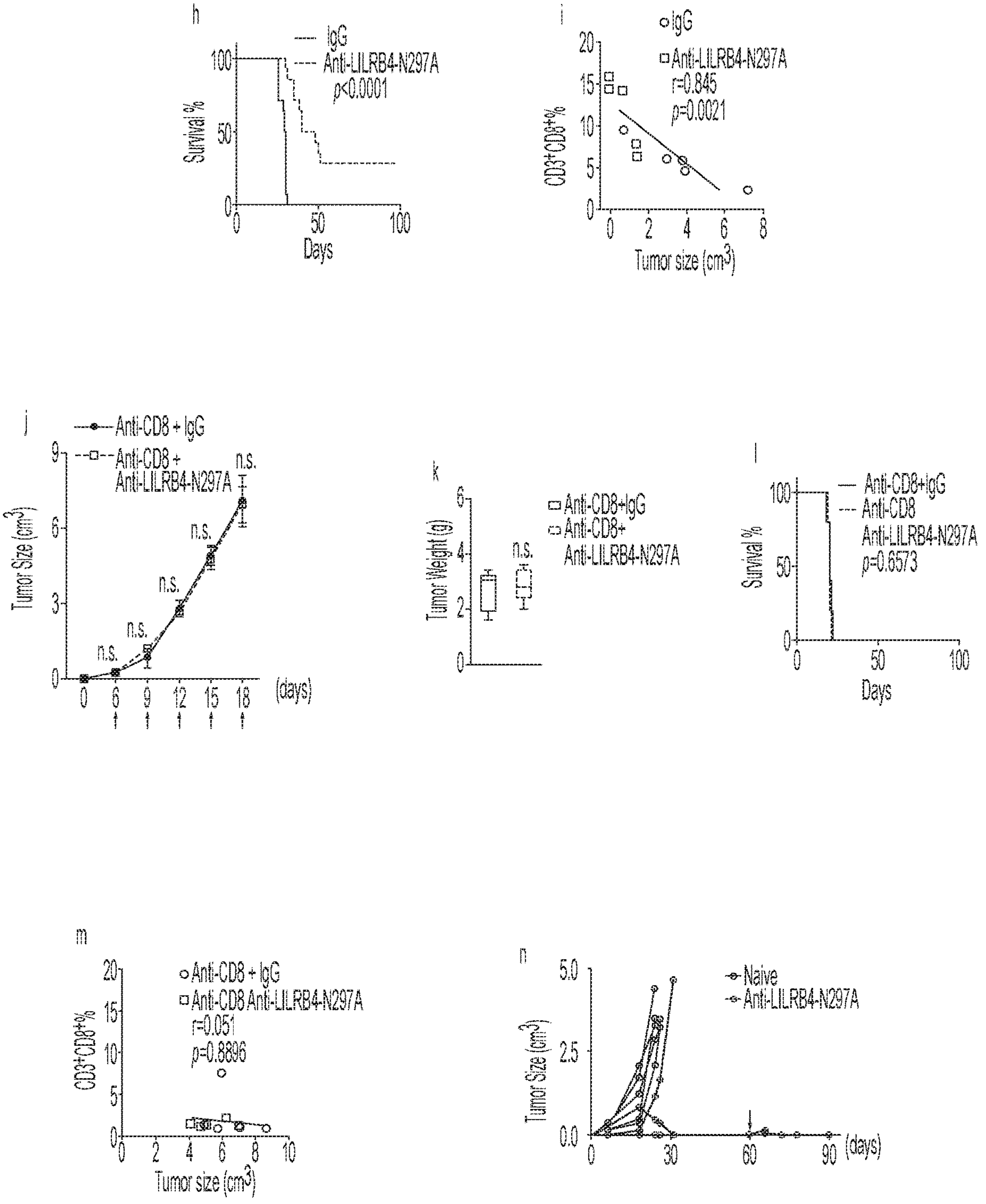
FIG. 12*h*: Mice treated with anti-LILRB4-N297A antibodies showed prolong mouse survival.
FIG. 12*i*: The percentages of $CD3^+CD8^+$ T cells in host spleen were determined by flow cytometry and were negatively correlated with tumor sizes.
FIG. 12*j*: C57b1/6 mice were subcutaneously implanted with human LILRB4-expressing mouse AML C1498 cells ($3\times10^6$ cells/mouse). All mice were treated with anti-CD8 antibodies at 3, 6, 9 and 12 days post inoculation of tumor cells. Anti-LILRB4-N297A antibodies or control IgG were intravascularly injected at 6, 9, 12, 15 and 18 days post inoculation of tumor cells. Tumor size was monitored every 3 days. Tumor size was calculated by (width×width×length). n.s., not significant.
FIG. 12*k*: Tumor weights were measured at 18 days post inoculation of tumor cells.
FIG. 12*m*: The percentage of $CD3^+CD8^+$ T cells in host spleen determined by flow cytometry was not correlated with tumor size.

To further validate the conclusion, the inventors subcutaneously implanted human LILRB4-expressing mouse C1498 AML cells (C1498-huLILRB4) into immune competent C57BL/6 mice. To exclude the anti-tumor effects from antibody-dependent cell-mediated cytotoxicity/phagocytosis or complement-dependent cytotoxicity (ADCC/ADCP/CDC), the inventors treated tumor-bearing mice with Fc glycosylation site mutated anti-LILRB4 antibody (anti-LILRB4-N297A) that is defective in ADCC/ADCP/CDC[33]. Compared with control IgG treatment, LILRB4 blockade was able to effectively lower tumor burdens (FIG. 12*f-h*) via an increase in effective-T cells (FIG. 12*i*). In contrast, depleting $CD8^+$ T cells eliminated the anti-tumor effects by the anti-LILRB4 antibody (FIG. 12*j-l*), suggesting that the tumor-supportive effect of LILRB4 depends on inhibition of T cells. To determine whether anti-LILRB4 antibody treatment generates memory T cells to prevent AML relapse, the inventors conducted adoptive transfer of spleen cells from anti-LILRB4 treated mice to normal recipient mice. Four out of five transplanted mice rejected the parent C1498 mouse leukemia cells and these mice also prevented the rechallenge by three times the numbers of leukemia cells (FIG. 12*n*). Together, these in vitro and in vivo results indicate that LILRB4 is a specific marker for monocytic AML, and LILRB4 signaling in tumor cells is required to suppress T cell-mediated anti-tumor immunity.

LILRB4 Supports Infiltration of Leukemia Cells.

Figure 13:
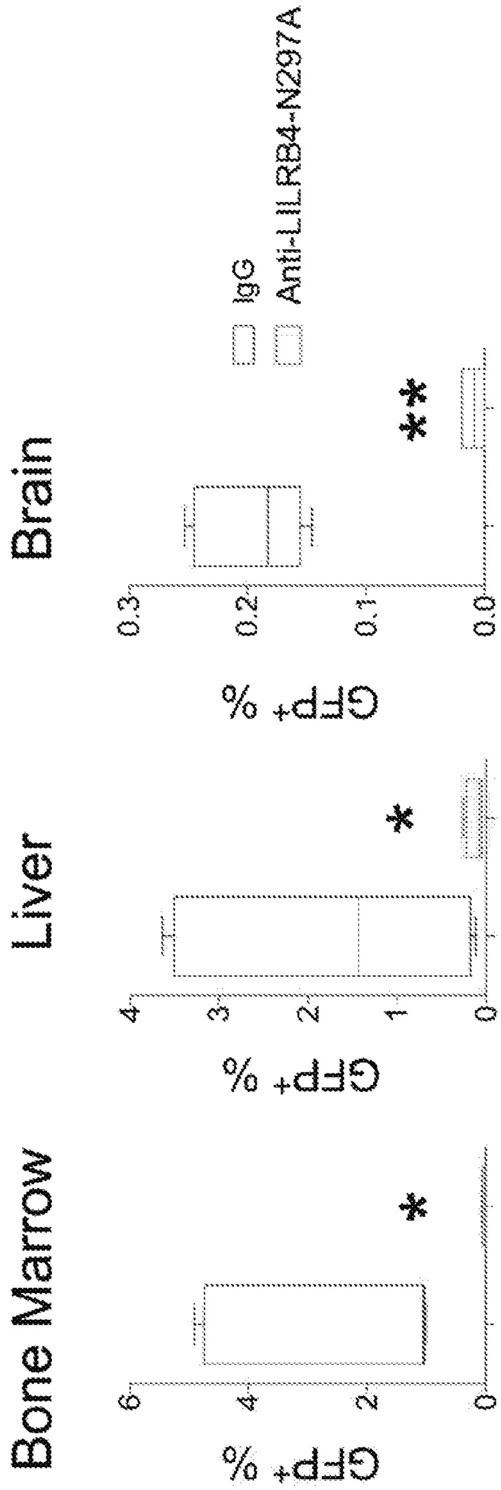
FIG. 13—Anti-LILRB4 antibodies reduce the percentage of GFP+ leukemia cells present in host tissues. C57b1/6 mice were subcutaneously implanted with human LILRb4-expressing mouse AML C1498 cells ($3\times10^6$ cells/mouse) that express GFP. Anti-LILRB4-N297A antibodies or control IgG were intravascularly injected at 6, 9, 12, 15, 18 and 21 days post inoculation of tumor cells. Anti-LILRB4 antibodies but not control IgG reduced the percentage of GFP+ leukemia cells present in host bone marrow, liver and brain as determined by flow cytometry. *, $p<0.05$, **, $p<0.01$.
Figures 14A, 14O:
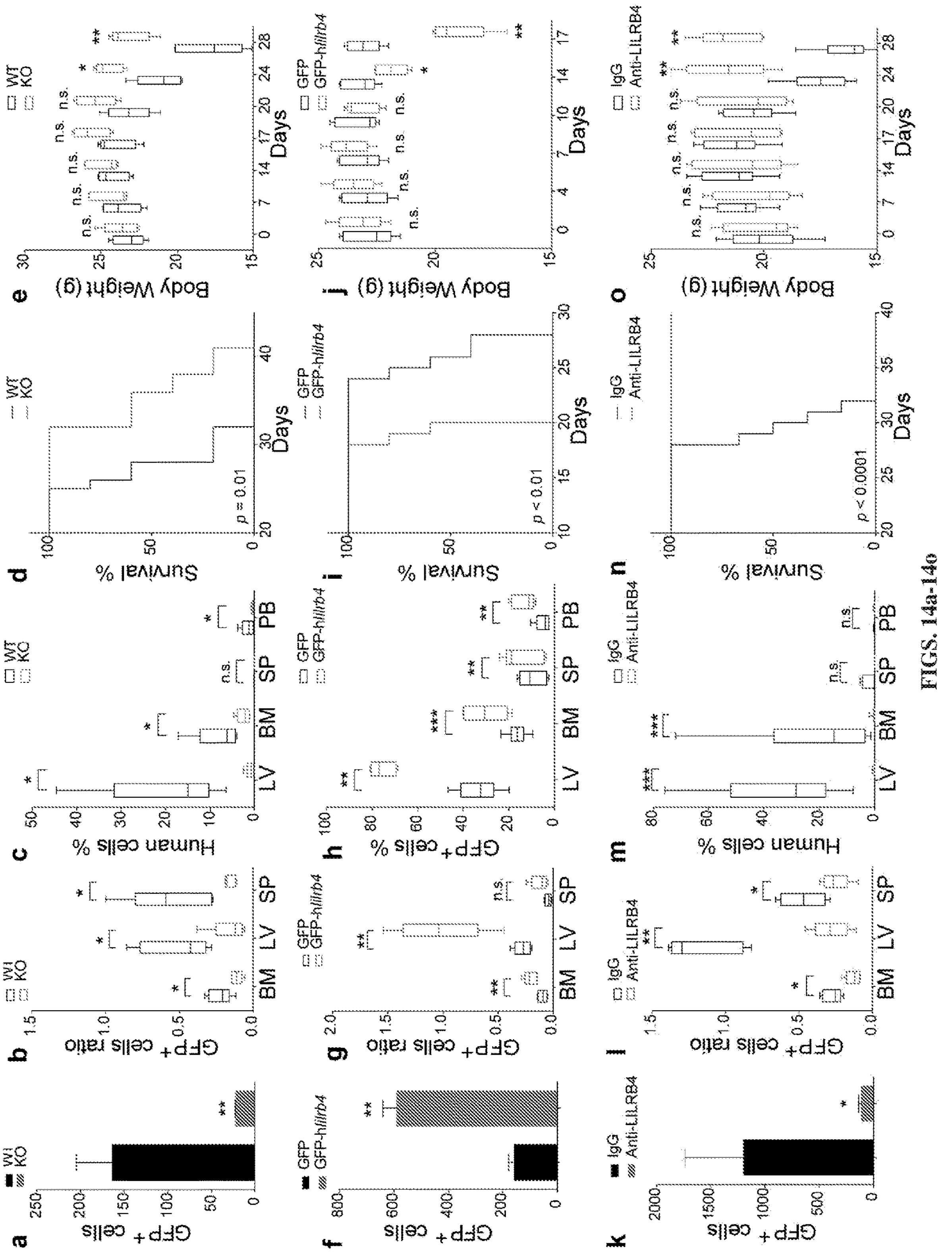
Figures 16A, 16B:
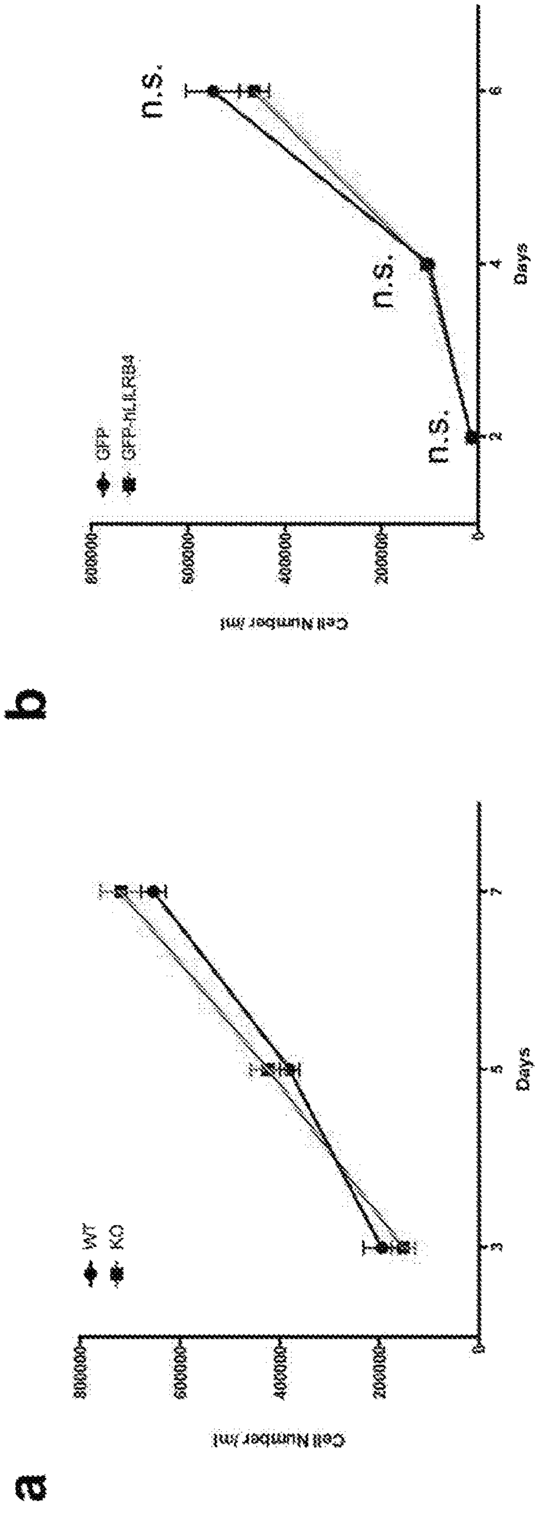
FIGS. 16*a*-16*b*—Modulation of LILRB4 expression doesn't affect proliferation of AML cells.

One of the characteristic feature of monocytic AML is enhanced extramedullary infiltration of tumor cells. The inventors observed that the antibody blockade of LILRB4 results in significant decrease of leukemic infiltration into internal organs, including bone marrow, liver, and brain (FIG. 13). The inventors hypothesized that, in addition to T cell inhibition, LILRB4 can promote leukemia infiltration for immune evasion. To test this hypothesis, they performed trans-endothelial migration and homing assays and monitored leukemia infiltration relative to LILRB4 expression. LILRB4 KO in human AML THP-1 cells decreased trans-endothelial migration in vitro (FIG. 14*a*), reduced short-term (20 hours) homing to liver and bone marrow (FIG. 14*b*), lowered long-term (21 days) engraftment to hematopoietic organs (FIG. 14*c*), prolonged survival of xenografted mice (FIG. 14*d*), and delayed the body weight loss (FIG. 14*e*). In contrast, forced expression of human LILRB4 in mouse AML C1498 or WEHI-3 cells had the opposite effects (FIGS. 14*f-j* and FIG. 15). Of note, KO or ectopic expression of LILRB4 did not significantly affect leukemia growth in vitro and in vivo (FIG. 16). Because NSG mice are defective of functional T cells, these results, especially those from the xenograft experiments, reveal a distinct role of LILRB4 in AML—to promote migration and leukemia infiltration. This is consistent with previous studies showing that the frequency of circulating $LILRB4^+$ AML blasts is significantly lower than that of the $LILRB4^-$ AML blasts[26] and $LILRB4^+$ chronic lymphocytic leukemia cells more commonly associate with lymphoid tissue involvement[12].

Figure 17:
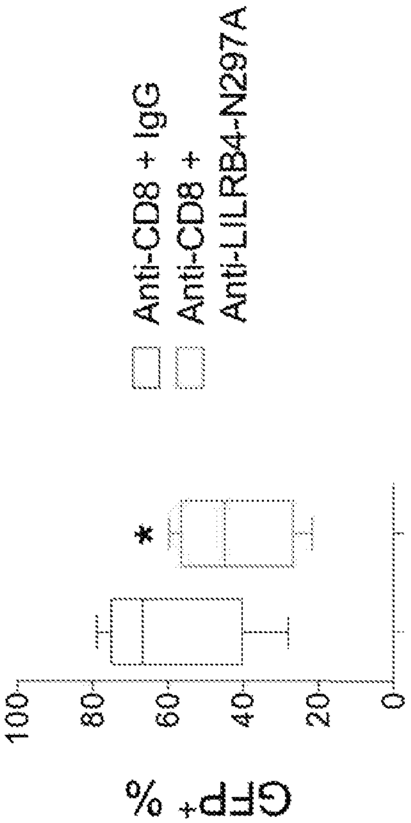
FIG. 17—Anti-LILRB4 antibody decreased leukemia cell infiltration in liver. C57b1/6 mice were subcutaneously implanted with human LILRB4-expressing mouse AML C1498 cells ($3\times10^6$ cells/mouse) that express GFP. All mice were treated with anti-CD8 antibodies at 3, 6, 9 and 12 days post inoculation of tumor cells. Anti-LILRB4-N297A antibodies or control IgG were intravascularly injected at 6, 9, 12, 15 and 18 days post inoculation of tumor cells. Anti-LILRB4 antibodies but not control IgG reduced the percentage of GFP+ leukemia cells in host liver as determined by flow cytometry. *, $p<0.05$.
Figure 18:
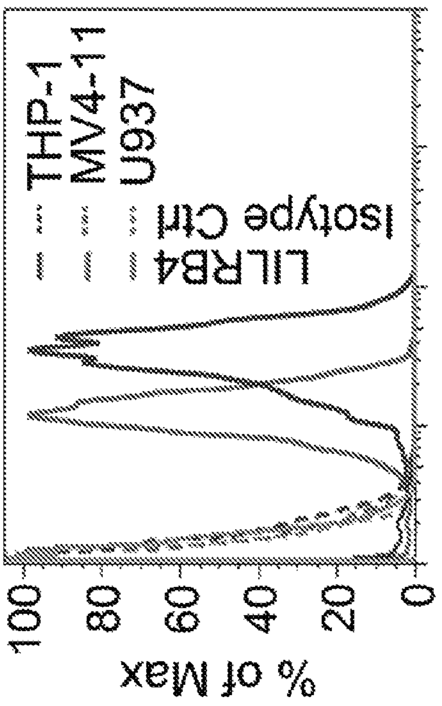
FIG. 18—LILRB4 expression on the indicated immortalized human AML cells as determined by flow cytometry. Isotype IgG was used as control.
Figure 19:
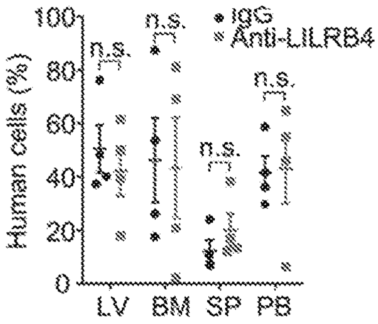
FIG. 19—Anti-LILRB4 antibodies do not act on LILRB4-negative cancer cells. NSG mice were injected with LILRB4-human AML U937 cells and then treated with anti-LILRB4 antibodies. IgG served as a control antibody. Mice were sacrificed at day 25 post-transplant for analysis of liver (LV), bone marrow (BM), spleen (SP), and peripheral blood (PB) by flow cytometry. The presence of human AML cells was detected by anti-human CD45 antibody staining. n.s., not significant.
Figures 20A, 20B, 20C, 20D:
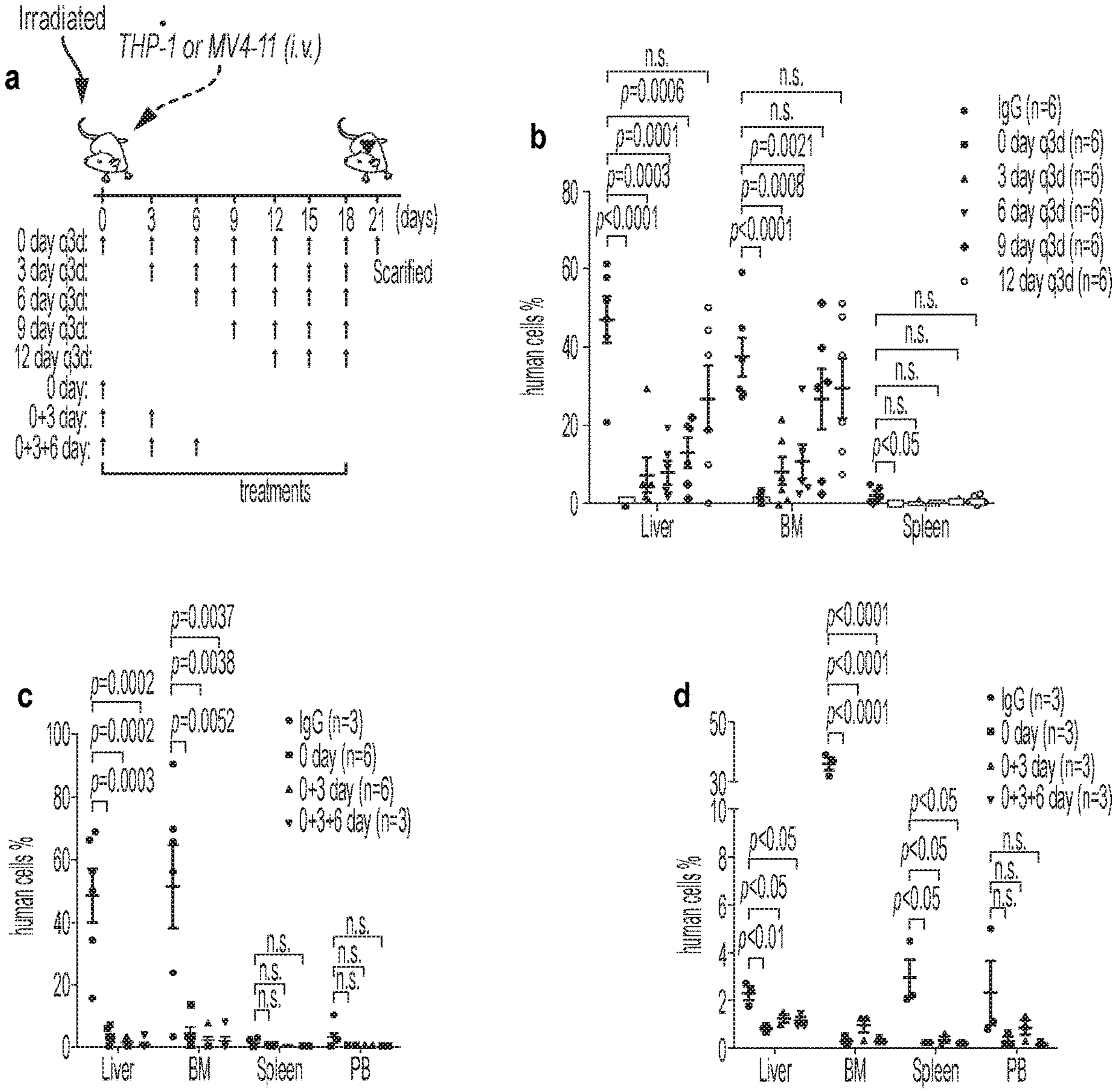
FIGS. 20*a*-20*b*—Anti-LILRB4 antibodies suppress human AML xenograft.
(FIGS. 20*c*-20*d*) Antibodies were administered at day 0, day 0+day 3, day 0+day 3+day 6, all similarly blocked AML development initiated by transplanted THP-1 cells (FIG. 20*c*) and MV4-11 cells (FIG. 20*d*).
Figure 21:
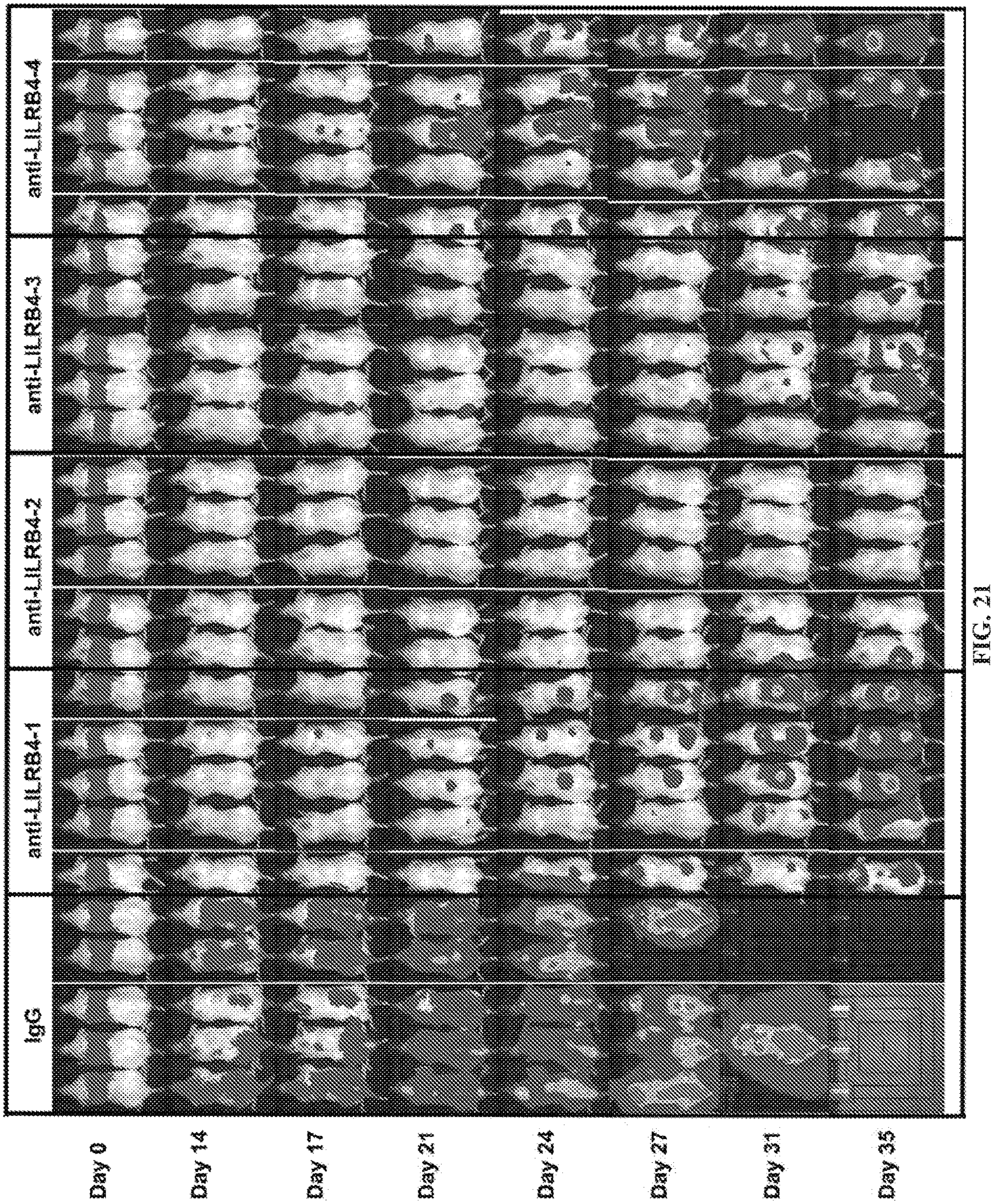
FIG. 21—Anti-LILRB4 antibodies suppress human AML xenograft. 20 μg of each antibody were administered at day 0 as indicated. THP-1 leukemia development monitored by whole animal bioluminescence imaging.
Figure 22:
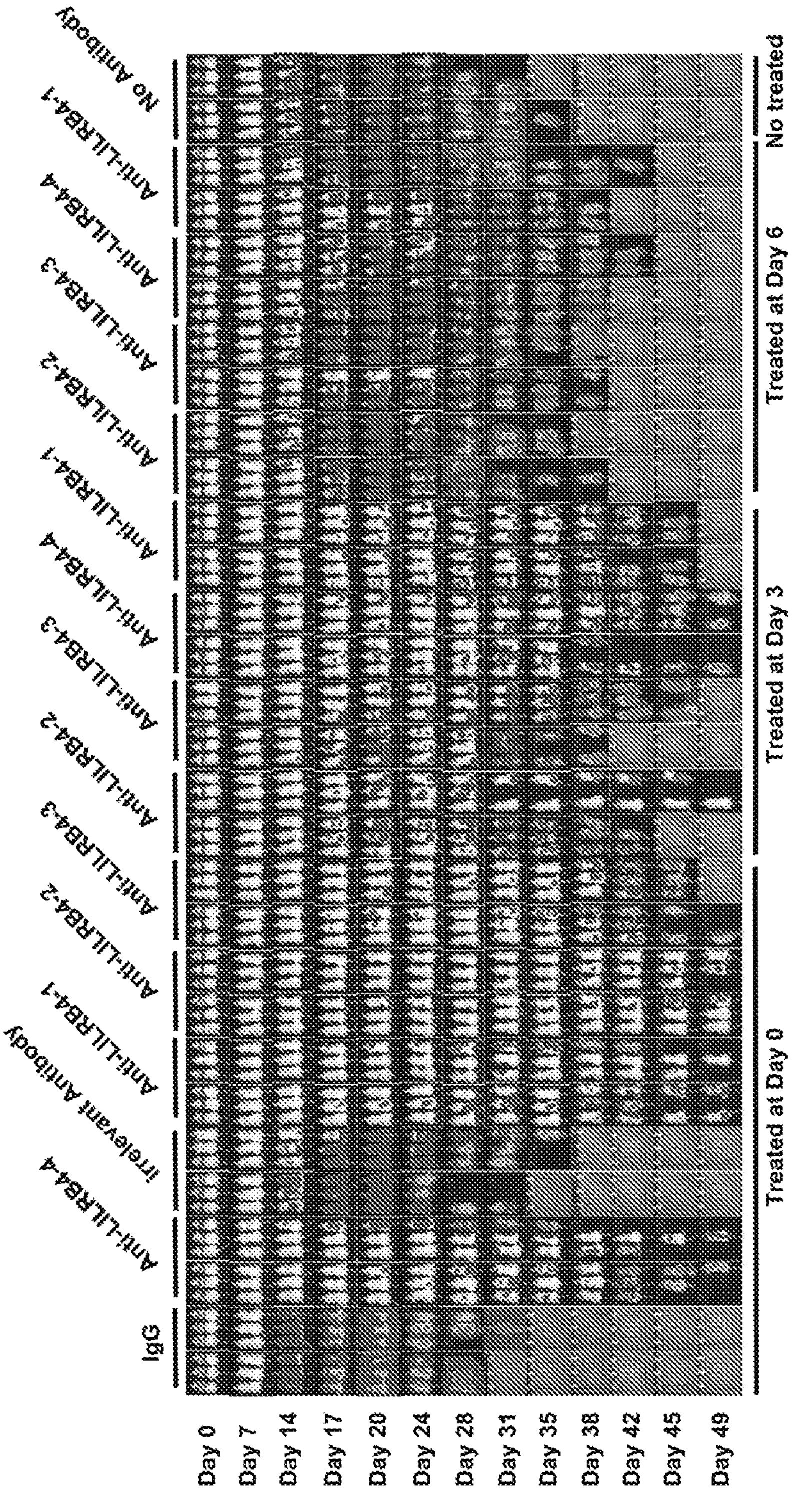
FIG. 22—Anti-LILRB4 antibodies suppress human AML xenograft. 200 μg of each antibody were administered at day 0, day 3 or day 6 as indicated. THP-1 leukemia development monitored by whole animal bioluminescence imaging.
Figures 23A, 23B, 23C:
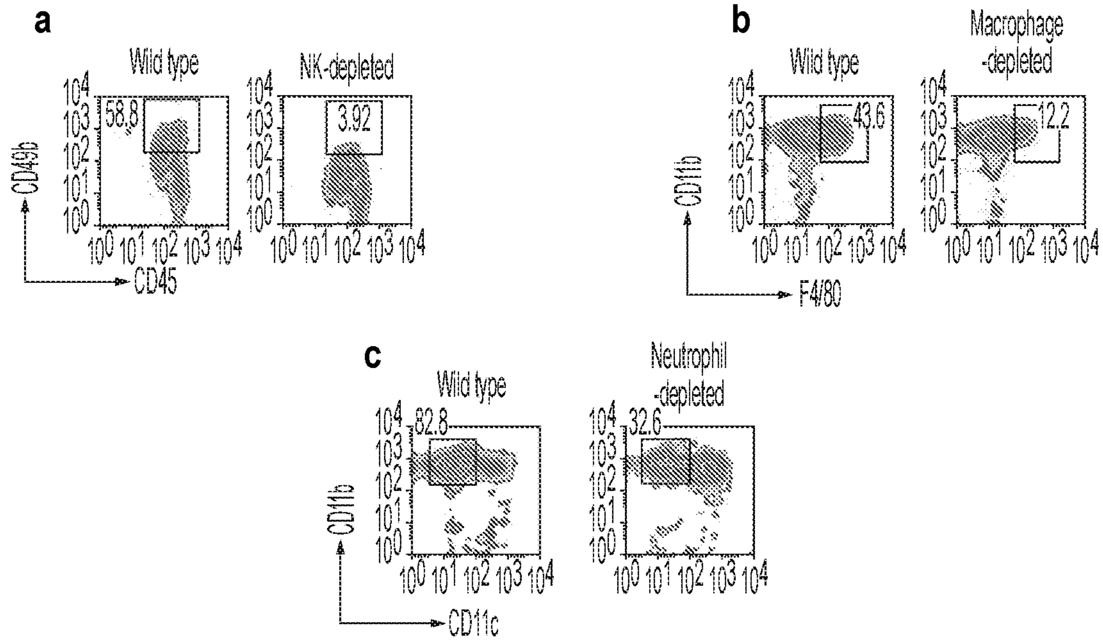
FIGS. 23*a-c*—Representative flow cytometry plots demonstrating successful reduction in (FIG. 23*a*) NK cell (CD45+CD49b+), (FIG. 23*b*) macrophage (CD11b+F4/80+), and (FIG. 23*c*) neutrophil (CD11b+CD11c−) frequency in NSG mice depleted of the respective immune cell subtype as compared to non-depleted (wild-type) NSG mice.

Although anti-LILRB4 antibody treatment did not reduce the size of subcutaneous C1498 tumor when CD8 T cells were depleted in C57b1/6 mice (FIG. 12*h*), treatment with anti-LILRB4 antibody did lead to decreased leukemia cell infiltration in liver (FIG. 17). To further investigate whether LILRB4 regulates cell migration/infiltration, the inventors treated LILRB4-positive (THP-1 and MV4-11) and LILRB4-negative (U937) human AML cells (FIG. 18) with anti-LILRB4 antibodies in in vitro transwell and in vivo homing assays and a xenograft model. The inventors found that antibody-mediated LILRB4 blockade had the same effect as LILRB4 KO for LILRB4-expressing MV4-11 and THP-1 AML cells (FIGS. 14*k-t*) but had no effect on U937 cells that do not express LILRB4 (FIG. 19). Importantly, whole animal and ex vivo bioluminescence imaging showed anti-LILRB4 antibody significantly blocked leukemia infiltration into lung, liver, bone marrow, brain, kidney, spleen and gastrointestinal tract (FIGS. 14*u-v*, FIG. 20, FIG. 21 and FIG. 22). To exclude the possibility that the observed migration-inhibitory effects may result from antibody-mediated effects by innate immune cells present in NSG mice, the inventors administered the glycosylation-deficient anti-LILRB4 antibody (anti-LILRB4-N297A) to NK cell-, macrophage-, and neutrophil-depleted NSG recipients that were transplanted with MV4-11 cells (FIGS. 23*a-c*). Anti-LILRB4-N297A antibody treatment significantly inhibited AML infiltration compared to isotype control in each of the innate immune cell-depleted conditions (FIGS. 14*w-z*).

Figures 14D, 14P:
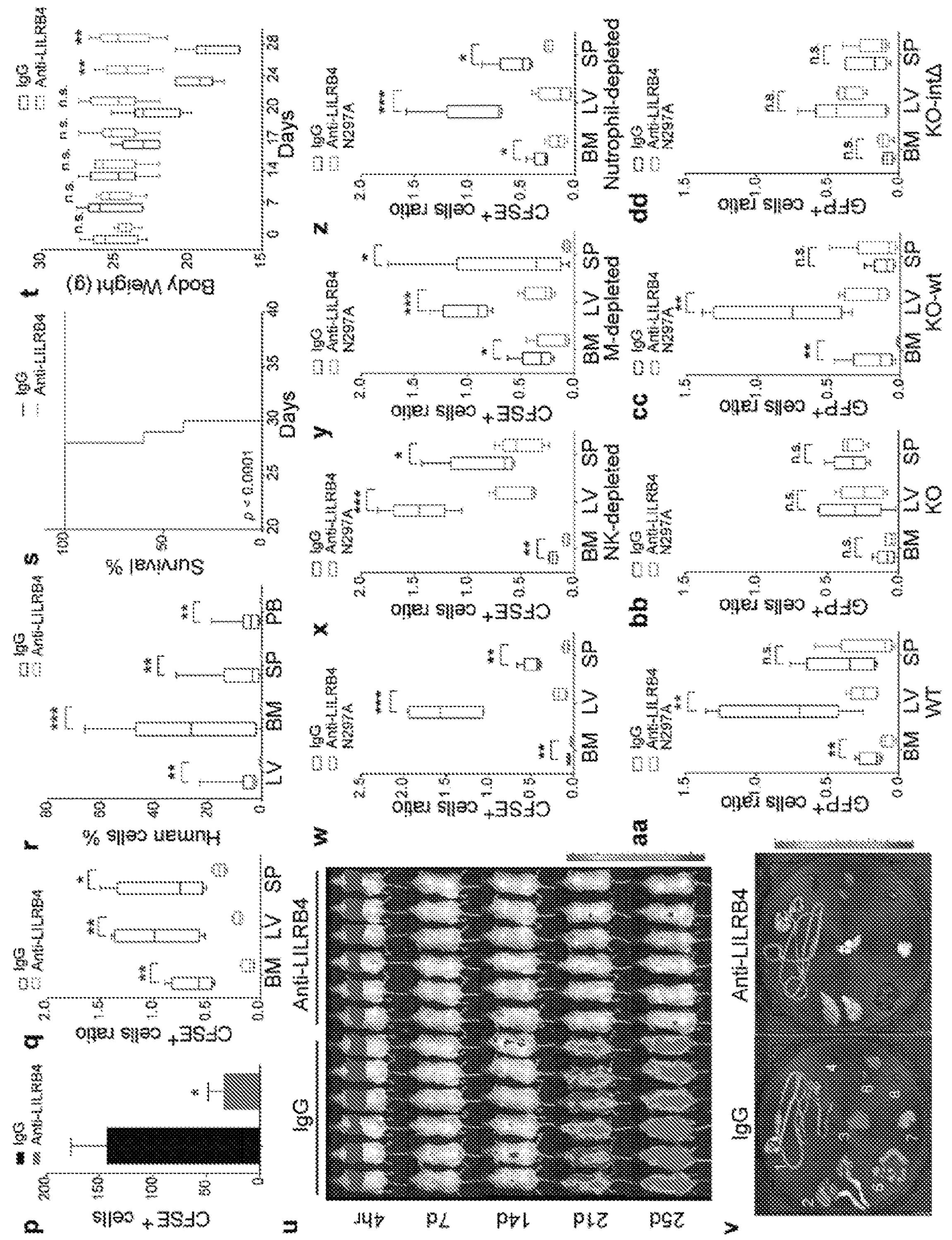
Figure 15:
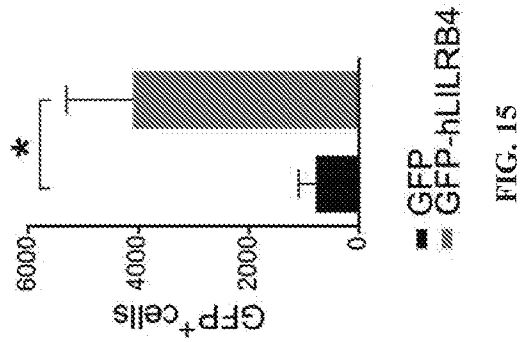
FIG. 15—Forced expression of human LILRB4 promotes transmigration of mouse AML WEHI-3 cells. *, $p<0.05$.

To determine whether LILRB4 intracellular signaling is required for leukemia cell migration, the inventors studied homing of THP-1 cells with wild-type (WT) or knockout (KO) of lilrb4 gene, and KO THP-1 cells rescued with wild-type lilrb4 expression (KO-wt) or with intracellular domain-deleted mutant lilrb4 expression (KO-intΔ). They further tested the effects of anti-LILRB4 antibody. The inventors found that anti-LILRB4 antibodies decreased the abilities of wild-type THP-1 and LILRB4 KO THP-1 cells that were reintroduced WT LILRB4 (KO-WT) homing to liver and bone marrow to the same level as LILRB4 KO or the KO THP-1 cells that were reintroduced the mutant LILRB4 lacking the intracellular domain (KO-intΔ) (FIG. 14*aa*, FIG. 14*cc*). In contrast, antibody treatment had no effect on the homing ability of LILRB4 KO THP-1 cells or KO-intΔ cells (FIG. 14*bb*, FIG. 14*dd*). Together, these results indicate that LILRB4 promotes migration of AML cells into internal organs including immune privileged sites and supports AML development.

APOE Activates LILRB4 to Support AML Infiltration.

Figure 24:
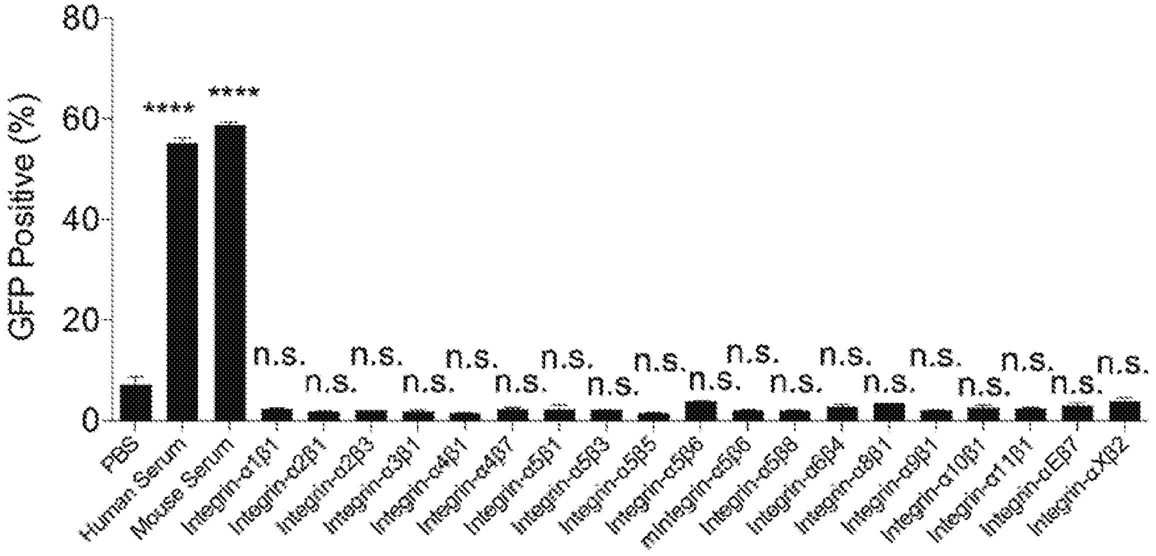
FIG. 24—Human and mouse integrin heterodimer proteins cannot activate LILRB4 reporter. Human and mouse serum were used as positive controls. n.s., not significant. ****, $p<0.0001$.

Anti-LILRB4 antibody blockade that efficiently suppresses immune inhibitory and migration functions of acute monocytic leukemia cells suggests that the function of LILRB4 on leukemia cell surface may be ligand dependent. The inventors sought to identify the extracellular binding protein(s) for LILRB4. Intergrin-$\alpha_v\beta_3$, was previously identified as the ligand for gp49B1, a mouse LILRB4 orthologue[34]. However, a variety of intergrin-αβ complexes did not activate human LILRB4 reporter cells (FIG. 24).

Figures 25A, 25B, 25C, 25D, 25E, 25F:
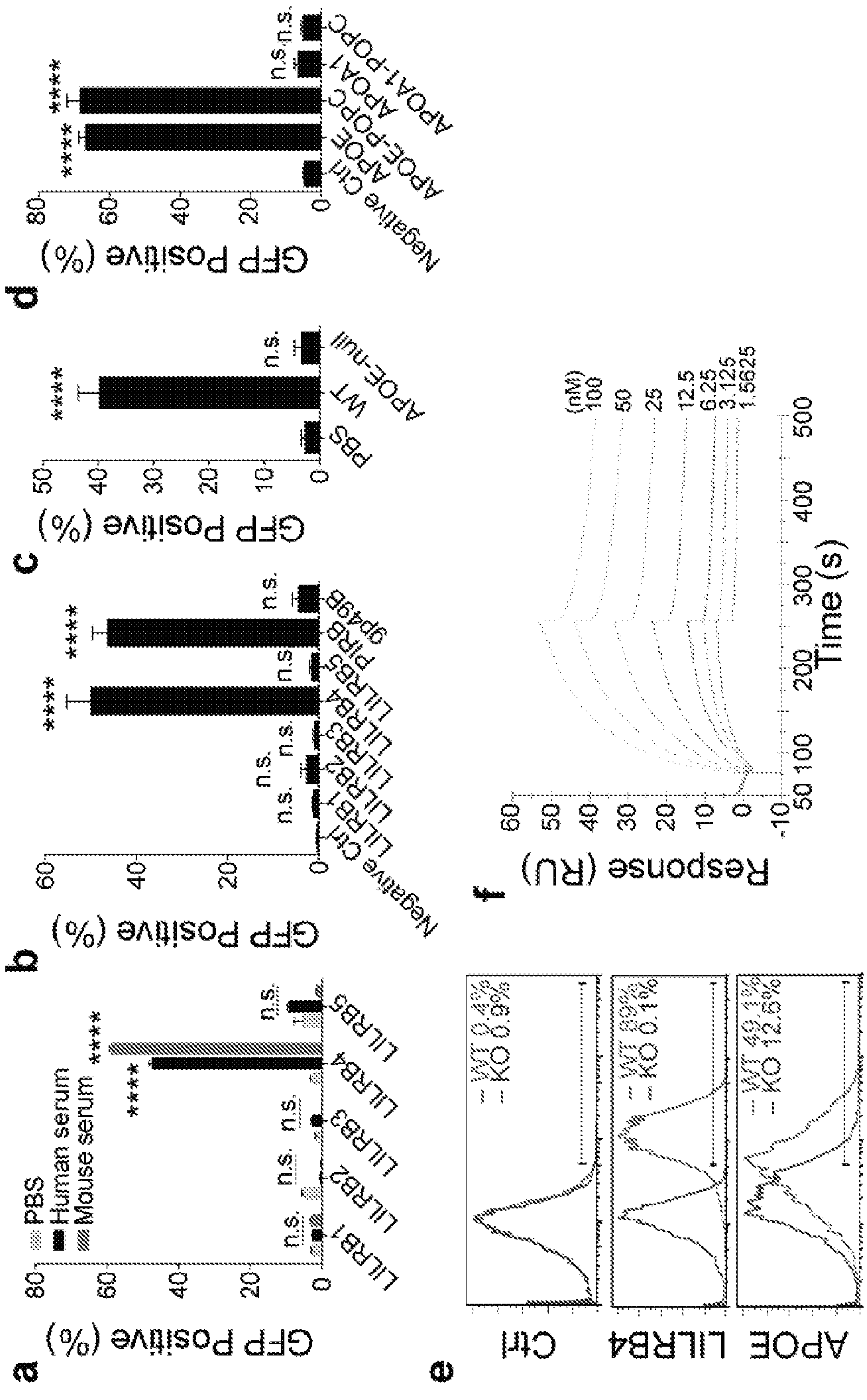
Figures 26A, 26B, 26C:
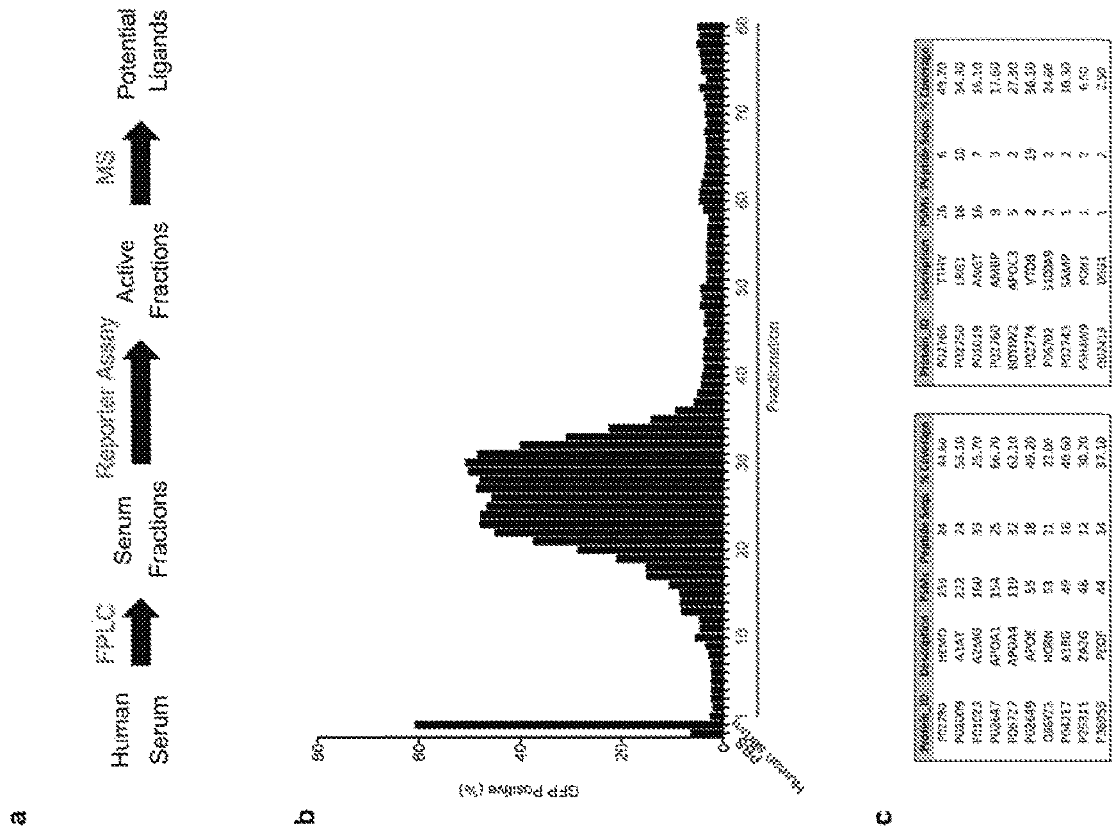
FIGS. 26*a*-26*c*—Identification of potential ligands of LILRB4 in human serum.
Figure 27:
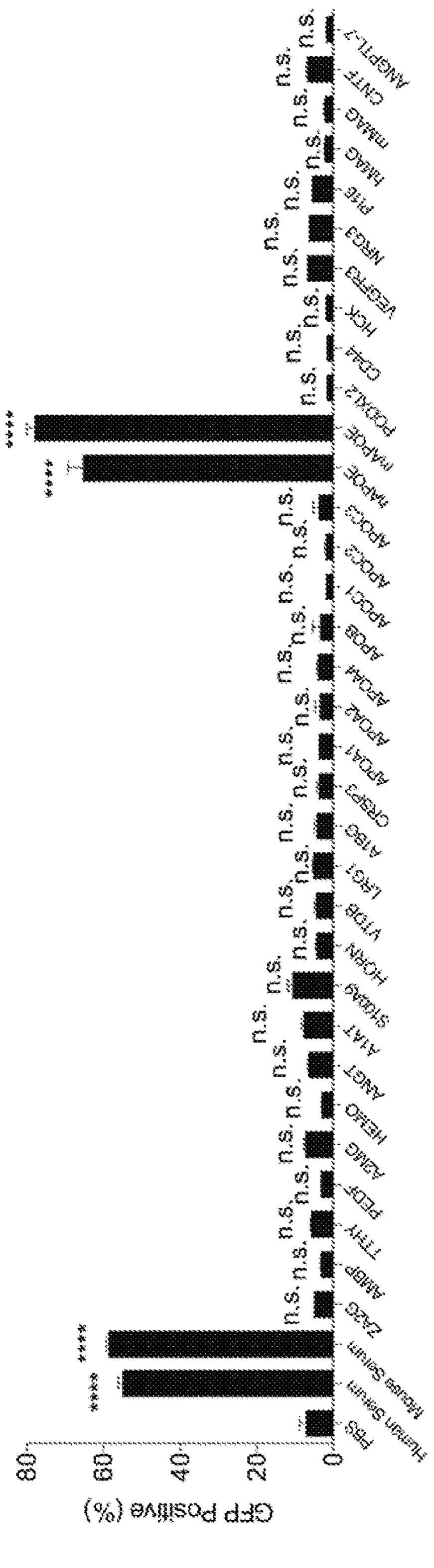
FIG. 27—Both Human and mouse APOE proteins can activate LILRB4 reporter. Human and mouse serum were used as positive controls. n.s., not significant. ****, $p<0.0001$.
Figures 28A, 28B:
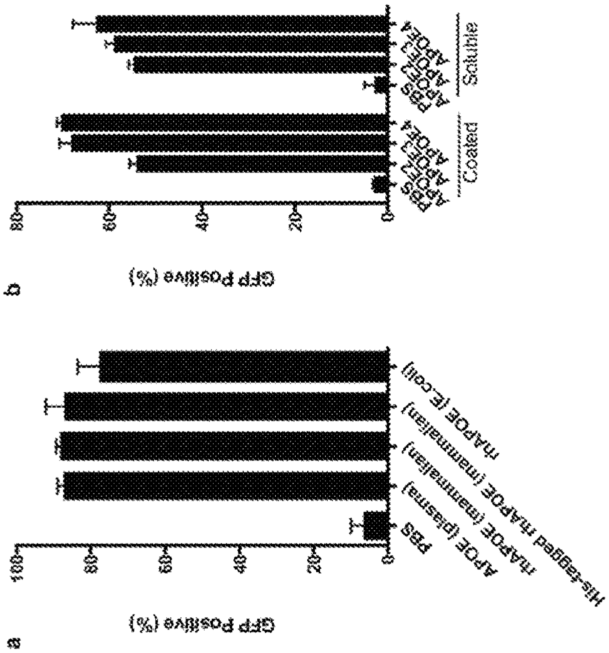
FIGS. 28*a*-28*b*—APOE proteins from different sources all activate LILRB4.

Surprisingly, the inventors found that human serum and mouse serum were capable of specifically stimulating the reporter for LILRB4 reporter but not other LILRBs (FIG. 25*a*). Through fast protein liquid chromatography (FPLC) fractionation followed by reporter assays and mass spectrometry (FIG. 26), they identified human and mouse APOE specifically activated LILRB4 reporter (FIG. 25*b* and FIG. 27). Purified APOE from different sources all activated LILRB4 (FIG. 28*a*). All three isoforms of human APOE activated LILRB4 in both immobilized and soluble conditions (FIG. 28*b*). Interestingly, recombinant APOE specifically activated the mouse PirB, but not gp49B1 (FIG. 25*b*) that is considered to be the mouse orthologue of LILRB4[28]. The serum from wild-type but not APOE-null mice activated the LILRB4 reporter (FIG. 25*c*). In addition, liposome-reconstituted APOE protein (APOE-POPC) had the same ability as lipid-free APOE protein in activation of LILRB4 reporter cells (FIG. 25*d*). The binding of APOE to THP-1 cells was significantly decreased by LILRB4 KO (FIG. 25*e*).

Figures 25G, 25H, 25I, 25J, 25K, 25L:
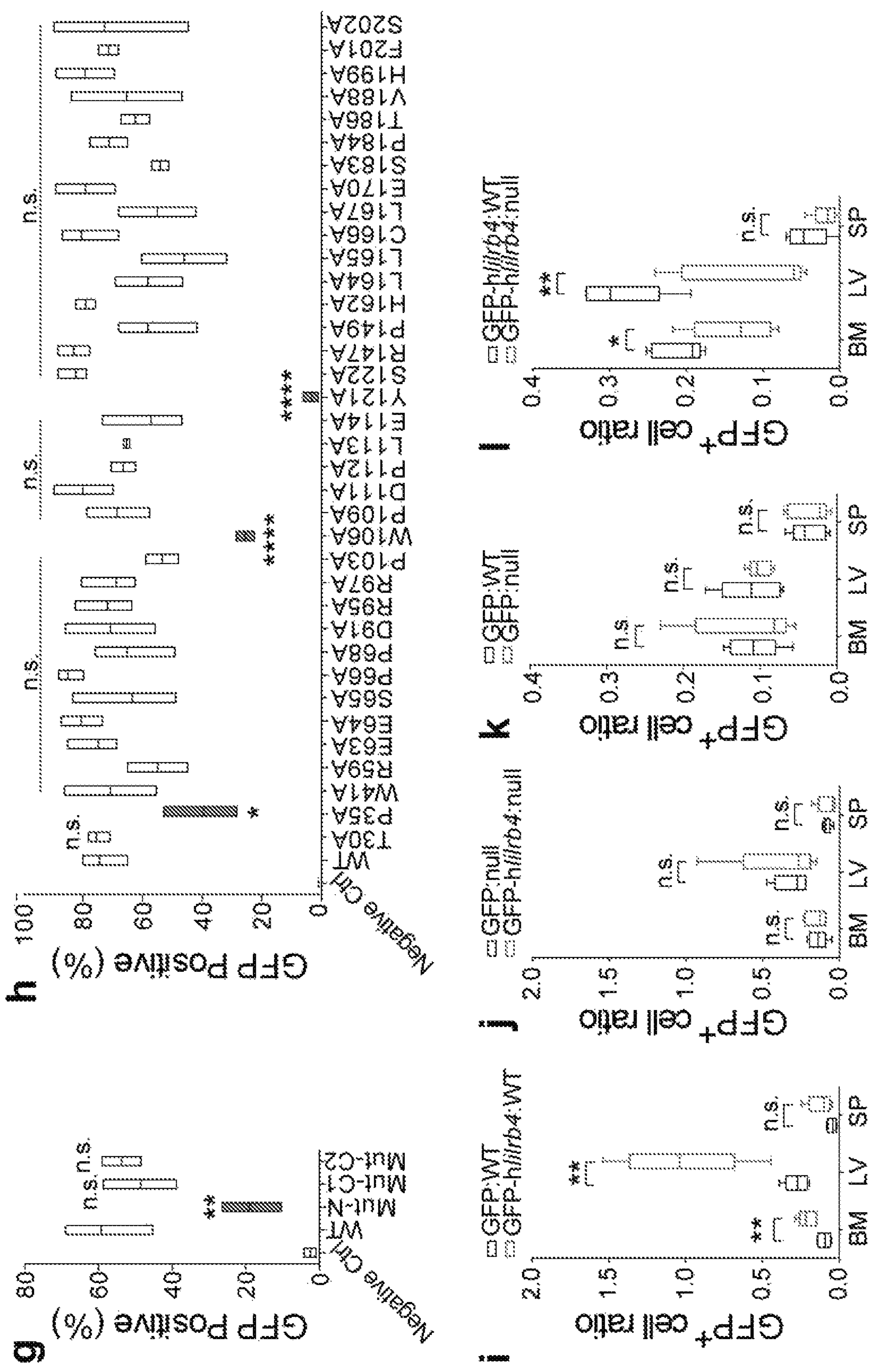
FIG. 25*g*: The activation of LILRB4 by APOE was reduced by mutation at N-terminal of APOE.
FIG. 25*h*: The activation of LILRB4 by APOE was reduced by the indicated single amino acid mutation of LILRB4.
FIG. 25*i*-FIG. 25*l*: APOE is necessary for LILRB4-mediated homing. Forced expression of human lilrb4 on mouse leukemia C1498 cells increases leukemia cell homing in wildtype (WT) recipient mice (n=5) (shown in FIG. 25*i*). However, forced lilrb4 expression doesn't increase homing in APOE-null (KO) recipient mice (n=5) (shown in FIG. 25*j*). Human lilrb4-expressing C1498 cells (1), but not control GFP-expressing C1498 cells (FIG. 25*k*), were less capable of homing in APOE-null (KO) mice (n=5) than in WT mice (n=5); Mice were sacrificed at 20 hrs after injection of leukemia cells. GFP was used to detect leukemia cells by flow cytometry.
Figures 29A, 29B, 29C, 29D, 29E, 29F, 29G:
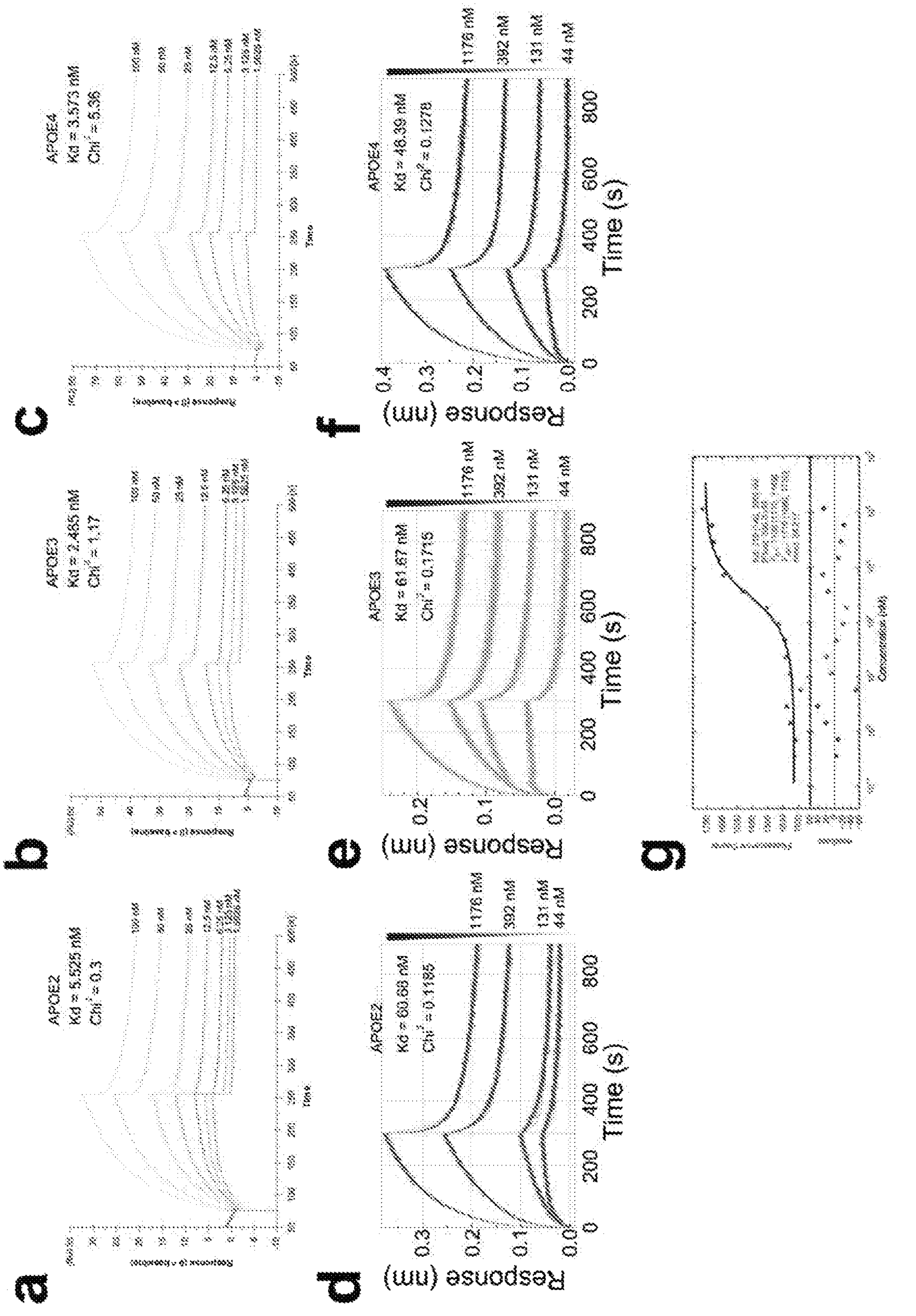
FIGS. 29*a*-29*g*—Three APOE isoforms bind to human LILRB4.

The inventors confirmed the specific binding of recombinant APOE to LILRB4 using surface plasmon resonance (SPR), bio-layer interferometry (Octet) and microscale thermophoresis (MST), with a dissociation constant of 2 nM as determined by SPR (FIG. 25*f* and FIG. 29). APOE contains two functional domains, the N-terminal domain that contains its receptor LDLR binding site (residues 136-150), and a C-terminal domain (residues 222-299). To determine which domain of APOE is required for binding to LILRB4, the inventors generated a N-terminal mutant (Mut-N: R142A/K143A/R145A/K146A/R147A/R150A) and two C-terminal mutants (Mut-C1: deletion of residues 245-299; and Mut-C2: deletion of residues 279-299) of human APOE. The N-terminal mutant significantly reduced the LILRB4 activation (FIG. 25*g*). The inventors further designed a series of site-specific mutations in amino acids potentially critical to the binding of ligand to LILRB4 based on the molecular modelling of LILRB4 to APOE (FIG. 30). They found that P35 and W106 in the first Ig-domain and Y121 in the linker region between two Ig-domains are critical for APOE activation of the LILRB4 reporter (FIG. 25*h*). APOE activation of the immune inhibitory receptor LILRB4 is in line with the well-documented immune-suppressive function of APOE[35, 36].

To further determine whether ApoE regulates LILRB4 function, the inventors compared the homing of mouse C1498 AML cells with and without ectopic-expressing LILRB4 in wild-type and apoe-knockout mice. Expression of LILRB4 significantly increased C1498 cell homing to bone marrow and liver in wild-type mice, but not in APOE-null recipients (FIGS. 25*i*-*l*). Together, APOE binds and activates LILRB4 to support migration of human acute monocytic leukemia cells.

LILRB4 Supports AML Infiltration and T Cell Inhibition Through Downstream Effectors in AML Cells.

Figures 31A, 31B:
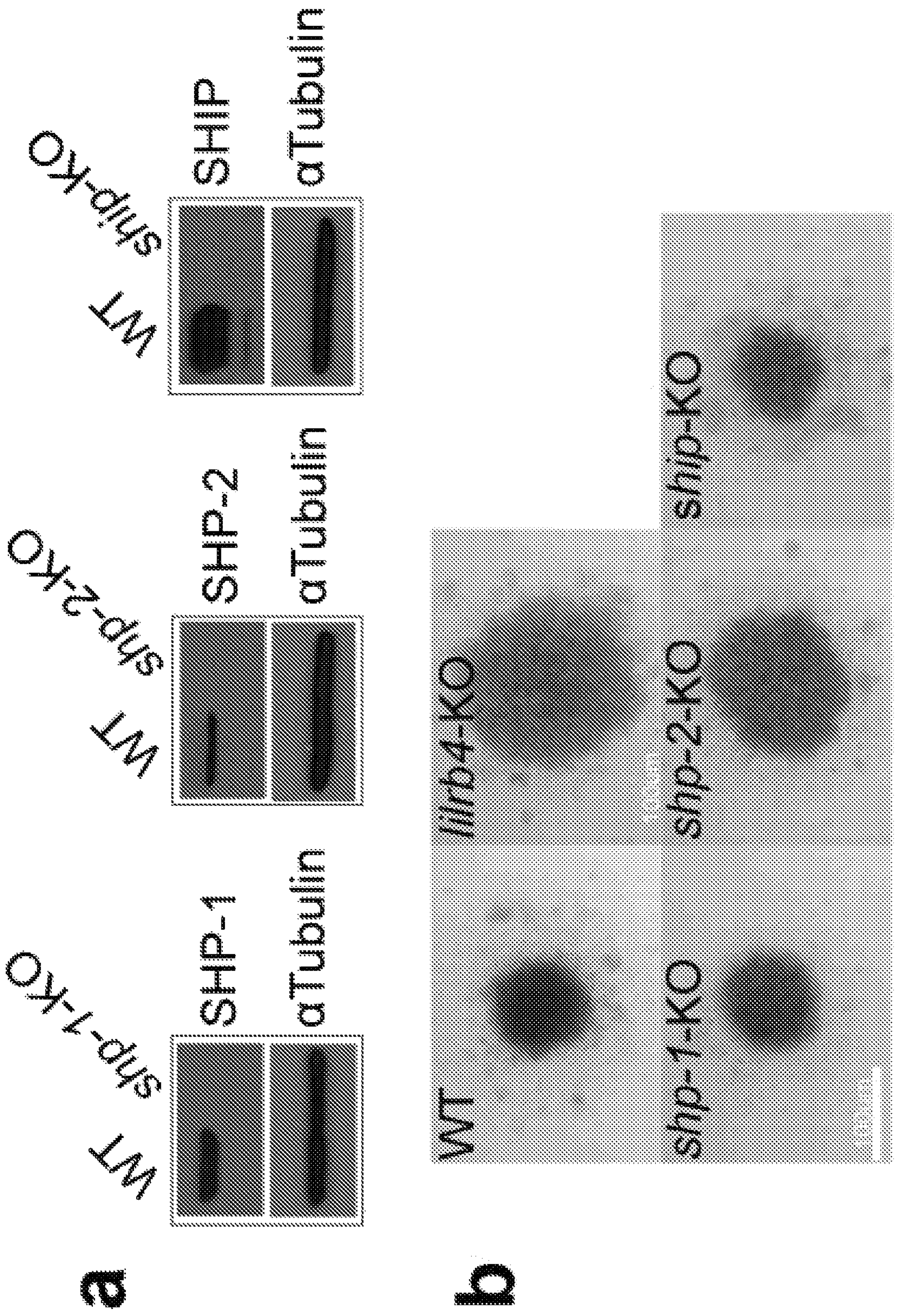
Figures 31C, 31D, 31E:
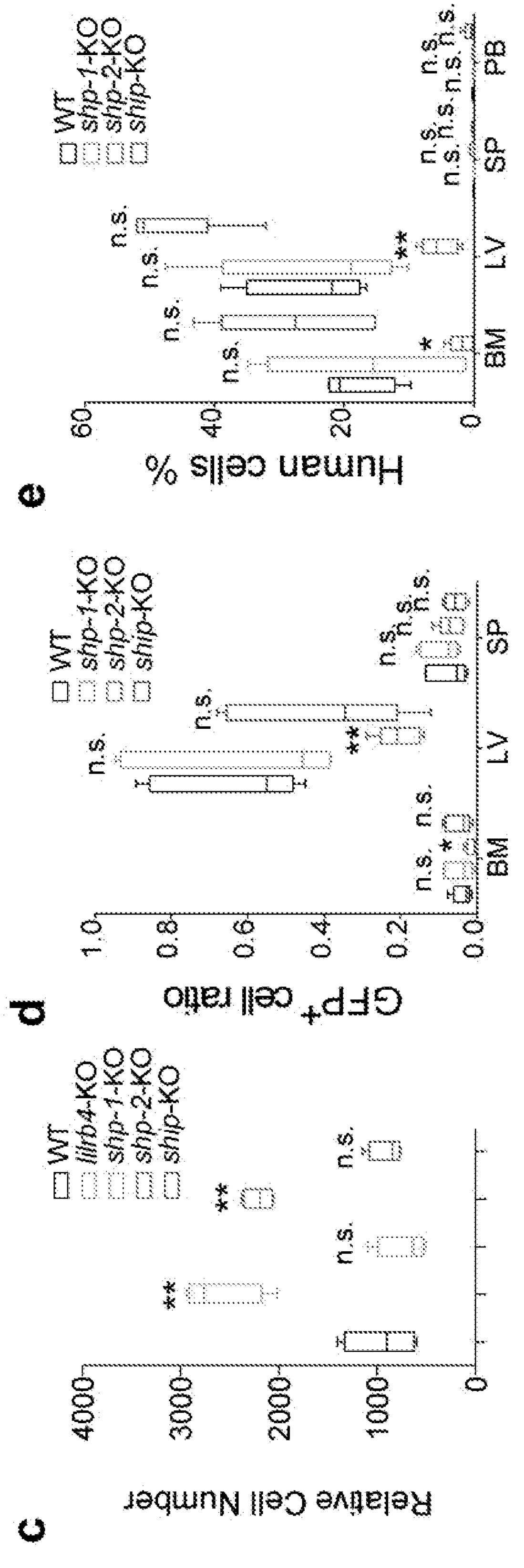
Figures 31F, 31G, 31H, 31I:
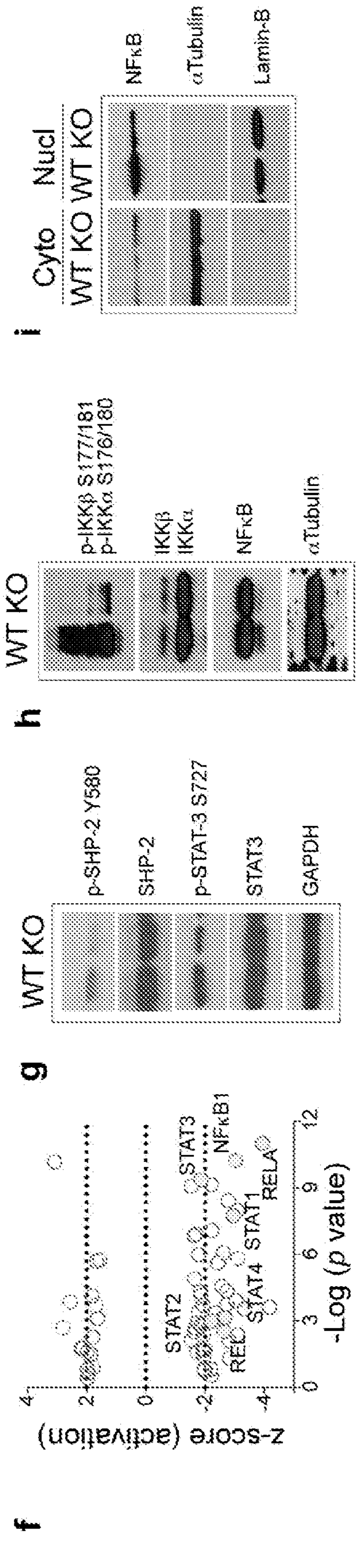
FIG. 31*f*: lilrb4-knockout (lilrb4-KO) and scramble control (WT) THP-1 cells were analyzed by RNA-seq. Loss of lilrb4 induced alterations in transcription factor activities (lilrb4-KO versus WT). Yellow dots highlighted the transcription factors involved in JAK/STATs and NFkB pathways.
FIG. 31*g*: Western blots show lilrb4-knockout (KO) decreases phosphorylation of SHP-2 and STAT-3 compared with that in scramble control (WT) THP-1 cells.
FIG. 31*h*: Western blots show lilrb4-knockout (KO) decreases phosphorylation of IKKs compared with that in scramble control (WT) THP-1 cells.
FIG. 31*i*: Western blots show expression of NFkB is decreased in the nuclear fraction in lilrb4-knockout (KO) compared with that in scramble control (WT) THP-1 cells.

The loss of function by intracellular domain deleted LILRB4 (FIGS. 7*e*-*g* and FIG. 14*dd*) suggests that the downstream signaling of LILRB4 is required for T cell suppression and leukemia infiltration. The intracellular domain of LILRB4 contains three ITIMs that may recruit phosphatases SHP-1, SHP-2 or SHIP, for downstream signalling. To determine whether one or more phosphatase(s) mediate LILRB4 functions, shp-1, shp-2 and ship, were individually deleted in THP-1 cells for T cell co-culture and migration assays by CRISPR/Cas9 technology. Loss of either SHP-2 rescued T cell suppression by THP-1 cells (FIGS. 31*a*-*c*). While, loss of SHP-2, but not SHP-1 or SHIP, decreased migration ability and engraftment of THP-1 cells (FIG. 31*d* and FIG. 31*e*). These results suggest that SHP-2 is a mediator of LILRB4 signaling to support leukemia migration and T cell suppression. The inventors further examined gene expression of wild-type and lilrb4-KO THP-1 cells by RNA-seq analysis. They found that 585 genes were significantly down-regulated, and 445 genes up-regulated, in lilrb4-KO THP-1 cells compared with wild-type counterparts. Consistent with the phenotypes the inventors observed, these lilrb4-regulated genes were particularly involved in cell migration, cytokine production and immunosuppressive IL10 signaling. Upstream regulator analysis in Ingenuity Pathway Analysis (IPA) showed that the activity of key transcription factors of JAK-STAT (STAT1, STAT2, STAT3 and STAT4) and NFkB (NFkB1, REL, and RELA) pathways, which are known as downstream signaling of SHP-2[37], were significantly inhibited by loss of lilrb4 (FIG. 31*f*). In parallel to the decrease of phosphorylation of SHP-2, activations of both JAK/STAT and NFkB pathways were down-regulated by loss of LILRB4 (FIGS. 31*g*-*i*). Inhibition of STATs in leukemia cells increased T cell proliferation (FIGS. 31*j*-*k*) and decreased transmigration in vitro (FIG. 31*l*) and leukemia development in vivo (FIG. 31*m*).

Figures 31V, 31W:
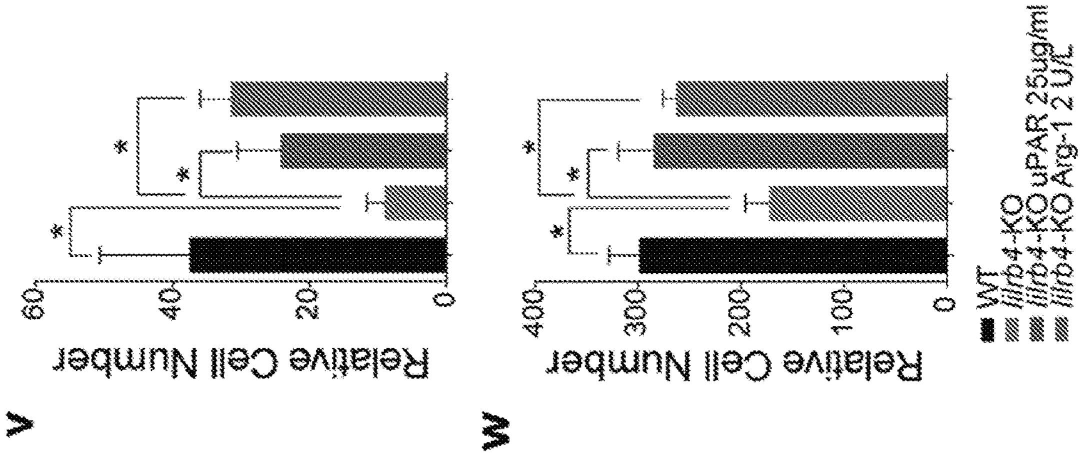
Figure 32:
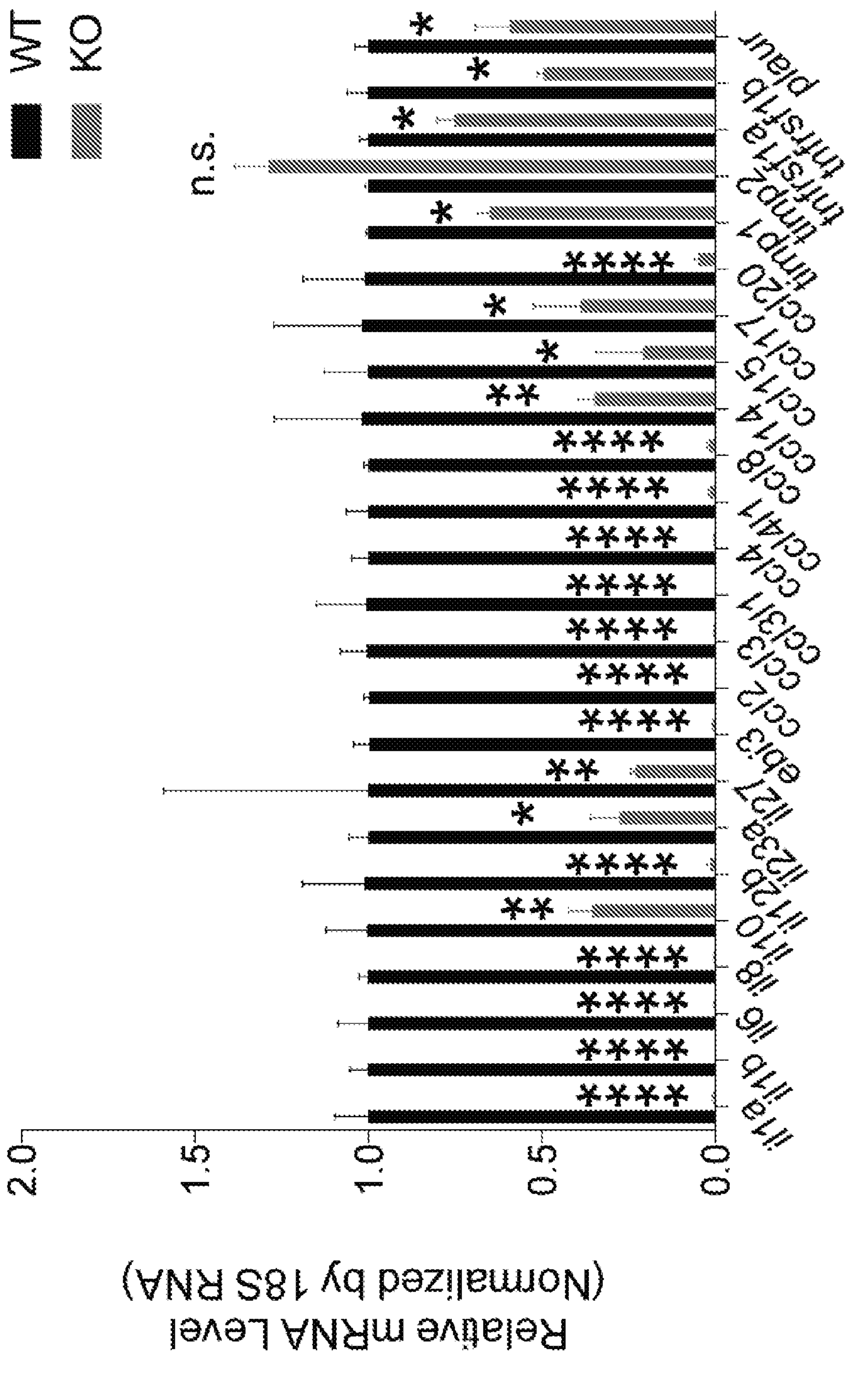
FIG. 32—qPCR shows lilrb4-knockout (KO) decreases gene expression of cytokines and chemokines compared with that in scramble control (WT) THP-1 cells.
Figure 33:
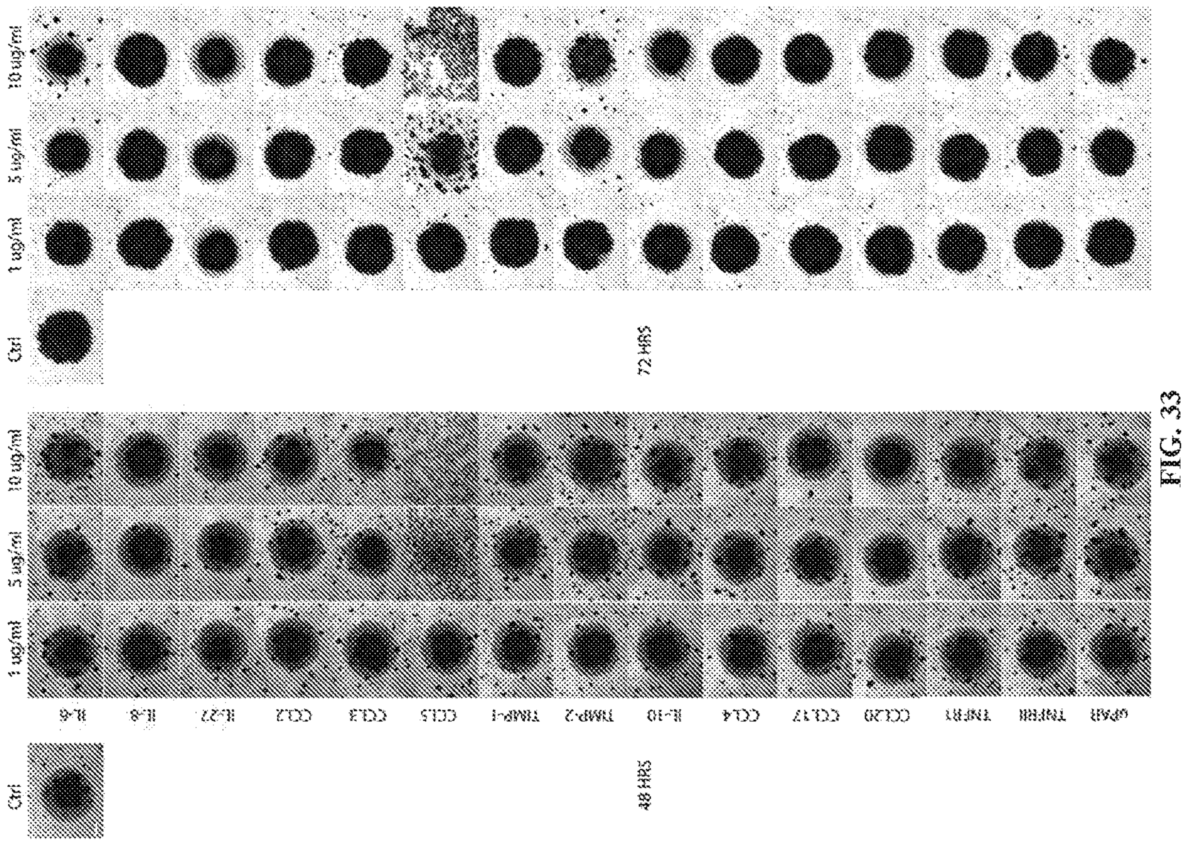
FIG. 33—Effects of cytokines on T cells. T cells isolated from healthy donors were cultured with anti-CD3/CD28-coated beads and rhIL-2 and supplemented with indicated proteins for 3 days. Representative cells were photographed using an inverted microscope.

The inventors' previous results that the separation of wild-type THP-1 cells and human T cells in transwells still enabled T cell inhibition (FIG. 7*g*-*h*) suggest that secreted proteins from leukemia cells are key effectors for immunosuppression. Consistent with this hypothesis, the inventors found the levels of mRNA of secreted proteins, involved in monocyte migration and immune modulation were down-regulated by loss of lilrb4 in monocytic AML cells (FIG. 32). Moreover, CCL2, CCL4, CCL5, IL-6R, IL-8, gp130, OSM, TIMP-1/2, TNF-RI/II and uPAR were decreased in the culture medium of lilrb4-KO cells compared with wild-type control cells (FIGS. 31*n*-*o*). Among these proteins, the uPAR (urokinase receptor), is in particularly higher expressed by monocytic AML cells[38], and is known to promote cancer invasion, metastasis, survival, and angiogenesis[39]. uPAR is a target of NFkB in human cancer cells[40-43] Consistent with a decrease of secreted uPAR, both mRNA and intracellular protein levels of uPAR decreased in lilrb4-KO cells (FIG. 32 and FIG. 31*p*). Next, the inventors found expression of arginase-1 is significantly decreased in lilrb4-KO cells (FIG. 31*p*); arginase-1 was reported to be upregulated by uPAR-mediated signalling and suppress T cell proliferation and CTL generation via increase of superoxide products in T cell microenvironment[4446]. Because it was reported that arginase-1 in AML cells can be secreted to inhibit T cell activity[47], the inventors measured the arginase-1 level in the culture medium and found that indeed the secreted arginase-1 from lilrb4-KO THP-1 cells also decreased (FIG. 31*q*). To determine if uPAR contributes to LILRB4-mediated T cell suppression, the inventors treated lilrb4-KO cells with additional uPAR proteins when co-cultured with T cells. Supplement of uPAR decreased T cell proliferation in the coculture in a dose-dependent manner (FIG. 31*r-s*); this effect of uPAR was likely through the coculture because uPAR does not efficiently directly decrease T cell proliferation (FIG. 33). Similarly, supplement of arginase-1 also decreased T cell proliferation in the coculture (FIGS. 31*t-u*). Moreover, supplement of either uPAR or arginase-1 increased the migration ability of THP-1 (FIG. 31*v*) or MV4-11 cells (FIG. 31*w*) across endothelial cells. These results suggest that LILRB4 may increase arginase-1 expression in AML cells via SHP-2/NFkB/uPAR/Arginase-1 signalling, which suppresses T cell activity and increases leukemia migration.

Figure 34:
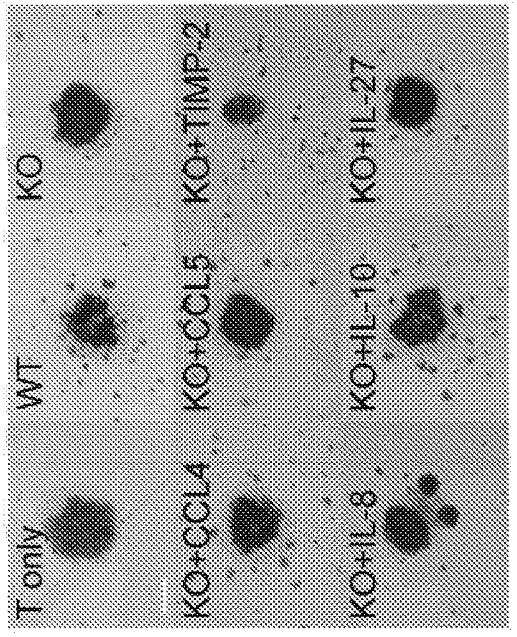
FIG. 34—Rescue of T cell-activating function of LILRB4 KO THP-1 cells by cytokines. T cells isolated from healthy donors were incubated in the lower chambers of a 96-well transwell plate. Irradiated lilrb4-WT or -KO THP-1 cells were incubated in the upper-chambers. Indicated proteins were supplemented in the upper-chamber with lilrb4-KO THP-1 cells. The pore size of the transwell membrane was 3 μm. E:T=2:1. After culture with anti-CD3/CD28-coated beads and rhIL-2 for 3 days, representative cells were photographed by using an inverted microscope. T only, no THP-1 cells in up-chamber. CCL4, 20 μg/ml, CCL5, 10 μg/ml, TIMP-2, 10 μg/ml, IL-8, 10 μg/ml, IL10, 20 μg/ml, IL-27, 10 μg/ml.
Figures 35A, 35B, 35C:
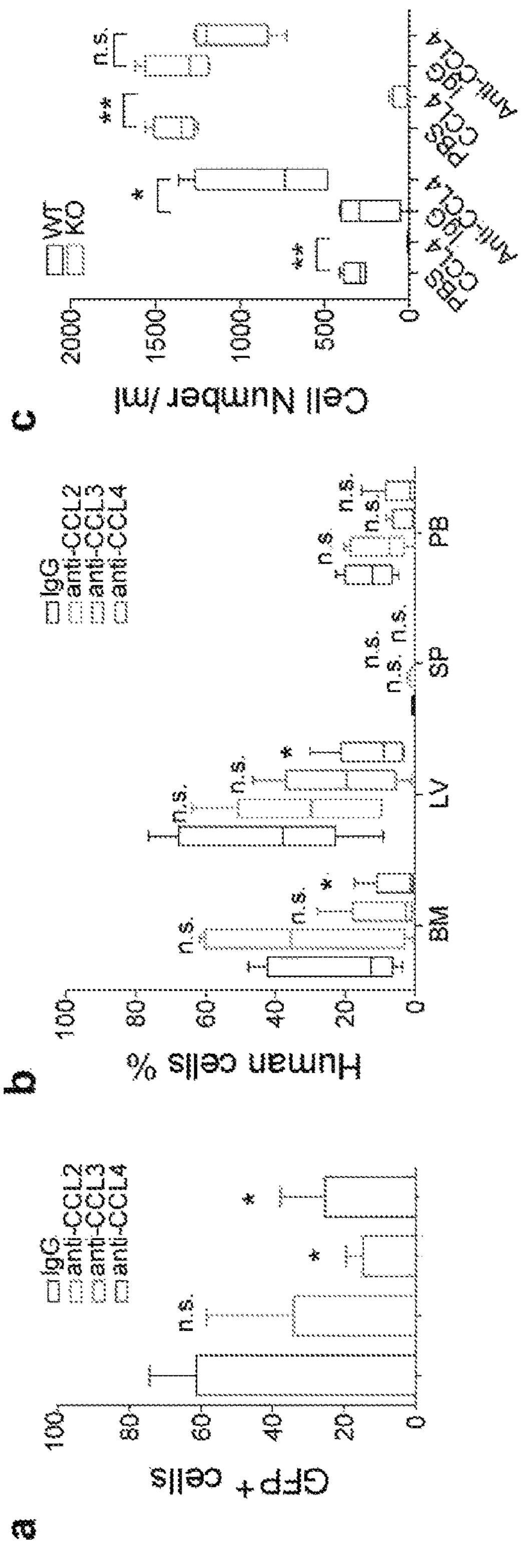
FIGS. 35*a*-35*c*—Effects of CCLs on AML cell infiltration.
Figure 36C:
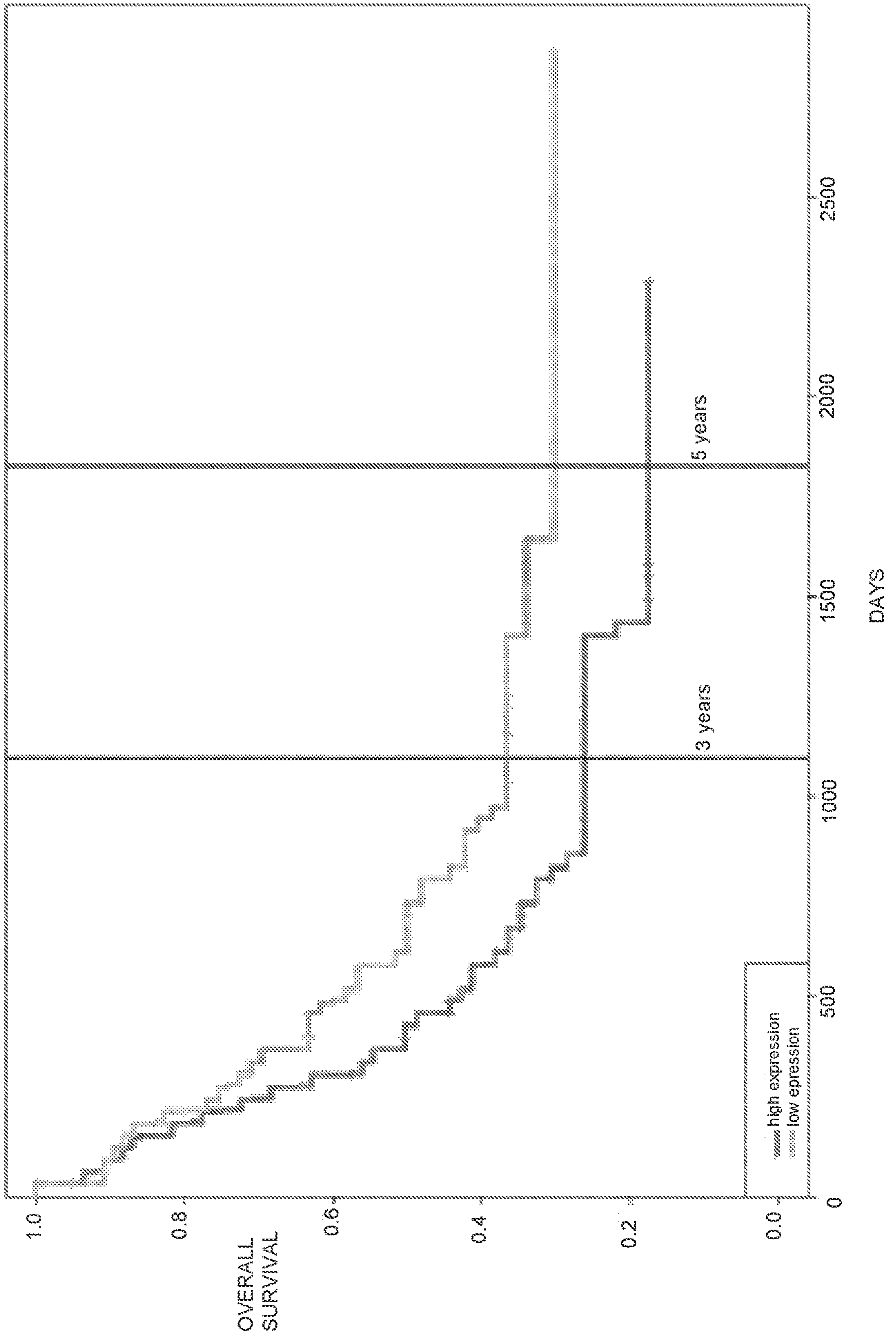
Figure 36D:
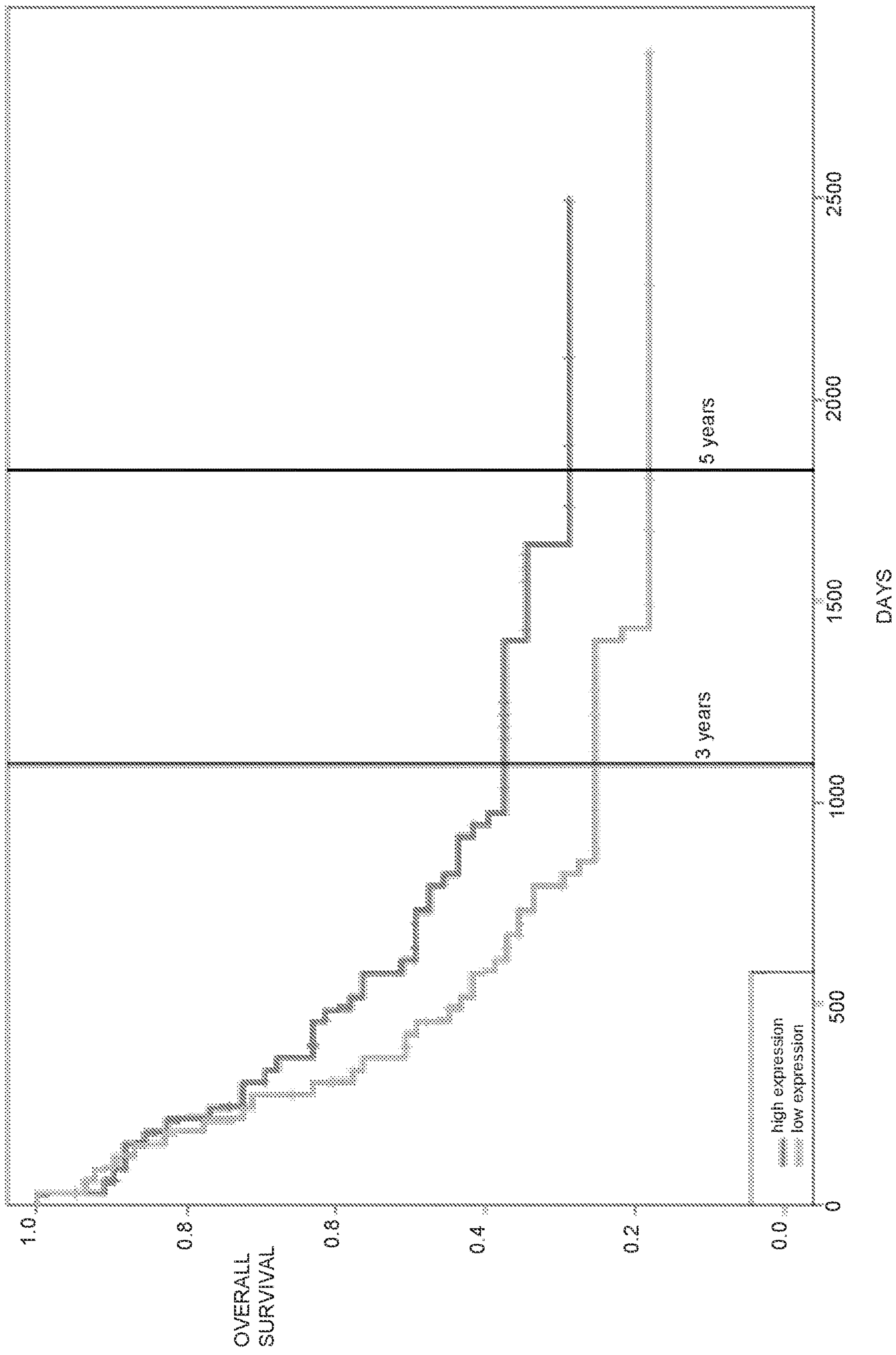

In addition to uPAR and arginase-1, EBI3, which forms heterodimer of IL-27 with IL27p28, was decreased by loss of lilrb4 (FIG. 32). Together with decrease of IL-10 (FIG. 32), these results suggest that LILRB4 controls expression of IL-27/IL-10 to suppress T cell proliferation and activation[48, 49] (FIG. 34). TIMP-2 is natural inhibitor for MMPs. Supplement of TIMP-2 in coculture (FIG. 34) or without THP-1 cells (FIG. 33) decreased T cell proliferation. Interestingly, CCL2, CCL3, CCL4 and CCL5, that have shared receptor CCRs controlling migration of monocytes and T cells[50], were down-regulated by loss of lilrb4. Treatment of THP-1 cells with individual neutralizing antibodies showed that CCL4, but not CCL2 and CCL3, promoted migration of leukemia cells and AML development in xenograft model (FIGS. 35*a-c*). In addition, consistent with a report that CCL4 directly induces apoptosis of T cells[51], the inventors found that supplement of CCL4 in T/THP-1 co-culture media suppressed T cell proliferation; and treatment of anti-CCL4 neutralizing antibodies rescued LILRB4-mediated T cell suppression (FIG. 34 and FIGS. 35*a-c*). These results suggest CCL4 is a key effector in LILRB4 signaling to control leukemia development and immune evasion.

In an attempt to validate the function of LILRB4 downstream effectors, the inventors performed gene expression analyses of lilrb4-KO versus wild-type THP-1 cells, human serum-treated versus non-treated THP-1 cells, and anti-LILRB4 antibody-treated versus control IgG-treated THP-1 cells with pre-treatment with human serum. They found that 44 genes, including 10 lilrb4-positively regulated and 34 lilrb4-negatively regulated genes, showed opposite trends in serum-activated and anti-LILRB4 treated samples (FIGS. 36*a-d*). The mRNA levels of these genes in human AML patient were also significant correlated with that of LILRB4 (FIGS. 36*a-d*). The expression of these LILRB4-positively regulated genes inversely correlated with patient survival (FIGS. 36*a-d*). In contrast, these LILRB4-negatively regulated genes positively correlated with patient survival (FIGS. 36*a-d*). Together, these results indicated that LILRB4 supports immune evasion and cancer infiltration via downstream signalling in leukemia cells.

In this study, the inventors sought to answer two major biological questions. First, given the generally inefficiency of existing immune checkpoint blockade therapies toward leukemia, does leukemia employ unique unknown tumor development and immune evasion mechanisms? Second, immune inhibitory ITIM-containing receptors often need to work together with activating receptors for immune regulation[52]. Can these receptors initiate immune-related primary signaling? Here, the inventors obtained positive answers to both questions. They identified new mechanisms for tumor progression and immune evasion of acute monocytic leukemia, and also demonstrated that an ITIM-containing receptor can initiate primary immune escape signaling in tumor cells. To evade immune attack, acute monocytic leukemia depends on LILRB4 for T cell inhibition; different from a previous finding[53], these data indicate that the intracellular signaling of LILRB4 in cancer cells is required for this immune suppression. Consistently, LILRB4 guides tumor cells to migrate to internal organs/tissues including the immune privileged sites. Of note, this also explained the characteristic extramedullary infiltration of monocytic AML.

The tumor invasion mechanisms for acute monocytic leukemia as the inventors demonstrated are unique. Different from the direct immune inhibition through cell-cell contact as exemplified by PD-L1/PD-1 engagement, these leukemia cells utilize LILRB4-mediated signaling to infiltrate into tissues and suppress T cell activities—thus to create a new immune suppressive microenvironment. These findings suggest that a tumor blockade strategy that is different from the existing ones is needed to treat acute monocytic leukemia.

Figures 37A, 37B, 37C:
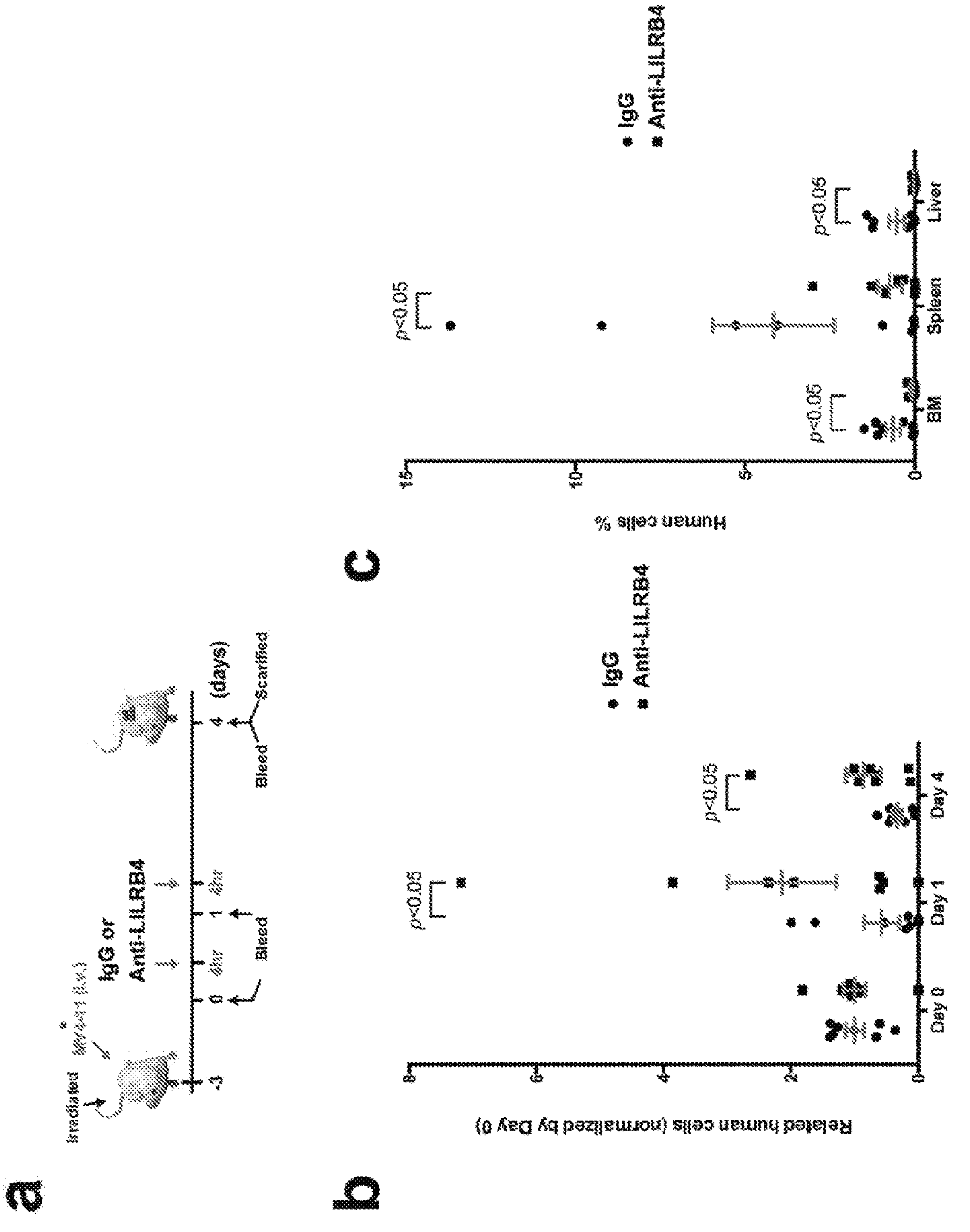
FIGS. 37*a*-37*c*—Anti-LILRB4 antibodies accelerate mobilization of MV4-11 cells to peripheral blood.
Figures 38A, 38B, 38C, 38D, 38E:
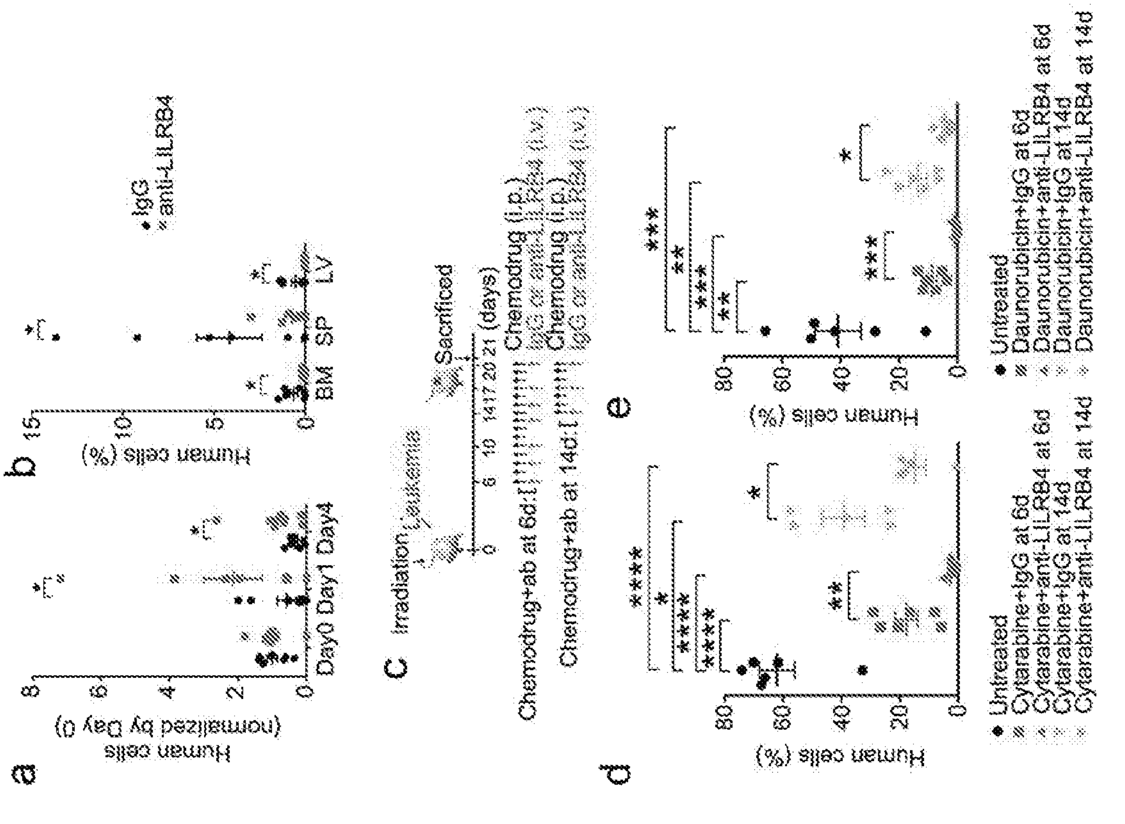
FIGS. 38*a*-38*e*—Synergistic effects of anti-LILRB4 and chemotherapy drugs.
Figure 39:
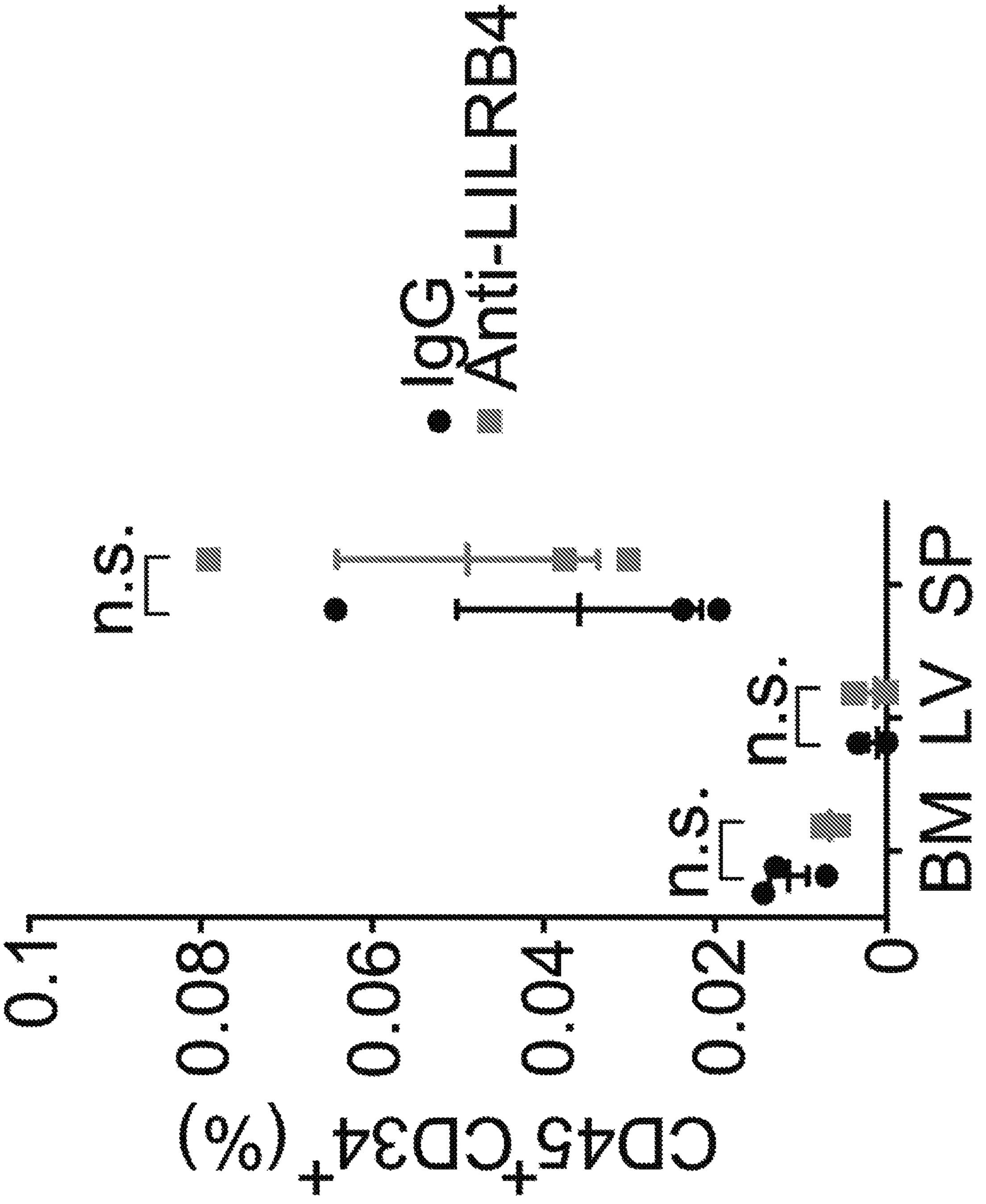
FIG. 39—Anti-LILRB4 antibody did not affect homing of normal HSCs. Human cord blood mononuclear cells ($1\times10^7$) were injected into NSG mice followed immediately by antibody treatment, and then the mice (n=3) were sacrificed at 20 hrs after transplant. The number of $CD45^+CD34^+$ HSCs in liver, spleen, and bone marrow were normalized to that in peripheral blood as determined by flow cytometry.
Figure 40C:
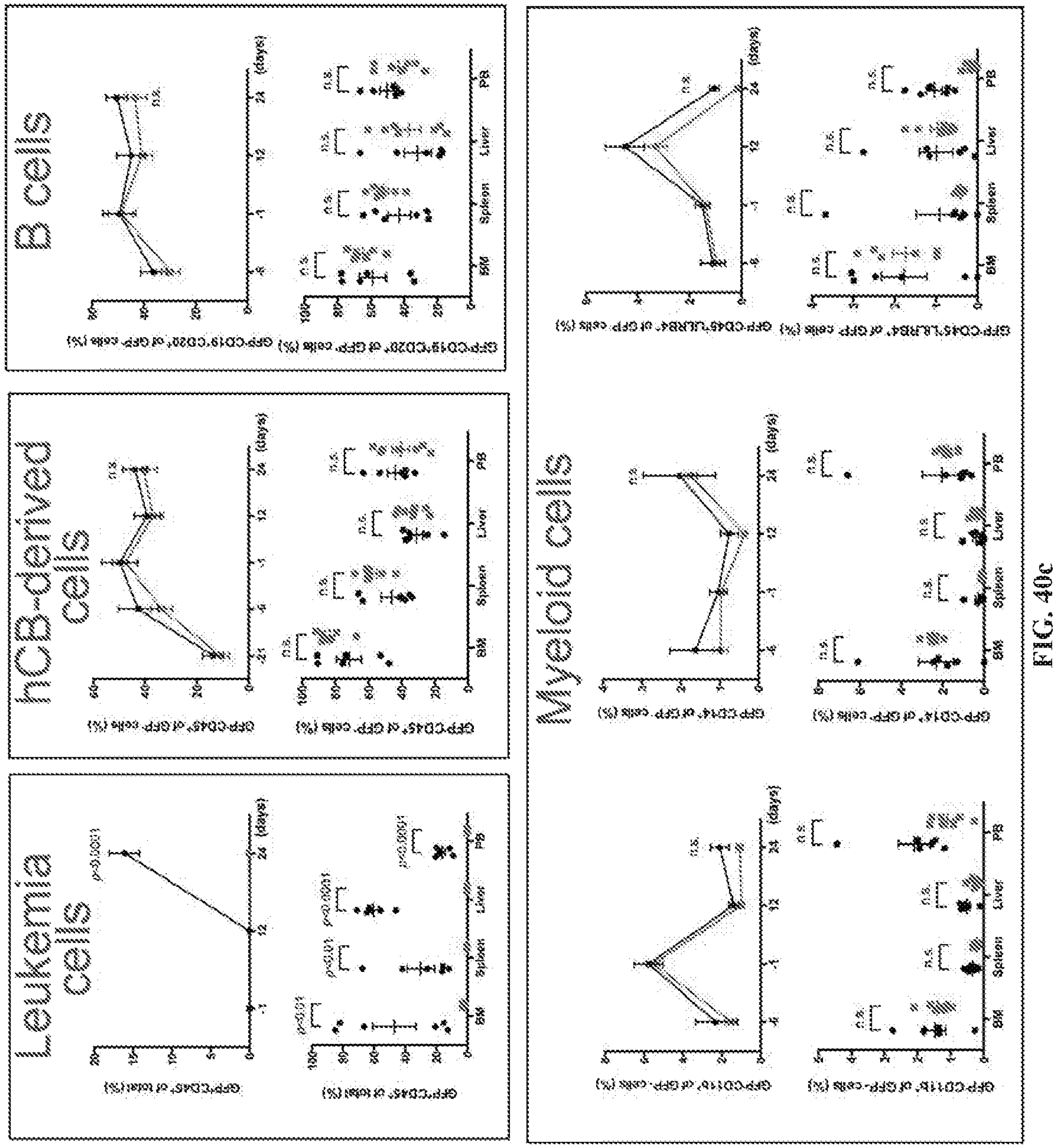
Figure 40C:
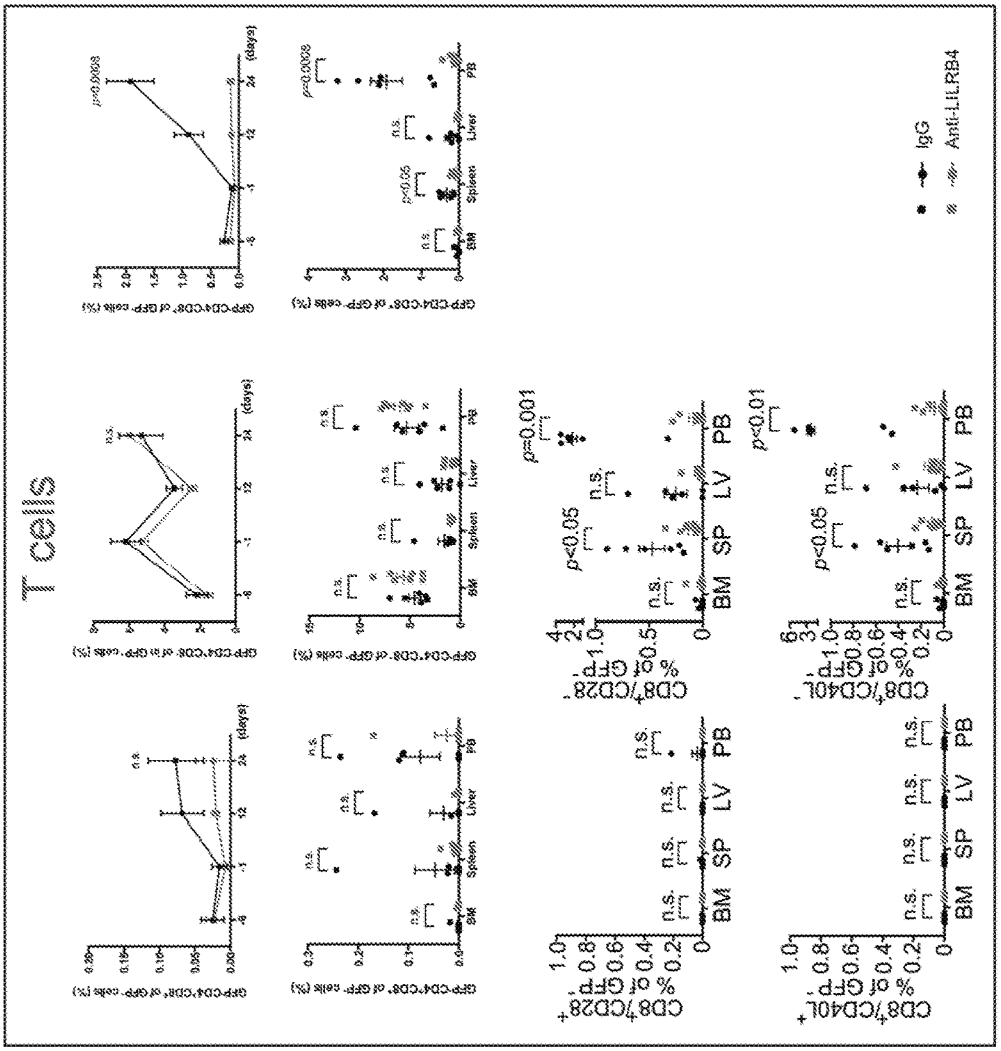

LILRB4 may become the Achilles' heel for acute monocytic leukemia and thus represents an ideal target for treating this disease. Targeting LILRB4 may reactivate multiple immune cell types including T cells and perhaps monocytes/macrophages, block tumor infiltration into tissues/organs, and directly kill tumor cells (by antibody-dependent cell-mediated cytotoxicity or phagocytosis), thus perfectly combining immunotherapy and targeted therapies. In addition, anti-LILRB4 may mobilize leukemia cells from bone marrow to peripheral blood (FIGS. 37*a-c*) and a combination of LILRB4 targeting with other therapies such as chemo-treatment can be beneficial as the anti-LILRB4 treatment results in migration of leukemia cells out of niche into the blood stream where these cells may be more susceptible to cytotoxic chemotherapy (FIGS. 38*a-e*). Importantly, the functional dependence of acute monocytic leukemia on LILRB4 suggests that the possibility of LILRB4 downregulation-led drug resistance for the LILRB4 blockade strategy is low. Even more, because LILRB4 is restrictively expressed on normal monocytic cells[22] but is expressed at higher levels on human monocytic AML cells, and anti-LILRB4 blocking antibody didn't affect normal HSC homing (FIG. 39) and normal haematopoiesis in human cord blood cell-reconstituted mice (FIG. 40), LILRB4 targeting may have minimal toxicity.

Besides AML, LILRB4 may play roles in other hematopoietic malignancies and solid cancers. LILRB4 is upregulated in chronic lymphocytic leukemia[12] and certain solid cancer cells[22 10, 16, 17]. LILRB4 is also expressed on tumor-associated macrophages, myeloid-derived suppressor cells, and tolerogenic dendritic cells[22 10, 16, 17], likely contributing to an immune-suppressive environment for many tumors. An extrapolation of these results in AML may suggest that LILRB4 potentially promotes metastasis of LILRB4-positive solid cancer cells. Moreover, monocytic cells are reported to be the source of IL-6, the main cytokine responsible for the life-threatening cytokine release syndrome associated with some immunotherapies[54]. Targeting these LILRB4-positive monocytic cells may thus control the cytokine release syndrome. Blocking LILRB4 signaling may prove to be a novel strategy for treating different types of cancers with minimal side effects.

Example 2—Materials and Methods

Mice. C57 BL/6J and NOD-scid IL2Rγ null (NSG) mice were purchased from and maintained at the animal core facility of University of Texas Southwestern Medical Center (UTSW). APOE-null mice were previously described[55]. All animal experiments were performed with the approval of the Committee on Animal Care.

Chimeric receptor reporter cells. The inventors constructed a stable chimeric receptor reporter cell system as described[2 31] to test the ability of a ligand to bind to the ECD of individual LILRBs, PirB, and gp49B1 and to trigger the activation or inhibition of the chimerically fused intracellular domain of paired immunoglobulin-like receptor β, which signals through the adaptor DAP-12 to activate the NFAT promoter. If an agonist or antagonist binds the ECD and activates or suppresses the chimeric signaling domain, an increase or decrease, respectively, in GFP expression is observed.

APOE competition assay was used to screen LILRB4 blocking antibodies. Briefly, APOE proteins were pre-coated on 96-well plate at 37° C. for 3 hrs. After 2 times washing by PBS, $2\times10^4$ LILRB4 reporter cells were seeded in each well; meanwhile, indicated anti-LILRB4 antibodies were added into culture media. After 16 hrs, the percentage of $GFP^+$ reporter cells was analysed by flow cytometry.

K562 co-culture assay was used to screen anti-LILRB4 antibodies that may enhance LILRB4 activity. Briefly, $2\times10^4$ LILRB4 reporter cells and $2\times10^4$ K562 cells were mixed and cultured in a well of 96-well plate; meanwhile, indicated anti-LILRB4 antibodies were added into culture media. After 16 hrs, the percentage of mouse $CD45^+$ $GFP^+$ cells was determined by flow cytometry.

Flow cytometry. For flow cytometry analyses of mouse AML cells, peripheral blood or bone marrow cells were stained with anti-Mac-1-APC (M1/70, BD Pharmingen), anti-Gr-1-PE (RB6-8C5, BD Pharmingen), anti-CD3-APC (145-2C11, BD Pharmingen), anti-B220-PE (RA3-6B2, BD Pharmingen), or anti-Kit-PE (B8, BD Pharmingen) monoclonal antibodies. For analysis of human hematopoietic engraftment in NSG mice, a previously published protocol was followed[2, 56, 57]. The inventors used anti-human CD45-PE (HI30, BD Pharmingen), anti-human CD34-FITC (555821, BD Pharmingen), anti-human CD19-PE (HIB19, eBioscience), anti-human CD20-PE (555623, BD Pharmingen), anti-human CD11b-APC (ICRF44, eBioscience), anti-human LILRB4-APC (ZM4.1, eBioscience), anti-human CD14-APC (61D3, eBioscience), anti-human CD4-APC (RPA-T4, eBioscience), anti-human CD8-PE (555367, BD Pharmingen), anti-human CD28-APC (CD28.2, eBioscience), and anti-human CD40L-APC (24-31, eBioscience) antibodies to quantify the engraftment of different human hematopoietic lineage cells.

Virus construction/infection and AML transplantation. For virus packaging, retroviral constructs MSCV-MLL-AF9-IRES-YFP, XZ201-IRES-GFP, XZ201-LILRB4-IRES-GFP were mixed with PCL-ECO (2:1), followed by transfection into 293T cells using Lipofectamine 2000 (Invitrogen, CA). Virus-containing supernatant was collected 48-72 hours post-transfection and used for infection as described previously[58]. Infected mouse $Lin^-$ cells ($3\times10^5$) or mouse leukemia C1498 cells ($1\times10^6$) were transplanted into lethally irradiated (1,000 rad) or sub-lethally irradiated (250 rad) C57BL/6J mice (6-8 weeks old) by retro-orbital injection. C1498 cells were purchased from ATCC. For the secondary transplantation, the inventors used FACS to isolate $YFP^+$ BM cells from primary recipient mice and transplanted 3000 cells into non-irradiated recipient mice including wild-type C57BL/6J and APOE-null mice. They monitored the survival, examined the size and histological properties of bone marrow, spleen, and liver, and analysed the numbers and infiltration of leukemia cells in peripheral blood, bone marrow, spleen, and liver. They also determined the different populations of leukemia cells using flow cytometry.

Human and mouse leukemia cells. Primary human AML samples were obtained from UTSW. Informed consent was obtained under a protocol reviewed and approved by the Institutional Review Board at UTSW. The UTSW cohort included 105 AML patients, representative of AML subtypes M1 (n=9), M2 (n=34), M3 (n=10), M4 (n=34), M5 (n=25), M6 (n=2), and M7 (n=1) and patients with undifferentiated leukemia (AUL; n=1) and transient myeloproliferative disorder (TAM; n=2). LILRB4 expression of samples were analysed by flow cytometry. Human leukemia cells (THP-1, MV4-11, and U937) and mouse leukemia cells (WEHI-3) (purchased from the ATCC) were cultured in RPMI-1640 supplemented with 10% FBS at 37° C. in 5% $CO_2$ and the normal level of $O_2$. Mouse leukemia cells (C1498) (purchased from the ATCC) were cultured in DMEM supplemented with 10% FBS at 37° C. in 5% $CO_2$ and the normal level of $O_2$.

TCGA analyses. Data were obtained from the TCGA acute myeloid leukemia database (Version: Oct. 29, 2015). The patients were classified into AML subtypes M0 (n=16), M1 (n=42), M2 (n=39), M3 (n=16), M4 (n=35), M5 (n=18), M6 (n=2), M7 (n=3); two cases were not classified by subtype. The levels of LILRB4 mRNA were determined by RNAseq (IlluminaHiSeq). RESM-normalized counts are reported, and data were visualized with UCSC Xena (xena.ucsc.edu). For analysis of overall survival, 160 patients with available survival data were separated into three groups based on whether they had high (n=55), moderate (n=48), or low (n=57) LILRB4 expression.

Bio-layer Interferometry. Binding interactions analyses between LILRB4-Fc with APOE2, APOE3, and APOE4 were performed on the Octet RED96 (ForteBio, Pall Corporation). All interaction studies were performed with the protein A dip-and-read biosensors (ForteBio). All binding experiments were performed using the Octet Red and kinetics buffer at 30° C. LILRB4-Fc coated biosensors (25 μg/ml LILRB4-Fc was loaded for 420 s) were washed in kinetics buffer before monitoring of association (300 s) and dissociation (600 s) of APOEs. Background wavelength shifts were measured from reference sensors that were loaded only with LILRB4-Fc.

Microscale Thermophoresis (MST). MST experiments were performed on a Monolith NT.115 system (NanoTemper Technologies) using 80% LED and 20% IR-laser power. Laser on and off times were set at 30 s and 5 s, respectively. Recombinant LILRB4-ECD protein (SinoBio) was labeled with 4488-NHS (NanoTemper Technologies) and applied at a final concentration of 5.9 nM. A two-fold dilution series was prepared for unlabeled His-APOE (#CI06, Novoprotein) in PBS and each dilution point was similarly transferred to LILRB4-ECD solution. The final concentrations of His-APOE ranged from 12 μM to 0.36 nM. Samples were filled into standard-treated capillaries (NanoTemper Technologies) for measurement.

Tumor cell/T cell co-culture assay. Human T cells isolated from health donor peripheral blood (PB009-1-0, Allcells) were co-cultured with irradiated (28 Gy) THP-1 cells in a U-bottom 96 well-plate for 3-7 days. Anti-CD3/CD28-coated beads (#11161D, Thermo Fisher), 50 U/ml recombinant human IL-2, and 5 ng/ml recombinant human IL-7 were supplemented to the medium. In some experiments, THP-1 cells were cultured in the upper chamber of transwell inserts (pore size is 3 μM, #09-761-80, Thermo Fisher) for the U-bottom 96 well-plate. For primary AML or B-ALL samples, patient $CD3^+$ T cells were collected and patient leukemia cells were sorted as $CD33^+$ and $CD19^+$ for AML and B-ALL, respectively.

$CD8^+$ T cells ($5\times10^4$ per well) isolated from hPBMCs of a healthy donor (Interstate Blood Bank) were stimulated with anti-CD3/CD28/CD137-coated beads (11163D, Thermo Fisher) or cultured without stimulation for 2 days in a 96-well plate. Then, $5\times10^3$ human leukemia THP-1-Luc-GFP cells and 50 to 500 μg/ml anti-LILRB4 antibody C84 or control antibody mIgG were added. Cell numbers were determined on day 7 in triplicate wells. Anti-CD8 and anti-CD28 were used to detect human CTL cells; THP-1 cells were positive for GFP. Cell supernatants from co-cultures of stimulated CTL cells and THP-1 cells treated with C84 or mIgG were used to examine cytokine production using human cytokine arrays (AAH-CYT-6, RayBiotech). The experiment was repeated three times with similar results.

Transwell assay. To test the cell plasticity, $1\times10^5$ MV4-11 cells were labelled with CFSE (Invitrogen) and treated with 100 μg/ml of anti-LILRB4 antibody C84 or control antibody mIgG and cultured in the upper chamber of well in a transwell plate (Corning). After 18 h, cells in lower chamber were counted. To test the ability of AML cells to migrate through endothelial cells, $3\times10^5$ human umbilical vein endothelial cells (HUVEC) cells were cultured on the transwell membrane. After 3 days, $1\times10^5$ CFSE-labelled MV4-11 cells were seeded in the upper chamber with 100 μg/ml of C84 or mIgG. After 18 h, cells in lower chamber were counted.

Homing and mobilization of leukemia and HSC cells. CFSE-labelled MV4-11 cells ($5\times10^6$ cells per mouse) were injected intravenously into NSG mice. Animals were treated with 200 μg of control antibody mIgG or anti-LILRB4 antibody C84 or 10% serum immediately after injection of leukemia cells. Mice were sacrificed after 8 or 20 h. Peripheral blood, bone marrow, liver, and spleen were harvested, and single-cell suspensions were examined by flow cytometry. CFSE or anti-human CD45 was used to detect human leukemia cells. Numbers of leukemia cells in recipient liver, spleen, and bone marrow are reported as a percentage relative to cell numbers in peripheral blood. To test HSC homing, $1\times10^7$ human cord blood mononuclear cells were injected intravenously into an NSG mouse. Mice were treated with 200 μg of mIgG or C84 immediately after injection of mononuclear cells and were sacrificed after 20 h. Anti-human CD45 and anti-human CD34 were used to detect human HSCs by flow cytometry. To test the homing of mouse leukemia cells, $5\times10^6$ C1498-GFP-hLILRB4 cells or C1498-GFP were injected intravenously into wild-type C57BL/6J or APOE-null mice. Mice were sacrificed after 20 h. GFP was used to detect leukemia cells by flow cytometry. The number of leukemia cells in recipient liver, spleen, and bone marrow were normalized to numbers in peripheral blood and are reported as a percentage. To test mobilization of leukemia cells, $5\times10^6$ MV4-11 cells were injected intravenously into each NSG mouse. Three days after transplantation, mice were injected intravenously with 200 μg C84 or mIgG. The day of first administration was assigned as day 0. Mice were then treated with another dose of 200 μg C84 or mIgG, respectively, on the next day. Leukemia cells in peripheral blood were examined at 4 hr (on day 0) and at 1 and 4 days after first administration of antibodies. Mice were sacrificed on day 4. Anti-human CD45 was used to detect human leukemia cells by flow cytometry.

Human AML xenograft. Xenografts were performed essentially as described[2, 3, 56, 59]. Briefly, 6-8 week-old NSG mice were used for transplantation. Human leukemia cells were resuspended in 200 μl PBS containing 1% FBS. Mice were given $1\times10^6$ human cultured leukemia cells or 5 to $10\times10^6$ human primary AML cells via tail-vein injection. One to four months after transplantation, the peripheral blood, bone marrow, spleen, and liver were assessed for the engraftment.

For hPBMC xenograft model, $1\times10^7$ human PBMCs were injected intravenously into each NSG mouse. Three weeks after implantation, mice had 30 to 50% engraftment of human T cells. At 3 weeks post implantation, $1\times10^6$ human AML THP-1 cells that stably express luciferase (THP-1-Luc-GFP cells) were subcutaneously implanted. Mice were immediately given 200 μg C84 or mIgG intravenously and were treated twice a week until euthanization. Tumor growth was monitored over time by luminescence imaging.

For the human cord blood (hCB) HSC reconstituted xenograft model, $3\times10^4$ human cord blood $CD34^+$ cells were injected intravenously via the retro-orbital route into sublethally irradiated (2.5 Gy) 6-8 weeks old NSG mice. Multi-lineage human hematopoietic reconstitution was confirmed at various time points between day 21 and day 41 post-transplantation by flow cytometry as described[56, 57, 60]. At day 42, $1\times10^6$ human THP-1-Luc-GFP cells were intravenously implanted. The mice were immediately given 200 μg C84 or mouse IgG by intravenous injection. Tumor growth was monitored over time by luminescence imaging. Multi-lineage human hematopoietic reconstitution was examined at various time points at day 12 to day 24 post-transplantation of leukemia cells by flow cytometry. CD19 and CD20 were used to identify human B cells; CD11b, CD14, and LILRB4 human myeloid cells; CD4, CD8, CD28, and CD40L populations of human T cells.

For survival curve experiments, the death of mice was recorded when the moribund animals were euthanized.

CRISPR/Cas9-based LILRB4 knockout in AML cells. THP1 cells were infected with doxycycline-inducible Cas9-expressing lentivirus (pCW-Cas9, Addgene 50661). After 1 μg/ml puromycin selection, the survived cells were infected with sgRNA-expressing lentivirus, produced by the plasmid modified from pSLQ1651 (Addgene 51024) by replacing the puro-mcherry with GFP for sorting. One control sgRNA (control sgRNA 5'-GAACGACTAGTTAGGCGTGTA-3' (SEQ ID NO:1)) and three LILRB4 targeting sgRNA (sgRNA1 5'-TGTTACTATCGCAGCCCTGT-3' (SEQ ID NO:2); sgRNA2 5'-GTAGGTCCCCCCGTGCACTG-3' (SEQ ID NO:3); sgRNA3 5'-CCTGTGACCTCAGTGCACGG-3' (SEQ ID NO:4);) which were designed by an online tool (http://crispr.mit-.edu), were cloned into the sgRNA plasmid, respectively. After treated with 1 μg/ml doxycycline for 1 week, these cells were staining with anti-LILRB4 antibody and the LILRB4 negative cells were sorted as LILRB4 knockout cells.

SDS-PAGE and Cytoplasmic/nuclear protein isolation. For SDS-PAGE, samples were mixed with 4×loading buffer with β-mercaptoethanol (BME) and loaded on 10% SDS gels. Nuclear and cytoplasmic cellular compartments were isolated by NE-nuclear/cytoplasmic extraction kit (#78833, Thermo Fisher) and these protein extracts were mixed with 4×loading buffer with β-mercaptoethanol (BME) and loaded on 10% SDS gels. Anti-SHP-1 (#3759), anti-SHP-2 (#3397), anti-SHIP (#2727), anti-phospho-SHP-2 (Tyr580) (#3703), anti-Nf-kB p65 (#8242), anti-IKKa (#11930), anti-IKKb (#8943), anti-phospho-IKKa/b (Ser176/180) (#2697), antiphospho-Stat1 (Tyr701) (#7649), anti-phospho-Stat-3 (Ser727) (#9134), anti-Lamin-B2 (#12255) and anti-Arginase-1 (#9819) were purchased from Cell Signaling Technology Inc. Anti-uPAR antibody (MON R-4-02, Thermo Fisher) and anti-alpha-tubulin (#MABT205, Sigma) were purchased from other companies.

RNA-seq analysis. RNA was purified from sorted cells with Qiagen RNeasy Mini Kit and then reverse-transcribed with SuperScript III Reverse Transcriptase (Invitrogen) according to the manufacturer's instructions. RNA-seq was performed at the UTSW Genomics and Microarray Core Facility. The cDNA was sonicated using a Covaris S2 ultrasonicator, and libraries were prepared with the KAPA High Throughput Library Preparation Kit. Samples were end-repaired and the 3' ends were adenylated and barcoded with multiplex adapters. PCR-amplified libraries were purified with AmpureXP beads and validated on the Agilent 2100 Bioanalyzer. Before being normalized and pooled, samples were quantified by Qubit (Invitrogen) and then run on an Illumina Hiseq 2500 instrument using PE100 SBS v3 reagents to generate 51-bp single-end reads. Before mapping, reads were trimmed to remove low-quality regions in the ends. Trimmed reads were mapped to the human genome (HM19) using TopHat v2.0.1227 with the UCSC iGenomes GTF file from Illumina.

Methods for data normalization and analysis are based on the use of "internal standards" that characterize some aspects of the system's behavior, such as technical variability, as presented elsewhere. Genes with $\log_2$ (fold change) >2, P<0.01 and RPKM>0.1 were deemed to be significantly differentially expressed between the two conditions, and used for pathway analysis and upstream transcription factor analysis. Pathway analysis was conducted using the DAVID (https://david.ncifcrf.gov/tools.jsp). Upstream transcription-factor analysis was conducted using QIAGEN's Ingenuity tool. Gene heat maps were clustered by hierarchical clustering (Cluster and Java Treeview).

Quantitative RT-PCR. Total RNA was extracted using RNAeasy kit (QIAGEN) and reverse transcribed into cDNA using SuperScript III Reverse Transcriptase (Invitrogen) according to the protocol provided. Real-time PCR was performed with the primers listed in Table 2 using SYBR Green Master Mix (Bio-Rad). mRNA levels were normalized to the level of GAPDH or 18S rRNA transcripts present in the same sample.

Statistical analyses. Data are expressed as means±SEM. Data were analysed by Student's t test and were considered statistically significant if $p<0.05$. The survival rates of the two groups were analysed using a log-rank test and were considered statistically significant if $p<0.05$. In all figures, * indicates $p<0.05$;  indicates $p<0.01$; * indicates $p<0.001$; **** indicates $p<0.0001$; otherwise, p values are represented as precise values.

TABLE 1

Eight AML patient samples from UTSW cohort were used for xenograft mouse model.

| Patient_ID | Age (yrs) | Gender | Specimen | FAB subtype | Blast type | Blast cells (%) | CD14 | CD33 | CD34 | CD36 | CD64 | CD117 | LILR B4 |
|---|---|---|---|---|---|---|---|---|---|---|---|---|---|
| 3605141020 | 57 | Female | BM | M4 | myeloblast | 30 | – | + | – | predom – | predom dim + | part dim + | – |
| | | | | | monoblast | 37 | partial + | + | – | variably + | variably + | – | + |
| 0245150122 | 29 | Female | BM | M4 | myeloblast | 15 | – | + | + | few + | few + | + | – |
| | | | | | monoblast | 54 | variably + | bright + | – | variably + | + | | dim + |
| 2990150813 | 55 | Male | BM | M4 | myeloblast | 28 | – | bright + | predom – | predom + | predom + | subset + | partial + |
| | | | | | monoblast | 40 | + | bright + | predom – | predom + | predom + | subset + | + |
| 3615141020 | 57 | Female | BM | M4 | myeloblast | 35 | – | + | – | – | dim + | variably + | – |
| | | | | | monoblast | 27 | partial + | + | – | partial + | + | – | + |
| 0237150120 | 17 | Male | BM | M5a | monoblast | 96 | predom – | variably + | predom – | part dim + | bright + | + | + |
| 0401150203 | 76 | Male | BM | M5a | myeloblast | 10 | – | + | + | – | few + | + | – |
| | | | | | monoblast | 74 | partial + | + | partial + | partial + | predom + | partial + | + |
| 2903140820 | 51 | Female | BM | M5b | myeloblast | 3 | – | variably + | + | – | – | + | – |
| | | | | | monoblast | 77 | variably + | + | – | – | + | partial + | + |
| 3986141117 | 13 | Male | BM | M5b | monoblast | 84 | sm sub + | + | – | – | + | predom – | + |

TABLE 2

Primers were used in qPCR

| Gene Name | Forward primer | | Reverse primer | |
|---|---|---|---|---|
| AIM2 | TGGCAAAACGTCTTCAGGAGG | SEQ ID NO:5 | AGCTTGACTTAGTGGCTTTGG | SEQ ID NO:6 |
| HOXA5 | AACTCATTTTGCGGTCGCTAT | SEQ ID NO:7 | TCCCTGAATTGCTCGCTCAC | SEQ ID NO:8 |
| IL12B | ACCCTGACCATCCAAGTCAAA | SEQ ID NO:9 | TTGGCCTCGCATCTTAGAAAG | SEQ ID NO:10 |
| IL27 | ACCGCTTTGCGGAATCTCA | SEQ ID NO:11 | AGGTCAGGGAAACATCAGGGA | SEQ ID NO:12 |
| IL6 | ACTCACCTCTTCAGAACGAATTG | SEQ ID NO:13 | CCATCTTTGGAAGGTTCAGGTTG | SEQ ID NO:14 |
| ITGAX | AGAGCTGTGATAAGCCAGTTCC | SEQ ID NO:15 | AATTCCTCGAAAGTGAAGTGTGT | SEQ ID NO:16 |
| CCL3 | AGTTCTCTGCATCACTTGCTG | SEQ ID NO:17 | CGGCTTCGCTTGGTTAGGAA | SEQ ID NO:18 |
| RGS16 | ATCAGAGTGGGCTGCGATA | SEQ ID NO:19 | CAGGTCGAACGACTCTCTCC | SEQ ID NO:20 |
| IL1B | ATGATGGCTTATTACAGTGGCAA | SEQ ID NO:21 | GTCGGAGATTCGTAGCTGGA | SEQ ID NO:22 |
| ICAM1 | ATGCCCAGACATCTGTGTCC | SEQ ID NO:23 | GGGGTCTCTATGCCCAACAA | SEQ ID NO:24 |
| CCL2 | CAGCCCAGATGCAATCAATGCC | SEQ ID NO:25 | TGGAATCCTGAACCCACTTCT | SEQ ID NO:26 |
| IER3 | CAGCCGCAGGGTTCTCTAC | SEQ ID NO:27 | GATCTGGCAGAAGACGATGGT | SEQ ID NO:28 |
| ITGA7 | CAGCGAGTGGACCAGATCC | SEQ ID NO:29 | CCAAAGAGGAGGTAGTGGCTATC | SEQ ID NO:30 |
| STAT1 | CAGCTTGACTCAAAATTCCTGGA | SEQ ID NO:31 | TGAAGATTACGCTTGCTTTTCCT | SEQ ID NO:32 |
| LIF | CCAACGRGACGGACTTCCC | SEQ ID NO:33 | TACACGACTATGCGGTACAGC | SEQ ID NO:34 |
| CCL14 | CCAAGCCCGGAATTGTCTTCA | SEQ ID NO:35 | GGGTTGGTACAGACGGAATGG | SEQ ID NO:36 |
| STAT2 | CCAGCTTTACTCGCACAGC | SEQ ID NO:37 | AGCCTTGGAATCATCACTCCC | SEQ ID NO:38 |
| CCL3L1 | CCGACAGATTCCACAGAA | SEQ ID NO:39 | TTGGTTAGGAAGATGACACT | SEQ ID NO:40 |
| BCL3 | CCGGAGGCGCTTTACTACC | SEQ ID NO:41 | TAGGGGTGTAGGCAGGTTCAC | SEQ ID NO:42 |
| SOCS3 | CCTGCGCCTCAAGACCTTC | SEQ ID NO:43 | GTCACTGCGCTCCAGTAGAA | SEQ ID NO:44 |
| CCL4L1 | CGCATCTCCTCCATACTC | SEQ ID NO:45 | ACCTAATACAATAATACAGCACAT | SEQ ID NO:46 |
| IL23A | CTCAGGGACAACAGTCAGTTC | SEQ ID NO:47 | ACAGGGCTATCAGGGAGCA | SEQ ID NO:48 |
| NDRG1 | CTCCTGCAAGAGTTTGATGTCC | SEQ ID NO:49 | TCATGCCGATGTCATGGTAGG | SEQ ID NO:50 |
| TMEM158 | CTGAACCGTAAGCCCATTGAG | SEQ ID NO:51 | CGCTCCACACCACGATGAC | SEQ ID NO:52 |
| CYTIP | CTGGGCCAGCGTATAGCTC | SEQ ID NO:53 | AGCAAGCTGCTTTCGTCCC | SEQ ID NO:54 |
| CCL4 | CTGTGCTGATCCCAGTGAATC | SEQ ID NO:55 | TCAGTTCAGTTCCAGGTCATACA | SEQ ID NO:56 |
| ITGA1 | GCTCCTCACTGTTGTTCTACG | SEQ ID NO:57 | CGGGCCGCTGAAAGTCATT | SEQ ID NO:58 |
| CCL17 | GGACCCCAACAACAAGAG | SEQ ID NO:59 | GTGAGGAGGCTTCAAGAC | SEQ ID NO:60 |
| BCL6 | GGAGTCGAGACATCTTGACTGA | SEQ ID NO:61 | ATGAGGACCGTTTTATGGGCT | SEQ ID NO:62 |
| CXCL10 | GTGGCATTCAAGGAGTACCTC | SEQ ID NO:63 | TGATGGCCTTCGATTCTGGATT | SEQ ID NO:64 |
| AREG | GTGGTGCTGTCGCTCTTGATA | SEQ ID NO:65 | CCCCAGAAAATGGTTCACGCT | SEQ ID NO:66 |
| BCL2A1 | TACAGGCTGGCTCAGGACTAT | SEQ ID NO:67 | CGCAACATTTTGTAGCACTCTG | SEQ ID NO:68 |
| CD300E | TCAGGCTGTTTGTCTCTGAAGG | SEQ ID NO:69 | CATGCTCTCATACTGACACCAC | SEQ ID NO:70 |
| EBI3 | TCATTGCCACGTACAGGCTC | SEQ ID NO:71 | GGGTCGGGCTTGATGATGTG | SEQ ID NO:72 |
| CCL15 | TCCCAGGCCCAGTTCATAAAT | SEQ ID NO:73 | TGCTTTGTGAGATGTAGGAGGT | SEQ ID NO:74 |
| TRAF1 | TCCTGTGGAAGATCACCAATGT | SEQ ID NO:75 | GCAGGCACAACTTGTAGCC | SEQ ID NO:76 |
| CCR7 | TGAGGTCACGGACGATTACAT | SEQ ID NO:77 | GTAGGCCCACGAAACAAATGAT | SEQ ID NO:78 |
| CCL20 | TGCTGTACCAAGAGTTTGCTC | SEQ ID NO:79 | CGCACACAGACAACTTTTTCTTT | SEQ ID NO:80 |
| CCL8 | TGGAGAGCTACACAAGAATCACC | SEQ ID NO:81 | TGGTCCAGATGCTTCATGGAA | SEQ ID NO:82 |
| IL1A | TGGTAGTAGCAACCAACGGGA | SEQ ID NO:83 | ACTTTGATTGAGGGCGTCATTC | SEQ ID NO:84 |
| CCL7 | TGTATATGTCATCTCAGT | SEQ ID NO:85 | TAATAACAATATGCTTCCA | SEQ ID NO:86 |
| STAT4 | TGTTGGCCCAATGGATTGAAA | SEQ ID NO:87 | GGAAACACGACCTAACTGTTCAT | SEQ ID NO:88 |
| NOS2 | TTCAGTATCACAACCTCAGCAAG | SEQ ID NO:89 | TGGACCTGCAAGTTAAAATCCC | SEQ ID NO:90 |
| IL8 | TTTTGCCAAGGAGTGCTAAAGA | SEQ ID NO:91 | AACCCTCTGCACCCAGTTTTC | SEQ ID NO:92 |
| GAPDH | GGAGCGAGATCCCTCCAAAAT | SEQ ID NO:93 | GGCTGTTGTCATACTTCTCATGG | SEQ ID NO:94 |
| ACTB | CATGTACGTTGCTATCCAGGC | SEQ ID NO:95 | CTCCTTAATGTCACGCACGAT | SEQ ID NO:96 |
| 18S RRNA | GTAACCCGTTGAACCCCATT | SEQ ID NO:97 | CCATCCAATCGGTAGTAGCG | SEQ ID NO:98 |
| STAT3 | CAGCAGCTTGACACACGGTA | SEQ ID NO:99 | AAACACCAAAGTGGCATGTGA | SEQ ID NO:100 |
| RIN2 | TTGCCTCGGAGATCGGAGAA | SEQ ID NO:101 | TTCCTCGGAATAGCCACCATC | SEQ ID NO:102 |
| RBP7 | CTCAGCGGTACTTGGACCC | SEQ ID NO:103 | CGAGTGGCAAAGTCAATACCT | SEQ ID NO:104 |
| LRP1 | CTATCGACGCCCCTAAGACTT | SEQ ID NO:105 | CATCGCTGGGCCTTACTCT | SEQ ID NO:106 |
| GREM1 | CGGAGCGCAAATACCTGAAG | SEQ ID NO:107 | GGTTGATGATGGTGCGACTGT | SEQ ID NO:108 |
| EVC2 | ACCACTTGGAATGAAATTGGACA | SEQ ID NO:107 | GCGGTGTGTTATAGGAGACTCT | SEQ ID NO:110 |
| TLR7 | TCCTTGGGGCTAGATGGTTTC | SEQ ID NO:111 | TCCACGATCACATGGTTCTTTG | SEQ ID NO:112 |
| IL10 | GACTTTAAGGGTTACCTGGGTTG | SEQ ID NO:113 | TCACATGCGCCTTGATGTCTG | SEQ ID NO:114 |
| CD48 | AGGTTGGGATTCGTGTCTGG | SEQ ID NO:115 | AGTTGTTTGTAGTTCTCAGGCAG | SEQ ID NO:116 |
| SLAMF7 | ACCCTCATCTATATCCTTTGGCA | SEQ ID NO:117 | CACCAACGGAACCGACCAG | SEQ ID NO:118 |
| KLHDC7B | GCACCATGCACAACTACCTGT | SEQ ID NO:119 | ATTCGCCACCGATGGCATAG | SEQ ID NO:120 |
| MTCP1 | TCACCAAGAGGGTATCTACCG | SEQ ID NO:121 | GTGCCCTTAGGAAACTCGTCT | SEQ ID NO:122 |
| WEE2 | GGACTCCCCTTAGCAACGTG | SEQ ID NO:123 | AGGACATTTGAGAGGGTGTGA | SEQ ID NO:124 |
| ADAM12 | CGAGGGGTGAGCTTATGGAAC | SEQ ID NO:125 | GCTTTCCCGTTGTAGTCGAATA | SEQ ID NO:126 |
| PLAUR | TGTAAGACCAACGGGGATTGC | SEQ ID NO:127 | AGCCAGTCCGATAGCTCAGG | SEQ ID NO:128 |
| TIMP1 | ACCACCTTATACCAGCGTTATGA | SEQ ID NO:129 | GGTGTAGACGAACCGGATGTC | SEQ ID NO:130 |
| TIMP2 | GCTGCGAGTGCAAGATCAC | SEQ ID NO:131 | TGGTGCCCGTTGATGTTCTTC | SEQ ID NO:132 |
| TNFRSF1A | TCACCGCTTCAGAAAACCACC | SEQ ID NO:133 | GGTCCACTGTGCAAGAAGAGA | SEQ ID NO:134 |
| TNFRSF1B | TGAAACATCAGACGTGGTGTG | SEQ ID NO:135 | TGCAAATATCCGTGGATGAAGTC | SEQ ID NO:136 |
| CCL5 | CCAGCAGTCGTCTTTGTCAC | SEQ ID NO:137 | CTCTGGGTTGGCACACACTT | SEQ ID NO:138 |
| ARG1 | GTGGAAACTTGCATGGACAAC | SEQ ID NO:139 | AATCCTGGCACATCGGGAATC | SEQ ID NO:140 |
| ARG2 | CGCGAGTGCATTCCATCCT | SEQ ID NO:141 | TCCAAAGTCTTTTAGGTGGCAG | SEQ ID NO:142 |

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

1. Dohner, H., Weisdorf, D. J. & Bloomfield, C. D. Acute Myeloid Leukemia. *N Engl J Med* 373, 1136-1152, doi:10.1056/NEJMra1406184 (2015).
2. Kang, X. et al. The ITIM-containing receptor LAIR1 is essential for acute myeloid leukaemia development. *Nat Cell Biol* 17, 665-677, doi:10.1038/ncb3158 (2015).
3. Zheng, J. et al. Inhibitory receptors bind ANGPTLs and support blood stem cells and leukaemia development. *Nature* 485, 656-660, doi:10.1038/nature11095 (2012).
4. Liu, X. et al. ANGPTL2/LILRB2 signaling promotes the propagation of lung cancer cells. *Oncotarget* (2014).
5. Wang, L. et al. Co-expression of immunoglobulin-like transcript 4 and angiopoietin-like proteins in human non-small cell lung cancer. *Mol Med Rep* 11, 2789-2796, doi:10.3892/mmr.2014.3029 (2015).
6. Zhang, P. et al. ILT4 drives B7-H3 expression via PI3K/AKT/mTOR signalling and ILT4/B7-H3 co-expression correlates with poor prognosis in non-small cell lung cancer. *FEBS Lett*, doi:10.1016/j.febslet.2015.06.037 (2015).
7. Naji, A., Menier, C., Maki, G., Carosella, E. D. & Rouas-Freiss, N. Neoplastic B-cell growth is impaired by HLA-G/ILT2 interaction. *Leukemia* 26, 1889-1892, doi:10.1038/leu.2012.62 (2012).
8. Harly, C. et al. Up-regulation of cytolytic functions of human Vdelta2-gamma T lymphocytes through engagement of ILT2 expressed by tumor target cells. *Blood* 117, 2864-2873, doi:10.1182/blood-2010-09-309781 (2011).
9. Urosevic, M., Kamarashev, J., Burg, G. & Dummer, R. Primary cutaneous CD8+ and CD56+ T-cell lymphomas express HLA-G and killer-cell inhibitory ligand, ILT2. *Blood* 103, 1796-1798, doi:10.1182/blood-2003-10-3372 (2004).
10. Zhang, Y. et al. Expression of immunoglobulin-like transcript (ILT)2 and ILT3 in human gastric cancer and its clinical significance. *Mol Med Rep* 5, 910-916, doi:10.3892/mmr.2012.744 (2012).
11. Heidenreich, S. et al. Impact of the NK cell receptor LIR-1 (ILT-2/CD85j/LILRB1) on cytotoxicity against multiple myeloma. *Clinical & developmental immunology* 2012, 652130, doi:10.1155/2012/652130 (2012).
12. Colovai, A. I. et al. Expression of inhibitory receptor ILT3 on neoplastic B cells is associated with lymphoid tissue involvement in chronic lymphocytic leukemia. *Cytometry B Clin Cytom* 72, 354-362, doi:10.1002/cyto.b.20164 (2007).
13. Liu, J. et al. Inhibitory receptor immunoglobulin-like transcript 4 was highly expressed in primary ductal and lobular breast cancer and significantly correlated with IL-10. Diagnostic pathology 9, 85, doi:10.1186/1746-1596-9-85 (2014).
14. Sun, Y., Liu, J., Gao, P., Wang, Y. & Liu, C. Expression of Ig-like transcript 4 inhibitory receptor in human non-small cell lung cancer. Chest 134, 783-788, doi:10.1378/chest.07-1100 (2008).
15. Pfistershammer, K. et al. Allogeneic disparities in immunoglobulin-like transcript 5 induce potent antibody responses in hematopoietic stem cell transplant recipients. *Blood* 114, 2323-2332, doi:10.1182/blood-2008-10-183814 (2009).
16. Suciu-Foca, N. et al. Soluble Ig-like transcript 3 inhibits tumor allograft rejection in humanized SCID mice and T cell responses in cancer patients. *J Immunol* 178, 7432-7441 (2007).
17. Cortesini, R. Pancreas cancer and the role of soluble immunoglobulin-like transcript 3 (ILT3). *JOP: Journal of the pancreas* 8, 697-703 (2007).
18. Chen, Z. et al. Signalling thresholds and negative B-cell selection in acute lymphoblastic leukaemia. *Nature* 521, 357-361, doi:10.1038/nature14231 (2015).
19. Ma, G. et al. Paired immunoglobin-like receptor-B regulates the suppressive function and fate of myeloid-derived suppressor cells. *Immunity* 34, 385-395, doi:10.1016/j.immuni.2011.02.004 (2011).
20. Hirayasu, K. & Arase, H. Functional and genetic diversity of leukocyte immunoglobulin-like receptor and implication for disease associations. *Journal of human genetics*, doi:10.1038/jhg.2015.64 (2015).
21. Trowsdale, J., Jones, D. C., Barrow, A. D. & Traherne, J. A. Surveillance of cell and tissue perturbation by receptors in the LRC. *Immunol Rev* 267, 117-136, doi:10.1111/imr.12314 (2015).
22. Kang, X. et al. Inhibitory leukocyte immunoglobulin-like receptors: Immune checkpoint proteins and tumor sustaining factors. *Cell Cycle* 15, 25-40, doi:10.1080/15384101.2015.1121324 (2016).
23. Sharma, P. & Allison, J. P. Immune checkpoint targeting in cancer therapy: toward combination strategies with curative potential. Cell 161, 205-214, doi:10.1016/j.cell.2015.03.030 (2015).
24. Chang, C. C. et al. Tolerization of dendritic cells by T(S) cells: the crucial role of inhibitory receptors ILT3 and ILT4. *Nat Immunol* 3, 237-243, doi:10.1038/ni760 (2002).
25. Vlad, G. et al. Membrane and soluble ILT3 are critical to the generation of T suppressor cells and induction of immunological tolerance. *Int Rev Immunol* 29, 119-132, doi:10.3109/08830180903281185 (2010).
26. Dobrowolska, H. et al. Expression of immune inhibitory receptor ILT3 in acute myeloid leukemia with monocytic differentiation. *Cytometry B Clin Cytom* 84, 21-29, doi:10.1002/cyto.b.21050 (2013).
27. Kubagawa, H., Burrows, P. D. & Cooper, M. D. A novel pair of immunoglobulin-like receptors expressed by B cells and myeloid cells. *Proc Natl Acad Sci USA* 94, 5261-5266 (1997).
28. Katz, H. R. et al. Mouse mast cell gp49B1 contains two immunoreceptor tyrosine-based inhibition motifs and suppresses mast cell activation when coligated with the high-affinity Fc receptor for IgE. *Proc Natl Acad Sci USA* 93, 10809-10814 (1996).
29. de Goeje, P. L. et al. Immunoglobulin-like transcript 3 is expressed by myeloid-derived suppressor cells and correlates with survival in patients with non-small cell lung cancer. Oncoimmunology 4, e1014242, doi:10.1080/2162402X.2015.1014242 (2015).

30. Mori, Y. et al. Inhibitory immunoglobulin-like receptors LILRB and PIR-B negatively regulate osteoclast development. *J Immunol* 181, 4742-4751 (2008).
31. Deng, M. et al. A motif in LILRB2 critical for Angptl2 binding and activation. *Blood* 124, 924-935, doi:10.1182/blood-2014-01-549162 (2014).
32. Mosier, D. E., Gulizia, R. J., Baird, S. M. & Wilson, D. B. Transfer of a functional human immune system to mice with severe combined immunodeficiency. *Nature* 335, 256-259, doi:10.1038/335256a0 (1988).
33. Ha, S. et al. Isolation and characterization of IgG1 with asymmetrical Fc glycosylation. *Glycobiology* 21, 1087-1096, doi:10.1093/glycob/cwr047 (2011).
34. Castells, M. C. et al. gp49B1-alpha(v)beta3 interaction inhibits antigen-induced mast cell activation. *Nat Immunol* 2, 436-442, doi:10.1038/87749 (2001).
35. Grainger, D. J., Reckless, J. & McKilligin, E. Apolipoprotein E modulates clearance of apoptotic bodies in vitro and in vivo, resulting in a systemic proinflammatory state in apolipoprotein E-deficient mice. *J Immunol* 173, 6366-6375 (2004).
36. Ali, K., Middleton, M., Pure, E. & Rader, D. J. Apolipoprotein E suppresses the type I inflammatory response in vivo. *Circ Res* 97, 922-927, doi:10.1161/01.res.0000187467.67684.43 (2005).
37. You, M., Flick, L. M., Yu, D. & Feng, G. S. Modulation of the nuclear factor kappa B pathway by Shp-2 tyrosine phosphatase in mediating the induction of interleukin (IL)-6 by IL-1 or tumor necrosis factor. *J Exp Med* 193, 101-110 (2001).
38. Bene, M. C. et al. CD87 (urokinase-type plasminogen activator receptor), function and pathology in hematological disorders: a review. *Leukemia* 18, 394-400, doi:10.1038/sj.leu. 2403250 (2004).
39. Su, S. C., Lin, C. W., Yang, W. E., Fan, W. L. & Yang, S. F. The urokinase-type plasminogen activator (uPA) system as a biomarker and therapeutic target in human malignancies. *Expert Opin Ther Targets* 20, 551-566, doi:10.1517/14728222.2016.1113260 (2016).
40. Wang, Y. et al. Identification of a novel nuclear factor-kappaB sequence involved in expression of urokinase-type plasminogen activator receptor. *Eur J Biochem* 267, 3248-3254 (2000).
41. Moreau, M., Mourah, S. & Dosquet, C. beta-Catenin and NF-kappaB cooperate to regulate the uPA/uPAR system in cancer cells. *Int J Cancer* 128, 1280-1292, doi:10.1002/ijc.25455 (2011).
42. Westhoff, M. A. et al. Inhibition of NF-kappaB signaling ablates the invasive phenotype of glioblastoma. *Mol Cancer Res* 11, 1611-1623, doi:10.1158/1541-7786.mcr-13-0435-t (2013).
43. Chang, H. J. et al. Triptolide inhibits tumor promoter-induced uPAR expression via blocking NF-kappaB signaling in human gastric AGS cells. *Anticancer Res* 27, 3411-3417 (2007).
44. Hu, J. et al. uPAR induces expression of transforming growth factor beta and interleukin-4 in cancer cells to promote tumor-permissive conditioning of macrophages. *Am J Pathol* 184, 3384-3393, doi:10.1016/j.ajpath.2014.08.003 (2014).
45. Ilkovitch, D. & Lopez, D. M. Urokinase-mediated recruitment of myeloid-derived suppressor cells and their suppressive mechanisms are blocked by MUC1/sec. *Blood* 113, 4729-4739, doi:10.1182/blood-2008-08-176438 (2009).
46. Billottet, C. et al. Modulation of several waves of gene expression during FGF-1 induced epithelial-mesenchymal transition of carcinoma cells. *J Cell Biochem* 104, 826-839, doi:10.1002/jcb.21667 (2008).
47. Mussai, F. et al. Acute myeloid leukemia creates an arginase-dependent immunosuppressive microenvironment. *Blood* 122, 749-758, doi:10.1182/blood-2013-01-480129 (2013).
48. Yoshida, H. & Hunter, C. A. The immunobiology of interleukin-27. *Annu Rev Immunol* 33, 417-443, doi:10.1146/annurev-immunol-032414-112134 (2015).
49. Fujisaki, J. et al. In vivo imaging of Treg cells providing immune privilege to the haematopoietic stem-cell niche. *Nature* 474, 216-219, doi:10.1038/nature10160 (2011).
50. Schlecker, E. et al. Tumor-infiltrating monocytic myeloid-derived suppressor cells mediate CCRS-dependent recruitment of regulatory T cells favoring tumor growth. *J Immunol* 189, 5602-5611, doi:10.4049/jimmunol.1201018 (2012).
51. Joosten, S. A. et al. Identification of a human CD8+ regulatory T cell subset that mediates suppression through the chemokine CC chemokine ligand 4. *Proc Natl Acad Sci USA* 104, 8029-8034, doi:10.1073/pnas.0702257104 (2007).
52. Long, E. O., Kim, H. S., Liu, D., Peterson, M. E. & Rajagopalan, S. Controlling natural killer cell responses: integration of signals for activation and inhibition. *Annu Rev Immunol* 31, 227-258, doi:10.1146/annurev-immunol-020711-075005 (2013).
53. Kim-Schulze, S. et al. Recombinant Ig-like transcript 3-Fc modulates T cell responses via induction of Th anergy and differentiation of CD8+T suppressor cells. *J Immunol* 176, 2790-2798 (2006).
54. Singh, N. et al. Monocyte lineage-derived IL-6 does not affect chimeric antigen receptor T-cell function. *Cytotherapy* 19, 867-880, doi:10.1016/j.jcyt.2017.04.001 (2017).
55. Piedrahita, J. A., Zhang, S. H., Hagaman, J. R., Oliver, P. M. & Maeda, N. Generation of mice carrying a mutant apolipoprotein E gene inactivated by gene targeting in embryonic stem cells. *Proc Natl Acad Sci USA* 89, 4471-4475 (1992).
56. Zhang, C. C., Kaba, M., Iizuka, S., Huynh, H. & Lodish, H. F. Angiopoietin-like 5 and IGFBP2 stimulate ex vivo expansion of human cord blood hematopoietic stem cells as assayed by NOD/SCID transplantation. Blood 111, 3415-3423, doi:blood-2007-11-122119 [pii] 10.1182/blood-2007-11-122119 [doi] (2008).
57. Zheng, J. et al. Ex vivo expanded hematopoietic stem cells overcome the MHC barrier in allogeneic transplantation. *Cell Stem Cell* 9, 119-130, doi:10.1016/j.stem.2011.06.003 (2011).
58. Zheng, J., Huynh, H., Umikawa, M., Silvany, R. & Zhang, C. C. Angiopoietin-like protein 3 supports the activity of hematopoietic stem cells in the bone marrow niche. *Blood* 117, 470-479, doi:10.1182/blood-2010-06-291716 (2011).
59. Lu, Z. et al. Fasting selectively blocks development of acute lymphoblastic leukemia via leptin-receptor upregulation. *Nat Med* 23, 79-90, doi:10.1038/nm.4252 (2017).
60. Huynh, H. et al. IGF binding protein 2 supports the survival and cycling of hematopoietic stem cells. *Blood* 118, 3236-3243, doi:10.1182/blood-2011-01-331876 (2011).

What is claimed is:

1. A method of identifying a modulator of Leukocyte Immunoglobulin-Like Receptor B4 (LILRB4) activation comprising:

(a) contacting a reporter cell with Apolipoprotein E (ApoE) and a candidate substance, wherein the reporter cell expresses a reporter gene that encodes a detectable reporter operably linked to a promoter regulated by activation of LILRB4; and (b) detecting a level of LILRB4 activation in the reporter cell, wherein an increase or decrease in the level of LILRB4 activation as compared to a reference level measured from a reporter cell not treated with said candidate substance indicates that the candidate substance is a modulator of LILRB4 activation in the reporter cell.

2. The method of claim 1, wherein the reporter cell expresses a receptor comprising an extracellular domain of LILRB4.

3. The method of claim 1, wherein the cell is a T-cell hybridoma or leukemia cell.

4. The method of claim 2, wherein the receptor further comprises an intracellular domain of paired immunoglobulin-like receptor β (PILRβ).

5. The method of claim 1, wherein the receptor is expressed in the cell through a viral expression vector.

6. The method of claim 5, wherein the viral expression vector is a retroviral expression vector.

7. The method of claim 1, wherein the level of LILRB4 activation is detected based on the morphology or mobility of the cell.

8. The method of claim 1, wherein the reporter cell expresses a reporter gene that encodes a detectable label or encodes a protein that utilizes or produces a detectable label and is operably linked to a promoter regulated by activation of the receptor.

9. The method of claim 8, wherein the promoter is a nuclear factor of activated T cells (NFAT) promoter.

10. The method of claim 8, wherein the promoter is a chemokine ligand 2 promoter, a chemokine ligand 4 promoter, a chemokine ligand 5 promoter, an Interleukin 6R promoter, an Interleukin 8 promoter, a glycoprotein 130 promoter, an Oncostatin M promoter, a Tissue Metalloproteinase Inhibitor ½ promoter, a Tumor Necrosis Factor receptor I/II promoter, a urokinase Plasminogen Activator Receptor uPAR promoter or an arginase-1 promoter.

11. The method of claim 8, wherein the detectable label is a colorometric label, fluorescent label, bioluminescent label, or chemiluminescent label.

12. The method of claim 8, wherein the detectable label is green fluorescent protein, yellow fluorescent protein, red fluorescent protein, or D-luciferin.

13. The method of claim 8, wherein the detectable label is GFP.

14. The method of claim 8, wherein detecting step comprises flow cytometry analysis or quantification of luminescence.

15. The method of claim 1, wherein the candidate substance is an antibody.

16. The method of claim 15, wherein the antibody is a monoclonal antibody, a chimeric antibody, a CDR-grafted antibody, a humanized antibody, a Fab, a Fab', a F(ab')2, a Fv, or a scFv.

17. The method of claim 15, wherein the antibody is a monoclonal antibody.

18. The method of claim 1, wherein the reference level is obtained in the reporter cell when it is contacted with only ApoE.

19. The method of claim 1, wherein the ApoE is recombinant.

20. The method of claim 1, wherein the ApoE is human ApoE or mouse ApoE.

21. The method of claim 20, wherein the human ApoE or mouse ApoE is isolated from human serum or mouse serum, respectively.

22. The method of claim 1, wherein the ApoE is further defined as ApoE2, ApoE3, or ApoE4.

23. The method of claim 1, wherein an increase in the level of LILRB4 activation as compared to the reference level indicates that the modulator is an agonist.

24. The method of claim 1, wherein a decrease in the level of LILRB4 activation as compared to the reference level indicates that the modulator is an antagonist.

25. The method of claim 1, wherein the candidate substance is linked to a substrate.

26. The method of claim 1, wherein the candidate substance is linked to a cell expressing FcR.

* * * * *

SEQUENCE LISTING

<160> NUMBER OF SEQ ID NOS: 196

<210> SEQ ID NO 1
<211> LENGTH: 21
<212> TYPE: DNA
<213> ORGANISM: Artificial Sequence
<220> FEATURE:
<223> OTHER INFORMATION: control sgRNA

<400> SEQUENCE: 1
gaacgactag ttaggcgtgt a 21

<210> SEQ ID NO 2
<211> LENGTH: 20
<212> TYPE: DNA
<213> ORGANISM: Artificial Sequence
<220> FEATURE:
<223> OTHER INFORMATION: sgRNA1

<400> SEQUENCE: 2
tgttactatc gcagccctgt 20

<210> SEQ ID NO 3
<211> LENGTH: 20
<212> TYPE: DNA
<213> ORGANISM: Artificial Sequence
<220> FEATURE:
<223> OTHER INFORMATION: sgRNA2

<400> SEQUENCE: 3
gtaggtcccc ccgtgcactg 20

<210> SEQ ID NO 4
<211> LENGTH: 20
<212> TYPE: DNA
<213> ORGANISM: Artificial Sequence
<220> FEATURE:
<223> OTHER INFORMATION: sgRNA3

<400> SEQUENCE: 4
cctgtgacct cagtgcacgg 20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tggcaaaacg tcttcaggag g 21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
agcttgactt agtggctttg g 21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aactcatttt gcggtcgcta t 21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tccctgaatt gctcgctcac 20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
accctgacca tccaagtcaa a 21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ttggcctcgc atcttagaaa g 21

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
accgctttgc ggaatctca 19

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
aggtcaggga aacatcaggg a 21

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
actcacctct tcagaacgaa ttg 23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ccatctttgg aaggttcagg ttg 23

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
agagctgtga taagccagtt cc 22

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
aattcctcga aagtgaagtg tgt 23

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
agttctctgc atcacttgct g 21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cggcttcgct tggttaggaa 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
atcagagctg ggctgcgata 20

<210> SEQ ID NO 20
<211> LENGTH: 20
<212> TYPE: DNA
<213> ORGANISM: Artificial Sequence
<220> FEATURE:
<223> OTHER INFORMATION: Primer -continued

<400> SEQUENCE: 20
caggtcgaac gactctctcc 20

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
atgatggctt attacagtgg caa 23

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gtcggagatt cgtagctgga 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atgcccagac atctgtgtcc 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggggtctcta tgcccaacaa 20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cagccagatg caatcaatgc c 21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tggaatcctg aacccacttc t 21

<210> SEQ ID NO 27

<211> LENGTH: 19
<212> TYPE: DNA
<213> ORGANISM: Artificial Sequence
<220> FEATURE:
<223> OTHER INFORMATION: Primer

<400> SEQUENCE: 27
cagccgcagg gttctctac 19

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
gatctggcag aagacgatgg t 21

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
cagcgagtgg accagatcc 19

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
ccaaagagga ggtagtggct atc 23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
cagcttgact caaaattcct gga 23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tgaagattac gcttgctttt cct 23

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
ccaacgtgac ggacttccc 19

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
tacacgacta tgcggtacag c 21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ccaagcccgg aattgtcttc a 21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
gggttggtac agacggaatg g 21

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
ccagctttac tcgcacagc 19

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
agccttggaa tcatcactcc c 21

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
ccgacagatt ccacagaa 18

<210> SEQ ID NO 40
<211> LENGTH: 20
<212> TYPE: DNA

<213> ORGANISM: Artificial Sequence
<220> FEATURE:
<223> OTHER INFORMATION: Primer

<400> SEQUENCE: 40
ttggttagga agatgacact 20

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
ccggaggcgc tttactacc 19

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
taggggtgta ggcaggttca c 21

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
cctgcgcctc aagaccttc 19

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gtcactgcgc tccagtagaa 20

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45
cgcatctcct ccatactc 18

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
acctaataca ataatacagc acat 24

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ctcagggaca acagtcagtt c 21

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
acagggctat cagggagca 19

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
ctcctgcaag agtttgatgt cc 22

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
tcatgccgat gtcatggtag g 21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
ctgaaccgta agcccattga g 21

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
cgctccacac cacgatgac 19

<210> SEQ ID NO 53
<211> LENGTH: 19
<212> TYPE: DNA
<213> ORGANISM: Artificial Sequence
<220> FEATURE:

<223> OTHER INFORMATION: Primer

<400> SEQUENCE: 53
ctgggccagc gtatagctc 19

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
agcaagctgc tttcgtccc 19

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
ctgtgctgat cccagtgaat c 21

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
tcagttcagt tccaggtcat aca 23

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
gctcctcact gttgttctac g 21

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
cgggccgctg aaagtcatt 19

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
ggaccccaac aacaagag 18

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
gtgaggaggc ttcaagac 18

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ggagtcgaga catcttgact ga 22

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
atgaggaccg ttttatgggc t 21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
gtggcattca aggagtacct c 21

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
tgatggcctt cgattctgga tt 22

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
gtggtgctgt cgctcttgat a 21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
ccccagaaaa tggttcacgc t 21

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
tacaggctgg ctcaggacta t 21

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
cgcaacattt tgtagcactc tg 22

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
tcaggctgtt tgtctctgaa gg 22

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
catgctctca tactgacacc ac 22

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
tcattgccac gtacaggctc 20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
gggtcgggct tgatgatgtg 20

<210> SEQ ID NO 73
<211> LENGTH: 21

<212> TYPE: DNA
<213> ORGANISM: Artificial Sequence
<220> FEATURE:
<223> OTHER INFORMATION: Primer

<400> SEQUENCE: 73
tcccaggccc agttcataaa t 21

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
tgctttgtga gatgtaggag gt 22

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
tcctgtggaa gatcaccaat gt 22

<210> SEQ ID NO 76
<211> LENGTH: 19
<212> TYPE: DNA
<213> ORGANISM: Artificial Sequence
<220> FEATURE:
<223> OTHER INFORMATION: Primer

<400> SEQUENCE: 76
gcaggcacaa cttgtagcc 19

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
tgaggtcacg gacgattaca t 21

<210> SEQ ID NO 78
<211> LENGTH: 22
<212> TYPE: DNA
<213> ORGANISM: Artificial Sequence
<220> FEATURE:
<223> OTHER INFORMATION: Primer

<400> SEQUENCE: 78
gtaggcccac gaaacaaatg at 22

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79

-continued tgctgtacca agagtttgct c 21

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
cgcacacaga caactttttc ttt 23

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
tggagagcta cacaagaatc acc 23

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
tggtccagat gcttcatgga a 21

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
tggtagtagc aaccaacggg a 21

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
actttgattg agggcgtcat tc 22

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
tgtatatgtc atctcagt 18

<210> SEQ ID NO 86
<211> LENGTH: 19
<212> TYPE: DNA
<213> ORGANISM: Artificial Sequence
<220> FEATURE:
<223> OTHER INFORMATION: Primer

<400> SEQUENCE: 86
taataacaat atgcttcca 19

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
tgttggccca atggattgaa a 21

<210> SEQ ID NO 88
<211> LENGTH: 23
<212> TYPE: DNA
<213> ORGANISM: Artificial Sequence
<220> FEATURE:
<223> OTHER INFORMATION: Primer

<400> SEQUENCE: 88
ggaaacacga cctaactgtt cat 23

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
ttcagtatca caacctcagc aag 23

<210> SEQ ID NO 90
<211> LENGTH: 22
<212> TYPE: DNA
<213> ORGANISM: Artificial Sequence
<220> FEATURE:
<223> OTHER INFORMATION: Primer

<400> SEQUENCE: 90
tggacctgca agttaaaatc cc 22

<210> SEQ ID NO 91
<211> LENGTH: 22
<212> TYPE: DNA
<213> ORGANISM: Artificial Sequence
<220> FEATURE:
<223> OTHER INFORMATION: Primer

<400> SEQUENCE: 91
ttttgccaag gagtgctaaa ga 22

<210> SEQ ID NO 92
<211> LENGTH: 21
<212> TYPE: DNA
<213> ORGANISM: Artificial Sequence
<220> FEATURE:
<223> OTHER INFORMATION: Primer

<400> SEQUENCE: 92
aaccctctgc acccagtttt c 21

<210> SEQ ID NO 93
<211> LENGTH: 21
<212> TYPE: DNA
<213> ORGANISM: Artificial Sequence
<220> FEATURE:
<223> OTHER INFORMATION: Primer

<400> SEQUENCE: 93
ggagcgagat ccctccaaaa t 21

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
ggctgttgtc atacttctca tgg 23

<210> SEQ ID NO 95
<211> LENGTH: 21
<212> TYPE: DNA
<213> ORGANISM: Artificial Sequence
<220> FEATURE:
<223> OTHER INFORMATION: Primer

<400> SEQUENCE: 95
catgtacgtt gctatccagg c 21

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
ctccttaatg tcacgcacga t 21

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
gtaacccgtt gaaccccatt 20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ccatccaatc ggtagtagcg 20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
cagcagcttg acacacggta 20

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
aaacaccaaa gtggcatgtg a 21

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ttgcctcgga gatcggagaa 20

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
ttcctcggaa tagccaccat c 21

<210> SEQ ID NO 103
<211> LENGTH: 19
<212> TYPE: DNA
<213> ORGANISM: Artificial Sequence
<220> FEATURE:
<223> OTHER INFORMATION: Primer

<400> SEQUENCE: 103
ctcagcggta cttggaccc 19

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
cgagtggcaa agtcaatacc t 21

<210> SEQ ID NO 105
<211> LENGTH: 21
<212> TYPE: DNA
<213> ORGANISM: Artificial Sequence
<220> FEATURE:
<223> OTHER INFORMATION: Primer

<400> SEQUENCE: 105
ctatcgacgc ccctaagact t 21

<210> SEQ ID NO 106

-continued

<211> LENGTH: 19
<212> TYPE: DNA
<213> ORGANISM: Artificial Sequence
<220> FEATURE:
<223> OTHER INFORMATION: Primer

<400> SEQUENCE: 106
catcgctggg ccttactct 19

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
cggagcgcaa atacctgaag 20

<210> SEQ ID NO 108
<211> LENGTH: 21
<212> TYPE: DNA
<213> ORGANISM: Artificial Sequence
<220> FEATURE:
<223> OTHER INFORMATION: Primer

<400> SEQUENCE: 108
ggttgatgat ggtgcgactg t 21

<210> SEQ ID NO 109
<211> LENGTH: 23
<212> TYPE: DNA
<213> ORGANISM: Artificial Sequence
<220> FEATURE:
<223> OTHER INFORMATION: Primer

<400> SEQUENCE: 109
accacttgga atgaaattgg aca 23

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
gcggtgtgtt ataggagact ct 22

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
tccttggggc tagatggttt c 21

<210> SEQ ID NO 112
<211> LENGTH: 22
<212> TYPE: DNA
<213> ORGANISM: Artificial Sequence
<220> FEATURE:
<223> OTHER INFORMATION: Primer

<400> SEQUENCE: 112
tccacgatca catggttctt tg 22

<210> SEQ ID NO 113
<211> LENGTH: 23
<212> TYPE: DNA
<213> ORGANISM: Artificial Sequence
<220> FEATURE:
<223> OTHER INFORMATION: Primer

<400> SEQUENCE: 113
gactttaagg gttacctggg ttg 23

<210> SEQ ID NO 114
<211> LENGTH: 21
<212> TYPE: DNA
<213> ORGANISM: Artificial Sequence
<220> FEATURE:
<223> OTHER INFORMATION: Primer

<400> SEQUENCE: 114
tcacatgcgc cttgatgtct g 21

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
aggttgggat tcgtgtctgg 20

<210> SEQ ID NO 116
<211> LENGTH: 23
<212> TYPE: DNA
<213> ORGANISM: Artificial Sequence
<220> FEATURE:
<223> OTHER INFORMATION: Primer

<400> SEQUENCE: 116
agttgtttgt agttctcagg cag 23

<210> SEQ ID NO 117
<211> LENGTH: 23
<212> TYPE: DNA
<213> ORGANISM: Artificial Sequence
<220> FEATURE:
<223> OTHER INFORMATION: Primer

<400> SEQUENCE: 117
accctcatct atatcctttg gca 23

<210> SEQ ID NO 118
<211> LENGTH: 19
<212> TYPE: DNA
<213> ORGANISM: Artificial Sequence
<220> FEATURE:
<223> OTHER INFORMATION: Primer

<400> SEQUENCE: 118
caccaacgga accgaccag 19

<210> SEQ ID NO 119
<211> LENGTH: 21
<212> TYPE: DNA

<213> ORGANISM: Artificial Sequence
<220> FEATURE:
<223> OTHER INFORMATION: Primer

<400> SEQUENCE: 119
gcaccatgca caactacctg t 21

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
attcgccacc gatggcatag 20

<210> SEQ ID NO 121
<211> LENGTH: 21
<212> TYPE: DNA
<213> ORGANISM: Artificial Sequence
<220> FEATURE:
<223> OTHER INFORMATION: Primer

<400> SEQUENCE: 121
tcaccaagag ggtatctacc g 21

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
gtgcccttag gaaactcgtc t 21

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
ggactcccct tagcaacgtg 20

<210> SEQ ID NO 124
<211> LENGTH: 21
<212> TYPE: DNA
<213> ORGANISM: Artificial Sequence
<220> FEATURE:
<223> OTHER INFORMATION: Primer

<400> SEQUENCE: 124
aggacatttg agagggtgtg a 21

<210> SEQ ID NO 125
<211> LENGTH: 21
<212> TYPE: DNA
<213> ORGANISM: Artificial Sequence
<220> FEATURE:
<223> OTHER INFORMATION: Primer

<400> SEQUENCE: 125
cgaggggtga gcttatggaa c 21

<210> SEQ ID NO 126
<211> LENGTH: 22
<212> TYPE: DNA
<213> ORGANISM: Artificial Sequence
<220> FEATURE:
<223> OTHER INFORMATION: Primer

<400> SEQUENCE: 126
gctttcccgt tgtagtcgaa ta 22

<210> SEQ ID NO 127
<211> LENGTH: 21
<212> TYPE: DNA
<213> ORGANISM: Artificial Sequence
<220> FEATURE:
<223> OTHER INFORMATION: Primer

<400> SEQUENCE: 127
tgtaagacca acggggattg c 21

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
agccagtccg atagctcagg 20

<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
accaccttat accagcgtta tga 23

<210> SEQ ID NO 130
<211> LENGTH: 21
<212> TYPE: DNA
<213> ORGANISM: Artificial Sequence
<220> FEATURE:
<223> OTHER INFORMATION: Primer

<400> SEQUENCE: 130
ggtgtagacg aaccggatgt c 21

<210> SEQ ID NO 131
<211> LENGTH: 19
<212> TYPE: DNA
<213> ORGANISM: Artificial Sequence
<220> FEATURE:
<223> OTHER INFORMATION: Primer

<400> SEQUENCE: 131
gctgcgagtg caagatcac 19

<210> SEQ ID NO 132
<211> LENGTH: 21
<212> TYPE: DNA
<213> ORGANISM: Artificial Sequence
<220> FEATURE:

-continued

<223> OTHER INFORMATION: Primer

<400> SEQUENCE: 132
tggtgcccgt tgatgttctt c 21

<210> SEQ ID NO 133
<211> LENGTH: 21
<212> TYPE: DNA
<213> ORGANISM: Artificial Sequence
<220> FEATURE:
<223> OTHER INFORMATION: Primer

<400> SEQUENCE: 133
tcaccgcttc agaaaaccac c 21

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
ggtccactgt gcaagaagag a 21

<210> SEQ ID NO 135
<211> LENGTH: 21
<212> TYPE: DNA
<213> ORGANISM: Artificial Sequence
<220> FEATURE:
<223> OTHER INFORMATION: Primer

<400> SEQUENCE: 135
tgaaacatca gacgtggtgt g 21

<210> SEQ ID NO 136
<211> LENGTH: 23
<212> TYPE: DNA
<213> ORGANISM: Artificial Sequence
<220> FEATURE:
<223> OTHER INFORMATION: Primer

<400> SEQUENCE: 136
tgcaaatatc cgtggatgaa gtc 23

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
ccagcagtcg tctttgtcac 20

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
ctctgggttg gcacacactt 20

<210> SEQ ID NO 139
<211> LENGTH: 21
<212> TYPE: DNA
<213> ORGANISM: Artificial Sequence
<220> FEATURE:
<223> OTHER INFORMATION: Primer

<400> SEQUENCE: 139
gtggaaactt gcatggacaa c 21

<210> SEQ ID NO 140
<211> LENGTH: 21
<212> TYPE: DNA
<213> ORGANISM: Artificial Sequence
<220> FEATURE:
<223> OTHER INFORMATION: Primer

<400> SEQUENCE: 140
aatcctggca catcgggaat c 21

<210> SEQ ID NO 141
<211> LENGTH: 19
<212> TYPE: DNA
<213> ORGANISM: Artificial Sequence
<220> FEATURE:
<223> OTHER INFORMATION: Primer

<400> SEQUENCE: 141
cgcgagtgca ttccatcct 19

<210> SEQ ID NO 142
<211> LENGTH: 22
<212> TYPE: DNA
<213> ORGANISM: Artificial Sequence
<220> FEATURE:
<223> OTHER INFORMATION: Primer

<400> SEQUENCE: 142
tccaaagtct tttaggtggc ag 22

<210> SEQ ID NO 143
<211> LENGTH: 1953
<212> TYPE: DNA
<213> ORGANISM: Homo sapiens
<220> FEATURE:
<221> NAME/KEY: source
<222> LOCATION: (1)..(1953)
<223> OTHER INFORMATION: cDNA LILRB1

<400> SEQUENCE: 143
atgaccccca tcctcacggt cctgatctgt ctcgggctga gtctgggccc ccggacccac 60
gtgcaggcag ggcacctccc caagcccacc ctctgggctg aaccaggctc tgtgatcacc 120
caggggagtc ctgtgaccct caggtgtcag gggggccagg agacccagga gtaccgtcta 180
tatagagaaa agaaaacagc accctggatt acacggatcc cacaggagct tgtgaagaag 240
ggccagttcc ccatcccatc catcacctgg gaacacacag ggcggtatcg ctgttactat 300
ggtagcgaca ctgcaggccg ctcagagagc agtgaccccc tggagctggt ggtgacagga 360
gcctacatca aacccaccct ctcagcccag cccagccccg tggtgaactc aggagggaat 420
gtaaccctcc agtgtgactc acaggtggca tttgatggct tcattctgtg taaggaagga 480
gaagatgaac acccacaatg cctgaactcc cagccccatg cccgtgggtc gtcccgcgcc 540
atcttctccg tgggccccgt gagcccgagt cgcaggtggt ggtacaggtg ctatgcttat 600

```
gactcgaact ctccctatga gtggtctcta cccagtgatc tcctggagct cctggtccta    660

ggtgtttcta agaagccatc actctcagtg cagccaggtc ctatcgtggc ccctgaggag    720

accctgactc tgcagtgtgg ctctgatgct ggctacaaca gatttgttct gtataaggac    780

ggggaacgtg acttccttca gctcgctggc gcacagcccc aggctgggct ctcccaggcc    840

aacttcaccc tgggccctgt gagccgctcc tacgggggcc agtacagatg ctacggtgca    900

cacaacctct cctccgagtg gtcggccccc agcgaccccc tggacatcct gatcgcagga    960

cagttctatg acagagtctc cctctcggtg cagccgggcc ccacggtggc ctcaggagag   1020

aacgtgaccc tgctgtgtca gtcacaggga tggatgcaaa ctttccttct gaccaaggag   1080

ggggcagctg atgacccatg gcgtctaaga tcaacgtacc aatctcaaaa ataccaggct   1140

gaattcccca tgggtcctgt gacctcagcc catgcgggga cctacaggtg ctacggctca   1200

cagagctcca aaccctacct gctgactcac cccagtgacc ccctggagct cgtggtctca   1260

ggaccgtctg gggccccag ctccccgaca acaggcccca cctccacatc tggccctgag   1320

gaccagcccc tcacccccac cggtcggat ccccagagtg gtctgggaag gcacctgggg   1380

gttgtgatcg gcatcttggt ggccgtcatc ctactgctcc tcctcctcct cctcctcttc   1440

ctcatcctcc gacatcgacg tcagggcaaa cactggacat cgacccagag aaaggctgat   1500

ttccaacatc ctgcaggggc tgtggggcca gagcccacag acagaggcct gcagtggagg   1560

tccagcccag ctgccgatgc ccaggaagaa aacctctatg ctgccgtgaa gcacacacag   1620

cctgaggatg gggtggagat ggacactcgg agcccacacg atgaagaccc ccaggcagtg   1680

acgtatgccg aggtgaaaca ctccagacct aggagagaaa tggcctctcc tccttcccca   1740

ctgtctgggg aattcctgga cacaaaggac agacaggcgg aagaggacag gcagatggac   1800

actgaggctg ctgcatctga agcccccag gatgtgacct acgcccagct gcacagcttg   1860

accctcagac gggaggcaac tgagcctcct ccatcccagg aagggccctc tccagctgtg   1920

cccagcatct acgccactct ggccatccac tag                               1953
```

<210> SEQ ID NO 144
<211> LENGTH: 650
<212> TYPE: PRT
<213> ORGANISM: Homo sapiens
<220> FEATURE:
<221> NAME/KEY: source
<222> LOCATION: (1)..(650)
<223> OTHER INFORMATION: LILRB1

<400> SEQUENCE: 144

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110
```

-continued

```
Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
```

530 535 540

Val Glu Met Asp Thr Arg Ser Pro His Asp Glu Asp Pro Gln Ala Val
545 550 555 560

Thr Tyr Ala Glu Val Lys His Ser Arg Pro Arg Arg Glu Met Ala Ser
565 570 575

Pro Pro Ser Pro Leu Ser Gly Glu Phe Leu Asp Thr Lys Asp Arg Gln
580 585 590

Ala Glu Glu Asp Arg Gln Met Asp Thr Glu Ala Ala Ala Ser Glu Ala
595 600 605

Pro Gln Asp Val Thr Tyr Ala Gln Leu His Ser Leu Thr Leu Arg Arg
610 615 620

Glu Ala Thr Glu Pro Pro Pro Ser Gln Glu Gly Pro Ser Pro Ala Val
625 630 635 640

Pro Ser Ile Tyr Ala Thr Leu Ala Ile His
645 650

<210> SEQ ID NO 145
<211> LENGTH: 438
<212> TYPE: PRT
<213> ORGANISM: Homo sapiens
<220> FEATURE:
<221> NAME/KEY: source
<222> LOCATION: (1)..(438)
<223> OTHER INFORMATION: Extracellular domain sequence of LILRB1

<400> SEQUENCE: 145

Gly His Leu Pro Lys Pro Thr Leu Trp Ala Glu Pro Gly Ser Val Ile
1 5 10 15

Thr Gln Gly Ser Pro Val Thr Leu Arg Cys Gln Gly Gly Gln Glu Thr
20 25 30

Gln Glu Tyr Arg Leu Tyr Arg Glu Lys Lys Thr Ala Leu Trp Ile Thr
35 40 45

Arg Ile Pro Gln Glu Leu Val Lys Lys Gly Gln Phe Pro Ile Pro Ser
50 55 60

Ile Thr Trp Glu His Ala Gly Arg Tyr Arg Cys Tyr Tyr Gly Ser Asp
65 70 75 80

Thr Ala Gly Arg Ser Glu Ser Ser Asp Pro Leu Glu Leu Val Val Thr
85 90 95

Gly Ala Tyr Ile Lys Pro Thr Leu Ser Ala Gln Pro Ser Pro Val Val
100 105 110

Asn Ser Gly Gly Asn Val Ile Leu Gln Cys Asp Ser Gln Val Ala Phe
115 120 125

Asp Gly Phe Ser Leu Cys Lys Glu Gly Glu Asp Glu His Pro Gln Cys
130 135 140

Leu Asn Ser Gln Pro His Ala Arg Gly Ser Ser Arg Ala Ile Phe Ser
145 150 155 160

Val Gly Pro Val Ser Pro Ser Arg Arg Trp Trp Tyr Arg Cys Tyr Ala
165 170 175

Tyr Asp Ser Asn Ser Pro Tyr Glu Trp Ser Leu Pro Ser Asp Leu Leu
180 185 190

Glu Leu Leu Val Leu Gly Val Ser Lys Lys Pro Ser Leu Ser Val Gln
195 200 205

Pro Gly Pro Ile Val Ala Pro Glu Glu Thr Leu Thr Leu Gln Cys Gly
210 215 220

Ser Asp Ala Gly Tyr Asn Arg Phe Val Leu Tyr Lys Asp Gly Glu Arg
225 230 235 240

```
Asp Phe Leu Gln Leu Ala Gly Ala Gln Pro Gln Ala Gly Leu Ser Gln
                245                 250                 255

Ala Asn Phe Thr Leu Gly Pro Val Ser Arg Ser Tyr Gly Gly Gln Tyr
            260                 265                 270

Arg Cys Tyr Gly Ala His Asn Leu Ser Ser Glu Trp Ser Ala Pro Ser
        275                 280                 285

Asp Pro Leu Asp Ile Leu Ile Ala Gly Gln Phe Tyr Asp Arg Val Ser
    290                 295                 300

Leu Ser Val Gln Pro Gly Pro Thr Val Ala Ser Gly Glu Asn Val Thr
305                 310                 315                 320

Leu Leu Cys Gln Ser Gln Gly Trp Met Gln Thr Phe Leu Leu Thr Lys
                325                 330                 335

Glu Gly Ala Ala Asp Asp Pro Trp Arg Leu Arg Ser Thr Tyr Gln Ser
            340                 345                 350

Gln Lys Tyr Gln Ala Glu Phe Pro Met Gly Pro Val Thr Ser Ala His
        355                 360                 365

Ala Gly Thr Tyr Arg Cys Tyr Gly Ser Gln Ser Ser Lys Pro Tyr Leu
    370                 375                 380

Leu Thr His Pro Ser Asp Pro Leu Glu Leu Val Val Ser Gly Pro Ser
385                 390                 395                 400

Gly Gly Pro Ser Ser Pro Thr Thr Gly Pro Thr Ser Thr Ser Gly Pro
                405                 410                 415

Glu Asp Gln Pro Leu Thr Pro Thr Gly Ser Asp Pro Gln Ser Gly Leu
            420                 425                 430

Gly Arg His Leu Gly Val
        435
```

<210> SEQ ID NO 146
<211> LENGTH: 1797
<212> TYPE: DNA
<213> ORGANISM: Homo sapiens
<220> FEATURE:
<221> NAME/KEY: source
<222> LOCATION: (1)..(1797)
<223> OTHER INFORMATION: LILRB2

<400> SEQUENCE: 146

```
atgaccccca tcgtcacagt cctgatctgt ctcgggctga gtctgggccc caggacccgc      60

gtgcagacag ggaccatccc caagcccacc ctgtgggctg agccagactc tgtgatcacc     120

caggggagtc ccgtcaccct cagttgtcag ggggagccttg aagcccagga gtaccgtcta    180

tatagggaga aaaaatcagc atcttggatt acacggatac gaccagagct tgtgaagaac     240

ggccagttcc acatcccatc catcacctgg gaacacacag ggcgatatgg ctgtcagtat     300

tacagccgcg ctcggtggtc tgagctcagt gaccccctgg tgctggtgat gacaggagcc     360

tacccaaaac ccaccctctc agcccagccc agccctgtgg tgacctcagg aggaagggtg     420

accctccagt gtgagtcaca ggtggcattt ggcggcttca ttctgtgtaa ggaaggagaa     480

gatgaacacc cacaatgcct gaactcccag ccccatgccc gtgggtcgtc ccgcgccatc     540

ttctccgtgg gccccgtgag cccgaatcgc aggtggtcgc acaggtgcta tggttatgac     600

ttgaactctc cctatgtgtg gtcttcaccc agtgatctcc tggagctcct ggtcccaggt     660

gtttctaaga agccatcact ctcagtgcag ccgggtcctg tcatggcccc tggggaaagc     720

ctgaccctcc agtgtgtctc tgatgtcggc tatgacagat ttgttctgta caaggagggg     780

gaacgtgacc ttcgccagct ccctggccgg cagccccagg ctgggctctc ccaggccaac     840
```

```
ttcaccctgg gccctgtgag ccgctcctac gggggccagt acagatgcta cggtgcacac     900

aacctctcct ctgagtgctc ggcccccagc gacccccctgg acatcctgat cacaggacag    960

atccgtggca cacccttcat ctcagtgcag ccaggcccca cagtggcctc aggagagaac    1020

gtgaccctgc tgtgtcagtc atggcggcag ttccacactt tccttctgac caaggcggga    1080

gcagctgatg ccccactccg tctaagatca atacacgaat atcctaagta ccaggctgaa    1140

ttccccatga gtcctgtgac ctcagcccac gcggggacct acaggtgcta cggctcactc    1200

aactccgacc cctacctgct gtctcacccc agtgagcccc tggagctcgt ggtctcagga    1260

ccctccatgg gttccagccc cccacccacc ggtcccatct ccacacctgc aggccctgag    1320

gaccagcccc tcacccccac tgggtcggat ccccaaagtg gtctgggaag gcacctgggg    1380

gttgtgatcg gcatcttggt ggccgtcgtc ctactgctcc tcctcctcct cctcctcttc    1440

ctcatcctcc gacatcgacg tcagggcaaa cactggacat cgacccagag aaaggctgat    1500

ttccaacatc ctgcaggggc tgtggggcca gagcccacag acagaggcct gcagtggagg    1560

tccagcccag ctgccgacgc ccaggaagaa aacctctatg ctgccgtgaa ggacacacag    1620

cctgaagatg gggtggagat ggacactcgg gctgctgcat ctgaagcccc ccaggatgtg    1680

acctacgccc agctgcacag cttgaccctc agacggaagg caactgagcc tcctccatcc    1740

caggaaaggg aacctccagc tgagcccagc atctacgcca ccctggccat ccactag       1797
```

<210> SEQ ID NO 147
<211> LENGTH: 598
<212> TYPE: PRT
<213> ORGANISM: Homo sapiens
<220> FEATURE:
<221> NAME/KEY: source
<222> LOCATION: (1)..(598)
<223> OTHER INFORMATION: LILRB2

<400> SEQUENCE: 147

```
Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
```

-continued

```
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
            580                 585                 590

Ala Thr Leu Ala Ile His
        595
```

-continued

<210> SEQ ID NO 148
<211> LENGTH: 440
<212> TYPE: PRT
<213> ORGANISM: Homo sapiens
<220> FEATURE:
<221> NAME/KEY: source
<222> LOCATION: (1)..(440)
<223> OTHER INFORMATION: Extracellular domain of LILRB2

<400> SEQUENCE: 148

Gln Thr Gly Thr Ile Pro Lys Pro Thr Leu Trp Ala Glu Pro Asp Ser
1 5 10 15

Val Ile Thr Gln Gly Ser Pro Val Thr Leu Ser Cys Gln Gly Ser Leu
20 25 30

Glu Ala Gln Glu Tyr Arg Leu Tyr Arg Glu Lys Lys Ser Ala Ser Trp
35 40 45

Ile Thr Arg Ile Arg Pro Glu Leu Val Lys Asn Gly Gln Phe His Ile
50 55 60

Pro Ser Ile Thr Trp Glu His Thr Gly Arg Tyr Gly Cys Gln Tyr Tyr
65 70 75 80

Ser Arg Ala Arg Trp Ser Glu Leu Ser Asp Pro Leu Val Leu Val Met
85 90 95

Thr Gly Ala Tyr Pro Lys Pro Thr Leu Ser Ala Gln Pro Ser Pro Val
100 105 110

Val Thr Ser Gly Gly Arg Val Thr Leu Gln Cys Glu Ser Gln Val Ala
115 120 125

Phe Gly Gly Phe Ile Leu Cys Lys Glu Gly Glu Glu Glu His Pro Gln
130 135 140

Cys Leu Asn Ser Gln Pro His Ala Arg Gly Ser Ser Arg Ala Ile Phe
145 150 155 160

Ser Val Gly Pro Val Ser Pro Asn Arg Arg Trp Ser His Arg Cys Tyr
165 170 175

Gly Tyr Asp Leu Asn Ser Pro Tyr Val Trp Ser Ser Pro Ser Asp Leu
180 185 190

Leu Glu Leu Leu Val Pro Gly Val Ser Lys Lys Pro Ser Leu Ser Val
195 200 205

Gln Pro Gly Pro Val Val Ala Pro Gly Glu Ser Leu Thr Leu Gln Cys
210 215 220

Val Ser Asp Val Gly Tyr Asp Arg Phe Val Leu Tyr Lys Glu Gly Glu
225 230 235 240

Arg Asp Leu Arg Gln Leu Pro Gly Arg Gln Pro Gln Ala Gly Leu Ser
245 250 255

Gln Ala Asn Phe Thr Leu Gly Pro Val Ser Arg Ser Tyr Gly Gly Gln
260 265 270

Tyr Arg Cys Tyr Gly Ala His Asn Leu Ser Ser Glu Cys Ser Ala Pro
275 280 285

Ser Asp Pro Leu Asp Ile Leu Ile Thr Gly Gln Ile Arg Gly Thr Pro
290 295 300

Phe Ile Ser Val Gln Pro Gly Pro Thr Val Ala Ser Gly Glu Asn Val
305 310 315 320

Thr Leu Leu Cys Gln Ser Trp Arg Gln Phe His Thr Phe Leu Leu Thr
325 330 335

Lys Ala Gly Ala Ala Asp Ala Pro Leu Arg Leu Arg Ser Ile His Glu
340 345 350

-continued

```
Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val
        435                 440


<210> SEQ ID NO 149
<211> LENGTH: 1896
<212> TYPE: DNA
<213> ORGANISM: Homo sapiens
<220> FEATURE:
<221> NAME/KEY: source
<222> LOCATION: (1)..(1896)
<223> OTHER INFORMATION: cDNA of LILRB3

<400> SEQUENCE: 149

atgacgcccg ccctcacagc cctgctctgc cttgggctga gtctgggccc caggacccgc      60

atgcaggcag ggcccttccc caaacccacc ctctgggctg agccaggctc tgtgatcagc     120

tgggggagcc ccgtgaccat ctggtgtcag ggggagcctgg aggcccagga gtaccaactg     180

gataaagagg gaagcccaga gccctgggac agaaataacc cactggaacc caagaacaag     240

gccagattct ccatcccatc catgacacag caccatgcag ggagataccg ctgccactat     300

tacagctctg caggctggtc agagcccagc gaccccctgg agctggtgat gacaggattc     360

tacaacaaac ccaccctctc agccctgccc agccctgtgg tggcctcagg ggggaatatg     420

accctccgat gtggctcaca gaagggatat caccattttg ttctgatgaa ggaaggagaa     480

caccagctcc cccggaccct ggactcacag cagctccaca gtggggggtt ccaggccctg     540

ttccctgtgg gccccgtgac ccccagccac aggtggaggt tcacatgcta ttactattat     600

acaaacaccc cctgggtgtg gtcccacccc agtgaccccc tggagattct gccctcaggc     660

gtgtctagga agccctccct cctgaccctg cagggccctg tcctggcccc tgggcagagc     720

ctgaccctcc agtgtggctc tgatgtcggc tacgacagat ttgttctgta taaggagggg     780

gaacgtgact tcctccagcg ccctggccag cagccccagg ctgggctctc ccaggccaac     840

ttcaccctgg gccctgtgag ccgctcctac gggggccagt acaggtgcta tggtgcacac     900

aacctctcct ccgagtggtc ggcccccagt gacccccctgg acatcctgat cacaggacag     960

atctatgaca ccgtctccct gtcagcacag ccgggcccca cagtggcctc aggagagaac    1020

atgaccctgc tgtgtcagtc acgggggtat tttgacactt tccttctgac caaagaaggg    1080

gcagcccatc ccccactgcg tctgagatca atgtacggag ctcataagta ccaggctgaa    1140

ttccccatga gtcctgtgac ctcagcccac gcggggacct acaggtgcta cggctcacgc    1200

agctccaacc cccacctgct gtctttcccc agtgagcccc tggaactcat ggtctcagga    1260

cactctggag gctccagcct cccacccaca gggccgccct ccacacctgg tctgggaaga    1320

tacctggagg ttttgattgg ggtctcggtg gccttcgtcc tgctgctctt cctcctcctc    1380

ttcctcctcc tcctccgtca gcgtcacagc aaacacagga catctgacca gagaaagact    1440

gatttccagc gtcctgcagg ggctgcggag acagagccca aggacagggg cctgctgagg    1500
```

```
aggtccagcc cagctgctga cgtccaggaa gaaaacctct atgctgctgt gaaggacaca   1560

cagtctgagg acagggtgga gctggacagt cagagcccac acgatgaaga cccccaggca   1620

gtgacgtatg ccccggtgaa acactccagt cctaggagag aaatggcctc tcctccctcc   1680

tcactgtctg gggaattcct ggacacaaag gacagacagg tggaagagga caggcagatg   1740

gacactgagg ctgctgcatc tgaagcctcc caggatgtga cctacgccca gctgcacagc   1800

ttgaccctta gacggaaggc aactgagcct cctccatccc aggaagggga acctccagct   1860

gagcccagca tctacgccac tctggccatc cactag                             1896


<210> SEQ ID NO 150
<211> LENGTH: 631
<212> TYPE: PRT
<213> ORGANISM: Homo sapiens
<220> FEATURE:
<221> NAME/KEY: source
<222> LOCATION: (1)..(631)
<223> OTHER INFORMATION: LILRB3

<400> SEQUENCE: 150

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Gln Glu Ala Gln Glu Tyr Arg Leu His Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Met Val Met Thr Gly Ala Tyr Ser Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Arg Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Tyr Thr Asn Thr Pro Trp Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asn Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
```

```
        275                 280                 285

Ser Asn Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser His Pro Ser Glu Pro Leu Glu Leu
                405                 410                 415

Val Val Ser Gly His Ser Gly Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe Leu Leu Leu
    450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
    530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
                565                 570                 575

Asp Arg Gln Met Asp Thr Glu Ala Ala Ala Ser Glu Ala Ser Gln Asp
            580                 585                 590

Val Thr Tyr Ala Gln Leu His Ser Leu Thr Leu Arg Arg Lys Ala Thr
        595                 600                 605

Glu Pro Pro Pro Ser Gln Glu Gly Glu Pro Pro Ala Glu Pro Ser Ile
    610                 615                 620

Tyr Ala Thr Leu Ala Ile His
625                 630


<210> SEQ ID NO 151
<211> LENGTH: 420
<212> TYPE: PRT
<213> ORGANISM: Homo sapiens
<220> FEATURE:
<221> NAME/KEY: source
<222> LOCATION: (1)..(420)
<223> OTHER INFORMATION: Extracellular domain of LILRB3

<400> SEQUENCE: 151
```

Gly Pro Phe Pro Lys Pro Thr Leu Trp Ala Glu Pro Gly Ser Val Ile
1 5 10 15

Ser Trp Gly Ser Pro Val Thr Ile Trp Cys Gln Gly Ser Gln Glu Ala
20 25 30

Gln Glu Tyr Arg Leu His Lys Glu Gly Ser Pro Glu Pro Leu Asp Arg
35 40 45

Asn Asn Pro Leu Glu Pro Lys Asn Lys Ala Arg Phe Ser Ile Pro Ser
50 55 60

Met Thr Glu His His Ala Gly Arg Tyr Arg Cys His Tyr Tyr Ser Ser
65 70 75 80

Ala Gly Trp Ser Glu Pro Ser Asp Pro Leu Glu Met Val Met Thr Gly
85 90 95

Ala Tyr Ser Lys Pro Thr Leu Ser Ala Leu Pro Ser Pro Val Val Ala
100 105 110

Ser Gly Gly Asn Met Thr Leu Arg Cys Gly Ser Gln Lys Gly Tyr His
115 120 125

His Phe Val Leu Met Lys Glu Gly Glu His Gln Leu Pro Arg Thr Leu
130 135 140

Asp Ser Gln Gln Leu His Ser Arg Gly Phe Gln Ala Leu Phe Pro Val
145 150 155 160

Gly Pro Val Thr Pro Ser His Arg Trp Arg Phe Thr Cys Tyr Tyr Tyr
165 170 175

Tyr Thr Asn Thr Pro Trp Val Trp Ser His Pro Ser Asp Pro Leu Glu
180 185 190

Ile Leu Pro Ser Gly Val Ser Arg Lys Pro Ser Leu Leu Thr Leu Gln
195 200 205

Gly Pro Val Leu Ala Pro Gly Gln Ser Leu Thr Leu Gln Cys Gly Ser
210 215 220

Asp Val Gly Tyr Asn Arg Phe Val Leu Tyr Lys Glu Gly Glu Arg Asp
225 230 235 240

Phe Leu Gln Arg Pro Gly Gln Gln Pro Gln Ala Gly Leu Ser Gln Ala
245 250 255

Asn Phe Thr Leu Gly Pro Val Ser Pro Ser Asn Gly Gly Gln Tyr Arg
260 265 270

Cys Tyr Gly Ala His Asn Leu Ser Ser Glu Trp Ser Ala Pro Ser Asp
275 280 285

Pro Leu Asn Ile Leu Met Ala Gly Gln Ile Tyr Asp Thr Val Ser Leu
290 295 300

Ser Ala Gln Pro Gly Pro Thr Val Ala Ser Gly Glu Asn Val Thr Leu
305 310 315 320

Leu Cys Gln Ser Trp Trp Gln Phe Asp Thr Phe Leu Leu Thr Lys Glu
325 330 335

Gly Ala Ala His Pro Pro Leu Arg Leu Arg Ser Met Tyr Gly Ala His
340 345 350

Lys Tyr Gln Ala Glu Phe Pro Met Ser Pro Val Thr Ser Ala His Ala
355 360 365

Gly Thr Tyr Arg Cys Tyr Gly Ser Tyr Ser Ser Asn Pro His Leu Leu
370 375 380

Ser His Pro Ser Glu Pro Leu Glu Leu Val Val Ser Gly His Ser Gly
385 390 395 400

Gly Ser Ser Leu Pro Pro Thr Gly Pro Pro Ser Thr Pro Gly Leu Gly
405 410 415

Arg Tyr Leu Glu
420

<210> SEQ ID NO 152
<211> LENGTH: 1347
<212> TYPE: DNA
<213> ORGANISM: Homo sapiens
<220> FEATURE:
<221> NAME/KEY: source
<222> LOCATION: (1)..(1347)
<223> OTHER INFORMATION: cDNA of LILRB4

<400> SEQUENCE: 152
atgatcccca ccttcacggc tctgctctgc ctcgggctga gtctgggccc caggacccac 60
atgcaggcag ggcccctccc caaacccacc ctctgggctg agccaggctc tgtgatcagc 120
tgggggaact ctgtgaccat ctggtgtcag ggcaccctgg aggctcggga gtaccgtctg 180
gataaagagg aaagcccagc accctgggac agacagaacc cactggagcc caagaacaag 240
gccagattct ccatcccatc catgacagag gactatgcag ggagataccg ctgttactat 300
cgcagccctg taggctggtc acagcccagt gacccccctgg agctggtgat gacaggagcc 360
tacagtaaac ccaccctttc agccctgccg agtcctcttg tgacctcagg aaagagcgtg 420
accctgctgt gtcagtcacg gagcccaatg gacacttttc ttctgatcaa ggagcgggca 480
gcccatcccc tactgcatct gagatcagag cacggagctc agcagcacca ggctgaattc 540
cccatgagtc ctgtgacctc agtgcacggg gggacctaca ggtgcttcag ctcacacggc 600
ttctcccact acctgctgtc acaccccagt gacccccctgg agctcatagt ctcaggatcc 660
ttggagggtc ccaggccctc acccacaagg tccgtctcaa cagctgcagg ccctgaggac 720
cagcccctca tgcctacagg gtcagtcccc cacagtggtc tgagaaggca ctgggaggta 780
ctgatcgggg tcttggtggt ctccatcctg cttctctccc tcctcctctt cctcctcctc 840
caacactggc gtcagggaaa acacaggaca ttggcccaga gacaggctga tttccaacgt 900
cctccagggg ctgccgagcc agagcccaag gacgggggcc tacagaggag gtccagccca 960
gctgctgacg tccagggaga aaacttctgt gctgccgtga agaacacaca gcctgaggac 1020
ggggtggaaa tggacactcg gcagagccca cacgatgaag acccccaggc agtgacgtat 1080
gccaaggtga aacactccag acctaggaga gaaatggcct ctcctccctc cccactgtct 1140
ggggaattcc tggacacaaa ggacagacag gcagaagagg acagacagat ggacactgag 1200
gctgctgcat ctgaagcccc ccaggatgtg acctacgccc ggctgcacag ctttaccctc 1260
agacagaagg caactgagcc tcctccatcc caggaagggg cctctccagc tgagcccagt 1320
gtctatgcca ctctggccat ccactaa 1347

<210> SEQ ID NO 153
<211> LENGTH: 448
<212> TYPE: PRT
<213> ORGANISM: Homo sapiens
<220> FEATURE:
<221> NAME/KEY: source
<222> LOCATION: (1)..(448)
<223> OTHER INFORMATION: LILRB4

<400> SEQUENCE: 153

Met Ile Pro Thr Phe Thr Ala Leu Leu Cys Leu Gly Leu Ser Leu Gly
1 5 10 15

Pro Arg Thr His Met Gln Ala Gly Pro Leu Pro Lys Pro Thr Leu Trp
20 25 30

```
Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Asp Pro
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
        355                 360                 365

Arg Arg Glu Met Ala Ser Pro Pro Ser Pro Leu Ser Gly Glu Phe Leu
    370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
                405                 410                 415

Ser Phe Thr Leu Arg Gln Lys Ala Thr Glu Pro Pro Pro Ser Gln Glu
            420                 425                 430

Gly Ala Ser Pro Ala Glu Pro Ser Val Tyr Ala Thr Leu Ala Ile His
        435                 440                 445
```

<210> SEQ ID NO 154
<211> LENGTH: 238
<212> TYPE: PRT
<213> ORGANISM: Homo sapiens
<220> FEATURE:
<221> NAME/KEY: source
<222> LOCATION: (1)..(238)
<223> OTHER INFORMATION: Extracellular domain of LILRB4

<400> SEQUENCE: 154

```
Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Glu Ser Pro Ala Pro Trp
        35                  40                  45

Asp Arg Gln Asn Pro Leu Glu Pro Lys Asn Lys Ala Arg Phe Ser Ile
    50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
            100                 105                 110

Val Thr Ser Gly Lys Ser Val Thr Leu Leu Cys Gln Ser Arg Ser Pro
        115                 120                 125

Met Asp Thr Phe Leu Leu Ile Lys Glu Arg Ala Ala His Pro Leu Leu
    130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
            180                 185                 190

Glu Leu Ile Val Ser Gly Ser Leu Glu Asp Pro Arg Pro Ser Pro Thr
        195                 200                 205

Arg Ser Val Ser Thr Ala Ala Gly Pro Glu Asp Gln Pro Leu Met Pro
    210                 215                 220

Thr Gly Ser Val Pro His Ser Gly Leu Arg Arg His Trp Glu
225                 230                 235
```

<210> SEQ ID NO 155
<211> LENGTH: 1773
<212> TYPE: DNA
<213> ORGANISM: Homo sapiens
<220> FEATURE:
<221> NAME/KEY: source
<222> LOCATION: (1)..(1773)
<223> OTHER INFORMATION: cDNA of LILRB5

<400> SEQUENCE: 155

```
atgaccctca ccctctcagt cctgatttgc ctcgggctga gtgtgggccc caggacctgc      60

gtgcaggcag gcaccctccc caaacccacc ctctgggctg agccagcctc tgtgatagct     120

cgggggaagc ccgtgaccct ctggtgtcag ggcccctgg agactgagga gtaccgtctg      180

gataaggagg gactcccatg ggcccggaag agacagaacc cactggagcc tggagccaag     240

gccaagttcc acattccatc cacggtgtat gacagtgcag ggcgataccg ctgctactat     300

gagacccctg caggctggtc agagcccagt gaccccctgg agctggtggc gacaggattc     360
```

```
tatgcagaac ccactctttt agccctgccg agtcctgtgg tggcctcagg aggaaatgtg    420
accctccagt gtgatacact ggacggactt ctcacgtttg ttcttgttga ggaagaacag    480
aagctcccca ggaccctgta ctcacagaag ctccccaaag ggccatccca ggccctgttc    540
cctgtgggtc ccgtgacccc cagctgcagg tggaggttca gatgctatta ctattacagg    600
aaaaaccctc aggtgtggtc gaaccccagt gacctcctgg agattctggt cccaggcgtg    660
tctaggaagc cctccctcct gatcccgcag ggctctgtcg tggcccgcgg aggcagcctg    720
accctgcagt gtcgctctga tgtcggctat gacatattcg ttctgtacaa ggagggggaa    780
catgacctcg tccagggctc tggccagcag ccccaggctg ggctctccca ggccaacttc    840
accctgggcc ctgtgagccg ctcccacggg ggccagtaca gatgctacgg tgcacacaac    900
ctctccccta ggtggtcggc ccccagcgac cccctggaca tcctgatcgc aggactgatc    960
cctgacatac ccgccctctc ggtgcagccg ggccccaagg tggcctcagg agagaacgtg   1020
accctgctgt gtcagtcatg gcatcagata gacactttct ttttgaccaa ggagggggca   1080
gcccatcccc cgctgtgtct aaagtcaaag taccagtctt atagacacca ggctgaattc   1140
tccatgagtc ctgtgacctc agcccagggt ggaacctacc gatgctacag cgcaatcagg   1200
tcctacccct acctgctgtc cagccctagt tacccccagg agctcgtggt ctcaggaccc   1260
tctggggatc ccagcctctc acctacaggc tccaccccca cacctggccc tgaggaccag   1320
cccctcaccc ccacggggtt ggatccccag agtggtctgg gaaggcacct gggggttgtg   1380
actggggtct cagtggcctt cgtcctgctg ctgttcctcc tcctcttcct cctcctccga   1440
catcggcatc agagcaaaca caggacatcg gcccatttct accgtcctgc aggggctgcg   1500
gggccagagc ccaaggacca gggcctgcag aagagggcca gcccagttgc tgacatccag   1560
gaggaaattc tcaatgctgc cgtgaaggac acacagccca aggacggggt ggagatggat   1620
gctccggctg ctgcatctga agccccccag gatgtgacct acgcccagct gcacagcttg   1680
accctcagac gggaggcaac tgagcctcct ccatcccagg aaagggaacc tccagctgaa   1740
cccagcatct acgcccccct ggccatccac tag                                1773
```

```
<210> SEQ ID NO 156
<211> LENGTH: 590
<212> TYPE: PRT
<213> ORGANISM: Homo sapiens
<220> FEATURE:
<221> NAME/KEY: source
<222> LOCATION: (1)..(590)
<223> OTHER INFORMATION: LILRB5

<400> SEQUENCE: 156

Met Thr Leu Thr Leu Ser Val Leu Ile Cys Leu Gly Leu Ser Val Gly
1               5                   10                  15

Pro Arg Thr Cys Val Gln Ala Gly Thr Leu Pro Lys Pro Thr Leu Trp
            20                  25                  30

Ala Glu Pro Ala Ser Val Ile Ala Arg Gly Lys Pro Val Thr Leu Trp
        35                  40                  45

Cys Gln Gly Pro Leu Glu Thr Glu Glu Tyr Arg Leu Asp Lys Glu Gly
    50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                85                  90                  95
```

-continued

```
Arg Cys Tyr Tyr Glu Thr Pro Ala Gly Trp Ser Glu Pro Ser Asp Pro
            100                 105                 110

Leu Glu Leu Val Ala Thr Gly Phe Tyr Ala Glu Pro Thr Leu Leu Ala
        115                 120                 125

Leu Pro Ser Pro Val Val Ala Ser Gly Gly Asn Val Thr Leu Gln Cys
    130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                165                 170                 175

Gln Ala Leu Phe Pro Val Gly Pro Val Thr Pro Ser Cys Arg Trp Arg
            180                 185                 190

Phe Arg Cys Tyr Tyr Tyr Tyr Arg Lys Asn Pro Gln Val Trp Ser Asn
        195                 200                 205

Pro Ser Asp Leu Leu Glu Ile Leu Val Pro Gly Val Ser Arg Lys Pro
    210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
                245                 250                 255

Lys Glu Gly Glu His Asp Leu Val Gln Gly Ser Gly Gln Gln Pro Gln
            260                 265                 270

Ala Gly Leu Ser Gln Ala Asn Phe Thr Leu Gly Pro Val Ser Arg Ser
        275                 280                 285

His Gly Gly Gln Tyr Arg Cys Tyr Gly Ala His Asn Leu Ser Pro Arg
    290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
            340                 345                 350

Phe Phe Leu Thr Lys Glu Gly Ala Ala His Pro Pro Leu Cys Leu Lys
        355                 360                 365

Ser Lys Tyr Gln Ser Tyr Arg His Gln Ala Glu Phe Ser Met Ser Pro
    370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415

Val Ser Gly Pro Ser Gly Asp Pro Ser Leu Ser Pro Thr Gly Ser Thr
            420                 425                 430

Pro Thr Pro Gly Pro Glu Asp Gln Pro Leu Thr Pro Thr Gly Leu Asp
        435                 440                 445

Pro Gln Ser Gly Leu Gly Arg His Leu Gly Val Val Thr Gly Val Ser
    450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                485                 490                 495

Ala Gly Ala Ala Gly Pro Glu Pro Lys Asp Gln Gly Leu Gln Lys Arg
            500                 505                 510

Ala Ser Pro Val Ala Asp Ile Gln Glu Glu Ile Leu Asn Ala Ala Val
```

```
        515                 520                 525

Lys Asp Thr Gln Pro Lys Asp Gly Val Glu Met Asp Ala Arg Ala Ala
    530                 535                 540

Ala Ser Glu Ala Pro Gln Asp Val Thr Tyr Ala Gln Leu His Ser Leu
545                 550                 555                 560

Thr Leu Arg Arg Glu Ala Thr Glu Pro Pro Pro Ser Gln Glu Arg Glu
                565                 570                 575

Pro Pro Ala Glu Pro Ser Ile Tyr Ala Pro Leu Ala Ile His
            580                 585                 590


<210> SEQ ID NO 157
<211> LENGTH: 435
<212> TYPE: PRT
<213> ORGANISM: Homo sapiens
<220> FEATURE:
<221> NAME/KEY: source
<222> LOCATION: (1)..(435)
<223> OTHER INFORMATION: Extracellular domain of LILRB5

<400> SEQUENCE: 157

Gly Thr Leu Pro Lys Pro Thr Leu Trp Ala Glu Pro Ala Ser Val Ile
1               5                   10                  15

Ala Arg Gly Lys Pro Val Thr Leu Trp Cys Gln Gly Pro Leu Glu Thr
            20                  25                  30

Glu Glu Tyr Arg Leu Asp Lys Glu Gly Leu Pro Trp Ala Arg Lys Arg
        35                  40                  45

Gln Asn Pro Leu Glu Pro Gly Ala Lys Ala Lys Phe His Ile Pro Ser
    50                  55                  60

Thr Val Tyr Asp Ser Ala Gly Arg Tyr Arg Cys Tyr Tyr Glu Thr Pro
65                  70                  75                  80

Ala Gly Trp Ser Glu Pro Ser Asp Pro Leu Glu Leu Val Ala Thr Gly
                85                  90                  95

Phe Tyr Ala Glu Pro Thr Leu Leu Ala Leu Pro Ser Pro Val Val Ala
            100                 105                 110

Ser Gly Gly Asn Val Thr Leu Gln Cys Asp Thr Leu Asp Gly Leu Leu
        115                 120                 125

Thr Phe Val Leu Val Glu Glu Glu Gln Lys Leu Pro Arg Thr Leu Tyr
    130                 135                 140

Ser Gln Lys Leu Pro Lys Gly Pro Ser Gln Ala Leu Phe Pro Val Gly
145                 150                 155                 160

Pro Val Thr Pro Ser Cys Arg Trp Arg Phe Arg Cys Tyr Tyr Tyr Tyr
                165                 170                 175

Arg Lys Asn Pro Gln Val Trp Ser Asn Pro Ser Asp Leu Leu Glu Ile
            180                 185                 190

Leu Val Pro Gly Val Ser Arg Lys Pro Ser Leu Leu Ile Pro Gln Gly
        195                 200                 205

Ser Val Val Ala Arg Gly Gly Ser Leu Thr Leu Gln Cys Arg Ser Asp
    210                 215                 220

Val Gly Tyr Asp Ile Phe Val Leu Tyr Lys Glu Gly Glu His Asp Leu
225                 230                 235                 240

Val Gln Gly Ser Gly Gln Gln Pro Gln Ala Gly Leu Ser Gln Ala Asn
                245                 250                 255

Phe Thr Leu Gly Pro Val Ser Arg Ser His Gly Gly Gln Tyr Arg Cys
            260                 265                 270

Tyr Gly Ala His Asn Leu Ser Pro Arg Trp Ser Ala Pro Ser Asp Pro
        275                 280                 285
```

```
Leu Asp Ile Leu Ile Ala Gly Leu Ile Pro Asp Ile Pro Ala Leu Ser
    290                 295                 300

Val Gln Pro Gly Pro Lys Val Ala Ser Gly Glu Asn Val Thr Leu Leu
305                 310                 315                 320

Cys Gln Ser Trp His Gln Ile Asp Thr Phe Phe Leu Thr Lys Glu Gly
                325                 330                 335

Ala Ala His Pro Pro Leu Cys Leu Lys Ser Lys Tyr Gln Ser Tyr Arg
            340                 345                 350

His Gln Ala Glu Phe Ser Met Ser Pro Val Thr Ser Ala Gln Gly Gly
        355                 360                 365

Thr Tyr Arg Cys Tyr Ser Ala Ile Arg Ser Tyr Pro Tyr Leu Leu Ser
    370                 375                 380

Ser Pro Ser Tyr Pro Gln Glu Leu Val Val Ser Gly Pro Ser Gly Asp
385                 390                 395                 400

Pro Ser Leu Ser Pro Thr Gly Ser Thr Pro Thr Pro Gly Pro Glu Asp
                405                 410                 415

Gln Pro Leu Thr Pro Thr Gly Leu Asp Pro Gln Ser Gly Leu Gly Arg
            420                 425                 430

His Leu Gly
        435


<210> SEQ ID NO 158
<211> LENGTH: 2526
<212> TYPE: DNA
<213> ORGANISM: Mus musculus
<220> FEATURE:
<221> NAME/KEY: source
<222> LOCATION: (1)..(2526)
<223> OTHER INFORMATION: cDNA of PirB

<400> SEQUENCE: 158

atgtcctgca ccttcacagc cctgctccgt cttggactga ctctgagcct ctggatccca     60

gtgctgacag ggtccctccc taagcctatc ctcagagtac agccagactc tgtggtctcc    120

aggaggacta aggtgacctt cttgtgtgaa gagacaattg gagccaatga gtaccgcctc    180

tataaagatg gaaagctata taaaaccgta acaaagaaca aacagaagcc agaaaacaag    240

gctgaattct cattctcaaa tgtagacctg agtaatgcag gtcaatatcg atgttcctac    300

agcacccagt ataaatcatc aggctacagt gacctcctgg agctggtggt gacaggacac    360

tactggacac ccagcctttt agcccaagcc agccctgtgg taacttcagg agggtatgtc    420

accctccagt gtgagtcctg gcacaacgat cacaagttca ttctgactgt agaaggacca    480

cagaagctct cgtggacaca agactcacag tataattact ctacaaggaa gtaccacgcc    540

ctgttctctg tgggccctgt gacccccaac cagagatgga tatgcagatg ttacagttat    600

gacaggaaca gaccatatgt gtggtcacct ccaagtgaat ccgtggagct cctggtctca    660

ggtaatctcc aaaaaccaac catcaaggct gaaccaggat ctgtgatcac ctccaaaaga    720

gcaatgacca tctggtgtca ggggaacctg gatgcagaag tatattttct gcataatgag    780

aaaagccaaa aaacacagag cacacagacc ctacaggagc ctgggaacaa gggcaagttc    840

ttcatccctt ctgtgacact acaacatgca gggcaatatc gctgttattg ttacggctca    900

gctggttggt cacagcccag tgacaccctg gagctggtgg tgacaggaat ctatgaatac    960

tatgaaccca ggctgtcagt actgcccagc cctgtggtga cagctggagg gaacatgaca   1020

ctccactgtg cctcagactt tccctacgat aaattcattc tcaccaagga agataagaaa   1080
```

-continued

```
ttcggcaact cactggacac agagcatata tcttctagtg gacagtaccg agccctgttt   1140

attataggac ccacaacccc aacccataca ggggcattca gatgttacgg ttactacaag   1200

aatgccccac agctgtggtc agtacctagt gctctccaac aaatactcat ctcagggctg   1260

tccaagaagc cctctctgct gactcaccaa ggccatatcc tggaccctgg aatgaccctc   1320

accctgcagt gtttctctga catcaactat gacagatttg ctctgcacaa ggtgggggga   1380

gctgacatca tgcagcactc tagccagcag actgacactg gcttctctgt ggccaacttc   1440

acactgggct atgtgagtag ctccactgga ggccaataca gatgctatgg tgcacacaac   1500

ctctcctctg agtggtcagc ctccagtgag cccctggaca tcctgatcac aggacagctc   1560

cctctcactc cttccctctc agtgcagcct aaccacacag tgcactcagg agagaccgtg   1620

agcctgctgt gttggtcaat ggactctgtg gatactttca ttctgtccaa ggagggatca   1680

gcccagcaac ccctgcgact aaaatcaaag tcccatgatc agcagtccca ggcagaattc   1740

tccatgagtg ctgtgacctc ccatctctca ggcacctaca ggtgctatgg agctcaagac   1800

tcatctttct acctcttgtc atctgccagt gcccctgtgg agctcacagt ctcaggaccc   1860

atcgaaacct ctaccccgcc acccacaatg tccatgccac taggtggact gcatatgtac   1920

ctgaaggctc tcattggagt gtctgtggcc ttcatcctgt tcctcttcat cttcatcttc   1980

attcttcttc gacgaagaca tcggggaaaa ttcaggaaag atgtccagaa agagaaagac   2040

ttgcaacttt cttcaggagc tgaagagccc ataaccagga aaggagaact ccagaagagg   2100

cccaacccag ctgctgccac ccaggaagaa agcctatatg cttcagtgga ggacatgcaa   2160

actgaggatg gagtggagct gaacagctgg acaccacctg aggaagatcc ccagggagag   2220

acttatgccc aggtgaaacc ctccaggctc aggaaggcag gacatgtctc accttctgtc   2280

atgtcaaggg aacaactgaa cacagaatat gaacaagcag aagagggcca aggagcaaac   2340

aatcaggctg ccgaatctgg ggagtcccag gatgtgacct atgcccagct gtgcagcagg   2400

acactcagac agggggcagc tgcatctcct ctctcccagg caggggaagc cccagaggag   2460

cccagtgtat atgctactct ggcggctgct cgtccagagg ctgttcccaa ggacatggag   2520

caatga                                                              2526
```

<210> SEQ ID NO 159
<211> LENGTH: 841
<212> TYPE: PRT
<213> ORGANISM: Mus musculus
<220> FEATURE:
<221> NAME/KEY: source
<222> LOCATION: (1)..(841)
<223> OTHER INFORMATION: PirB

<400> SEQUENCE: 159

```
Met Ser Cys Thr Phe Thr Ala Leu Leu Arg Leu Gly Leu Thr Leu Ser
1               5                   10                  15

Leu Trp Ile Pro Val Leu Thr Gly Ser Leu Pro Lys Pro Ile Leu Arg
            20                  25                  30

Val Gln Pro Asp Ser Val Val Ser Arg Arg Thr Lys Val Thr Phe Leu
        35                  40                  45

Cys Glu Glu Thr Ile Gly Ala Asn Glu Tyr Arg Leu Tyr Lys Asp Gly
    50                  55                  60

Lys Leu Tyr Lys Thr Val Thr Lys Asn Lys Gln Lys Pro Glu Asn Lys
65                  70                  75                  80

Ala Glu Phe Ser Phe Ser Asn Val Asp Leu Ser Asn Ala Gly Gln Tyr
                85                  90                  95
```

-continued

```
Arg Cys Ser Tyr Ser Thr Gln Tyr Lys Ser Ser Gly Tyr Ser Asp Leu
            100                 105                 110

Leu Glu Leu Val Val Thr Gly His Tyr Trp Thr Pro Ser Leu Leu Ala
        115                 120                 125

Gln Ala Ser Pro Val Val Thr Ser Gly Gly Tyr Val Thr Leu Gln Cys
    130                 135                 140

Glu Ser Trp His Asn Asp His Lys Phe Ile Leu Thr Val Glu Gly Pro
145                 150                 155                 160

Gln Lys Leu Ser Trp Thr Gln Asp Ser Gln Tyr Asn Tyr Ser Thr Arg
                165                 170                 175

Lys Tyr His Ala Leu Phe Ser Val Gly Pro Val Thr Pro Asn Gln Arg
            180                 185                 190

Trp Ile Cys Arg Cys Tyr Ser Tyr Asp Arg Asn Arg Pro Tyr Val Trp
        195                 200                 205

Ser Pro Pro Ser Glu Ser Val Glu Leu Leu Val Ser Gly Asn Leu Gln
    210                 215                 220

Lys Pro Thr Ile Lys Ala Glu Pro Gly Ser Val Ile Thr Ser Lys Arg
225                 230                 235                 240

Ala Met Thr Ile Trp Cys Gln Gly Asn Leu Asp Ala Glu Val Tyr Phe
                245                 250                 255

Leu His Asn Glu Lys Ser Gln Lys Thr Gln Ser Thr Gln Thr Leu Gln
            260                 265                 270

Glu Pro Gly Asn Lys Gly Lys Phe Phe Ile Pro Ser Val Thr Leu Gln
        275                 280                 285

His Ala Gly Gln Tyr Arg Cys Tyr Cys Tyr Gly Ser Ala Gly Trp Ser
    290                 295                 300

Gln Pro Ser Asp Thr Leu Glu Leu Val Val Thr Gly Ile Tyr Glu Tyr
305                 310                 315                 320

Tyr Glu Pro Arg Leu Ser Val Leu Pro Ser Pro Val Val Thr Ala Gly
                325                 330                 335

Gly Asn Met Thr Leu His Cys Ala Ser Asp Phe Pro Tyr Asp Lys Phe
            340                 345                 350

Ile Leu Thr Lys Glu Asp Lys Lys Phe Gly Asn Ser Leu Asp Thr Glu
        355                 360                 365

His Ile Ser Ser Ser Gly Gln Tyr Arg Ala Leu Phe Ile Ile Gly Pro
    370                 375                 380

Thr Thr Pro Thr His Thr Gly Ala Phe Arg Cys Tyr Gly Tyr Tyr Lys
385                 390                 395                 400

Asn Ala Pro Gln Leu Trp Ser Val Pro Ser Ala Leu Gln Gln Ile Leu
                405                 410                 415

Ile Ser Gly Leu Ser Lys Lys Pro Ser Leu Leu Thr His Gln Gly His
            420                 425                 430

Ile Leu Asp Pro Gly Met Thr Leu Thr Leu Gln Cys Phe Ser Asp Ile
        435                 440                 445

Asn Tyr Asp Arg Phe Ala Leu His Lys Val Gly Gly Ala Asp Ile Met
    450                 455                 460

Gln His Ser Ser Gln Gln Thr Asp Thr Gly Phe Ser Val Ala Asn Phe
465                 470                 475                 480

Thr Leu Gly Tyr Val Ser Ser Ser Thr Gly Gly Gln Tyr Arg Cys Tyr
                485                 490                 495

Gly Ala His Asn Leu Ser Ser Glu Trp Ser Ala Ser Ser Glu Pro Leu
            500                 505                 510
```

```
Asp Ile Leu Ile Thr Gly Gln Leu Pro Leu Thr Pro Ser Leu Ser Val
        515                 520                 525

Gln Pro Asn His Thr Val His Ser Gly Glu Thr Val Ser Leu Leu Cys
    530                 535                 540

Trp Ser Met Asp Ser Val Asp Thr Phe Ile Leu Ser Lys Glu Gly Ser
545                 550                 555                 560

Ala Gln Gln Pro Leu Arg Leu Lys Ser Lys Ser His Asp Gln Gln Ser
                565                 570                 575

Gln Ala Glu Phe Ser Met Ser Ala Val Thr Ser His Leu Ser Gly Thr
            580                 585                 590

Tyr Arg Cys Tyr Gly Ala Gln Asp Ser Ser Phe Tyr Leu Leu Ser Ser
        595                 600                 605

Ala Ser Ala Pro Val Glu Leu Thr Val Ser Gly Pro Ile Glu Thr Ser
    610                 615                 620

Thr Pro Pro Pro Thr Met Ser Met Pro Leu Gly Gly Leu His Met Tyr
625                 630                 635                 640

Leu Lys Ala Leu Ile Gly Val Ser Val Ala Phe Ile Leu Phe Leu Phe
                645                 650                 655

Ile Phe Ile Phe Ile Leu Leu Arg Arg Arg His Arg Gly Lys Phe Arg
            660                 665                 670

Lys Asp Val Gln Lys Glu Lys Asp Leu Gln Leu Ser Ser Gly Ala Glu
        675                 680                 685

Glu Pro Ile Thr Arg Lys Gly Glu Leu Gln Lys Arg Pro Asn Pro Ala
    690                 695                 700

Ala Ala Thr Gln Glu Glu Ser Leu Tyr Ala Ser Val Glu Asp Met Gln
705                 710                 715                 720

Thr Glu Asp Gly Val Glu Leu Asn Ser Trp Thr Pro Pro Glu Glu Asp
                725                 730                 735

Pro Gln Gly Glu Thr Tyr Ala Gln Val Lys Pro Ser Arg Leu Arg Lys
            740                 745                 750

Ala Gly His Val Ser Pro Ser Val Met Ser Arg Glu Gln Leu Asn Thr
        755                 760                 765

Glu Tyr Glu Gln Ala Glu Glu Gly Gln Gly Ala Asn Asn Gln Ala Ala
    770                 775                 780

Glu Ser Gly Glu Ser Gln Asp Val Thr Tyr Ala Gln Leu Cys Ser Arg
785                 790                 795                 800

Thr Leu Arg Gln Gly Ala Ala Ala Ser Pro Leu Ser Gln Ala Gly Glu
                805                 810                 815

Ala Pro Glu Glu Pro Ser Val Tyr Ala Thr Leu Ala Ala Ala Arg Pro
            820                 825                 830

Glu Ala Val Pro Lys Asp Met Glu Gln
        835                 840


<210> SEQ ID NO 160
<211> LENGTH: 618
<212> TYPE: PRT
<213> ORGANISM: Mus musculus
<220> FEATURE:
<221> NAME/KEY: source
<222> LOCATION: (1)..(618)
<223> OTHER INFORMATION: Extracellular domain of PirB

<400> SEQUENCE: 160

Ser Leu Pro Lys Pro Ile Leu Arg Val Gln Pro Asp Ser Val Val Ser
1               5                   10                  15

Arg Arg Thr Lys Val Thr Phe Leu Cys Glu Glu Thr Ile Gly Ala Asn
```

-continued

```
            20                  25                  30

Glu Tyr Arg Leu Tyr Lys Asp Gly Lys Leu Tyr Lys Thr Val Thr Lys
        35                  40                  45

Asn Lys Gln Lys Pro Glu Asn Lys Ala Glu Phe Ser Phe Ser Asn Val
    50                  55                  60

Asp Leu Ser Asn Ala Gly Gln Tyr Arg Cys Ser Tyr Ser Thr Gln Tyr
65                  70                  75                  80

Lys Ser Ser Gly Tyr Ser Asp Leu Leu Glu Leu Val Val Thr Gly His
                85                  90                  95

Tyr Trp Thr Pro Ser Leu Leu Ala Gln Ala Ser Pro Val Val Thr Ser
            100                 105                 110

Gly Gly Tyr Val Thr Leu Gln Cys Glu Ser Trp His Asn Asp His Lys
        115                 120                 125

Phe Ile Leu Thr Val Glu Gly Pro Gln Lys Leu Ser Trp Thr Gln Asp
    130                 135                 140

Ser Gln Tyr Asn Tyr Ser Thr Arg Lys Tyr His Ala Leu Phe Ser Val
145                 150                 155                 160

Gly Pro Val Thr Pro Asn Gln Arg Trp Ile Cys Arg Cys Tyr Ser Tyr
                165                 170                 175

Asp Arg Asn Arg Pro Tyr Val Trp Ser Pro Pro Ser Glu Ser Val Glu
            180                 185                 190

Leu Leu Val Ser Gly Asn Leu Gln Lys Pro Thr Ile Lys Ala Glu Pro
        195                 200                 205

Gly Ser Val Ile Thr Ser Lys Arg Ala Met Thr Ile Trp Cys Gln Gly
    210                 215                 220

Asn Leu Asp Ala Glu Val Tyr Phe Leu His Asn Glu Lys Ser Gln Lys
225                 230                 235                 240

Thr Gln Ser Thr Gln Thr Leu Gln Glu Pro Gly Asn Lys Gly Lys Phe
                245                 250                 255

Phe Ile Pro Ser Val Thr Leu Gln His Ala Gly Gln Tyr Arg Cys Tyr
            260                 265                 270

Cys Tyr Gly Ser Ala Gly Trp Ser Gln Pro Ser Asp Thr Leu Glu Leu
        275                 280                 285

Val Val Thr Gly Ile Tyr Glu Tyr Tyr Glu Pro Arg Leu Ser Val Leu
    290                 295                 300

Pro Ser Pro Val Val Thr Ala Gly Gly Asn Met Thr Leu His Cys Ala
305                 310                 315                 320

Ser Asp Phe Pro Tyr Asp Lys Phe Ile Leu Thr Lys Glu Asp Lys Lys
                325                 330                 335

Phe Gly Asn Ser Leu Asp Thr Glu His Ile Ser Ser Ser Gly Gln Tyr
            340                 345                 350

Arg Ala Leu Phe Ile Ile Gly Pro Thr Thr Pro Thr His Thr Gly Ala
        355                 360                 365

Phe Arg Cys Tyr Gly Tyr Tyr Lys Asn Ala Pro Gln Leu Trp Ser Val
    370                 375                 380

Pro Ser Ala Leu Gln Gln Ile Leu Ile Ser Gly Leu Ser Lys Lys Pro
385                 390                 395                 400

Ser Leu Leu Thr His Gln Gly His Ile Leu Asp Pro Gly Met Thr Leu
                405                 410                 415

Thr Leu Gln Cys Phe Ser Asp Ile Asn Tyr Asp Arg Phe Ala Leu His
            420                 425                 430

Lys Val Gly Gly Ala Asp Ile Met Gln His Ser Ser Gln Gln Thr Asp
        435                 440                 445
```

```
Thr Gly Phe Ser Val Ala Asn Phe Thr Leu Gly Tyr Val Ser Ser Ser
    450                 455                 460

Thr Gly Gly Gln Tyr Arg Cys Tyr Gly Ala His Asn Leu Ser Ser Glu
465                 470                 475                 480

Trp Ser Ala Ser Ser Glu Pro Leu Asp Ile Leu Ile Thr Gly Gln Leu
                485                 490                 495

Pro Leu Thr Pro Ser Leu Ser Val Gln Pro Asn His Thr Val His Ser
            500                 505                 510

Gly Glu Thr Val Ser Leu Leu Cys Trp Ser Met Asp Ser Val Asp Thr
        515                 520                 525

Phe Ile Leu Ser Lys Glu Gly Ser Ala Gln Gln Pro Leu Arg Leu Lys
    530                 535                 540

Ser Lys Ser His Asp Gln Gln Ser Gln Ala Glu Phe Ser Met Ser Ala
545                 550                 555                 560

Val Thr Ser His Leu Ser Gly Thr Tyr Arg Cys Tyr Gly Ala Gln Asp
                565                 570                 575

Ser Ser Phe Tyr Leu Leu Ser Ser Ala Ser Ala Pro Val Glu Leu Thr
            580                 585                 590

Val Ser Gly Pro Ile Glu Thr Ser Thr Pro Pro Pro Thr Met Ser Met
        595                 600                 605

Pro Leu Gly Gly Leu His Met Tyr Leu Lys
    610                 615
```

<210> SEQ ID NO 161
<211> LENGTH: 1008
<212> TYPE: DNA
<213> ORGANISM: Mus musculus
<220> FEATURE:
<221> NAME/KEY: source
<222> LOCATION: (1)..(1008)
<223> OTHER INFORMATION: cDNA of gp49B1

<400> SEQUENCE: 161

```
atgatcgcca tgctcacagt gctgctatac cttggtctta ttctggaacc caggactgca     60

gtacaggcag gacacctccc aaagcccatc atctgggctg agccaggctc tgtgatcgct    120

gcgtatacat ctgtgattac ctggtgtcag ggttcctggg aggcccagta ttatcatctg    180

tataaagaga aaagtgtaaa tccttgggac actcaagtcc ctctggaaac caggaataag    240

gccaagttca acattccaag catgacaacc tcatatgcag gcatatataa gtgttactat    300

gagagtgctg ctggcttctc agagcacagt gatgccatgg agctggtgat gacaggagca    360

tatgaaaatc ccagcctgtc agtctatccc agctctaatg tgacctctgg agtttccata    420

tcctttagtt gcagctcatc catagtattt ggcagattca ttctgatcca ggaaggaaag    480

catggcctct cttggaccct ggactcacag catcaggcca atcagccatc ctatgctact    540

tttgttctgg atgctgttac tcccaaccac aatggaacat tcagatgcta tggctacttt    600

agaaatgaac cacaggtgtg gtcaaaacca agtaactccc tagacctcat gatctcagaa    660

accaaggacc agtcctctac acccactgaa gatggactgg aaacatacca gaagattttg    720

attggagtcc tggtgtcatt cctcctgctt ttcttcctcc tgctttttct catcctcatc    780

ggataccagt atgggcacaa aaagaaggct aatgcttctg tgaagaacac acaatctgag    840

aacaatgcag agctgaacag ttggaaccca caaaatgaag acccccaggg aattgtctac    900

gcccaggtaa aaccctccag gcttcagaag gacactgcat gcaaagagac ccaggatgta    960

acctatgccc agttgtgcat caggacacag gaacagaaca acagctga                1008
```

<210> SEQ ID NO 162
<211> LENGTH: 335
<212> TYPE: PRT
<213> ORGANISM: Mus musculus
<220> FEATURE:
<221> NAME/KEY: source
<222> LOCATION: (1)..(335)
<223> OTHER INFORMATION: gp49B1

<400> SEQUENCE: 162

Met Ile Ala Met Leu Thr Val Leu Leu Tyr Leu Gly Leu Ile Leu Glu
1 5 10 15

Pro Arg Thr Ala Val Gln Ala Gly His Leu Pro Lys Pro Ile Ile Trp
20 25 30

Ala Glu Pro Gly Ser Val Ile Ala Ala Tyr Thr Ser Val Ile Thr Trp
35 40 45

Cys Gln Gly Ser Trp Glu Ala Gln Tyr Tyr His Leu Tyr Lys Glu Lys
50 55 60

Ser Val Asn Pro Trp Asp Thr Gln Val Pro Leu Glu Thr Arg Asn Lys
65 70 75 80

Ala Lys Phe Asn Ile Pro Ser Met Thr Thr Ser Tyr Ala Gly Ile Tyr
85 90 95

Lys Cys Tyr Tyr Glu Ser Ala Ala Gly Phe Ser Glu His Ser Asp Ala
100 105 110

Met Glu Leu Val Met Thr Gly Ala Tyr Glu Asn Pro Ser Leu Ser Val
115 120 125

Tyr Pro Ser Ser Asn Val Thr Ser Gly Val Ser Ile Ser Phe Ser Cys
130 135 140

Ser Ser Ser Ile Val Phe Gly Arg Phe Ile Leu Ile Gln Glu Gly Lys
145 150 155 160

His Gly Leu Ser Trp Thr Leu Asp Ser Gln His Gln Ala Asn Gln Pro
165 170 175

Ser Tyr Ala Thr Phe Val Leu Asp Ala Val Thr Pro Asn His Asn Gly
180 185 190

Thr Phe Arg Cys Tyr Gly Tyr Phe Arg Asn Glu Pro Gln Val Trp Ser
195 200 205

Lys Pro Ser Asn Ser Leu Asp Leu Met Ile Ser Glu Thr Lys Asp Gln
210 215 220

Ser Ser Thr Pro Thr Glu Asp Gly Leu Glu Thr Tyr Gln Lys Ile Leu
225 230 235 240

Ile Gly Val Leu Val Ser Phe Leu Leu Leu Phe Phe Leu Leu Leu Phe
245 250 255

Leu Ile Leu Ile Gly Tyr Gln Tyr Gly His Lys Lys Lys Ala Asn Ala
260 265 270

Ser Val Lys Asn Thr Gln Ser Glu Asn Asn Ala Glu Leu Asn Ser Trp
275 280 285

Asn Pro Gln Asn Glu Asp Pro Gln Gly Ile Val Tyr Ala Gln Val Lys
290 295 300

Pro Ser Arg Leu Gln Lys Asp Thr Ala Cys Lys Glu Thr Gln Asp Val
305 310 315 320

Thr Tyr Ala Gln Leu Cys Ile Arg Thr Gln Glu Gln Asn Asn Ser
325 330 335

<210> SEQ ID NO 163
<211> LENGTH: 215

<212> TYPE: PRT
<213> ORGANISM: Mus musculus
<220> FEATURE:
<221> NAME/KEY: source
<222> LOCATION: (1)..(215)
<223> OTHER INFORMATION: Extracellular domain of gp49B1

<400> SEQUENCE: 163

```
Gly His Leu Pro Lys Pro Ile Ile Trp Ala Glu Pro Gly Ser Val Ile
1               5                   10                  15

Ala Ala Tyr Thr Ser Val Ile Thr Trp Cys Gln Gly Ser Trp Glu Ala
            20                  25                  30

Gln Tyr Tyr His Leu Tyr Lys Glu Lys Ser Val Asn Pro Trp Asp Thr
        35                  40                  45

Gln Val Pro Leu Glu Thr Arg Asn Lys Ala Lys Phe Asn Ile Pro Ser
    50                  55                  60

Met Thr Thr Ser Tyr Ala Gly Ile Tyr Lys Cys Tyr Tyr Glu Ser Ala
65                  70                  75                  80

Ala Gly Phe Ser Glu His Ser Asp Ala Met Glu Leu Val Met Thr Gly
                85                  90                  95

Ala Tyr Glu Asn Pro Ser Leu Ser Val Tyr Pro Ser Ser Asn Val Thr
            100                 105                 110

Ser Gly Val Ser Ile Ser Phe Ser Cys Ser Ser Ser Ile Val Phe Gly
        115                 120                 125

Arg Phe Ile Leu Ile Gln Glu Gly Lys His Gly Leu Ser Trp Thr Leu
    130                 135                 140

Asp Ser Gln His Gln Ala Asn Gln Pro Ser Tyr Ala Thr Phe Val Leu
145                 150                 155                 160

Asp Ala Val Thr Pro Asn His Asn Gly Thr Phe Arg Cys Tyr Gly Tyr
                165                 170                 175

Phe Arg Asn Glu Pro Gln Val Trp Ser Lys Pro Ser Asn Ser Leu Asp
            180                 185                 190

Leu Met Ile Ser Glu Thr Lys Asp Gln Ser Ser Thr Pro Thr Glu Asp
        195                 200                 205

Gly Leu Glu Thr Tyr Gln Lys
    210                 215
```

<210> SEQ ID NO 164
<211> LENGTH: 864
<212> TYPE: DNA
<213> ORGANISM: Homo sapiens
<220> FEATURE:
<221> NAME/KEY: source
<222> LOCATION: (1)..(864)
<223> OTHER INFORMATION: cDNA of Lair1

<400> SEQUENCE: 164

```
atgtctcccc accccaccgc cctcctgggc ctagtgctct gcctggccca gaccatccac     60

acgcaggagg aagatctgcc cagaccctcc atctcggctg agccaggcac cgtgatcccc    120

ctggggagcc atgtgacttt cgtgtgccgg ggcccggttg ggttcaaac attccgcctg    180

gagagggaca gtagatccac atacaatgat actgaagatg tgtctcaagc tagtccatct    240

gagtcagagg ccagattccg cattgactca gtaagagaag gaaatgccgg gctttatcgc    300

tgcatctatt ataagccccc taaatggtct gagcagagtg actacctgga gctgctggtg    360

aaagaaagct ctggaggccc ggactccccg gacacagagc ccggctcctc agctggaccc    420

acgcagaggc cgtcggacaa cagtcacaat gagcatgcac ctgcttccca aggcctgaaa    480
```

```
gctgagcatc tgtatattct catcggggtc tcagtggtct tcctcttctg tctcctcctc    540

ctggtcctct tctgcctcca tcgccagaat cagataaagc aggggccccc cagaagcaag    600

gacgaggagc agaagccaca gcagaggcct gacctggctg ttgatgttct agagaggaca    660

gcagacaagg ccacagtcaa tggacttcct gagaaggaca gagagacgga cacctcggcc    720

ctggctgcag ggagttccca ggaggtgacg tatgctcagc tggaccactg ggccctcaca    780

cagaggacag cccgggctgt gtccccacag tccacaaagc ccatggccga gtccatcacg    840

tatgcagccg ttgccagaca ctga                                           864


<210> SEQ ID NO 165
<211> LENGTH: 287
<212> TYPE: PRT
<213> ORGANISM: Homo sapiens
<220> FEATURE:
<221> NAME/KEY: source
<222> LOCATION: (1)..(287)
<223> OTHER INFORMATION: Lair1

<400> SEQUENCE: 165

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
        35                  40                  45

Cys Arg Gly Pro Val Gly Val Gln Thr Phe Arg Leu Glu Arg Glu Ser
    50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Ser Glu Gly Asn Ala
                85                  90                  95

Gly Pro Tyr Arg Cys Ile Tyr Tyr Lys Pro Pro Lys Trp Ser Glu Gln
            100                 105                 110

Ser Asp Tyr Leu Glu Leu Leu Val Lys Glu Thr Ser Gly Gly Pro Asp
        115                 120                 125

Ser Pro Asp Thr Glu Pro Gly Ser Ser Ala Gly Pro Thr Gln Arg Pro
    130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
        275                 280                 285
```

-continued

<210> SEQ ID NO 166
<211> LENGTH: 144
<212> TYPE: PRT
<213> ORGANISM: Homo sapiens
<220> FEATURE:
<221> NAME/KEY: source
<222> LOCATION: (1)..(144)
<223> OTHER INFORMATION: Extracellular domain of Lair1

<400> SEQUENCE: 166

```
Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
        115                 120                 125

Asn Glu His Ala Pro Ala Ser Gln Gly Leu Lys Ala Glu His Leu Tyr
    130                 135                 140
```

<210> SEQ ID NO 167
<211> LENGTH: 792
<212> TYPE: DNA
<213> ORGANISM: Mus musculus
<220> FEATURE:
<221> NAME/KEY: source
<222> LOCATION: (1)..(792)
<223> OTHER INFORMATION: cDNA of Lair1

<400> SEQUENCE: 167

```
atgtcacttc atccagttat cctgctggtg cttgtgctgt gcctgggatg gaaaattaac      60

acacaggagg gttctctgcc tgatattacc atcttcccta attcaagtct tatgatctcc     120

caagggactt ttgtaactgt tgtgtgctca tactctgata aacacgactt gtataacatg     180

gtccgcctgg agaaggacgg cagcaccttt atggaaaaga gcactgagcc ttataaaaca     240

gaggatgaat ttgagattgg gccagtgaat gaaaccatta ctggacatta tagctgtatc     300

tattcgaagg ggattacctg gtccgaacgt agtaagacgc tggagctaaa ggtgatcaaa     360

gaaaatgtca tccagactcc tgccccaggt ccaacctcag atacatcttg gctaaagaca     420

tacagcattt acatttttac tgtggtctct gtgattttcc tcctttgtct ttccgccctt     480

ctgttctgct tcctcaggca ccgtcagaaa aagcagggac tcccaaacaa caaaagacag     540

cagcagaggc cagaagagag gctaaatcta gctactaatg gcctggagat gactccagac     600

atagttgcag atgacaggct tcctgaggac agatggacag aaacctggac cccagttgca     660

ggagaccttc aagaggtgac gtatatccag ctggaccatc actccctcac acagagggca     720

gtcggagctg tgacctcaca gagcacagat atggctgagt ccagcacata tgcagccatc     780

atcagacact ga                                                         792
```

<210> SEQ ID NO 168
<211> LENGTH: 263
<212> TYPE: PRT
<213> ORGANISM: Mus musculus
<220> FEATURE:
<221> NAME/KEY: source
<222> LOCATION: (1)..(263)
<223> OTHER INFORMATION: Lair

<400> SEQUENCE: 168

```
Met Ser Leu His Pro Val Ile Leu Leu Val Leu Val Leu Cys Leu Gly
1               5                   10                  15

Trp Lys Ile Asn Thr Gln Glu Gly Ser Leu Pro Asp Ile Thr Ile Phe
            20                  25                  30

Pro Asn Ser Ser Leu Met Ile Ser Gln Gly Thr Phe Val Thr Val Val
        35                  40                  45

Cys Ser Tyr Ser Asp Lys His Asp Leu Tyr Asn Met Val Arg Leu Glu
    50                  55                  60

Lys Asp Gly Ser Thr Phe Met Glu Lys Ser Thr Glu Pro Tyr Lys Thr
65                  70                  75                  80

Glu Asp Glu Phe Glu Ile Gly Pro Val Asn Glu Thr Ile Thr Gly His
                85                  90                  95

Tyr Ser Cys Ile Tyr Ser Lys Gly Ile Thr Trp Ser Glu Arg Ser Lys
            100                 105                 110

Thr Leu Glu Leu Lys Val Ile Lys Glu Asn Val Ile Gln Thr Pro Ala
        115                 120                 125

Pro Gly Pro Thr Ser Asp Thr Ser Trp Leu Lys Thr Tyr Ser Ile Tyr
    130                 135                 140

Ile Phe Thr Val Val Ser Val Ile Phe Leu Leu Cys Leu Ser Ala Leu
145                 150                 155                 160

Leu Phe Cys Phe Leu Arg His Arg Gln Lys Lys Gln Gly Leu Pro Asn
                165                 170                 175

Asn Lys Arg Gln Gln Gln Arg Pro Glu Glu Arg Leu Asn Leu Ala Thr
            180                 185                 190

Asn Gly Leu Glu Met Thr Pro Asp Ile Val Ala Asp Asp Arg Leu Pro
        195                 200                 205

Glu Asp Arg Trp Thr Glu Thr Trp Thr Pro Val Ala Gly Asp Leu Gln
    210                 215                 220

Glu Val Thr Tyr Ile Gln Leu Asp His His Ser Leu Thr Gln Arg Ala
225                 230                 235                 240

Val Gly Ala Val Thr Ser Gln Ser Thr Asp Met Ala Glu Ser Ser Thr
                245                 250                 255

Tyr Ala Ala Ile Ile Arg His
            260
```

<210> SEQ ID NO 169
<211> LENGTH: 123
<212> TYPE: PRT
<213> ORGANISM: Mus musculus
<220> FEATURE:
<221> NAME/KEY: source
<222> LOCATION: (1)..(123)
<223> OTHER INFORMATION: Extracellular domain of Lair1

<400> SEQUENCE: 169

```
Gln Glu Gly Ser Leu Pro Asp Ile Thr Ile Phe Pro Asn Ser Ser Leu
1               5                   10                  15
```

```
Met Ile Ser Gln Gly Thr Phe Val Thr Val Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
    50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr
        115                 120


<210> SEQ ID NO 170
<211> LENGTH: 1470
<212> TYPE: DNA
<213> ORGANISM: Homo sapiens
<220> FEATURE:
<221> NAME/KEY: source
<222> LOCATION: (1)..(1470)
<223> OTHER INFORMATION: cDNA of LILRA1

<400> SEQUENCE: 170

atgaccccca tcgtcacagt cctgatctgt ctcaggctga gtctgggccc ccggacccac      60

gtgcaggcag ggaccctccc caagcccaca ctctgggctg agccaggctc tgtgatcacc     120

caggggagtc ccgtgaccct ctggtgtcag ggggatcctgg agacccagga gtaccgtctg    180

tatagagaaa agaaaacagc accctggatt acacggatcc cacaggagat tgtgaagaag     240

ggccagttcc ccatcccatc catcacctgg gaacacacag ggcggtatcg ctgtttctac     300

ggtagccaca ctgcaggctg gtcagagccc agtgaccccc tggagctggt ggtgacagga     360

gcctacatca aacccaccct ctcagctcta cccagccctg tggtgacctc aggagggaac     420

gtgaccctcc attgtgtctc acaggtggca tttggcagct tcattctgtg taaggaagga     480

gaagatgaac acccacaatg cctgaactca cagccccgta cccatgggtg gtcccgggcc     540

atcttctctg tgggccccgt gagcccgagt cgcaggtggt cgtacaggtg ctatgcttat     600

gactcgaact ctccccatgt gtggtctcta cccagtgatc tcctggagct cctggtccta     660

ggtgtttcta agaagccatc actctcagtg cagccaggtc ctatagtggc ccctggggag     720

agcctgaccc tccagtgtgt ttctgatgtc agctacgaca gatttgttct gtataaggag     780

ggagaacgtg acttcctcca gctccctggc ccacagcccc aggctgggct ctcccaggcc     840

aacttcaccc tgggccctgt gagccgctcc tacgggggcc agtacagatg ctccggtgca     900

tacaacctct cctccgagtg gtcggccccc agcgaccccc tggacatcct gatcgcagga     960

cagttccgtg gcagaccctt catctcggtg catccgggcc ccacggtggc ctcaggagag    1020

aacgtgaccc tgctgtgtca gtcatggggg ccgttccaca ctttccttct gaccaaggcg    1080

ggagcagctg atgcccccct ccgtctcaga tcaatacacg aatatcctaa gtaccaggct    1140

gaattcccta tgagtcctgt gacctcagcc cactcgggga cctacaggtg ctacggctca    1200

ctcagctcca acccctacct gctgtctcac cccagtgact ccctggagct catggtctca    1260

ggagcagctg agaccctcag cccaccacaa aacaagtccg attccaaggc tggagcagct    1320

aacaccctca gcccatcaca aaacaagact gcctcacacc cccaggatta cacagtggag    1380
```

-continued

```
aatctcatcc gcatgggcat agctggcttg gtcctggtgg tcctcgggat tctgctattt   1440

gaggctcagc acagccagag aagcctctga                                    1470


<210> SEQ ID NO 171
<211> LENGTH: 489
<212> TYPE: PRT
<213> ORGANISM: Homo sapiens
<220> FEATURE:
<221> NAME/KEY: source
<222> LOCATION: (1)..(489)
<223> OTHER INFORMATION: LILRA1

<400> SEQUENCE: 171

Met Thr Pro Ile Val Thr Val Leu Ile Cys Leu Arg Leu Ser Leu Gly
1               5                   10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
        35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
                245                 250                 255

Leu Tyr Lys Glu Gly Glu Arg Asp Phe Leu Gln Leu Pro Gly Pro Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Ser Gly Ala Tyr Asn Leu Ser
    290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
                325                 330                 335
```

```
Ala Ser Gly Glu Asn Val Thr Leu Leu Cys Gln Ser Trp Gly Pro Phe
            340                 345                 350

His Thr Phe Leu Leu Thr Lys Ala Gly Ala Ala Asp Ala Pro Leu Arg
        355                 360                 365

Leu Arg Ser Ile His Glu Tyr Pro Lys Tyr Gln Ala Glu Phe Pro Met
    370                 375                 380

Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
                405                 410                 415

Leu Met Val Ser Gly Ala Ala Glu Thr Leu Ser Pro Pro Gln Asn Lys
            420                 425                 430

Ser Asp Ser Lys Ala Gly Ala Ala Asn Thr Leu Ser Pro Ser Gln Asn
        435                 440                 445

Lys Thr Ala Ser His Pro Gln Asp Tyr Thr Val Glu Asn Leu Ile Arg
    450                 455                 460

Met Gly Ile Ala Gly Leu Val Leu Val Val Leu Gly Ile Leu Leu Phe
465                 470                 475                 480

Glu Ala Gln His Ser Gln Arg Ser Leu
                485


<210> SEQ ID NO 172
<211> LENGTH: 445
<212> TYPE: PRT
<213> ORGANISM: Homo sapiens
<220> FEATURE:
<221> NAME/KEY: source
<222> LOCATION: (1)..(445)
<223> OTHER INFORMATION: Extracellular domain of LILRA1

<400> SEQUENCE: 172

Pro Arg Thr His Val Gln Ala Gly Thr Leu Pro Lys Pro Thr Leu Trp
1               5                   10                  15

Ala Glu Pro Gly Ser Val Ile Thr Gln Gly Ser Pro Val Thr Leu Trp
            20                  25                  30

Cys Gln Gly Ile Leu Glu Thr Gln Glu Tyr Arg Leu Tyr Arg Glu Lys
        35                  40                  45

Lys Thr Ala Pro Trp Ile Thr Arg Ile Pro Gln Glu Ile Val Lys Lys
    50                  55                  60

Gly Gln Phe Pro Ile Pro Ser Ile Thr Trp Glu His Thr Gly Arg Tyr
65                  70                  75                  80

Arg Cys Phe Tyr Gly Ser His Thr Ala Gly Trp Ser Glu Pro Ser Asp
                85                  90                  95

Pro Leu Glu Leu Val Val Thr Gly Ala Tyr Ile Lys Pro Thr Leu Ser
            100                 105                 110

Ala Leu Pro Ser Pro Val Val Thr Ser Gly Gly Asn Val Thr Leu His
        115                 120                 125

Cys Val Ser Gln Val Ala Phe Gly Ser Phe Ile Leu Cys Lys Glu Gly
    130                 135                 140

Glu Asp Glu His Pro Gln Cys Leu Asn Ser Gln Pro Arg Thr His Gly
145                 150                 155                 160

Trp Ser Arg Ala Ile Phe Ser Val Gly Pro Val Ser Pro Ser Arg Arg
                165                 170                 175

Trp Ser Tyr Arg Cys Tyr Ala Tyr Asp Ser Asn Ser Pro His Val Trp
            180                 185                 190

Ser Leu Pro Ser Asp Leu Leu Glu Leu Leu Val Leu Gly Val Ser Lys
```

```
        195                 200                 205

Lys Pro Ser Leu Ser Val Gln Pro Gly Pro Ile Val Ala Pro Gly Glu
    210                 215                 220

Ser Leu Thr Leu Gln Cys Val Ser Asp Val Ser Tyr Asp Arg Phe Val
225                 230                 235                 240

Leu Tyr Lys Glu Gly Glu Arg Asp Phe Leu Gln Leu Pro Gly Pro Gln
                245                 250                 255

Pro Gln Ala Gly Leu Ser Gln Ala Asn Phe Thr Leu Gly Pro Val Ser
            260                 265                 270

Arg Ser Tyr Gly Gly Gln Tyr Arg Cys Ser Gly Ala Tyr Asn Leu Ser
        275                 280                 285

Ser Glu Trp Ser Ala Pro Ser Asp Pro Leu Asp Ile Leu Ile Ala Gly
    290                 295                 300

Gln Phe Arg Gly Arg Pro Phe Ile Ser Val His Pro Gly Pro Thr Val
305                 310                 315                 320

Ala Ser Gly Glu Asn Val Thr Leu Leu Cys Gln Ser Trp Gly Pro Phe
                325                 330                 335

His Thr Phe Leu Leu Thr Lys Ala Gly Ala Ala Asp Ala Pro Leu Arg
            340                 345                 350

Leu Arg Ser Ile His Glu Tyr Pro Lys Tyr Gln Ala Glu Phe Pro Met
        355                 360                 365

Ser Pro Val Thr Ser Ala His Ser Gly Thr Tyr Arg Cys Tyr Gly Ser
    370                 375                 380

Leu Ser Ser Asn Pro Tyr Leu Leu Ser His Pro Ser Asp Ser Leu Glu
385                 390                 395                 400

Leu Met Val Ser Gly Ala Ala Glu Thr Leu Ser Pro Pro Gln Asn Lys
                405                 410                 415

Ser Asp Ser Lys Ala Gly Ala Ala Asn Thr Leu Ser Pro Ser Gln Asn
            420                 425                 430

Lys Thr Ala Ser His Pro Gln Asp Tyr Thr Val Glu Asn
        435                 440                 445


<210> SEQ ID NO 173
<211> LENGTH: 1452
<212> TYPE: DNA
<213> ORGANISM: Homo sapiens
<220> FEATURE:
<221> NAME/KEY: source
<222> LOCATION: (1)..(1452)
<223> OTHER INFORMATION: cDNA of LILRA2

<400> SEQUENCE: 173

atgaccccca tcctcacggt cctgatctgt ctcgggctga gtctgggccc caggacccac      60

gtgcaggcag ggcacctccc caagcccacc ctctgggctg agccaggctc tgtgatcatc     120

cagggaagtc ctgtgaccct caggtgtcag gggagccttc aggctgagga gtaccatcta     180

tatagggaaa acaaatcagc atcctgggtt agacggatac aagagcctgg gaagaatggc     240

cagttcccca tcccatccat cacctgggaa cacgcagggc ggtatcactg tcagtactac     300

agccacaatc actcatcaga gtacagtgac cccctggagc tggtggtgac aggagcctac     360

agcaaaccca ccctctcagc tctgcccagc cctgtggtga cctcaggagg gaacgtgacc     420

ctccagtgtg tctcacaggt ggcatttgac ggcttcattc tgtgtaagga aggagaagat     480

gaacacccac aacgcctgaa ctcccattcc catgcccgtg ggtggtcctg ggccatcttc     540

tccgtgggcc ccgtgagccc gagtcgcagg tggtcgtaca ggtgctatgc ttatgactcg     600
```

```
aactctccct atgtgtggtc tctacccagt gatctcctgg agctcctggt cccaggtgtt    660

tctaagaagc catcactctc agtgcagcca ggtcctatgg tggcccctgg ggagagcctg    720

accctccagt gtgtctctga tgtcggctac gacagatttg ttctgtataa ggagggagaa    780

cgtgacttcc tccagcgccc tggttggcag ccccaggctg ggctctccca ggccaacttc    840

accctgggcc ctgtgagccc ctcccacggg ggccagtaca gatgctacag tgcacacaac    900

ctctcctccg agtggtcggc ccccagtgac cccctggaca tcctgatcac aggacagttc    960

tatgacagac cctctctctc ggtgcagccg gtccccacag tagccccagg aaagaacgtg   1020

accctgctgt gtcagtcacg gggcagttc cacactttcc ttctgaccaa ggagggggca   1080

ggccatcccc cactgcatct gagatcagag caccaagctc agcagaacca ggctgaattc   1140

cgcatgggtc ctgtgacctc agcccacgtg ggacctaca gatgctacag ctcactcagc   1200

tccaacccct acctgctgtc tctccccagt gacccccctgg agctcgtggt ctcagaagca   1260

gctgagaccc tcagcccatc acaaaacaag acagactcca cgactacatc cctaggccaa   1320

cacccccagg attacacagt ggagaatctc atccgcatgg gtgtggctgg cttggtcctg   1380

gtggtcctcg ggattctgct atttgaggct cagcacagcc agagaagcct acaagatgca   1440

gccgggaggt ga                                                        1452
```

```
<210> SEQ ID NO 174
<211> LENGTH: 483
<212> TYPE: PRT
<213> ORGANISM: Homo sapiens
<220> FEATURE:
<221> NAME/KEY: source
<222> LOCATION: (1)..(483)
<223> OTHER INFORMATION: LILRA2

<400> SEQUENCE: 174

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190

Tyr Arg Cys Tyr Ala Tyr Asp Ser Asn Ser Pro Tyr Val Trp Ser Leu
```

```
        195                 200                 205

Pro Ser Asp Leu Leu Glu Leu Leu Val Pro Gly Val Ser Lys Lys Pro
    210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
                245                 250                 255

Lys Glu Gly Glu Arg Asp Phe Leu Gln Arg Pro Gly Trp Gln Pro Gln
            260                 265                 270

Ala Gly Leu Ser Gln Ala Asn Phe Thr Leu Gly Pro Val Ser Pro Ser
        275                 280                 285

His Gly Gly Gln Tyr Arg Cys Tyr Ser Ala His Asn Leu Ser Ser Glu
    290                 295                 300

Trp Ser Ala Pro Ser Asp Pro Leu Asp Ile Leu Ile Thr Gly Gln Phe
305                 310                 315                 320

Tyr Asp Arg Pro Ser Leu Ser Val Gln Pro Val Pro Thr Val Ala Pro
                325                 330                 335

Gly Lys Asn Val Thr Leu Leu Cys Gln Ser Arg Gly Gln Phe His Thr
            340                 345                 350

Phe Leu Leu Thr Lys Glu Gly Ala Gly His Pro Pro Leu His Leu Arg
        355                 360                 365

Ser Glu His Gln Ala Gln Gln Asn Gln Ala Glu Phe Arg Met Gly Pro
    370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
                405                 410                 415

Val Ser Glu Ala Ala Glu Thr Leu Ser Pro Ser Gln Asn Lys Thr Asp
            420                 425                 430

Ser Thr Thr Thr Ser Leu Gly Gln His Pro Gln Asp Tyr Thr Val Glu
        435                 440                 445

Asn Leu Ile Arg Met Gly Val Ala Gly Leu Val Leu Val Val Leu Gly
    450                 455                 460

Ile Leu Leu Phe Glu Ala Gln His Ser Gln Arg Ser Leu Gln Asp Ala
465                 470                 475                 480

Ala Gly Arg


<210> SEQ ID NO 175
<211> LENGTH: 426
<212> TYPE: PRT
<213> ORGANISM: Homo sapiens
<220> FEATURE:
<221> NAME/KEY: source
<222> LOCATION: (1)..(426)
<223> OTHER INFORMATION: Extracellular domain of LILRA2

<400> SEQUENCE: 175

Gly His Leu Pro Lys Pro Thr Leu Trp Ala Glu Pro Gly Ser Val Ile
1               5                   10                  15

Ile Gln Gly Ser Pro Val Thr Leu Arg Cys Gln Gly Ser Leu Gln Ala
            20                  25                  30

Glu Glu Tyr His Leu Tyr Arg Glu Asn Lys Ser Ala Ser Trp Val Arg
        35                  40                  45

Arg Ile Gln Glu Pro Gly Lys Asn Gly Gln Phe Pro Ile Pro Ser Ile
    50                  55                  60
```

```
Thr Trp Glu His Ala Gly Arg Tyr His Cys Gln Tyr Tyr Ser His Asn
65                  70                  75                  80

His Ser Ser Glu Tyr Ser Asp Pro Leu Glu Leu Val Val Thr Gly Ala
                85                  90                  95

Tyr Ser Lys Pro Thr Leu Ser Ala Leu Pro Ser Pro Val Val Thr Leu
            100                 105                 110

Gly Gly Asn Val Thr Leu Gln Cys Val Ser Gln Val Ala Phe Asp Gly
        115                 120                 125

Phe Ile Leu Cys Lys Glu Gly Glu Asp Glu His Pro Gln Arg Leu Asn
    130                 135                 140

Ser His Ser His Ala Arg Gly Trp Ser Trp Ala Ile Phe Ser Val Gly
145                 150                 155                 160

Pro Val Ser Pro Ser Arg Arg Trp Ser Tyr Arg Cys Tyr Ala Tyr Asp
                165                 170                 175

Ser Asn Ser Pro Tyr Val Trp Ser Leu Pro Ser Asp Leu Leu Glu Leu
            180                 185                 190

Leu Val Pro Gly Val Ser Lys Lys Pro Ser Leu Ser Val Gln Pro Gly
        195                 200                 205

Pro Met Val Ala Pro Gly Glu Ser Leu Thr Leu Gln Cys Val Ser Asp
    210                 215                 220

Val Gly Tyr Asp Arg Phe Val Leu Tyr Lys Glu Gly Glu Arg Asp Phe
225                 230                 235                 240

Leu Gln Arg Pro Gly Trp Gln Pro Gln Ala Gly Leu Ser Gln Ala Asn
                245                 250                 255

Phe Thr Leu Gly Pro Val Ser Pro Ser His Gly Gly Gln Tyr Arg Cys
            260                 265                 270

Tyr Ser Ala His Asn Leu Ser Ser Glu Trp Ser Ala Pro Ser Asp Pro
        275                 280                 285

Leu Asp Ile Leu Ile Thr Gly Gln Phe Tyr Asp Arg Pro Ser Leu Ser
    290                 295                 300

Val Gln Pro Val Pro Thr Val Ala Pro Gly Lys Asn Val Thr Leu Leu
305                 310                 315                 320

Cys Gln Ser Arg Gly Gln Phe His Thr Phe Leu Leu Thr Lys Glu Gly
                325                 330                 335

Ala Gly His Pro Pro Leu His Leu Arg Ser Glu His Gln Ala Gln Gln
            340                 345                 350

Asn Gln Ala Glu Phe Arg Met Gly Pro Val Thr Ser Ala His Val Gly
        355                 360                 365

Thr Tyr Arg Cys Tyr Ser Ser Leu Ser Ser Asn Pro Tyr Leu Leu Ser
    370                 375                 380

Leu Pro Ser Asp Pro Leu Glu Leu Val Val Ser Glu Ala Ala Glu Thr
385                 390                 395                 400

Leu Ser Pro Ser Gln Asn Lys Thr Asp Ser Thr Thr Thr Ser Leu Gly
                405                 410                 415

Gln His Pro Gln Asp Tyr Thr Val Glu Asn
            420                 425
```

```
<210> SEQ ID NO 176
<211> LENGTH: 1320
<212> TYPE: DNA
<213> ORGANISM: Homo sapiens
<220> FEATURE:
<221> NAME/KEY: source
<222> LOCATION: (1)..(1320)
<223> OTHER INFORMATION: cDNA of LILRA3
```

<400> SEQUENCE: 176
atgaccccca tcctcacggt cctgatctgt ctcgggctga gcctggaccc caggacccac 60
gtgcaggcag ggcccctccc caagcccacc ctctgggctg agccaggctc tgtgatcacc 120
caagggagtc ctgtgaccct caggtgtcag gggagcctgg agacgcagga gtaccatcta 180
tatagagaaa agaaaacagc actctggatt acacggatcc cacaggagct tgtgaagaag 240
ggccagttcc ccatcctatc catcacctgg gaacatgcag ggcggtattg ctgtatctat 300
ggcagccaca ctgcaggcct ctcagagagc agtgaccccc tggagctggt ggtgacagga 360
gcctacagca aacccaccct ctcagctctg cccagccctg tggtgacctc aggagggaat 420
gtgaccatcc agtgtgactc acaggtggca tttgatggct tcattctgtg taaggaagga 480
gaagatgaac acccacaatg cctgaactcc cattcccatg cccgtgggtc atcccgggcc 540
atcttctccg tgggccccgt gagcccaagt cgcaggtggt cgtacaggtg ctatggttat 600
gactcgcgcg ctccctatgt gtggtctcta cccagtgatc tcctggggct cctggtccca 660
ggtgtttcta agaagccatc actctcagtg cagccgggtc ctgtcgtggc ccctggggag 720
aagctgacct tccagtgtgg ctctgatgcc ggctacgaca gatttgttct gtacaaggag 780
tggggacgtg acttcctcca gcgccctggc cggcagcccc aggctgggct ctcccaggcc 840
aacttcaccc tgggccctgt gagccgctcc tacgggggcc agtacacatg ctccggtgca 900
tacaacctct cctccgagtg gtcggccccc agcgaccccc tggacatcct gatcacagga 960
cagatccgtg ccagaccctt cctctccgtg cggccgggcc ccacagtggc ctcaggagag 1020
aacgtgaccc tgctgtgtca gtcacaggga gggatgcaca ctttcctttt gaccaaggag 1080
ggggcagctg attccccgct gcgtctaaaa tcaaagcgcc aatctcataa gtaccaggct 1140
gaattcccca tgagtcctgt gacctcggcc cacgcgggga cctacaggtg ctacggctca 1200
ctcagctcca acccctacct gctgactcac cccagtgacc ccctggagct cgtggtctca 1260
ggagcagctg agaccctcag cccaccacaa aacaagtccg actccaaggc tggtgagtga 1320

<210> SEQ ID NO 177
<211> LENGTH: 439
<212> TYPE: PRT
<213> ORGANISM: Homo sapiens
<220> FEATURE:
<221> NAME/KEY: source
<222> LOCATION: (1)..(439)
<223> OTHER INFORMATION: LILRA3

<400> SEQUENCE: 177

Met Thr Pro Ile Leu Thr Val Leu Ile Cys Leu Gly Leu Ser Leu Asp
1 5 10 15

Pro Arg Thr His Val Gln Ala Gly Pro Leu Pro Lys Pro Thr Leu Trp
20 25 30

Ala Glu Pro Gly Ser Val Ile Thr Gln Gly Ser Pro Val Thr Leu Arg
35 40 45

Cys Gln Gly Ser Leu Glu Thr Gln Glu Tyr His Leu Tyr Arg Glu Lys
50 55 60

Lys Thr Ala Leu Trp Ile Thr Arg Ile Pro Gln Glu Leu Val Lys Lys
65 70 75 80

Gly Gln Phe Pro Ile Leu Ser Ile Thr Trp Glu His Ala Gly Arg Tyr
85 90 95

Cys Cys Ile Tyr Gly Ser His Thr Ala Gly Leu Ser Glu Ser Ser Asp
100 105 110

```
Pro Leu Glu Leu Val Val Thr Gly Ala Tyr Ser Lys Pro Thr Leu Ser
        115                 120                 125

Ala Leu Pro Ser Pro Val Val Thr Ser Gly Gly Asn Val Thr Ile Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
    210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435
```

<210> SEQ ID NO 178
<211> LENGTH: 416
<212> TYPE: PRT
<213> ORGANISM: Homo sapiens
<220> FEATURE:
<221> NAME/KEY: source
<222> LOCATION: (1)..(416)
<223> OTHER INFORMATION: Extracellular domain of LILRA3

<400> SEQUENCE: 178

```
Gly Pro Leu Pro Lys Pro Thr Leu Trp Ala Glu Pro Gly Ser Val Ile
1               5                   10                  15

Thr Gln Gly Ser Pro Val Thr Leu Arg Cys Gln Gly Ser Leu Glu Thr
```

```
            20                  25                  30

Gln Glu Tyr His Leu Tyr Arg Glu Lys Lys Thr Ala Leu Trp Ile Thr
        35                  40                  45

Arg Ile Pro Gln Glu Leu Val Lys Lys Gly Gln Phe Pro Ile Leu Ser
    50                  55                  60

Ile Thr Trp Glu His Ala Gly Arg Tyr Cys Cys Ile Tyr Gly Ser His
65                  70                  75                  80

Thr Ala Gly Leu Ser Glu Ser Ser Asp Pro Leu Glu Leu Val Val Thr
                85                  90                  95

Gly Ala Tyr Ser Lys Pro Thr Leu Ser Ala Leu Pro Ser Pro Val Val
            100                 105                 110

Thr Ser Gly Gly Asn Val Thr Ile Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser His Ser His Ala Arg Gly Ser Ser Arg Ala Ile Phe Ser
145                 150                 155                 160

Val Gly Pro Val Ser Pro Ser Arg Arg Trp Ser Tyr Arg Cys Tyr Gly
                165                 170                 175

Tyr Asp Ser Arg Ala Pro Tyr Val Trp Ser Leu Pro Ser Asp Leu Leu
            180                 185                 190

Gly Leu Leu Val Pro Gly Val Ser Lys Lys Pro Ser Leu Ser Val Gln
        195                 200                 205

Pro Gly Pro Val Val Ala Pro Gly Glu Lys Leu Thr Phe Gln Cys Gly
    210                 215                 220

Ser Asp Ala Gly Tyr Asp Arg Phe Val Leu Tyr Lys Glu Trp Gly Arg
225                 230                 235                 240

Asp Phe Leu Gln Arg Pro Gly Arg Gln Pro Gln Ala Gly Leu Ser Gln
                245                 250                 255

Ala Asn Phe Thr Leu Gly Pro Val Ser Arg Ser Tyr Gly Gly Gln Tyr
            260                 265                 270

Thr Cys Ser Gly Ala Tyr Asn Leu Ser Ser Glu Trp Ser Ala Pro Ser
        275                 280                 285

Asp Pro Leu Asp Ile Leu Ile Thr Gly Gln Ile Arg Ala Arg Pro Phe
    290                 295                 300

Leu Ser Val Arg Pro Gly Pro Thr Val Ala Ser Gly Glu Asn Val Thr
305                 310                 315                 320

Leu Leu Cys Gln Ser Gln Gly Gly Met His Thr Phe Leu Leu Thr Lys
                325                 330                 335

Glu Gly Ala Ala Asp Ser Pro Leu Arg Leu Lys Ser Lys Arg Gln Ser
            340                 345                 350

His Lys Tyr Gln Ala Glu Phe Pro Met Ser Pro Val Thr Ser Ala His
        355                 360                 365

Ala Gly Thr Tyr Arg Cys Tyr Gly Ser Leu Ser Ser Asn Pro Tyr Leu
    370                 375                 380

Leu Thr His Pro Ser Asp Pro Leu Glu Leu Val Val Ser Gly Ala Ala
385                 390                 395                 400

Glu Thr Leu Ser Pro Pro Gln Asn Lys Ser Asp Ser Lys Ala Gly Glu
                405                 410                 415
```

<210> SEQ ID NO 179
<211> LENGTH: 1500
<212> TYPE: DNA
<213> ORGANISM: Homo sapiens
<220> FEATURE:
<221> NAME/KEY: source
<222> LOCATION: (1)..(1500)
<223> OTHER INFORMATION: cDNA of LILRA4

<400> SEQUENCE: 179

```
atgaccctca ttctcacaag cctgctcttc tttgggctga gcctgggccc caggacccgg     60

gtgcaggcag aaaacctact caaacccatc ctgtgggccg agccaggtcc cgtgatcacc    120

tggcataacc ccgtgaccat ctggtgtcag ggcaccctgg aggcccaggg gtaccgtctg    180

gataaagagg gaaactcaat gtcgaggcac atattaaaaa cactggagtc tgaaaacaag    240

gtcaaactct ccatcccatc catgatgtgg gaacatgcag ggcgatatca ctgttactat    300

cagagccctg caggctggtc agagcccagc gaccccctgg agctggtggt gacagcctac    360

agcagaccca ccctgtccgc actgccaagc cctgtggtga cctcaggagt gaacgtgacc    420

ctccggtgtg cctcacggct gggactgggc aggttcactc tgattgagga aggagaccac    480

aggctctcct ggaccctgaa ctcacaccaa cacaaccatg gaaagttcca ggccctgttc    540

cccatgggcc ccctgacctt cagcaacagg ggtacattca gatgctacgg ctatgaaaac    600

aacaccccat acgtgtggtc ggaacccagt gacccccctgc agctactggt gtcaggcgtg    660

tctaggaagc cctccctcct gaccctgcag ggccctgtcg tgacccccgg agagaatctg    720

accctccagt gtggctctga tgtcggctac atcagataca ctctgtacaa ggagggggcc    780

gatggcctcc cccagcgccc tggccggcag ccccaggctg ggctctccca ggccaacttc    840

accctgagcc ctgtgagccg ctcctacggg ggccagtaca gatgctacgg cgcacacaac    900

gtctcctccg agtggtcggc cccccagtgac cccctggata tcctgatcgc aggacagatc    960

tctgacagac cctccctctc agtgcagccg ggccccacgg tgacctcagg agagaaggtg   1020

accctgctgt gtcagtcatg ggacccgatg ttcactttcc ttctgaccaa ggagggggca   1080

gcccatcccc cgttgcgtct gagatcaatg tacggagctc ataagtacca ggctgaattc   1140

cccatgagtc ctgtgacctc agcccacgcg gggacctaca ggtgctacgg ctcacgcagc   1200

tccaacccct acctgctgtc tcaccccagt gagcccctgg agctcgtggt ctcaggagca   1260

actgagaccc tcaatccagc acaaaagaag tcagattcca agactgcccc acacctccag   1320

gattacacag tggagaatct catccgcatg ggtgtggctg gcttggtcct gctgttcctc   1380

gggattctgt tatttgaggc tcagcacagc cagagaagcc ccccaaggtg cagccaggag   1440

gcaaacagca gaaaggacaa tgcacccttc agagtggtgg agccttggga acagatctga   1500
```

<210> SEQ ID NO 180
<211> LENGTH: 499
<212> TYPE: PRT
<213> ORGANISM: Homo sapiens
<220> FEATURE:
<221> NAME/KEY: source
<222> LOCATION: (1)..(499)
<223> OTHER INFORMATION: LILRA4

<400> SEQUENCE: 180

```
Met Thr Leu Ile Leu Thr Ser Leu Leu Phe Phe Gly Leu Ser Leu Gly
1               5                   10                  15

Pro Arg Thr Arg Val Gln Ala Glu Asn Leu Pro Lys Pro Ile Leu Trp
            20                  25                  30

Ala Glu Pro Gly Pro Val Ile Thr Trp His Asn Pro Val Thr Ile Trp
        35                  40                  45

Cys Gln Gly Thr Leu Glu Ala Gln Gly Tyr Arg Leu Asp Lys Glu Gly
```

```
    50                  55                  60

Asn Ser Met Ser Arg His Ile Leu Lys Thr Leu Glu Ser Glu Asn Lys
65                  70                  75                  80

Val Lys Leu Ser Ile Pro Ser Met Met Trp Glu His Ala Gly Arg Tyr
                85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
        115                 120                 125

Pro Ser Pro Val Val Thr Ser Gly Val Asn Val Thr Leu Arg Cys Ala
    130                 135                 140

Ser Arg Leu Gly Leu Gly Arg Phe Thr Leu Ile Glu Glu Gly Asp His
145                 150                 155                 160

Arg Leu Ser Trp Thr Leu Asn Ser His Gln His Asn His Gly Lys Phe
                165                 170                 175

Gln Ala Leu Phe Pro Met Gly Pro Leu Thr Phe Ser Asn Arg Gly Thr
            180                 185                 190

Phe Arg Cys Tyr Gly Tyr Glu Asn Asn Thr Pro Tyr Val Trp Ser Glu
        195                 200                 205

Pro Ser Asp Pro Leu Gln Leu Leu Val Ser Gly Val Ser Arg Lys Pro
    210                 215                 220

Ser Leu Leu Thr Leu Gln Gly Pro Val Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
            260                 265                 270

Ala Gly Leu Ser Gln Ala Asn Phe Thr Leu Ser Pro Val Ser Arg Ser
        275                 280                 285

Tyr Gly Gly Gln Tyr Arg Cys Tyr Gly Ala His Asn Val Ser Ser Glu
    290                 295                 300

Trp Ser Ala Pro Ser Asp Pro Leu Asp Ile Leu Ile Ala Gly Gln Ile
305                 310                 315                 320

Ser Asp Arg Pro Ser Leu Ser Val Gln Pro Gly Pro Thr Val Thr Ser
                325                 330                 335

Gly Glu Lys Val Thr Leu Leu Cys Gln Ser Trp Asp Pro Met Phe Thr
            340                 345                 350

Phe Leu Leu Thr Lys Glu Gly Ala Ala His Pro Pro Leu Arg Leu Arg
        355                 360                 365

Ser Met Tyr Gly Ala His Lys Tyr Gln Ala Glu Phe Pro Met Ser Pro
    370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
            420                 425                 430

Ser Lys Thr Ala Pro His Leu Gln Asp Tyr Thr Val Glu Asn Leu Ile
        435                 440                 445

Arg Met Gly Val Ala Gly Leu Val Leu Leu Phe Leu Gly Ile Leu Leu
    450                 455                 460

Phe Glu Ala Gln His Ser Gln Arg Ser Pro Pro Arg Cys Ser Gln Glu
465                 470                 475                 480
```

```
Ala Asn Ser Arg Lys Asp Asn Ala Pro Phe Arg Val Val Glu Pro Trp
                485                 490                 495

Glu Gln Ile


<210> SEQ ID NO 181
<211> LENGTH: 423
<212> TYPE: PRT
<213> ORGANISM: Homo sapiens
<220> FEATURE:
<221> NAME/KEY: source
<222> LOCATION: (1)..(423)
<223> OTHER INFORMATION: Extracellular domain of LILRA4

<400> SEQUENCE: 181

Glu Asn Leu Pro Lys Pro Ile Leu Trp Ala Glu Pro Gly Pro Val Ile
1               5                   10                  15

Thr Trp His Asn Pro Val Thr Ile Trp Cys Gln Gly Thr Leu Glu Ala
            20                  25                  30

Gln Gly Tyr Arg Leu Asp Lys Glu Gly Asn Ser Met Ser Arg His Ile
        35                  40                  45

Leu Lys Thr Leu Glu Ser Glu Asn Lys Val Lys Leu Ser Ile Pro Ser
    50                  55                  60

Met Met Trp Glu His Ala Gly Arg Tyr His Cys Tyr Tyr Gln Ser Pro
65                  70                  75                  80

Ala Gly Trp Ser Glu Pro Ser Asp Pro Leu Glu Leu Val Val Thr Ala
                85                  90                  95

Tyr Ser Arg Pro Thr Leu Ser Ala Leu Pro Ser Pro Val Val Thr Ser
            100                 105                 110

Gly Val Asn Val Thr Leu Arg Cys Ala Ser Arg Leu Gly Leu Gly Arg
        115                 120                 125

Phe Thr Leu Ile Glu Glu Gly Asp His Arg Leu Ser Trp Thr Leu Asn
    130                 135                 140

Ser His Gln His Asn His Gly Lys Phe Gln Ala Leu Phe Pro Met Gly
145                 150                 155                 160

Pro Leu Thr Phe Ser Asn Arg Gly Thr Phe Arg Cys Tyr Gly Tyr Glu
                165                 170                 175

Asn Asn Thr Pro Tyr Val Trp Ser Glu Pro Ser Asp Pro Leu Gln Leu
            180                 185                 190

Leu Val Ser Gly Val Ser Arg Lys Pro Ser Leu Leu Thr Leu Gln Gly
        195                 200                 205

Pro Val Val Thr Pro Gly Glu Asn Leu Thr Leu Gln Cys Gly Ser Asp
    210                 215                 220

Val Gly Tyr Ile Arg Tyr Thr Leu Tyr Lys Glu Gly Ala Asp Gly Leu
225                 230                 235                 240

Pro Gln Arg Pro Gly Arg Gln Pro Gln Ala Gly Leu Ser Gln Ala Asn
                245                 250                 255

Phe Thr Leu Ser Pro Val Ser Arg Ser Tyr Gly Gly Gln Tyr Arg Cys
            260                 265                 270

Tyr Gly Ala His Asn Val Ser Ser Glu Trp Ser Ala Pro Ser Asp Pro
        275                 280                 285

Leu Asp Ile Leu Ile Ala Gly Gln Ile Ser Asp Arg Pro Ser Leu Ser
    290                 295                 300

Val Gln Pro Gly Pro Thr Val Thr Ser Gly Glu Lys Val Thr Leu Leu
305                 310                 315                 320

Cys Gln Ser Trp Asp Pro Met Phe Thr Phe Leu Leu Thr Lys Glu Gly
```

-continued

```
                325                 330                 335

Ala Ala His Pro Pro Leu Arg Leu Arg Ser Met Tyr Gly Ala His Lys
            340                 345                 350

Tyr Gln Ala Glu Phe Pro Met Ser Pro Val Thr Ser Ala His Ala Gly
        355                 360                 365

Thr Tyr Arg Cys Tyr Gly Ser Arg Ser Ser Asn Pro Tyr Leu Leu Ser
    370                 375                 380

His Pro Ser Glu Pro Leu Glu Leu Val Val Ser Gly Ala Thr Glu Thr
385                 390                 395                 400

Leu Asn Pro Ala Gln Lys Lys Ser Asp Ser Lys Thr Ala Pro His Leu
                405                 410                 415

Gln Asp Tyr Thr Val Glu Asn
            420


<210> SEQ ID NO 182
<211> LENGTH: 900
<212> TYPE: DNA
<213> ORGANISM: Homo sapiens
<220> FEATURE:
<221> NAME/KEY: source
<222> LOCATION: (1)..(900)
<223> OTHER INFORMATION: cDNA of LILRA5

<400> SEQUENCE: 182

atggcaccat ggtctcatcc atctgcacag ctgcagccag tgggaggaga cgccgtgagc      60

cctgccctca tggttctgct ctgcctcggg ctgagtctgg gccccaggac ccacgtgcag     120

gcagggaacc tctccaaagc caccctctgg gctgagccag gctctgtgat cagccggggg     180

aactctgtga ccatccggtg tcaggggacc ctggaggccc aggaataccg tctggttaaa     240

gagggaagcc cagaaccctg ggacacacag aacccactgg agcccaagaa caaggccaga     300

ttctccatcc catccatgac agagcaccat gcagggagat accgctgtta ctactacagc     360

cctgcaggct ggtcagagcc cagcgacccc ctggagctgg tggtgacagg attctacaac     420

aaacccaccc tctcagccct gcccagtcct gtggtgacct caggagagaa cgtgaccctc     480

cagtgtggct cacggctgag attcgacagg ttcattctga ctgaggaagg agaccacaag     540

ctctcctgga ccttggactc acagctgacc cccagtgggc agttccaggc cctgttccct     600

gtgggccctg tgacccccag ccacaggtgg atgctcagat gctatggctc tcgcaggcat     660

atcctgcagg tatggtcaga acccagtgac ctcctggaga ttccggtctc aggagcagct     720

gataacctca gtccgtcaca aaacaagtct gactctggga ctgcctcaca ccttcaggat     780

tacgcagtag agaatctcat ccgcatgggc atggccggct tgatcctggt ggtccttggg     840

attctgatat ttcaggattg gcacagccag agaagccccc aagctgcagc tggaaggtga     900


<210> SEQ ID NO 183
<211> LENGTH: 299
<212> TYPE: PRT
<213> ORGANISM: Homo sapiens
<220> FEATURE:
<221> NAME/KEY: source
<222> LOCATION: (1)..(299)
<223> OTHER INFORMATION: LILRA5

<400> SEQUENCE: 183

Met Ala Pro Trp Ser His Pro Ser Ala Gln Leu Gln Pro Val Gly Gly
1               5                   10                  15

Asp Ala Val Ser Pro Ala Leu Met Val Leu Leu Cys Leu Gly Leu Ser
            20                  25                  30
```

```
Leu Gly Pro Arg Thr His Val Gln Ala Gly Asn Leu Ser Lys Ala Thr
        35                  40                  45

Leu Trp Ala Glu Pro Gly Ser Val Ile Ser Arg Gly Asn Ser Val Thr
    50                  55                  60

Ile Arg Cys Gln Gly Thr Leu Glu Ala Gln Glu Tyr Arg Leu Val Lys
65                  70                  75                  80

Glu Gly Ser Pro Glu Pro Trp Asp Thr Gln Asn Pro Leu Glu Pro Lys
                85                  90                  95

Asn Lys Ala Arg Phe Ser Ile Pro Ser Met Thr Glu His His Ala Gly
            100                 105                 110

Arg Tyr Arg Cys Tyr Tyr Tyr Ser Pro Ala Gly Trp Ser Glu Pro Ser
        115                 120                 125

Asp Pro Leu Glu Leu Val Val Thr Gly Phe Tyr Asn Lys Pro Thr Leu
    130                 135                 140

Ser Ala Leu Pro Ser Pro Val Val Thr Ser Gly Glu Asn Val Thr Leu
145                 150                 155                 160

Gln Cys Gly Ser Arg Leu Arg Phe Asp Arg Phe Ile Leu Thr Glu Glu
                165                 170                 175

Gly Asp His Lys Leu Ser Trp Thr Leu Asp Ser Gln Leu Thr Pro Ser
            180                 185                 190

Gly Gln Phe Gln Ala Leu Phe Pro Val Gly Pro Val Thr Pro Ser His
        195                 200                 205

Arg Trp Met Leu Arg Cys Tyr Gly Ser Arg Arg His Ile Leu Gln Val
    210                 215                 220

Trp Ser Glu Pro Ser Asp Leu Leu Glu Ile Pro Val Ser Gly Ala Ala
225                 230                 235                 240

Asp Asn Leu Ser Pro Ser Gln Asn Lys Ser Asp Ser Gly Thr Ala Ser
                245                 250                 255

His Leu Gln Asp Tyr Ala Val Glu Asn Leu Ile Arg Met Gly Met Ala
            260                 265                 270

Gly Leu Ile Leu Val Val Leu Gly Ile Leu Ile Phe Gln Asp Trp His
        275                 280                 285

Ser Gln Arg Ser Pro Gln Ala Ala Ala Gly Arg
    290                 295
```

```
<210> SEQ ID NO 184
<211> LENGTH: 227
<212> TYPE: PRT
<213> ORGANISM: Homo sapiens
<220> FEATURE:
<221> NAME/KEY: source
<222> LOCATION: (1)..(227)
<223> OTHER INFORMATION: Extracellular domain of LILRA5

<400> SEQUENCE: 184

Gly Asn Leu Ser Lys Ala Thr Leu Trp Ala Glu Pro Gly Ser Val Ile
1               5                   10                  15

Ser Arg Gly Asn Ser Val Thr Ile Arg Cys Gln Gly Thr Leu Glu Ala
            20                  25                  30

Gln Glu Tyr Arg Leu Val Lys Glu Gly Ser Pro Glu Pro Trp Asp Thr
        35                  40                  45

Gln Asn Pro Leu Glu Pro Lys Asn Lys Ala Arg Phe Ser Ile Pro Ser
    50                  55                  60

Met Thr Glu His His Ala Gly Arg Tyr Arg Cys Tyr Tyr Tyr Ser Pro
65                  70                  75                  80
```

-continued

```
Ala Gly Trp Ser Glu Pro Ser Asp Pro Leu Glu Leu Val Val Thr Gly
                85                  90                  95

Phe Tyr Asn Lys Pro Thr Leu Ser Ala Leu Pro Ser Pro Val Val Thr
            100                 105                 110

Ser Gly Glu Asn Val Thr Leu Gln Cys Gly Ser Arg Leu Arg Phe Asp
        115                 120                 125

Arg Phe Ile Leu Thr Glu Glu Gly Asp His Lys Leu Ser Trp Thr Leu
    130                 135                 140

Asp Ser Gln Leu Thr Pro Ser Gly Gln Phe Gln Ala Leu Phe Pro Val
145                 150                 155                 160

Gly Pro Val Thr Pro Ser His Arg Trp Met Leu Arg Cys Tyr Gly Ser
                165                 170                 175

Arg Arg His Ile Leu Gln Val Trp Ser Glu Pro Ser Asp Leu Leu Glu
            180                 185                 190

Ile Pro Val Ser Gly Ala Ala Asp Asn Leu Ser Pro Ser Gln Asn Lys
        195                 200                 205

Ser Asp Ser Gly Thr Ala Ser His Leu Gln Asp Tyr Ala Val Glu Asn
    210                 215                 220

Leu Ile Arg
225


<210> SEQ ID NO 185
<211> LENGTH: 1446
<212> TYPE: DNA
<213> ORGANISM: Homo sapiens
<220> FEATURE:
<221> NAME/KEY: source
<222> LOCATION: (1)..(1446)
<223> OTHER INFORMATION: cDNA of LILRA6

<400> SEQUENCE: 185

atgaccccca ccctcgcagc cctgctctgc ctagggctga gtctgggccc caggacccac      60

gtgcaggcag ggcccttccc caaacccacc ctctgggctg agccaggctc tgtgatcagc     120

tgggggagcc ccgtgaccat ctggtgtcag ggggagcctgg aggcccagga gtaccgactg     180

gataaagagg gaagcccaga gccctgggac agaaataacc cactggaacc caagaacaag     240

gccagattct ccatcccatc cataacagag caccatgcgg ggagataccg ctgccactat     300

tacagctctg caggctggtc agagcccagc gacccccctgg agctggtgat gacaggagcc     360

tatagcaaac ccaccctctc agccctgccc agccctgtgg tggcctcagg ggggaatatg     420

accctccaat gtggctcaca gaagggatat caccattttg ttctgatgaa ggaaggagaa     480

caccagctcc cccggaccct ggactcacag cagctccaca gtggggggtt ccaggccctg     540

ttccctgtgg gccccgtgaa ccccagccac aggtggaggt tcacatgcta ttactattat     600

atgaacaccc cccgggtgtg gtcccacccc agtgaccccc tggagattct gccctcaggc     660

gtgtctagga agccctccct cctgaccctg cagggccctg tcctggcccc tgggcagagc     720

ctgaccctcc agtgtggctc tgatgtcggc tacgacagat ttgttctgta taaggagggg     780

gaacgtgact tcctccagcg ccctggccag cagccccagg ctgggctctc ccaggccaac     840

ttcaccctgg gccctgtgag cccctcccac gggggccagt acaggtgcta tggtgcacac     900

aacctctcct ccgagtggtc ggcccccagc gacccccctga acatcctgat ggcaggacag     960

atctatgaca ccgtctccct gtcagcacag ccgggcccca cagtggcctc aggagagaac    1020

gtgaccctgc tgtgtcagtc atggtggcag tttgacactt tccttctgac caaagaaggg    1080

gcagcccatc ccccactgcg tctgagatca atgtacggag ctcataagta ccaggctgaa    1140
```

```
ttccccatga gtcctgtgac ctcagcccac gcggggacct acaggtgcta cggctcatac   1200

agctccaacc cccacctgct gtctttcccc agtgagcccc tggaactcat ggtctcagga   1260

cactctggag gctccagcct cccacccaca gggccgccct ccacacctgc ctcacacgcc   1320

aaggattaca cagtggagaa tctcatccgc atgggcatgg caggcttggt cctggtgttc   1380

ctcgggattc tgttatttga ggctcagcac agccagagaa acccccaaga tgcagccggg   1440

aggtga                                                              1446
```

```
<210> SEQ ID NO 186
<211> LENGTH: 481
<212> TYPE: PRT
<213> ORGANISM: Homo sapiens
<220> FEATURE:
<221> NAME/KEY: source
<222> LOCATION: (1)..(481)
<223> OTHER INFORMATION: LILRA6

<400> SEQUENCE: 186

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Gln Leu Asp Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Gln His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Tyr Thr Asn Thr Pro Arg Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285
```

```
Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Arg Gly Tyr Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Gly Ser Ser Leu Pro Pro Thr Gly Pro
            420                 425                 430

Pro Ser Thr Pro Ala Ser His Ala Lys Asp Tyr Thr Val Glu Asn Leu
        435                 440                 445

Ile Arg Met Gly Met Ala Gly Leu Val Leu Val Phe Leu Gly Ile Leu
    450                 455                 460

Leu Phe Glu Ala Gln His Ser Gln Arg Asn Pro Gln Asp Ala Ala Gly
465                 470                 475                 480

Arg


<210> SEQ ID NO 187
<211> LENGTH: 424
<212> TYPE: PRT
<213> ORGANISM: Homo sapiens
<220> FEATURE:
<221> NAME/KEY: source
<222> LOCATION: (1)..(424)
<223> OTHER INFORMATION: LILRA6

<400> SEQUENCE: 187

Gly Pro Phe Pro Lys Pro Thr Leu Trp Ala Glu Pro Gly Ser Val Ile
1               5                   10                  15

Ser Trp Gly Ser Pro Val Thr Ile Trp Cys Gln Gly Ser Leu Glu Ala
            20                  25                  30

Gln Glu Tyr Gln Leu Asp Lys Glu Gly Ser Pro Glu Pro Leu Asp Arg
        35                  40                  45

Asn Asn Pro Leu Glu Pro Lys Asn Lys Ala Arg Phe Ser Ile Pro Ser
    50                  55                  60

Met Thr Gln His His Ala Gly Arg Tyr Arg Cys His Tyr Tyr Ser Ser
65                  70                  75                  80

Ala Gly Trp Ser Glu Pro Ser Asp Pro Leu Glu Leu Val Met Thr Gly
                85                  90                  95

Phe Tyr Asn Lys Pro Thr Leu Ser Ala Leu Pro Ser Pro Val Val Ala
            100                 105                 110

Ser Gly Gly Asn Met Thr Leu Arg Cys Gly Ser Gln Lys Gly Tyr His
        115                 120                 125

His Phe Val Leu Met Lys Glu Gly Glu His Gln Leu Pro Arg Thr Leu
    130                 135                 140

Asp Ser Gln Gln Leu His Ser Gly Gly Phe Gln Ala Leu Phe Pro Val
145                 150                 155                 160
```

```
Gly Pro Val Thr Pro Ser His Arg Trp Arg Phe Thr Cys Tyr Tyr Tyr
                165                 170                 175

Tyr Thr Asn Thr Pro Arg Val Trp Ser His Pro Ser Asp Pro Leu Glu
            180                 185                 190

Ile Leu Pro Ser Gly Val Ser Arg Lys Pro Ser Leu Leu Thr Leu Gln
        195                 200                 205

Gly Pro Val Leu Ala Pro Gly Gln Ser Leu Thr Leu Gln Cys Gly Ser
    210                 215                 220

Asp Val Gly Tyr Asp Arg Phe Val Leu Tyr Lys Glu Gly Glu Arg Asp
225                 230                 235                 240

Phe Leu Gln Arg Pro Gly Gln Gln Pro Gln Ala Gly Leu Ser Gln Ala
                245                 250                 255

Asn Phe Thr Leu Gly Pro Val Ser Pro Ser His Gly Gly Gln Tyr Arg
            260                 265                 270

Cys Tyr Gly Ala His Asn Leu Ser Ser Glu Trp Ser Ala Pro Ser Asp
        275                 280                 285

Pro Leu Asn Ile Leu Met Ala Gly Gln Ile Tyr Asp Thr Val Ser Leu
    290                 295                 300

Ser Ala Gln Pro Gly Pro Thr Val Ala Ser Gly Glu Asn Val Thr Leu
305                 310                 315                 320

Leu Cys Gln Ser Arg Gly Tyr Phe Asp Thr Phe Leu Leu Thr Lys Glu
                325                 330                 335

Gly Ala Ala His Pro Pro Leu Arg Leu Arg Ser Met Tyr Gly Ala His
            340                 345                 350

Lys Tyr Gln Ala Glu Phe Pro Met Ser Pro Val Thr Ser Ala His Ala
        355                 360                 365

Gly Thr Tyr Arg Cys Tyr Gly Ser Tyr Ser Ser Asn Pro His Leu Leu
    370                 375                 380

Ser Phe Pro Ser Glu Pro Leu Glu Leu Met Val Ser Gly His Ser Gly
385                 390                 395                 400

Gly Ser Ser Leu Pro Pro Thr Gly Pro Pro Ser Thr Pro Ala Ser His
                405                 410                 415

Ala Lys Asp Tyr Thr Val Glu Asn
            420


<210> SEQ ID NO 188
<211> LENGTH: 675
<212> TYPE: DNA
<213> ORGANISM: Mus musculus
<220> FEATURE:
<221> NAME/KEY: source
<222> LOCATION: (1)..(675)
<223> OTHER INFORMATION: PILRbeta

<400> SEQUENCE: 188

atggctttgc tgatctcgct tcctggaggg actccagcca tggctcaggt cctgcttctg      60

ctctcatcag gctgtctgca tgctggaaat tcagaaagat acaacagaaa aaatggcttt     120

ggggtcaacc aacctgaacg ctgctctgga gtccagggtg gctccatcga catccccttc     180

tccttctatt tcccctggaa gttggccaag gatccacaga tgagcatagc ctggaaatgg     240

aaggatttcc atggggaagt catctacaac tcctccctgc ctttcataca tgagcacttc     300

aagggccggc tcatcctgaa ctggacacag ggtcagacat ctggagtcct cagaatcctg     360

aacttgaagg agtctgacca agcccagtac tttagtcgag ttaatctgca gtcgacagaa     420

ggcatgaagt tgtggcagtc aattcctgga acccaactca acgtgaccca agcactcaac     480
```

```
accaccatga ggagcccctt catcgtcacc tctgaattca ccacagctgg cctggagcac    540

acaagcgacc agaggaatcc ttcactgatg aacctgggag ccatggtcac gatgctcctg    600

gctaaagttt tggtcatagt cctagtctat ggatggatga tcttcctgag gtggaagcaa    660

aggccagcac actaa                                                     675


<210> SEQ ID NO 189
<211> LENGTH: 224
<212> TYPE: PRT
<213> ORGANISM: Mus musculus
<220> FEATURE:
<221> NAME/KEY: source
<222> LOCATION: (1)..(224)
<223> OTHER INFORMATION: PILRbeta

<400> SEQUENCE: 189

Met Ala Leu Leu Ile Ser Leu Pro Gly Gly Thr Pro Ala Met Ala Gln
1               5                   10                  15

Val Leu Leu Leu Leu Ser Ser Gly Cys Leu His Ala Gly Asn Ser Glu
            20                  25                  30

Arg Tyr Asn Arg Lys Asn Gly Phe Gly Val Asn Gln Pro Glu Arg Cys
        35                  40                  45

Ser Gly Val Gln Gly Gly Ser Ile Asp Ile Pro Phe Ser Phe Tyr Phe
    50                  55                  60

Pro Trp Lys Leu Ala Lys Asp Pro Gln Met Ser Ile Ala Trp Lys Trp
65                  70                  75                  80

Lys Asp Phe His Gly Glu Val Ile Tyr Asn Ser Ser Leu Pro Phe Ile
                85                  90                  95

His Glu His Phe Lys Gly Arg Leu Ile Leu Asn Trp Thr Gln Gly Gln
            100                 105                 110

Thr Ser Gly Val Leu Arg Ile Leu Asn Leu Lys Glu Ser Asp Gln Ala
        115                 120                 125

Gln Tyr Phe Ser Arg Val Asn Leu Gln Ser Thr Glu Gly Met Lys Leu
    130                 135                 140

Trp Gln Ser Ile Pro Gly Thr Gln Leu Asn Val Thr Gln Ala Leu Asn
145                 150                 155                 160

Thr Thr Met Arg Ser Pro Phe Ile Val Thr Ser Glu Phe Thr Thr Ala
                165                 170                 175

Gly Leu Glu His Thr Ser Asp Gln Arg Asn Pro Ser Leu Met Asn Leu
            180                 185                 190

Gly Ala Met Val Thr Met Leu Leu Ala Lys Val Leu Val Ile Val Leu
        195                 200                 205

Val Tyr Gly Trp Met Ile Phe Leu Arg Trp Lys Gln Arg Pro Ala His
    210                 215                 220


<210> SEQ ID NO 190
<211> LENGTH: 24
<212> TYPE: DNA
<213> ORGANISM: Mus musculus
<220> FEATURE:
<221> NAME/KEY: source
<222> LOCATION: (1)..(24)
<223> OTHER INFORMATION: Intracellular domain of PILRbeta

<400> SEQUENCE: 190

aggtggaagc aaaggccagc acac                                            24


<210> SEQ ID NO 191
```

<211> LENGTH: 8
<212> TYPE: PRT
<213> ORGANISM: Mus musculus
<220> FEATURE:
<221> NAME/KEY: source
<222> LOCATION: (1)..(8)
<223> OTHER INFORMATION: Intracellular domain of PILRbeta

<400> SEQUENCE: 191

Arg Trp Lys Gln Arg Pro Ala His
1               5

<210> SEQ ID NO 192
<211> LENGTH: 900
<212> TYPE: DNA
<213> ORGANISM: Artificial Sequence
<220> FEATURE:
<223> OTHER INFORMATION: Chimeric LILRB4-PLILRbeta receptor

<400> SEQUENCE: 192
atggatccca aaggatccct ttcctggaga atacttctgt ttctctccct ggcttttgag 60
ttgagctacg gactcgagca ggcagggccc ctccccaaac ccaccctctg ggctgagcca 120
ggctctgtga tcagctgggg gaactctgtg accatctggt gtcaggggac cctggaggct 180
cgggagtacc gtctggataa agaggaaagc ccagcaccct gggacagaca gaacccactg 240
gagcccaaga acaaggccag attctccatc ccatccatga cagaggacta tgcagggaga 300
taccgctgtt actatcgcag ccctgtaggc tggtcacagc ccagtgaccc cctggagctg 360
gtgatgacag gagcctacag taaacccacc ctttcagccc tgccgagtcc tcttgtgacc 420
tcaggaaaga gcgtgaccct gctgtgtcag tcacggagcc caatggacac ttttcttctg 480
atcaaggagc gggcagccca tcccctactg catctgagat cagagcacgg agctcagcag 540
caccaggctg aattccccat gagtcctgtg acctcagtgc acgggggggac ctacaggtgc 600 ttcagctcac acggcttctc ccactacctg ctgtcacacc ccagtgaccc cctggagctc 660
atagtctcag gatccttgga gggtcccagg ccctcaccca caaggtccgt ctcaacagct 720
gcaggccctg aggaccagcc cctcatgcct acagggtcag tcccccacag tggtctgaga 780
aggcactggg agctcgagct gggagccatg gtcacgatgc tcctggctaa agttttggtc 840
atagtcctag tctatggatg gatgatcttc ctgaggtgga agcaaaggcc agcacactaa 900

<210> SEQ ID NO 193
<211> LENGTH: 299
<212> TYPE: PRT
<213> ORGANISM: Artificial Sequence
<220> FEATURE:
<223> OTHER INFORMATION: Chimeric LILRB4-PLILRbeta receptor

<400> SEQUENCE: 193

Met Asp Pro Lys Gly Ser Leu Ser Trp Arg Ile Leu Leu Phe Leu Ser
1               5                   10                  15

Leu Ala Phe Glu Leu Ser Tyr Gly Leu Glu Gln Ala Gly Pro Leu Pro
            20                  25                  30

Lys Pro Thr Leu Trp Ala Glu Pro Gly Ser Val Ile Ser Trp Gly Asn
        35                  40                  45

Ser Val Thr Ile Trp Cys Gln Gly Thr Leu Glu Ala Arg Glu Tyr Arg
    50                  55                  60

Leu Asp Lys Glu Glu Ser Pro Ala Pro Trp Asp Arg Gln Asn Pro Leu
65                  70                  75                  80

Glu Pro Lys Asn Lys Ala Arg Phe Ser Ile Pro Ser Met Thr Glu Asp

```
                85                  90                  95

Tyr Ala Gly Arg Tyr Arg Cys Tyr Tyr Arg Ser Pro Val Gly Trp Ser
            100                 105                 110

Gln Pro Ser Asp Pro Leu Glu Leu Val Met Thr Gly Ala Tyr Ser Lys
        115                 120                 125

Pro Thr Leu Ser Ala Leu Pro Ser Pro Leu Val Thr Ser Gly Lys Ser
    130                 135                 140

Val Thr Leu Leu Cys Gln Ser Arg Ser Pro Met Asp Thr Phe Leu Leu
145                 150                 155                 160

Ile Lys Glu Arg Ala Ala His Pro Leu Leu His Leu Arg Ser Glu His
                165                 170                 175

Gly Ala Gln Gln His Gln Ala Glu Phe Pro Met Ser Pro Val Thr Ser
            180                 185                 190

Val His Gly Gly Thr Tyr Arg Cys Phe Ser Ser His Gly Phe Ser His
        195                 200                 205

Tyr Leu Leu Ser His Pro Ser Asp Pro Leu Glu Leu Ile Val Ser Gly
    210                 215                 220

Ser Leu Glu Asp Pro Arg Pro Ser Pro Thr Arg Ser Val Ser Thr Ala
225                 230                 235                 240

Ala Gly Pro Glu Asp Gln Pro Leu Met Pro Thr Gly Ser Val Pro His
                245                 250                 255

Ser Gly Leu Arg Arg His Trp Glu Leu Glu Leu Gly Ala Met Val Thr
            260                 265                 270

Met Leu Leu Ala Lys Val Leu Val Ile Val Leu Val Tyr Gly Trp Met
        275                 280                 285

Ile Phe Leu Arg Trp Lys Gln Arg Pro Ala His
    290                 295
```

<210> SEQ ID NO 194
<211> LENGTH: 18
<212> TYPE: DNA
<213> ORGANISM: Artificial Sequence
<220> FEATURE:
<223> OTHER INFORMATION: NFAT promoter

<400> SEQUENCE: 194
tgaaaatgaa aatgaaaa 18

<210> SEQ ID NO 195
<211> LENGTH: 954
<212> TYPE: DNA
<213> ORGANISM: Homo sapiens

<400> SEQUENCE: 195
atgaaggttc tgtgggctgc gttgctggtc acattcctgg caggatgcca ggccaaggtg 60
gagcaagcgg tggagacaga gccggagccc gagctgcgcc agcagaccga gtggcagagc 120
ggccagcgct gggaactggc actgggtcgc ttttgggatt acctgcgctg ggtgcagaca 180
ctgtctgagc aggtgcagga ggagctgctc agctcccagg tcacccagga actgagggcg 240
ctgatggacg agaccatgaa ggagttgaag gcctacaaat cggaactgga ggaacaactg 300
accccggtgg cggaggagac gcgggcacgg ctgtccaagg agctgcaggc ggcgcaggcc 360
cggctgggcg cggacatgga ggacgtgtgc ggccgcctgg tgcagtaccg cggcgaggtg 420
caggccatgc tcggccagag caccgaggag ctgcgggtgc gcctcgcctc ccacctgcgc 480
aagctgcgta agcggctcct ccgcgatgcc gatgacctgc agaagcgcct ggcagtgtac 540

-continued

```
caggccgggg cccgcgaggg cgccgagcgc ggcctcagcg ccatccgcga gcgcctgggg    600

cccctggtgg aacagggccg cgtgcgggcc gccactgtgg gctccctggc cggccagccg    660

ctacaggagc gggcccaggc ctggggcgag cggctgcgcg cgcggatgga ggagatgggc    720

agccggaccc gcgaccgcct ggacgaggtg aaggagcagg tggcggaggt gcgcgccaag    780

ctggaggagc aggcccagca gatacgcctg caggccgagg ccttccaggc ccgcctcaag    840

agctggttcg agcccctggt ggaagacatg cagcgccagt gggccgggct ggtggagaag    900

gtgcaggctg ccgtgggcac cagcgccgcc cctgtgccca gcgacaatca ctga          954
```

<210> SEQ ID NO 196
<211> LENGTH: 317
<212> TYPE: PRT
<213> ORGANISM: Homo sapiens

<400> SEQUENCE: 196

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270
```

-continued

```
Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315
```